US010413505B1

(12) United States Patent
Moshal et al.

(10) Patent No.: US 10,413,505 B1
(45) Date of Patent: *Sep. 17, 2019

(54) PHARMACEUTICAL COMPOSITIONS AND METHODS OF USING THE SAME

(71) Applicant: GENUS LIFESCIENCES INC., Allentown, PA (US)

(72) Inventors: Jeffrey M. Moshal, Allentown, PA (US); Michael Libman, Allentown, PA (US)

(73) Assignee: GENUS LIFESCIENCES INC., Allentown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/934,562

(22) Filed: Mar. 23, 2018

Related U.S. Application Data

(63) Continuation-in-part of application No. 15/434,014, filed on Feb. 15, 2017, now Pat. No. 10,231,961, which is a continuation-in-part of application No. 15/427,011, filed on Feb. 7, 2017, now Pat. No. 10,149,843.

(51) Int. Cl.

| | |
|---|---|
| *A61K 31/46* | (2006.01) |
| *A61K 9/00* | (2006.01) |
| *A61P 23/02* | (2006.01) |
| *A61M 19/00* | (2006.01) |
| *A61B 17/24* | (2006.01) |
| *A61B 1/233* | (2006.01) |

(52) U.S. Cl.
CPC ............ *A61K 9/0043* (2013.01); *A61B 17/24* (2013.01); *A61K 31/46* (2013.01); *A61M 19/00* (2013.01); *A61P 23/02* (2018.01); *A61B 1/233* (2013.01); *A61B 2017/246* (2013.01)

(58) Field of Classification Search
CPC .............................. A61K 31/46; A61K 9/0043
See application file for complete search history.

(56) References Cited

U.S. PATENT DOCUMENTS

| | | | |
|---|---|---|---|
| 4,248,855 A | 2/1981 | Blank et al. | |
| 5,002,974 A | 3/1991 | Geria | |
| 5,276,032 A | 1/1994 | King et al. | |
| 5,563,153 A | 10/1996 | Mueller et al. | |
| 5,589,156 A | 12/1996 | Henry | |
| 5,610,184 A | 3/1997 | Shahinian, Jr. | |
| 5,773,023 A | 6/1998 | Deckner et al. | |
| 5,858,996 A | 1/1999 | Tsao | |
| 6,391,888 B1 | 5/2002 | Gleich | |
| 6,413,499 B1 | 7/2002 | Clay | |
| 6,461,644 B1 | 10/2002 | Jackson et al. | |
| 6,491,940 B1 | 12/2002 | Levin | |
| 6,562,326 B1 | 5/2003 | Miller | |
| 7,713,440 B2 | 5/2010 | Anderson | |
| 7,799,337 B2 | 9/2010 | Levin | |
| 7,855,296 B1 | 12/2010 | Kunetsov | |
| 8,231,588 B2 | 7/2012 | Xia | |
| 8,449,863 B2 | 5/2013 | Anderson | |
| 8,622,993 B2 | 1/2014 | Frey, II et al. | |
| 8,623,412 B2 | 1/2014 | Farid et al. | |
| 8,715,706 B2 | 5/2014 | Barak | |
| 8,765,177 B2 | 7/2014 | Levine et al. | |
| 8,808,732 B2 | 8/2014 | Dong | |
| 8,876,794 B2 | 11/2014 | Xia | |
| 9,227,031 B2 | 1/2016 | Shahaf et al. | |
| 9,308,208 B2 | 4/2016 | Wensley et al. | |
| 9,339,617 B2 | 5/2016 | Shahaf et al. | |
| 9,867,815 B1 | 1/2018 | Moshal et al. | |
| 10,016,407 B1 | 7/2018 | Moshal et al. | |
| 10,149,843 B1 | 12/2018 | Moshal et al. | |
| 10,231,961 B1 | 3/2019 | Moshal et al. | |
| 2014/0018328 A1 | 1/2014 | Harrison et al. | |
| 2014/0187481 A1 | 7/2014 | Tucker et al. | |
| 2014/0228782 A1 | 8/2014 | Barak | |
| 2014/0377368 A1 | 12/2014 | Kiehm et al. | |
| 2015/0045775 A1 | 2/2015 | Xia | |
| 2015/0165136 A1 | 6/2015 | Galgon et al. | |
| 2015/0250887 A1 | 9/2015 | Battaglia et al. | |
| 2015/0258287 A1 | 9/2015 | Shahaf et al. | |
| 2015/0290438 A1 | 10/2015 | Gerrans et al. | |
| 2015/0297845 A1 | 10/2015 | Shahaf et al. | |
| 2015/0306362 A1 | 10/2015 | Battaglia | |
| 2015/0342986 A1 | 12/2015 | Abrahmsohn | |
| 2015/0343063 A1 | 12/2015 | Nelson et al. | |
| 2015/0359738 A1 | 12/2015 | Mulvahill | |
| 2016/0030723 A1 | 2/2016 | Bedrosian | |
| 2016/0106937 A1 | 4/2016 | Shahaf et al. | |
| 2019/0060302 A1 | 2/2019 | Moshal et al. | |

OTHER PUBLICATIONS

Abdel-Rahman et al., "Teratogenic Effect of Ketamine and Cocaine in CF-1 Mice", Teratology, 2000, vol. 61, pp. 291-296.
Abel et al., "Effects of Cocaine Hydrochloride on Reproductive Function and Sexual Behavior of Male Rats and on the Behavior of Their Offspring", Journal of Andrology, vol. 10, No. 1, Jan./Feb. 1989, pp. 17-27.
Addis et al., "Fetal effects of cocaine: an updated meta-analysis", Reproductive Toxicology, 2001, vol. 15, pp. 341-369.
Alexander et al., "Pseudocholinesterase Deficiency Clinical Presentation", Medscape Reference, Jan. 13, 2012, WebMD, LLC, 4 pages.
Alleweireldt et al., "Blockade or stimulation of $D_1$ dopamine receptors attenuates cue reinstatement of extinguished cocaine-seeking behavior in rats", Psychopharmacology, 2002, vol. 159, pp. 284-293.
Ama et al., "Implications of Pharmacogenomics for Anesthesia Providers", AANA Journal, Oct. 2010, vol. 78, No. 5, pp. 393-399.
Ambre et al., "Ecgonine Methyl Ester, A Major Metabolite of Cocaine", Journal of Analytical Toxicology, vol. 6, Jan./Feb. 1982, pp. 26-29.
Ambre et al., "Urinary Excretion of Ecgonine Methyl Ester, a Major Metabolite of Cocaine in Humans", Journal of Analytical Toxicology, vol. 8, Jan./Feb. 1984, pp. 23-25.
Ambre et al., "The Urinary Excretion of Cocaine and Metabolites in Humans: A Kinetic Analysis of Published Data", Journal of Analytical Toxicology, vol. 9, Nov./Dec. 1985, pp. 241245.

(Continued)

*Primary Examiner* — James D. Anderson
(74) *Attorney, Agent, or Firm* — K&L Gates LLP

(57) ABSTRACT

Novel pharmaceutical compositions including cocaine hydrochloride and methods of treating patients using those pharmaceutical compositions are described.

16 Claims, 34 Drawing Sheets

(56) References Cited

OTHER PUBLICATIONS

Ambre et al., "Urinary Excretion of Cocaine, Benzoylecgonine, and Ecgonine Methyl Ester in Humans", Journal of Analytical Toxicology, vol. 12, Nov./Dec. 1988, pp. 301-306.
Aoki et al., "Participation of CYP2A in Cocaine-Induced Hepatotoxicity in Female Mice", Pharmacology & Toxicology, 2000, vol. 87, pp. 26-32.
Astrom et al., "The toxicity of some local anesthetics after application on different mucous membranes and its relation to anesthetic action on the nasal mucosa of the rabbit", The Journal of Pharmacology Experimental Therapeutics, 1961, vol. 132, pp. 87-90.
Atlas et al., "Effects of intravenous cocaine on reproductive function in the mated rabbit", Am J Obstet Gynecol, Dec. 1991, pp. 1785-1790.
Bailey, D., "Cocaine and cocaethylene binding in human serum", Am J Clin Pathol, 1995, vol. 104, pp. 180-186.
Bailey, D., "Cocaine and cocaethylene binding to human milk", Am J Clin Pathol, 1998, vol. 110, pp. 491-494.
Bailey, D., "Amitriptyline and procainamide inhibition of cocaine and cocaethylene degradation in human serum in vitro", J Anal Toxicol, Mar./Apr. 1999, vol. 23, pp. 99-102.
Bailey, D., "Procainamide inhibition of human hepatic degradation of cocaine and cocaethylene in vitro. J Anal Toxicol", May/Jun. 1999, vol. 23, pp. 173-176.
Bailey et al., "The effect of lovastatin and thioridazine on the degradation of cocaine in human serum in vitro", Ther Drug Monit, Apr. 2005, vol. 27, No. 2, pp. 168-170.
Baker et al., "Disulfiram effects on responses to intravenous cocaine administration", Drug Alcohol Depend, Mar. 16, 2007, vol. 87 (2-3), pp. 202-209.
Bandstra et al., "Prenatal drug exposure: infant and toddler outcomes", J Addict Dis, 2010, vol. 29, pp. 245-258.
Barker et al., "Norepinephrine and serotonin transporters: molecular targets of antidepressant drugs", Psychopharmacology: The Fourth Generation of Progress, Bloom F.E. and Kupfer D.J., eds., New York: Raven, 1995, pp. 321-333.
Barat et al., "Development and Validation of a High-performance Liquid Chromatography Method for the Determination of Cocaine, its Metabolites and Lidocaine", Journal of Applied Toxicology, 1996, vol. 16(3), pp. 215-219.
Barat et al., "Kinetics and Rat Locomotor Activity Following Cocaine and Lidocaine Administration", Journal of Applied Toxicology, 1998, vol. 18, pp. 227-232.
Barron et al., "Effects of Neonatal Cocaine Exposure on Two Measures of Balance and Coordination", Neurotoxicology and Teratology, 1994, vol. 16, No. 1, pp. 89-94.
Barron et al., "Neonatal Cocaine Exposure, Activity, and Responsivity to Cocaine in a Rodent Model", Neurotoxicology and Teratology, 1994, vol. 16, No. 4, pp. 401-409.
Barron et al., "Behavioral Effects of Neonatal Cocaine Exposure Using a Rodent Model", Pharmacology Biochemistry and Behavior, 1995, vol. 50, No. 1, pp. 107-114.
Barron et al., "Neonatal cocaine exposure and activity rhythms in rats", Behavioural Brain Research, 1996, 74, pp. 167-174.
Barroso-Moguel et al., "Testicular lesions by chronic administration of cocaine in rats", J Appl Toxicol, 1994, vol. 14(1), pp. 37-41.
Barroso-Moguel et al., "Experimental nephropathy by chronic administration of cocaine in rats", Toxicology, 1995, 98, pp. 41-46.
Barroso-Moguel et al., "Alveolar lesions induced by systemic administration of cocaine to rats", Toxicology Letters, 1999, 110, pp. 113-118.
Barroso-Moguel et al., "Brain lesions induced by chronic cocaine administration to rats", Progress in Neuro-Psychopharmacology & Biological Psychiatry, 2002, 26, pp. 59-63.
Bashkatova et al., "Nitric Oxide and Oxidative Stress in the Brain of Rats Exposed In Utero to Cocaine", Annals New York Academy of Sciences, 2006, 1074, pp. 632-642.
Bateman et al., "Dose-response effect of cocaine on newborn head circumference", Pediatrics, Sep. 3, 2000, vol. 6, No. 3, http://www.pediatrics.org/cgi/content/full/106/3/e33, 6 pages.

Beckman et al., "Hemodynamic and Electrophysiological Actions of Cocaine, Effects of Sodium Bicarbonate as an Antidote in Dogs", Circulation, May 1991, vol. 83, No. 5, pp. 1799-1807.
Bedford et al., "Local Anesthetic Effects of Cocaine and Several Extracts of the Coca Leaf (*E. coca*)", Pharmacology, Biochemistry & Behavior, 1984, vol. 20, pp. 819-821.
Bedotto et al., "Cocaine and Cardiovascular Function in Dogs: Effects on Heart and Peripheral Circulation", JACC, Jun. 1988, vol. 11, No. 6, pp. 1337-1342.
Behnke et al., "Incidence and description of structural brain abnormalities in newborns exposed to cocaine", The Journal of Pediatrics, Feb. 1998, vol. 132, No. 2, pp. 291-294.
Behnke et al., "The search for congenital malformations in newborns with fetal cocaine exposure", Pediatrics, May 2001, vol. 107 No. 5, 6 pages.
Benuck et al., "Oxidative Metabolism of Cocaine: Comparison of Brain and Liver (42822)", Proceedings of the Society for Experimental Biology and Medicine, Feb. 1989, vol. 190, pp. 7-13.
Benzaquen et al., "Effects of cocaine on the coronary arteries", American Heart Journal, Sep. 2001, vol. 142, No. 3, pp. 402-410.
Berul et al., "Effects of cocaine hydrochloride on the male reproductive system", Life Sciences, 1989, vol. 45, No. 1, pp. 91-95.
Beuming et al., "The binding sites for cocaine and dopamine in the dopamine transporter overlap", Nature Neuroscience, Jul. 2008, vol. 11, No. 7, pp. 780-789.
Billman et al., "Cocaine-induced ventricular fibrillation: protection afforded by the calcium antagonist verapamil", The FASEB Journal, Nov. 1988, vol. 2, pp. 2990-2995.
Bingol et al. "Teratogenicity of cocaine in humans", The Journal of Pediatrics, Jan. 1987, vol. 110, No. 1, pp. 93-96.
Blaho et al., "Blood cocaine and metabolite concentrations, clinical findings, and outcome of patients presenting to an ED", Am J Emerg Med, 2000, vol. 18, No. 5, pp. 593-598.
Bonate et al., "Preliminary Physiologically Based Pharmacokinetic Model for Cocaine in the Rat: Model Development and Scale-Up to Humans", Journal of Pharmaceutical Sciences, Aug. 1996, vol. 85, No. 8, pp. 878-883.
Boni et al., "Cocaine Inhalation in the Rat: Pharmacokinetics and Cardiovascular Response", The Journal of Pharmacology and Experimental Therapeutics, 1991, vol. 257, No. 1, pp. 307-315.
Booze et al., "Dose-Response Cocaine Pharmacokinetics and Metabolite Profile Following Intravenous Administration and Arterial Sampling in Unanesthetized, Freely Moving Male Rats", Neurotoxicology and Teratology, 1997, vol. 19. No. 1, pp. 7-15.
Bornheim, L., "Effect of Cytochrome P450 Inducers on Cocaine-Mediated Hepatotoxicity", Toxicology and Applied Pharmacology, 1998, vol. 150, pp. 158-165.
Bosron et al., "Human liver cocaine carboxylesterases", NIDA Research Monograph, No. 173, NIH Archives, 1997, pp. 27-34.
Boyer et al., "Enzymatic Basis for the Transesterification of Cocaine in the Presence of Ethanol: Evidence for the Participation of Microsomal Carboxylesterases", The Journal of Pharmacology and Experimental Therapeutics, 1992, vol. 260, No. 3, pp. 939-946.
Boyer et al., "Pharmacokinetic analysis of the metabolism of cocaine to norcocaine and N-hydroxynorcocaine in mice", Drug Metabolism and Disposition, Nov. 1992, vol. 20, No. 6, pp. 863-868.
Bradberry et al., "Cocaine and Cocaethylene: Microdialysis Comparison of Brain Drug Levels and Effects on Dopamine and Serotonin", Journal of Neurochemistry, 1993, vol. 60, No. 4, pp. 1429-1435.
Brittebo, E., "Binding of cocaine in the liver, olfactory mucosa, eye, and fur of pigmented mice", Toxicology and Applied Pharmacology, Nov. 1988, vol. 96, Issue 2, pp. 315-323.
Bromley et al., "Cocaine absorption from the nasal mucosa", Anaesthesia, 1988, vol. 43, pp. 356-358.
Browne et al., "The influence of plasma butyrylcholinesterase concentration on the in vitro hydrolysis of cocaine in human plasma", Biopharm Drug Dispos, 1998, 19, pp. 309-314.
Brzezinski et al., "Purification and characterization of a human liver carboxylesterase that catalyzes the production of benzoylecgonine and the formation of cocaethylene from alcohol and cocaine", Biochem Pharmacol, 1994, vol. 48, No. 9, pp. 1747-1755.

(56) References Cited

OTHER PUBLICATIONS

Caine et al., "Lack of Self-Administration of Cocaine in Dopamine D1 Receptor Knock-Out Mice", J Neurosci, Nov. 28, 2007, 27(48), 28 pages.

Cañez et al., "Cocaine impairs gonadotropin secretion in oophorectomized monkeys", American Journal of Obstetrics and Gynecology, 1992, vol. 167, No. 6, pp. 1785-1793.

Carmona et al., "Butyrylcholinesterase accelerates cocaine metabolism: in vitro and in vivo effects in nonhuman primates and humans", Drug Metabolism and Disposition, 2000, vol. 28, No. 3, pp. 367-371.

Cascales et al., "Cocaine-induced liver injury in mice elicits specific changes in DNA ploidy and induces programmed death of hepatocytes", Hepatology, 1994, vol. 20, No. 4, pp. 992-1001.

Catlow et al., "Heightened cocaine-induced locomotor activity in adolescent compared to adult female rats", J Psychopharmacol, Sep. 2005, vol. 19, No. 5, 8 pages.

Catravas et al., "Acute cocaine intoxication in the conscious dog: studies on the mechanism of lethality", J Pharmacol Exp Ther, 1981, vol. 217, No. 2, pp. 350-356.

Chan et al., "Induction of Rat Hepatic Cytochrome P-450 by Ketamine and its Toxicological Implications", Journal of Toxicology and Environmental Health, Part A, 2005, vol. 68, pp. 1581-1597.

Chaney et al., "Cocaine convulsions in a breast-feeding baby", J Pediatr, Jan. 1988, vol. 112, No. 1, pp. 134-135.

Chasnoff et al., "Cocaine intoxication in a breast-fed infant", Pediatrics, Dec. 1987, vol. 80, No. 6, pp. 836-838.

Chasnoff, "Maternal cocaine use and genitourinary tract malformations", Teratology, 1988, vol. 37, pp. 201-204.

Chavez et al., "Maternal cocaine use during early pregnancy as a risk factor for congenital urogenital anomalies", JAMA, Aug. 11, 1989, vol. 262, No. 6, pp. 795-798.

Chen et al., "Cocaine exposure during the brain growth spurt: Studies of neonatal survival, somatic growth, and brain development", Neurotoxicology and Teratology, Jul. 1993, vol. 15, pp. 267-273.

Chen et al., "Cocaine attenuates puberty acceleration in female house mice", Pharmacology Biochemistry and Behavior, Feb. 1993, vol. 44, pp. 281-285.

Chen et al., "Effect of cocaine on the production of puberty-accelerating pheromone by male mice", Pharmacology Biochemistry and Behavior, 1993, vol. 46, pp. 835-839.

Chen et al., "Effect of chronic cocaine on reproduction in female house mice", Pharmacology Biochemistry and Behavior, 1994, vol. 48, No. 4, pp. 909-913.

Chen et al., "Cocaine impairs follicular phase pulsatile gonadotropin secretion in rhesus monkeys", Journal of the Society for Gynecologic Investigation, Nov./Dec. 1998, vol. 5, No. 6, pp. 311-316.

Chiriboga et al., "Dose-response effect of fetal cocaine exposure on newborn neurologic function", Pediatrics, Jan. 1999, vol. 103, No. 1, pp. 79-86.

Chow et al., "Kinetics of cocaine distribution, elimination, and chronotropic effects", Clin Pharmacol Ther, Sep. 1985, vol. 38, No. 3, pp. 318-324.

Chow et al., "Direct transport of cocaine from the nasal cavity to brain following intranasal cocaine administration in rats", Journal of Pharmaceutical Sciences, Aug. 1999, vol. 88, No. 8, pp. 754-758.

Church et al., "Dose-dependent consequences of cocaine on pregnancy outcome in the Long-Evans rat", Neurotoxicology and Teratology, 1988, vol. 10, pp. 51-58.

Church et al., "Prenatal cocaine exposure in the Long-Evans rat: I. Dose-dependent effects on gestation, mortality, and postnatal maturation", Neurotoxicology Teratology, 1990, vol. 12, pp. 327-334.

Church et al., "Prenatal cocaine exposure in the Long-Evans rat: II. Dose-dependent effects on offspring behavior", Neurotoxicology Teratology, 1990, vol. 12, pp. 335-343.

Clarkson et al., "Analysis of the Ionic Basis for Cocaine's Biphasic Effect on Action Potential Duration in Guinea-pig Ventricular Myocytes", Journal of Molecular and Cellular Cardiology, May 1996, vol. 28, pp. 667-678.

Cocaine Hydrochloride, Topical Solution package insert, Lannett Company, Inc., Philadelphia, PA, Mar. 2008, 2 pages.

Cocaine Hydrochloride, Topical Solution package insert, Roxane Laboratories, Inc., Columbus, OH, Feb. 2006, 2 pages.

Collins et al., "Intranasal cocaine in humans: effects of sex and menstrual cycle", Pharmacology, Biochemistry and Behavior, 2007, vol. 86, pp. 117-124.

Cone et al., "Simultaneous measurement of cocaine, cocaethylene, their metabolites, and "crack" pyrolysis products by gas chromatography—mass spectrometry", Clinical Chemistry, 1994, vol. 40, No. 7, pp. 1299-1305.

Cone, E., "Pharmacokinetics and pharmacodynamics of cocaine", Journal of Analytical Toxicology, Oct. 1995, vol. 19, pp. 459-478.

Cone et al., "Cocaine metabolism and urinary excretion after different routes of administration", Therapeutic Drug Monitoring, 1998, vol. 20, pp. 556-560.

Cressman et al., "Motherisk Update: Maternal cocaine use during breastfeeding", Canadian Family Physician, Nov. 2012, vol. 58, pp. 1218-1219.

Cressman et al., "Cocaine abuse during pregnancy", J Obstet Gynaecol Can, Jul. 2014, vol. 36, No. 7, pp. 628-631.

Crumb et al., "Characterization of cocaine-induced block of cardiac sodium channels", Biophysical Journal, Mar. 1990, vol. 57, pp. 590-599.

Davies et al., "Physiological parameters in laboratory animals and humans", Pharmaceutical Research, 1993, vol. 10, No. 7, pp. 1093-1095.

Dean et al., "Human liver cocaine esterases: ethanol-mediated formation of ethylcocaine", The FASEB Journal, Sep. 1991, vol. 5, pp. 2735-2739.

DeVane et al., "Tissue distribution of cocaine in the pregnant rat", Life Sciences, 1989, vol. 45, No. 14, pp. 1271-1276.

Dickson et al., "The routine analysis of breast milk for drugs of abuse in a clinical toxicology laboratory", Journal of Forensic Sciences, 1994, vol. 39, No. 1, pp. 207-214.

Dierschke et al. "Induced follicular atresia in rhesus monkeys: strength-duration relationships of the estrogen stimulus", Endocrinology, 1985, vol. 117, No. 4, pp. 1397-1403.

Dietrich et al. "Acute or repeated cocaine administration generates reactive oxygen species and induces antioxidant enzyme activity in dopaminergic rat brain structures", Neuropharmacology, 2005, vol. 48, No. 7, pp. 965-974.

Dow-Edwards et al., "Comparison of oral and subcutaneous routes of cocaine administration on behavior, plasma drug concentration and toxicity in female rats", Pharmacology Biochemistry and Behavior, 1989, vol. 33, pp. 167-173.

Dow-Edwards et al., "Adult reactivity in rats exposed to cocaine during two early postnatal periods", Neurotoxicology and Teratology, 1995, vol. 17, No. 5, pp. 553-559.

Edwards et al., "Protein binding of cocaine in human serum", Pharmaceutical Research, 1988, vol. 5, No. 7, pp. 440-442.

Egashira et al., "Effects of cocaine on epicardial coronary artery reactivity in miniature swine after endothelial injury and high cholesterol feeding: in vivo and in vitro analysis", Journal of Clinical Investigation, Oct. 1991, vol. 88, No. 4, pp. 1307-1314.

Egashira et al., "Effects of cocaine on excitation-contraction coupling of aortic smooth muscle from the ferret", Journal of Clinical Investigation, Apr. 1991, vol. 87, No. 4, pp. 1322-1328.

Einer-Jensen et al., "Local Transfer of Diazepam, but Not of Cocaine, from the Nasal Cavities to the Brain Arterial Blood in Rats", Pharmacology & Toxicology, 2000, vol. 87, pp. 276-278.

El-Bizri et al., "Effects of cocaine on rat embryo development in vivo and in cultures", Pediatric Research, 1991, vol. 29, No. 2, pp. 187-190.

Erzouki et al., "Comparison of the Effects of Cocaine and its Metabolites on Cardiovascular Function in Anesthetized Rats", Journal of Cardiovascular Pharmacology, 1993, vol. 22, No. 4, pp. 557-563.

(56) References Cited

OTHER PUBLICATIONS

Evans et al., "Cocaine-induced hepatotoxicity in mice", Toxicology and Applied Pharmacology, 1978, vol. 45, No. 3, pp. 739-754.
Evans et al., "The effects of smoked cocaine during the follicular and luteal phases of the menstrual cycle in women", Psychopharmacology, 2002, vol. 159, pp. 397-406.
Evans et al., "Pharmacokinetics of Intravenous Cocaine Across the Menstrual Cycle in Rhesus Monkeys", Neuropsychopharmacology, 2004, vol. 29, pp. 1889-1900.
Evans et al., "Pharmacokinetics of repeated doses of intravenous cocaine across the menstrual cycle in rhesus monkeys", Pharmacology, Biochemistry and Behavior, 2006, vol. 83, pp. 56-66.
Evans et al., "Exogenous progesterone attenuates the subjective effects of smoked cocaine in women, but not in men", Neuropsychopharmacology, 2006, vol. 31, pp. 659-674.
Evans et al, "Does the response to cocaine differ as a function of sex or hormonal status in human and non-human primates?", Hormones and Behavior, 2010, vol. 58, pp. 13-21.
Eyler et al., "Birth outcome from a prospective, matched study of prenatal crack/cocaine use: I. Interactive and dose effects on health and growth", Pediatrics, Feb. 1998, vol. 101, No. 2, pp. 229-237.
Eyler et al., "Birth outcome from a prospective, matched study of prenatal crack/cocaine use: II. Interactive and dose effects on Neurobehavioral Assessment", Pediatrics, Feb. 1998, vol. 101, No. 2, pp. 237-241.
Fantel et al., "The teratogenicity of cocaine", Teratology, 1982, vol. 26, pp. 17-19.
Fattinger et al., "Nasal mucosal versus gastrointestinal absorption of nasally administered cocaine", Eur J Clin Pharmacol, 2000, vol. 56, pp. 305-310.
Ferreira et al., "Effects of Cocaine and its Major Metabolites on the HERG-Encoded Potassium Channel", The Journal of Pharmacology and Experimental Therapeutics, 2001, vol. 299, No. 1, pp. 220-226.
Filip et al., "Contribution of Serotonin (5-Hydroxytryptamine; 5-HT) 5-HT2 Receptor Subtypes to the Hyperlocomotor Effects of Cocaine: Acute and Chronic Pharmacological Analyses", The Journal of Pharmacology and Experimental Therapeutics, 2004, vol. 310, No. 3, pp. 1246-1254.
Fineschi et al., "Markers of cardiac oxidative stress and altered morphology after intraperitoneal cocaine injection in a rat model", Int J Legal Med, 2001, vol. 114, pp. 323-330.
Finnell et al., "Preliminary evidence for a cocaine-induced embryopathy in mice", Toxicology and Applied Pharmacology, 1990, vol. 103, pp. 228-237.
Fish et al., "Excretion of cocaine and its metabolites in man", J Pharm Pharmacol, 1969, vol. 21, Suppl., 135 S-138 S.
Fleming et al., "Pharmacology and therapeutic applications of cocaine", Anesthesiology, 1990, vol. 73, pp. 518-531.
Fraker et al., "Mechanism of Cocaine-Induced Myocardial Depression in Dogs", Circulation, Mar. 1990, vol. 81, No. 3, pp. 1012-1016.
Frank et al., "Level of In Utero Cocaine Exposure and Neonatal Ultrasound Findings", Pediatrics, Nov. 1999, vol. 104, 5 Pt 1, 10 pages.
Frank et al., "Growth, Development, and Behavior in Early Childhood Following Prenatal Cocaine Exposure: A Systematic Review", JAMA, Mar. 28, 2001, vol. 285, No. 12, 23 pages.
Frantz et al., "Behavioral and Neurochemical Responses to Cocaine in Periadolescent and Adult Rats", Neuropsychopharmacology, 2007, vol. 32, pp. 625-637.
Freitas et al., "Oxidative stress in the hippocampus after pilocarpine-induced status epilepticus in Wistar rats", FEBS Journal, 2005, vol. 272, pp. 1307-1312.
Garhart et al., "Cocaine-induced changes in perfusion pressure and bile flow in perfused rat livers", Biochemical Pharmacology, 1989, vol. 38, No. 13, pp. 2139-2145.
George et al., "Cocaine Toxicity: Genetic differences in cocaine-induced lethality in rats", Pharmacology Biochemistry and Behavior, 1991, vol. 38, pp. 893-895.
George et al., "Effects of long-term cocaine exposure on spermatogenesis and fertility in peripubertal male rats", Journal of Urology, Jan. 1996, vol. 155, 1, pp. 327-331.
Golden, et al., "Acute Cocaine-Induced Seizures: Differential Sensitivity of Six Inbred Mouse Strains", Neuropsychopharmacology, 2001, vol. 24, No. 3, pp. 291-299.
González et al., "Psychostimulant-induced testicular toxicity in mice: Evidence of cocaine and caffeine effects on the local dopaminergic system", Nov. 11, 2015, PLOS ONE, vol. 10, pp. 1-18.
Gordon, et al., "Changes in testosterone levels in the rat Following intraperitoneal cocaine HCl", Intern. J. Neuroscience, 1980, vol. 11, pp. 139-141.
Greinwald et al., "Absorption of topical cocaine in rhinologic procedures", Laryngoscope, Oct. 1996, vol. 106, pp. 1223-1225.
Hackett et al., "Pseudocholinesterase deficiency: a case report and literature review", Open Journal of Anesthesiology, 2012, vol. 2, pp. 188-194.
Hale et al., "Adverse effects of cocaine on cardiovascular dynamics, myocardial blood flow, and coronary artery diameter in an experimental model", American Heart Journal, Nov. 1989, pp. 927-933.
Hamilton et al., "Cocaine and benzoylecgonine excretion in humans", Journal of Forensic Sciences, 1977, vol. 22, pp. 697-707.
Hardman, "The Pharmacological Basis of Therapeutics", 10th ed. McGraw-Hill, New York, 2001, p. 1945.
Hatfield et al., "Biochemical and molecular analysis of carboxylesterase-mediated hydrolysis of cocaine and heroin", British Journal of Pharmacology, 2010, vol. 160, pp. 1916-1928.
Hayase et al., "Role of cocaethylene in toxic symptoms due to repeated subcutaneous cocaine administration modified by oral doses of ethanol", The Journal of Toxicological Sciences, 1999, vol. 24, No. 3, pp. 227-235.
Hayes et al., "Intravenous cocaine causes epicardial coronary vasoconstriction in the intact dog", Jun. 1991, American Heart Journal, vol. 121, No. 6, pp. 1639-1648.
He et al., "Neurobehavioral deficits in neonatal rhesus monkeys exposed to cocaine in utero", Neurotoxicology and Teratology, 2004, vol. 26, pp. 13-21.
Hearn et al., "Cocaethylene is More Potent Than Cocaine in Mediating Lethality", Pharmacology Biochemistry & Behavior, vol. 39, 1991, pp. 531-533.
Hebra et al., "Systemic and Mesenteric Vascular Effects of Platelet-activating Factor and Cocaine", The American Surgeon, vol. 59, Jan. 1993, pp. 50-54.
Hedaya et al., "Cocaine Pharmacokinetics/Pharmacodynamics in Awake Freely Moving Rats", Pharmaceutical Research, vol. 14, No. 8, 1997, pp. 1099-1102.
Heesch et al., "Effects of cocaine on anterior pituitary and gonadal hormones", The Journal of Pharmacology and Experimental Therapeutics, 1996, vol. 278, No. 3, pp. 1195-1200.
Henderson et al., "Incorporation of isotopically labeled cocaine and metabolites into human hair: 1. dose-response relationships", Journal of Analytical Toxicology, 1996, No. 20, pp. 1-12.
Herculiani et al., "Effects of Chronic Exposure to Crack Cocaine on the Respiratory Tract of Mice", Toxicologic Pathology, 2009, vol. 37, No. 3, pp. 324-332.
Hime et al., "Analysis of cocaine and cocaethylene in blood and tissues by GC-NPD and GC-ion trap mass spectrometry", Journal of Analytical Toxicology, 1991, vol. 15, pp. 241-245.
Honoré et al., "Effects of Cocaine on Basal and Pulsatile Prolactin Levels in Rhesus Monkeys", J Soc Gynecol Investig, vol. 8, No. 6, Nov./Dec. 2001, pp. 351-357.
Howell et al., "Fetal development in rhesus monkeys exposed prenatally to cocaine", Neurotoxicology Teratology, 2001, vol. 23, pp. 133-140.
Hoyme et al., "Prenatal cocaine exposure and fetal vascular disruption", Pediatrics, May 1990, vol. 85, pp. 743-747.
Huang et al., "Effect of cocaine and methylecgonidine on intracellular $Ca^{2+}$ and myocardial contraction in cardiac myocytes", Am. J. Physiol, 1997, vol. 273, Heart Circ. Physiol. 42, pp. H893-H901.
Huestis et al., "Cocaine and metabolites urinary excretion after controlled smoked administration", Journal of Analytical Toxicology, Oct. 2007, vol. 31, pp. 462-468.

(56) References Cited

OTHER PUBLICATIONS

Hunter et al., "Effects of cocaine administration during early organogenesis on prenatal development and postnatal growth in mice", Fundamental and Applied Toxicology, 1995, vol. 28, pp. 177-186.
Inaba et al., "Metabolism of cocaine in man", Clin Pharmacol Ther, May 1978, vol. 23, No. 5, pp. 547-552.
Isenschmid et al., "Concentration of cocaine and metabolites in plasma of humans following intravenous administration and smoking of cocaine", Journal of Analytical Toxicology, Sep./Oct. 1992, vol. 16, pp. 311-314.
Jatlow, P., "Cocaine: analysis, pharmacokinetics, and metabolic disposition", The Yale Journal of Biology and Medicine, 1988; vol. 61, pp. 105-113.
Javaid et al., "Cocaine Plasma Concentration: Relation to Physiological and Subjective Effects in Humans", Science, vol. 202, Oct. 1978, pp. 227-228.
Javaid et al., "Kinetics of cocaine in humans after Intravenous and intranasal administration", Biopharmaceutics & Drug Disposition, 1983, vol. 4, pp. 9-18.
Jeffcoat et al. "Cocaine disposition in humans after intravenous injection, nasal insufflation (snorting), or smoking", Drug Metabolism and Disposition, 1989, vol. 17, No. 2, pp. 153-159.
Jennings et al., "Cocaine-Induced Platelet Defects", Stroke, Sep. 1993, vol. 24, No. 9, pp. 1352-1359.
Johns et al., "Prenatal exposure to Cocaine I: Effects on gestation, development, and activity in Sprague-Dawley rats", Neurotoxicology and Teratology, 1992, vol. 14, pp. 337-342.
Johns et al., "Prenatal Exposure to Cocaine II: Effects on open-field activity and cognitive behavior in Sprague-Dawley rats", Neurotoxicology and Teratology, 1992, vol. 14, pp. 343-349.
Jones, W., "Cocaine use and the breastfeeding mother", The Practicing Midwife, Jan. 2015, vol. 18, 1, pp. 19-22.
Jufer et al., "Cocaine and metabolite concentrations in plasma during repeated oral administration: development of a human laboratory model of chronic cocaine use", Journal of Analytical Toxicology, Oct. 1998, vol. 22, pp. 435-444.
Kanel et al., "Cocaine-induced liver cell injury: Comparison of morphological features in man and in experimental models", Hepatology, vol. 11, No. 4, 1990, pp. 646-651.
Kapur et al. "Brain hemorrhages in cocaine-exposed human fetuses", Teratology, 1991, vol. 44, pp. 11-18.
Katz, et al., "Comparative behavioral pharmacology and toxicology of cocaine and its ethanol-derived metabolite, cocaine ethyl-ester (cocaethylene)", Life Sciences, vol. 50, No. 18, 1992, pp. 1351-1361.
Kaufmann et al., "Cocaine Inhibits Mating-Induced, but not Human Chorionic Gonadotropin-Stimulated, Ovulation in the Rabbit", Biology of Reproduction, 1992, vol. 46, pp. 641-647.
Keller et al., "Acute cardiotoxic effects of cocaine and a hyperadrenergic state in anesthetized dogs", International Journal of Cardiology, 1994, vol. 24, pp. 19-28.
Khroyan et al., "Attenuation of relapse to cocaine seeking by dopamine D1 receptor agonists and antagonists in non-human primates" Psychopharmacology, 2003, vol. 168, pp. 124-131.
King, et al., "Cocaine Disrupts Estrous Cyclicity and Alters the Reproductive Neuroendocrine Axis in the Rat", Neuroendocrinology, 1990, vol. 51, pp. 15-22.
King et al., "Chronic Cocaine Disruption of Estrous Cyclicity in the Rat: Dose-Dependent Effects", The Journal of Pharmacology and Experimental Therapeutics, 1993, vol. 264, No. 1, pp. 29-34.
King et al., "Effect of acute administration of cocaine on pituitary gonadotrophin secretion in female rats", Reproduction, 2001, vol. 122, pp. 723-729.
Knuepfer M., "Cardiovascular disorders associated with cocaine use: myths and truths", Pharmacology & Therapeutics, 2003, vol. 97, pp. 181-222.
Kolbrich et al., "Major and minor metabolites of cocaine in human plasma following controlled subcutaneous cocaine administration", Journal of Analytical Toxicology, Oct. 2006, vol. 30, pp. 501-510.

Kordon et al., "Role of hypothalamic monoaminergic neurones in the gonadotrophin release-regulating mechanisms", Neuropharmacology, 1972, vol. 11, pp. 153-162.
Kosten et al., "Gender differences in response to intranasal cocaine administration to humans", Biol Psychiatry, 1996, vol. 39, pp. 147-148.
Kozanian et al., "Ontogeny of Methamphetamine- and Cocaine-Induced One-Trial Behavioral Sensitization in Preweanling and Adolescent Rats", Behav Pharmacol, Aug. 2012, vol. 23, No. 4, 24 pages.
Kuhn et al., "Effect of Cocaine on the Coronary Circulation and Systemic Hemodynamics in Dogs", JACC, Nov. 15, 1990, vol. 16. No. 6, pp. 1481-1491.
Kuhn et al., "Cocaine Use during Pregnancy and Intrauterine Growth Retardation: New Insights Based on Maternal Hair Tests", American Journal of Epidemiology, 2000, vol. 152, No. 2, pp. 112-119.
Labib et al., "Oral cocaine produces dose-related hepatotoxicity in male mice", Toxicology Letters, 2001, vol. 125, pp. 29-37.
Ladona et al., "Cocaine metabolism in human fetal and adult liver microsomes is related to cytochrome P450 3A expression", Life Sciences, 2000, vol. 68, pp. 431-443.
Lambert et al., "Developmental and behavioral consequences of prenatal cocaine exposure: a review", J Perinatol, Nov. 2012, vol. 32, No. 11, 17 pages.
Lang et al., "Acquired pseudocholinesterase deficiency", Current Anaesthesia & Critical Care, 2010 vol. 21, pp. 297-298.
Lattanzio et al., "Cocaine Increases Intracellular Calcium and Reactive Oxygen Species, Depolarizes Mitochondria, and Activates Genes Associated With Heart Failure and Remodeling", Cardiovascular Toxicology, 2005, vol. 5, No. 4, pp. 377-389.
LeDuc et al., "Norcocaine and N-hydroxynorcocaine formation in human liver microsomes: role of cytochrome P-450 3A4", Pharmacology, 1993, vol. 46, pp. 294-300.
Li et al., "Histopathological changes in the testes of prepubertal male rats after chronic administration of cocaine", Journal of Environmental Pathology, Toxicology and Oncology, 1997, vol. 16, No. 1, pp. 67-71.
Li et al., "Effect of Cocaine on Testicular Blood Flow in Rats: Evaluation by Percutaneous Injection of Xenon-133", Journal of Environmental Pathology, Toxicology and Oncology, 1999, vol. 18, No. 1, pp. 73-77.
Liao et al., "A preliminary study of cocaine absorption from the nasal mucosa", Laryngoscope, Jan. 1999, vol. 109, pp. 98-102.
Lima et al., "Effects of acute systemic cocaine administration on the cortisol, ACTH and prolactin levels of black tufted-ear marmosets", Psychoneuroendocrinology, 2008, vol. 33, pp. 321-327.
Little et al., Is there a cocaine syndrome? Dysmorphic and anthropometric assessment of infants exposed to cocaine, Teratology, 1996, vol. 54, pp. 145-149.
Lluch et al., "Role of dopamine and glutamate receptors in cocaine-induced social effects in isolated and grouped male OF1 mice", Pharmacology, Biochemistry and Behavior, vol. 82, 2005, pp. 478-487.
Long et al., "Medicinal use of cocaine: a shifting paradigm over 25 years", The Laryngoscope, Sep. 2004, vol. 114, pp. 1625-1629.
Lutiger et al., Relationship Between Gestational Cocaine Use and Pregnancy Outcome: A Meta-Analysis, Teratology, 1991, vol. 44, pp. 405-414.
Ma et al., "Cocaine pharmacodynamics after intravenous and oral administration in rats: relation to pharmacokinetics", Psychopharmacology, 1999, vol. 144, pp. 323-332.
Macedo et al., "Cocaine alters catalase activity in prefrontal cortex and striatum of mice", Neuroscience Letters, 2005, vol. 387, pp. 53-56.
Mahalik et al., "Teratogenic potential of cocaine hydrochloride in CF-1 mice", Journal of Pharmaceutical Sciences, Jun. 1980, vol. 69, No. 6, pp. 703-706.
Maiorana et al., "Heterozygous pseudocholinesterase deficiency: a case report and review of the literature", J Oral Maxillofac Surg, 2003, vol. 61, pp. 845-847.

(56) References Cited

OTHER PUBLICATIONS

Matsubara et al., "In vivo and n vitro studies on cocaine metabolism: ecgonine methyl ester as a major metabolite of cocaine", Forensic Science International, vol. 26, 1984, pp. 169-180.

Matsuzaki et al., "Comparison of the Convulsant Effects of Cocaine and Pseudococaine in the Rhesus Monkey", Brain Research Bulletin, vol. 2, 1977, pp. 417-424.

Matsuzaki, M., "Alteration in pattern of eeg activities and convulsant effect of cocaine following chronic administration in the rhesus monkey", Electroencephalography and Clinical Neurophysiology, 1978, vol. 45, pp. 1-15.

Mattes et al., "Cocaine and butyrylcholinesterase (BChE): determination of enzymatic parameters", Life Sciences, 1996, vol. 58, No. 13, PL257-PL261.

Matthews et al., "Interactions of cocaine and cocaine congeners with sodium channels", Biochemical Pharmacology, 1983, vol. 32, No. 3, pp. 455-460.

McCance-Katz et al., "Disulfiram effects on acute cocaine administration", Drug and Alcohol Dependence, 1998, vol. 52, pp. 27-39.

McCarthy et al., "The distribution of cocaine in mice differs by age and strain", Neurotoxicology and Teratology, 2004, vol. 26, pp. 839-848.

McClung et al., "Regulation of dopaminergic transmission and cocaine reward by the Clock gene", PNAS, Jun. 28, 2005, vol. 102, No. 26, pp. 9377-9381.

Mehanny et al., "Teratogenic effect of cocaine and diazepam in CF1 mice", Teratology, 1991, vol. 43, pp. 11-17.

Mehta et al., "Electrocardiographic effects of intravenous cocaine: an experimental study in a canine model", Journal of Cardiovascular Pharmacology, vol. 41, 2003, pp. 25-30.

Mello et al., "Acute effects of cocaine on prolactin and gonadotropins in female rhesus monkey during the follicular phase of the menstrual cycle", The Journal of Pharmacology and Experimental Therapeutics, 1990, vol. 254, No. 3, pp. 815-823.

Mello et al., "Acute Effects of Cocaine on Anterior Pituitary Hormones in Male and Female Rhesus Monkeys", The Journal of Pharmacology and Experimental Therapeutics, vol. 266, No. 2, 1993, pp. 804-811.

Mello et al., "The Effects of Cocaine on Basal and Human Chorionic Gonadotropin-Stimulated Ovarian Steroid Hormones in Female Rhesus Monkeys", The Journal of Pharmacology and Experimental Therapeutics, 2000, vol. 294, No. 3, pp. 1137-1145.

Mello et al., "The Effects of Cocaine on Gonadal Steroid Hormones and LH in Male and Female Rhesus Monkeys", Neuropsychopharmacology, 2004, vol. 29, pp. 2024-2034.

Mendelson et al., "Cocaine pharmacokinetics in men and in women during the follicular and luteal phases of the menstrual cycle", Neuropsychopharmacology, 1999, vol. 21, No. 2, pp. 294-303.

Mendelson et al., "Effects of cocaine on luteinizing hormone in women during the follicular and luteal phases of the menstrual cycle and in men", Journal of Pharmacology and Experimental Therapeutics, 2001, vol. 296, No. 3, pp. 972-979.

Mets et al., "Lethal Toxicity from Equimolar Infusions of Cocaine and Cocaine Metabolites in Conscious and Anesthetized Rats", Anesth Analg, 1995, vol. 81, pp. 1033-1038.

Minnes et al., "Dysmorphic and anthropometric outcomes in 6-year-old prenatally cocaine-exposed children", Neurotoxicol Teratol, 2006, vol. 28, 19 pages.

Mirsa et al. "Disposition and Metabolism of [3H]Cocaine in Acutely and Chronically treated Dogs", Xenobiotica, 1976, vol. 6, No. 9, 537-552.

Mizugaki et al., "The Distribution of [11C] Cocaine in Normal and Cocaine-sensitization Mice", Nucl. Med. Biol., vol. 21, No. 6, 1994, pp. 793-799.

Mo et al., "Role of Nitric Oxide in Cocaine-Induced Acute Hypertension", AJH, 1998, vol. 11, pp. 708-714.

Morishima et al., "Gender-related differences in cocaine toxicity in the rat", J Lab Clin Med, Aug. 1993, vol. 122, No. 2, pp. 157-163.

Morishima et al., "Species- Gender-, and Pregnancy-Related Differences in the Pharmacokinetics and Pharmacodynamics of Cocaine", Biological Mechanisms and Perinatal Exposure to Abused Drugs, NIDA Research Monograph, 1995, pp. 2-21.

Morishima et al., "The Comparative Toxicity of Cocaine and Its Metabolites in Conscious Rats", Anesthesiology, Jun. 1999, vol. 90, No. 6, pp. 1684-1690.

Moritz et al., "Role of reactive oxygen species in cocaine-induced cardiac dysfunction", Cardiovascular Research, 2003, vol. 59, pp. 834-843.

Morris et al., "The effect of chronic cocaine exposure during pregnancy on maternal and infant outcomes in the rhesus monkey," Neurotoxicol Teratol. 1996, vol. 18, No. 2, pp. 147-154.

Morris et al., "The effect of chronic cocaine exposure during pregnancy on the acquisition of operant behaviors by rhesus monkey offspring", Neurotoxicology and Teratology, 1996, vol. 18, No. 2, pp. 155-166.

Morris et al., "The effect of chronic cocaine exposure throughout pregnancy on maternal and infant outcomes in the rhesus monkey", Neurotoxicology and Teratology, 1997, vol. 19, No. 1, p. 47-57.

Muir et al., "Cocaine potentiates the blood pressure and cerebral blood flow response to norepinephrine in rats", European Journal of Pharmacology, 1993, vol. 249, pp. 287-292.

Murphy et al., "The rabbit as a model for studies for cocaine exposure in utero", Laboratory Animal Science, 1995, vol. 45, No. 2, pp. 163-168.

Nayak et al., "Physiological disposition and biotransformation of [3H] cocaine in acutely and chronically treated rats", The Journal of Pharmacology and Experimental Therapeutics, vol. 196, No. 3, 1976, pp. 556-569.

Noorily et al. "Cocaine, Lidocaine, Tetracaine: Which is Best for Topical Nasal Anesthesia", Anesth Analg, 1995, vol. 81, pp. 724-727.

O'Leary et al., "Role of voltage-gated sodium, potassium and calcium channels in the development of cocaine-associated cardiac arrhythmias", British Journal of Clinical Pharmacology, 2010, vol. 69, No. 5, pp. 427-442.

Pacifici et al., "Immunosuppression and oxidative stress induced by acute and chronic exposure to cocaine in rat", International Immunopharmacology, 2003, vol. 3, pp. 581-592.

Pagel et al., "Systemic and Coronary Hemodynamic Effects of Repetitive Cocaine Administration in Conscious Dogs", Journal of Cardiovascular Pharmacology, 1994, vol. 24, pp. 443-453.

Pal et al., "MDR- and CYP3A4-Mediated Drug—Drug Interactions", J Neuroimmune Pharmacol, 2006, vol. 1, pp. 323-339.

Pan et al., "Sensitive and specific high-performance liquid chromatographic assay with ultraviolet detection for the determination of cocaine and its metabolites in rat plasma", Journal of Chromatography B, 1997, vol. 703, pp. 129-138.

Pan et al., "An Animal Model for Simultaneous Pharmacokinetic/Pharmacodynamic Investigations: Application to Cocaine", Journal of Pharmacological and Toxicological Methods, 1998, vol. 39, No. 1, pp. 1-8.

Pan et al., "Cocaine and Alcohol Interactions in the Rat: Effect of Cocaine and Alcohol Pretreatments on Cocaine Pharmacokinetics and Pharmacodynamics", Journal of Pharmaceutical Sciences, Dec. 1999, vol. 88, No. 12, pp. 1266-1274.

Parlaman et al., "Pharmacokinetic profile of cocaine following intravenous administration in the female rabbit", European Journal of Pharmacology, 2007, vol. 563, pp. 124-129.

Parker et al., "Factors affecting serum protein binding of cocaine in humans", The Journal of Pharmacology and Experimental Therapeutics, 1995, vol. 275, No. 2, pp. 605-610.

Pellinen et al., Cocaine N-demethylation and the metabolism-related hepatotoxicity can be prevented by cytochrome P450 3A inhibitors, European Journal of Pharmacology, 1994, vol. 270, pp. 35-43.

Pellinen et al., "Regenerative Changes in Hepatic Morphology and Enhanced Expression of CYP2B10 and CYP3A During Daily Administration of Cocaine", Hepatology, 1996, vol. 23, No. 3, pp. 515-523.

Phillips et al., "Cocaine Cardiotoxicity a Review of the Pathophysiology, Pathology, and Treatment Options", Am J Cardiovasc Drugs, 2009; vol. 9, No. 3, pp. 177-196.

(56) References Cited

OTHER PUBLICATIONS

Pires et al., "Repeated inhalation of crack-cocaine affects spermatogenesis in young and adult mice", Inhalation Toxicology, 2012, vol. 24, No. 7, pp. 439-446.
Pitts et al., "Cardiovascular Effects of Cocaine in Anesthetized and Conscious Rats", Life Sciences, 1987, vol. 40, pp. 1099-1111.
Poet et al., "Participation of cytochromes P4502B and P4503A in cocaine toxicity in rat hepatocytes", Drug Metabolism and Disposition, 1996, vol. 24, No. 1, pp. 74-80.
Poon et al., "Autonomic mechanisms in the acute cardiovascular effects of cocaine in conscious rats", European Journal of Pharmacology, 1998, vol. 363, pp. 147-152.
Potter et al., "Effects of follicular-phase cocaine administration on menstrual and ovarian cyclicity in rhesus monkeys", Am J Obstet Gynecol, 1998, vol. 178, Part 1, pp. 118-125.
Potter et al., "Low-dose follicular-phase cocaine administration disrupts menstrual and ovarian cyclicity in rhesus monkeys", J Soc Gynecol Investig, Mar./Apr. 1999, vol. 6, No. 2, pp. 88-94.
Powers et al., "Subacute Cocaine Treatment Changes Expression of Mouse Liver Cytochrome P450 Isoforms", Pharmacology, 1999, vol. 58, pp. 87-100.
Qiu et al., "Differential effects of cocaine and cocaethylene on intracellular $Ca^{2+}$ and myocardial contraction in cardiac myocytes", Br. J. Pharmacol., 1993, vol. 109, pp. 293-298.
Quinones-Jenab et al., "Cocaine Affects Progesterone Plasma Levels in Female Rats", Pharmacology Biochemistry and Behavior, 2000, vol. 66, No. 2, pp. 449-453.
Raje et al., "Evaluation of the Blood-Brain Barrier Transport, Population Pharmacokinetics, and Brain Distribution of Benztropine Analogs and Cocaine Using in Vitro and in Vivo Techniques", The Journal of Pharmacology and Experimental Therapeutics, 2003, vol. 307, No. 2, pp. 801-808.
Rhee et al., "Toxic Effects of Cocaine to the Cardiovascular System in Conscious and Anesthetized Rats and Rabbits: Evidence for a Direct Effect on the Myocardium", NeuroToxicology, 1990, vol. 11, pp. 361-366.
Riezzo et al., "Side Effects of Cocaine Abuse: Multiorgan Toxicity and Pathological Consequences", Current Medicinal Chemistry, 2012, vol. 19, pp. 5624-5646.
Roberts et al., "Human microsomal N-oxidative metabolism of cocaine", Drug Metabolism and Disposition, 1991, vol. 19, No. 6, pp. 1046-1051.
Roberts et al., "Cocaethylene hepatotoxicity in mice", Biochemical Pharmacology, 1992, vol. 43, No. 9, pp. 1989-1995.
Rofael et al., "Development and Validation of a High-performance Liquid Chromatography Method for the Determination of Cocaine, its Metabolites and Ketamine", Journal of Applied Toxicology, 2002, vol. 22, pp. 123-128.
Rofael et al., "The role of ketamine on plasma cocaine pharmacokinetics in rat", Toxicology Letters, 2002, vol. 129, pp. 167-176.
Rosenkranz, et al., "The carcinogenic potential of cocaine", Cancer Letters, 1990, vol. 52, pp. 243-246.
Roth et al., "Cocaine Hepatotoxicity: Influence of Hepatic Enzyme Inducing and Inhibiting Agents on the Site of Necrosis", Hepatology, vol. 15, No. 5, 1992, pp. 934-940.
Rothman et al., "Amphetamine-Type Central Nervous System Stimulants Release Norepinephrine More Potently Than They Release Dopamine and Serotonin", Synapse, 2001, vol. 39, pp. 32-41.
Rump et al. "Pseudocholinesterase-Activity Reduction during Cardiopulmonary Bypass: The Role of Dilutional Processes and Pharmacological Agents", Gen. Pharmac., 1999, vol. 32, No. 1, pp. 65-69.
Ruth et al., "An Analysis of Cocaine Effects on Locomotor Activities and Heart Rate in Four Inbred Mouse Strains", Pharmacology Biochemistry & Behavior, 1998, vol. 29, pp. 157-162.
Saady et al., "Cocaine, Ecgonine Methyl Ester, and Benzoylecgonine Plasma Profiles in Rhesus Monkeys", Journal of Analytical Toxicology, Nov./Dec. 1995, vol. 19, pp. 571-575.
Salvadori et al., "Cocaine Mutagenicity and Hepatocarcinogenicity Evaluations in Rodents", Teratogenesis, Carcinogenesis, and Mutagenesis, 1998, vol. 18, pp. 199-208.
Sarper et al., "Assessment of Splanchnic Blood Flow in Alcohol and Drug Abuse Using Radionuclide Angiography", Journal of Substance Abuse, 1993, vol. 5, pp. 295-303.
Schindler et al., "Effects of cocaine and cocaine metabolites on cardiovascular function in squirrel monkeys", European Journal of Pharmacology, 2001, vol. 431, pp. 53-59.
Schindler et al., "Interactions between Cocaine and Dopamine Agonists on Cardiovascular Function in Squirrel Monkeys", The Journal of Pharmacology and Experimental Therapeutics, 2002, vol. 300, No. 1, pp. 180-187.
Schwartz et al., "Acute effects of cocaine on catecholamines and cardiac electrophysiology in the conscious dog", The Canadian Journal of Cardiology, May 1988, vol. 4, No. 4, pp. 188-192.
Schwartz et al., "In vitro competitive inhibition of plasma cholinesterase by cocaine: normal and variant genotypes", Clinical Toxicology, 1996, vol. 34, No. 1, pp. 77-81.
Schwartz et al., "Cardiovascular Effects of Cocaine", Circulation, 2010, vol. 122, pp. 2558-2569.
Seifen et al., "Cardiovascular and Lethal Effects of Cocaine in Anesthetized Dogs and Guinea-Pigs", Arch. int. Pharmacodyn., 1989, vol. 300, pp. 241-253.
Shannon et al., "Coronary Vascular Responses to Short-term Cocaine Administration in Conscious Baboons Compared With Dogs", Journal of the American College of Cardiology, Apr. 2000, vol. 35, No. 5, pp. 1347-1354.
Shen et al., "Comparative metabolic capabilities and inhibitory profiles of CYP2D6.1, CYP2D6.10, and CYP2D6.17", Drug Metabolism and Disposition, 2007, vol. 35, No. 8, pp. 1292-1300.
Shuster et al., "Liver damage from cocaine in mice", Life Sciences, 1977, vol. 20, pp. 1035-1041.
Smith et al., "Drug abuse and reproduction", Fertility and Sterility, Sep. 1987, vol. 48, No. 33, pp. 355-373.
Smith et al., "Tachyphylaxis in Cardiovascular Responses to Cocaine in Conscious Rats", Journal of Cardiovascular Pharmacology, 1993, vol. 21, pp. 272-277.
Smith et al., "Urinary excretion of ecgonine and five other cocaine metabolites following controlled oral, intravenous, intranasal, and smoked administration of cocaine", Journal of Analytical Toxicology, Mar. 2010, vol. 34, pp. 57-63.
Soliday et al., "Pseudocholinesterase deficiency: a comprehensive review of genetic, acquired, and drug influences", AANA Journal, 2010, vol. 78, No. 4, pp. 313-320.
Sora et al., "Cocaine reward models: Conditioned place preference can be established in dopamine- and in serotonin-transporter knockout mice", Proc. Natl. Acad. Sci. USA, Jun. 1998, vol. 95, pp. 7699-7704.
Spear et al., "Effects of Prenatal Cocaine Exposure on Behavior During the Early Postnatal Period", Neurotoxicology and Teratology, 1989, vol. 11, pp. 57-63.
Sprauve et al., "Adverse perinatal outcome in parturients who use crack cocaine", Obstetrics & Gynecology, 1997, vol. 89, pp. 674-678.
Steger et al., "Interactions of cocaine and $\Delta^9$-tetrahydrocannabinol with the Hypothalamic-hypophysial axis of the female rat", Fertility and Sterility, May 1981, vol. 35, No. 5, pp. 567-572.
Stewart et al., "Hydrolysis of cocaine in human plasma by cholinesterase", Life Sciences, 1977, vol. 20, pp. 1557-1563.
Stewart et al., "Cocaine metabolism: cocaine and norcocaine hydrolysis by liver and serum esterases", Clin. Pharmacol. Ther., Apr. 1979, vol. 25, No. 4, pp. 464-468.
Sukbuntherng et al., "Quantitative Determination of Cocaine, Cocaethylene (Ethylcocaine), and Metabolites in Plasma and Urine by High-Performance Liquid Chromatography", Journal of Pharmaceutical Sciences, vol. 84, No. 7, Jul. 1995, pp. 799-804.
Sun et al., "High-performance liquid chromatographic determination of cocaine and its metabolites in serum microsamples with fluorimetric detection and its application to pharmacokinetics in rats", Journal of Chromatography B, 2000, vol. 745, pp. 315-323.
Sun et al., "Simultaneous pharmacokinetic modeling of cocaine and its metabolites, norcocaine and benzoylecgonine, after intravenous

(56) References Cited

OTHER PUBLICATIONS and oral Administration in rats", Drug Metabolism and Disposition, 2001, vol. 29, No. 9, pp. 1183-1189.
Tella et al., "Pathophysiological and Pharmacological Mechanisms of Acute Cocaine Toxicity in Conscious Rats", The Journal of Pharmacology and Experimental Therapeutics, 1992, vol. 262, No. 3, pp. 936-946.
Tella S., "Effects of Monoamine Reuptake Inhibitors on Cocaine Self-Administration in Rats", Pharmacology Biochemistry and Behavior, 1995, vol. 51, No. 4, pp. 687-692.
Temsey-Armos et al., "The Effects of Cocaine on Cardiac Electrophysiology in Conscious, Unsedated Dogs", Journal of Cardiovascular Pharmacology, 1992, vol. 19, pp. 883-891.
Tepperman, J., "Metabolic and Endocrine Physiology", 4th Edition, Year Book Medical Publishers, Inc., Chicago, 1981, pp. 130-132.
Tisdale et al., "Electrophysiologic and Electrocardiographic Pharmacodynamics of Cocaine", Pharmacotherapy, 1996, vol. 16, No. 3, pp. 438-445.
Toennes et al., "Studies on Metabolic Pathways of Cocaine and its Metabolites Using Microsome Preparations from Rat Organs", Chem. Res. Toxicol., 2003, vol. 16, pp. 375-381.
Tournier et al., "Interaction of drugs of abuse and maintenance treatments with human P-glycoprotein (ABCB1) and breast cancer resistance protein (ABCG2)", International Journal of Neuropsychopharmacology, 2010, vol. 13, pp. 905-915.
Turillazzi et al., "Cardiovascular Effects of Cocaine: Cellular, Ionic and Molecular Mechanisms", Current Medicinal Chemistry, 2012, vol. 19, pp. 5664-5676.
Van Dyke et al., "Cocaine: plasma concentrations after intranasal application in man", Science, 1976, vol. 91, pp. 859-861.
Van Dyke et al., "Oral cocaine: plasma concentrations and central effects", Science, Apr. 1978, vol. 200, pp. 211-213.
Verlander et al., "The clinical use of cocaine", Otolaryngologic Clinics of North America, 1981, vol. 14, pp. 521-531.
Visalli et al., "Gender differences in cocaine pharmacokinetics in CF-1 mice", Toxicology Letters, 2005, vol. 155, pp. 35-40.
Volkow et al., "Distribution and kinetics of carbon-11-cocaine in the human body measured with PET", The Journal of Nuclear Medicine, Apr. 1992, vol. 33, No. 4, pp. 521-525.
Vorhees et al., "Evaluation of neonatal exposure to cocaine on learning, activity, startle, scent marking, immobility, and plasma cocaine concentrations", Neurotoxicology and Teratology, 2000, vol. 22, pp. 255-265.
Wang et al., "Cocaine enhances myocarditis induced by encephalomyocarditis virus in murine model", AJP-Heart Circ Physiol, Mar. 2002, vol. 282, pp. H956-H963.
Warner et al., "Mechanisms of cocaine hydrolysis and metabolism in vitro and in vivo: a clarification", Therapeutic Drug Monitoring, 2000 vol. 22, pp. 266-270.
Webster et al., "Cocaine as a cause of congenital malformations of vascular origin: Experimental evidence in the rat", Teratology, 1990, vol. 41, pp. 689-697.
Weese-Mayer et al., "Effects of prenatal cocaine exposure on perinatal morbidity and postnatal growth in the rabbit", Dev Pharmacol Ther, 1991, vol. 4, pp. 221-230.
Wiggins et al., "Pharmacokinetics of cocaine: basic studies of route, dosage, pregnancy and lactation", NeuroToxicology, 1989, vol. 10, pp. 367-381.
Wilkinson et al., "Intranasal and oral cocaine kinetics", Clin. Pharmacol. Ther., Mar. 1980, vol. 27, No. 3, pp. 386-394.
Wilson et al., "Acute Pharmacological Activity of Intravenous cocaine in the rhesus monkey", Psychopharmacology Communications, 1976, vol. 2, No. 3, pp. 251-261.
Wilson et al., "Tolerance Develops to the Sympathomimetic but not the Local Anesthetic Effects of Cocaine", Clinical Toxicology, 2000, vol. 38, No. 7, pp. 719-727.
Wilson et al., "Cocaine, Ethanol, and Cocaethylene Cardiotoxicity in an Animal Model of Cocaine and Ethanol Abuse", Academic Emergency Medicine, Mar. 2001, vol. 8, No. 3, pp. 211-222.

Winecker et al., "Detection of cocaine and its metabolites in breast milk", J Forensic Sci., 2001, vol. 46, No. 5, pp. 1221-1223.
Wnhusen et al., "Methylphenidate and cocaine: a placebo-controlled drug interaction study", Pharmacology, Biochemistry and Behavior, 2006, vol. 85, pp. 29-38.
Wise, R., "Neural Mechanisms of the Reinforcing Action of Cocaine", NIDA Research Monograph, 1984, vol. 50, 19 pages.
Yang et al., "Effect of cocaine on germ cell apoptosis in rats at different ages", Asian J Androl, 2006, vol. 8, No. 5, pp. 569-575.
Yao et al., "Characterization of Differential Cocaine Metabolism in Mouse and Rat through Metabolomics-Guided Metabolite Profiling", Drug Metabolism and Disposition, Jan. 2013, vol. 41, pp. 79-88.
Ye et al., "Cocaine and lidocaine have additive inhibitory effects on the GABAA current of acutely dissociated hippocampal pyramidal neurons", Brain Research, 1999, vol. 821, pp. 26-32.
Yelian et al., "The effects of in vitro cocaine exposure on human sperm motility, intracellular calcium, and oocyte penetration", Fertility and Sterility, 1994, vol. 61, No. 5, pp. 915-921.
Zhang et al., "Permeation and metabolism of cocaine in the nasal mucosa", Eur J Drug Metab Pharmacokinet, 2012, vol. 37, pp. 255-262.
Zimring et al., "Intracoronary Versus Intravenous Effects of Cocaine on Coronary Flow and Ventricular Function", Circulation, vol. 89, No. 4, Apr. 1994, pp. 1819-1828.
Zombeck et al., "Evaluation of a pharmacokinetic hypothesis for reduced locomotor stimulation from methamphetamine and cocaine in adolescent versus adult male C57BL/6J mice", Psychopharmacology, 2009, vol. 201, pp. 589-599.
Zombeck et al., "Patterns of neural activity associated with differential acute locomotor stimulation to cocaine and methamphetamine in adolescent versus adult male C57BL/6J mice", Neuroscience, Feb. 17, 2010, vol. 165, No. 4, 26 pages.
Zombeck et al., "Acute locomotor responses to cocaine in adolescents versus adults from 4 divergent inbred mouse strains", Genes Brain Behav., Nov. 2010, vol. 9, No. 8, 15 pages.
Boehrer et al., "Influence of Labetalol on Cocaine-Induced Coronary Vasoconstriction in Humans", The American Journal of Medicine, Jun. 1993, vol. 94, pp. 608-610.
Brogan et al. "Alleviation of Cocaine-Induced Coronary Vasoconstriction by Nitroglycerin", Aug. 1991, JACC, vol. 18, No. 2, p. 581-586.
Brogan et al. "Recurrent Coronary Vasoconstriction Caused by Intranasal Cocaine: Possible Role for Metabolites", Apr. 1992, Annals of Internal Medicine, vol. 116, No. 7, p. 556-561.
Campbell et al., "Comparison of the vasoconstrictive and anesthetic effects of intranasally applied cocaine vs. xylometazoline/lidocaine solution", Otolaryngology—Head Neck Surg, vol. 107, No. 5, Nov. 1992, pp. 697-700.
Cara et al., "Pain during awake nasal intubation after topical cocaine or phenylephrine/lidocaine spray", Anaesthesia, 2003, 58, pp. 775-803.
Chiu et al., "Myocardial Infarction With Topical Cocaine Anesthesia for Nasal Surgery", Arch Otolaryngol Neck Surg, Sep. 1986, vol. 112, pp. 988-990.
El-Din et al., "Severe hypertension during anaesthesia for dacryocystorhinostomy", Anaesthesia, 1985, vol. 40, pp. 787-789.
Flores et al., "Effect of Cocaine on Coronary Artery Dimensions in Atherosclerotic Coronary Artery Disease: Enhanced Vasoconstriction at Sites of Significant Stenoses", JACC. vol. 16, No. 1, Jul. 1990, pp. 74-79.
Green, K., "Reduction of nasal fractures under local anaesthetic", Rhinology, 2001, vol. 39, pp. 43-46.
Gurudevan et al., "Cocaine-Induced Vasoconstriction in the Human Coronary Microcirculation", Circulation, Aug. 6, 2013, pp. 598-604.
Hacker et al., "Effects of Nasopharyngeal Cocaine of Pharyngeal Benzocaine of Esophageal Motility", The American Journal of Gastroenterology, 1987, vol. 82, No. 2, pp. 127-129.
Hari et al., "Acute angle closure glaucoma precipitated by intranasal application of cocaine", The Journal of Laryngology and Otology, Mar. 1999, vol. 113, pp. 250-251.

(56) References Cited

OTHER PUBLICATIONS

Jonathan et al., "Comparison of cocaine and lignocaine as intranasal local anaesthetics", The Journal of Laryngology and Otology, Jul. 1988, vol. 102, pp. 628-629.
Laffey et al., "Prolonged Perioperative Myocardial Ischemia in a Young Male: Due to Topical Intranasal Cocaine?" Journal of Clinical Anesthesia, 1999, vol. 11, 419-424.
Lange et al., "Cocaine-Induced Coronary-Artery Vasoconstriction", The New England Journal of Medicine, Dec. 7, 1989, vol. 321, No. 23, pp. 1557-1562.
Lange et al., "Potentiation of Cocaine-Induced Coronary Vasoconstriction by Beta-Adrenergic Blockade", Annals of Internal Medicine, Jun. 15, 1990, vol. 112, No. 12, pp. 897-903.
Latore et al., "Cocaine or phenylephrine/lignocaine for nasal fibreoptic intubation", European Journal of Anaesthesiology, 1996, vol. 13, pp. 577-581.
Lenders et al., "Coronary spasm after the topical use of cocaine in nasal surgery", Am J Case Rep, 2013, vol. 14, pp. 76-79.
Le Pelley et al., "Anesthésie de contact á la cocaïne pour chirurgie endonasale. Cinétique et tolérance clinique d'une solution concentrée", Ann Fr Anesth Réanim, 1995, vol. 14, abstract, 1 page.
Lips et al., "The Effects of Formulation and Addition of Adrenaline to Cocaine for Haemostasis in Intranasal Surgery", Anaesth Intens Care, 1987, vol. 15, pp. 141-146.
Littlewood et al., "Myocardial Ischemia with Epinephrine and Cocaine during septoplasty", Otolarynology/Head and Neck Surgery Report, 1987, vol. 139, No. 5, pp. 15-18.
Lormans et al., "Ventricular Fibrillation following Local Application of Cocaine and Epinephrine for Nasal Surgery", ORL, 1992, vol. 54, pp. 160-162.
Makaryus et al., "Acute Myocardial Infarction Following the Use of Intranasal Anesthetic Cocaine", Southern Medical Journal, Jul. 2006, vol. 99, No. 7, pp. 759-761.
Minor et al., "Cocaine-induced Myocardial Infarction in Patients with Normal Coronary Arteries", Annals of Internal Medicine, 1991, vol. 115, pp. 797-806.
Molitnero et al., "Coronary-Artery Vasoconstriction Induced by Cocaine, Cigarette Smoking, or Both", The New England Journal of Medicine, Feb. 17, 1994, vol. 330, No. 7, pp. 454-459.
Noorily et al. "Intranasal anesthetic effects of lidocaine and tetracaine compared", Otolaryngology/Head and Neck Surgery, Oct. 1995, vol. 113, No. 4 pp. 370-374.
Oleson et al., "Human Experimental Pain Models for Assessing the Therapeutic Efficacy of Analgesic Drugs", Pharmacol Rev, 2012, vol. 64, pp. 722-779.
Owen et al., "Fractured-nose reduction under local anaesthesia. Is it acceptable to the patient?" Rhinology, 1992, vol. 30, pp. 89-96.
Pirwitz et al., "Influence of Cocaine, Ethanol, or Their Combination on Epicardial Coronary Arterial Dimensions in Humans", Arch Intern Med, Jun. 12, 1995, vol. 155, pp. 1186-1191.
Rezvani et al., "Cocaine Toxicity After Laryngoscopy in an Infant", Can J Clin Pharmacol, Jul. 4, 2006, vol. 13(2), Summer 2006, pp. e232-e235.
Rhidian et al., "Chest pain in the recovery room, following topical intranasal cocaine solution use", BMJ Case Rep, 2015, 2 pages.
Schou et al., "Unexpected Cocaine Intoxication in a Fourteen Month Old Child Following Topical Administration", Journal of Toxicology: Clinical Toxicology, 1987, vol. 25, No. 5, pp. 419-422.
Schubert et al., "Cocaine toxicity in an infant following intranasal instillation of a four percent cocaine solution", Pediatric Emergency Care, 1992, vol. 8, No. 2, pp. 81-82.
Tarver et al., "A comparison of cocaine vs. lidocaine with oxymetazoline for use in nasal procedures", Otolaryngology—Head and Neck Surgery, 1993, vol. 109, No. 4, pp. 653-659.
Torres et al., "Toxicidade Cardiovascular da Cocaína de Natureza Iatrogénica. Caso Clínico [85]", Rev Port Cardiol, 2007, vol. 26, No. 12, pp. 1395-1404.
Valdes et al., "Topical cocaine vs adrenaline in endoscopic sinus surgery: a blinded randomized controlled study", International Forum of Allergy & Rhinology, Aug. 2014, vol. 4, No. 8, pp. 646-650.
Vongpatanasin et al., "Comparison of Cocaine-Induced Vasoconstriction of Left and Right Coronary Arterial Systems", Brief Reports, Excerpta Medica, Inc., 1997, pp. 492-493.
Vongpatanasin et al., "Cocaine Stimulates the Human Cardiovascular System via a Central Mechanism of Action", Circulation, Aug. 3, 1999, pp. 497-502.
Vongpatanasin et al., "Effects of Cocaine on Heart Rate Variability in Healthy Subjects", The American Journal of Cardiology, Feb. 1, 2004, vol. 93, pp. 385-388.
Waldron et al., "Reduction of fractured nasal bones; local versus general anaesthesia", Clin. Otolaryngol., 1989, 14, pp. 357-359.
Das Gupta, "Stability of cocaine hydrochloride solutions at various pH values as determined by high-pressure liquid chromatography", International Journal of Pharmaceutics, Elsevier Biomedical Press, vol. 10, 1982, pp. 249-257.
Cocaine Hydrochloride, Topical Solution CII Product Label, Lannett Company, Inc., 2008, 7 pages.
Lannett Company, Inc. (sponsor), "Topical Application of Cocaine HCI 4%, or 10%, or Placebo Solution in Local (Topical) Anesthesia", ClincalTrials.gov, NCT02500836, first posted Jul. 17, 2015, update posted May 16, 2017, 11 pages.
Pharmaceutical Project Solutions (sponsor), "Topical Anesthetic for Procedures Through the Nose", ClincalTrials.gov, NCT02667054, first posted Jan. 28, 2016, update posted May 17, 2016, 9 pages.
Darpo et al., "Improving the precision of QT measurements", Cardiology Journal, 2011, vol. 18, No. 4, pp. 401-410.
Cocaine Hydrochloride Topical Solution, FDA prescribing information, side effects and uses, Lannett Company, Inc., 2016, 9 pages.
Glomerular Filtration Rate (GFR)—The National Kidney Foundation, accessed at http://web.archive.org/web/20150906064515/https://www.kidney.org/atoz/content/gfr, 2015, 9 pages.
History of Changes for Study: NCT01746940, Topical Application of Cocaine HCI 4% and 10% on Safety and Efficacy in Local (Topical) Anesthesia, Clinical Trials.gov, Lannett Company, Inc., Oct. 22, 2013, V2, 10 pages.
Naughton et al., "Drug-Induced Nephrotoxicity", American Family Physician, Sep. 15, 2008, vol. 78. No. 6, pp. 743-750.

PHARMACEUTICAL COMPOSITIONS AND METHODS OF USING THE SAME

CROSS-REFERENCE TO RELATED APPLICATIONS

This application claims priority under 35 U.S.C. § 120 as a continuation-in-part of co-pending U.S. patent application Ser. No. 15/434,014, filed Feb. 15, 2017, the entire disclosure of which is hereby incorporated herein by reference in its entirety. U.S. patent application Ser. No. 15/434,014 is a continuation-in-part application, and claims the benefit of the filing date under 35 U.S.C. § 120, of U.S. patent application Ser. No. 15/427,011, filed on Feb. 7, 2017.

FIELD OF THE TECHNOLOGY

The present disclosure relates to novel pharmaceutical compositions and methods of treating subjects using those compositions.

DESCRIPTION OF THE BACKGROUND OF THE TECHNOLOGY

Anesthesia is a partial or complete loss of sensation or feeling induced by the administration of various substances. Types of anesthesia are usually classified in one of three main groups: general anesthesia, local anesthesia, and spinal anesthesia. General anesthetics act primarily on the brain, rendering people both insensible to pain and unconscious. Local anesthetics affect only part of the body, and the patient remains conscious. Certain local anesthetics are administered by applying a gel or cream onto the skin or mucosa, while others are injected. When local anesthetics are applied directly to the skin or mucosa they are also referred to as topical anesthetics. Topical anesthetics are absorbed through the skin or mucosa and interact with nerve endings in the dermis. Once topical anesthetics are absorbed, they cause a depolarization of sensory nerves within the outer dermis, temporarily deactivating the sensory nerves. While the anesthetic effect is present, the deactivated sensory nerves do not transmit impulses to the brain, and painful sensations within the anesthetized body region are temporarily decreased or eliminated.

Topical anesthetics are routinely used to provide anesthesia for the skin, eyes, ears, nasal mucosa, oral mucosa, and bronchotracheal area. Topical anesthetics avoid the pain and tissue distortion associated with invasive, injected forms of anesthesia.

Topical nasal anesthesia is used for the management of both routine and emergency procedures, including nasal examination, management of nasal and facial trauma, outpatient and in-patient sino-nasal procedures, and management of facial and nasal abscesses.

Two classes of topical nasal anesthetics are available: amides (e.g., lidocaine) and esters (e.g., benzocaine, tetracaine, cocaine). The mechanism of action of both amides and esters are similar; each prevents conduction in nerve fibers by reversibly blocking sodium channels and preventing the transient rise in sodium conductance necessary for generation of an action potential. The primary mechanism of local anesthetics, in general, is to interfere with $Na^+$ channel activity, thereby preventing depolarization of target cells and reducing or blocking nerve conduction. Sodium channels are responsible for controlling $Na^+$ ion conductance in excitable cells such as neurons and myocardial cells.

Depending on the indication, topical nasal anesthesia may be obtained by the use of topical sprays, cotton swabs, nasal injections, regional nerve blocks, or with a combination of these approaches.

Anesthetics are sometimes combined with a vasoconstrictor to reduce the risk of anesthetic toxicity. The vasoconstrictor reduces systemic absorption of the anesthetic and increases the anesthetic's local tissue retention time. Increased retention time allows the anesthetic to metabolize more slowly, until local vasoconstriction is reversed. Oxymetazoline, epinephrine, or another adrenergic agonist is sometimes used in combination with a topical nasal anesthetic to increase vasoconstriction and to prolong the anesthetic effect by decreasing the rate of systemic absorption.

Epinephrine is commonly used in combination with an anesthetic for intravenous administration in concentrations ranging from 0.0000001% to 0.0001% weight by volume. However, because epinephrine is one of the most powerful alpha 1 agonists, significant cardiovascular side effects may occur, with an increased risk of hypertension, stroke, arrhythmia, or infarction, particularly in individuals with a history of cardiovascular disease.

Cocaine is a naturally-derived compound with anesthetic properties, and it can also be made synthetically. Cocaine prevents conduction in nerve fibers by reversibly blocking sodium channels and preventing the transient rise in sodium conductance necessary for generation of an action potential. Cocaine passes into $Na^+$ channels and binds to the inside of the cell membrane, inhibiting further conduction of $Na^+$ ions through the membrane of electrically active cells, such as nerve cells. Thus, for example, when cocaine is topically applied to a nasal mucous membrane, it is absorbed into the underlying tissue and prevents generation of nerve impulses in electrically active cells, producing a desensitizing effect in the affected cells and tissues of the nasal cavity. The onset and duration of the anesthetic effect of cocaine is dependent on the administered dose and the manner of administration.

Cocaine has no anesthetic effect when applied to intact skin, but is readily absorbed from denuded areas and through mucous membranes. Cocaine has properties that can make it useful as an active agent in topical anesthetic compositions administered prior to diagnostic or surgical procedures performed on highly vascularized regions of a human body (e.g., the nose, throat, larynx, and lower respiratory passages). Cocaine has vasoconstrictor activity which can reduce operative bleeding, and it exhibits both a short time to the onset of localized anesthetic effect and a short duration of action.

Many anesthetic pharmaceutical compositions have poor stability, and hence it may be necessary to prepare the compositions just prior to use. This can be inconvenient or impossible depending on the application and the available facilities. Further, certain topical anesthetics are administered using a tape-shaped medicament, which is unsuited for anesthetizing certain body mucosa (e.g., nasal passages, ear canals, throat, mouth, and eyes).

Accordingly, there is a need for a local anesthetic composition that exhibits advantageous stability and produces vasoconstriction during local anesthesia without systemic negative side effects that can be produced by epinephrine.

SUMMARY

It is understood that the inventions disclosed and described in this specification are not limited to the embodiments described in this Summary.

A non-limiting aspect of the present disclosure is directed to a ready to use pharmaceutical composition comprising about 4% cocaine hydrochloride, by weight, and a preservative in an aqueous solution, wherein a pH of the pharmaceutical composition is 2 to 4. The pharmaceutical composition exhibits advantageous stability, and the cocaine hydrochloride concentration in the pharmaceutical composition remains greater than about 3.4%, by weight, after the composition has been stored for 12 months at a temperature ranging from 23° C. to 27° C. and a relative humidity ranging from 55% to 65%.

Another non-limiting aspect of the present disclosure is directed to a ready to use pharmaceutical composition comprising about 4% cocaine hydrochloride, by weight, and a preservative in an aqueous solution, wherein a pH of the pharmaceutical composition is 2 to 4, and wherein the cocaine hydrochloride concentration in the pharmaceutical composition remains at greater than about 3.4%, by weight, after the composition has been stored for 6 months at a temperature ranging from 28° C. to 32° C. and a relative humidity ranging from 60% to 70%.

Yet another non-limiting aspect of the present disclosure is directed to a ready to use pharmaceutical composition comprising about 4% cocaine hydrochloride, by weight, and a preservative in an aqueous solution, and wherein the cocaine hydrochloride concentration in the pharmaceutical composition remains greater than about 3.4%, by weight, after the composition has been stored for 1 month at a temperature ranging from 38° C. to 42° C. and a relative humidity ranging from 70% to 80%.

An additional non-limiting aspect according to the present disclosure is directed to a storage stable pharmaceutical composition comprising about 4% cocaine hydrochloride, by weight, and a preservative in an aqueous solution, wherein a pH of the pharmaceutical composition is 2 to 4, and wherein the pharmaceutical composition comprises no more than 7% of total impurities, by weight, after the composition has been stored for 20 months at a temperature ranging from 23° C. to 27° C. and a relative humidity ranging from 55% to 65%.

A further non-limiting aspect according to the present disclosure is directed to a storage stable pharmaceutical composition comprising about 4% cocaine hydrochloride, by weight, and a preservative in an aqueous solution, wherein a pH of the pharmaceutical composition is 2 to 4, and wherein the pharmaceutical composition comprises no more than 8% of total impurities, by weight, after the composition has been stored for 12 months at a temperature ranging from 28° C. to 32° C. and a relative humidity ranging from 60% to 70%.

Yet a further non-limiting aspect according to the present disclosure is directed to a storage stable pharmaceutical composition comprising about 4% cocaine hydrochloride, by weight, and a preservative in an aqueous solution, wherein a pH of the pharmaceutical composition is 2 to 4, and wherein the pharmaceutical composition comprises no more than 10% of total impurities, by weight, after the composition has been stored for 6 months at a temperature ranging from 38° C. to 42° C. and a relative humidity ranging from 70% to 80%.

An additional non-limiting aspect according to the present disclosure is directed to a pharmaceutical composition for reducing sensation in a body region of a subject, wherein the pharmaceutical composition comprises about 4% cocaine hydrochloride, by weight, and a preservative, in an aqueous solution, and wherein the pharmaceutical composition results in a cocaine $AUC_{inf}$ in the subject ranging from 30.8 ng*h/mL to 79.0 ng*h/mL following a topical application of the pharmaceutical composition to the subject for about 20 minutes.

Another non-limiting aspect according to the present disclosure is directed to a pharmaceutical composition for reducing sensation in a body region of a subject, the pharmaceutical composition comprising about 4% cocaine hydrochloride, by weight, and a preservative, in an aqueous solution, and wherein the pharmaceutical composition results in a cocaine $C_{max}$ ranging from 19.7 ng/mL to 54.3 ng/mL in the subject following a topical application of the pharmaceutical composition to the subject for about 20 minutes.

An additional non-limiting aspect according to the present disclosure is directed to a pharmaceutical composition for reducing sensation in a body region of a subject, wherein the pharmaceutical composition comprises about 4% cocaine hydrochloride, by weight, and a preservative, in an aqueous solution, and wherein the pharmaceutical composition results in a cocaine $T_{max}$ of 0.09 h to 0.77 h in the subject following a topical application of the pharmaceutical composition to the subject for about 20 minutes.

One further non-limiting aspect according to the present disclosure is directed to a pharmaceutical composition for reducing sensation in a body region of a subject, the pharmaceutical composition comprising about 4% cocaine hydrochloride, by weight, and a preservative, in an aqueous solution, and wherein the pharmaceutical composition results in an absorptivity factor for cocaine in the subject ranging from 0.640 $h^{-1}$ to 0.687 $h^{-1}$ following a topical application of the pharmaceutical composition to the subject for about 20 minutes.

Yet a further non-limiting aspect according to the present disclosure is directed to a method of administering a topical anesthetic solution comprising cocaine hydrochloride to a subject to provide a reduction in sensation in a body region of the subject. The method comprises soaking absorbent articles with a solution comprising about 4%, by weight, cocaine hydrochloride, and contacting the absorbent articles with a nasal mucous membrane of the subject for at least about 20 minutes, wherein the method achieves a cocaine $AUC_{inf}$ in the subject ranging from 30.8 ng*h/mL to 79.0 ng*h/mL.

Another aspect of the present disclosure is directed to a method of administering a topical anesthetic solution comprising cocaine hydrochloride to a subject to reduce sensation in a body region of the subject, wherein the method comprises soaking absorbent articles with a solution comprising about 4%, by weight, cocaine hydrochloride, and contacting the absorbent articles with a nasal mucous membrane of the subject for at least about 20 minutes, wherein the method achieves a cocaine $T_{max}$ in the subject ranging from 0.09 h to 0.77 h.

Yet another non-limiting aspect of the present disclosure is directed to a method of administering a topical anesthetic solution comprising cocaine hydrochloride to a subject to reduce sensation in a body region of the subject, wherein the method comprises soaking absorbent articles with a solution comprising about 4%, by weight, cocaine hydrochloride and contacting the absorbent articles with a nasal mucous membrane of the subject for at least about 20 minutes, wherein the method achieves a cocaine $C_{max}$ in the subject ranging from 19.7 ng/mL to 54.3 ng/mL.

One additional non-limiting aspect of the present disclosure is directed to a method of administering a topical anesthetic solution comprising cocaine hydrochloride to a subject, the method comprising soaking absorbent articles with a solution comprising about 4%, by weight, cocaine hydrochloride, and contacting the absorbent articles with a nasal mucous membrane of the subject for at least about 20 minutes, wherein the method achieves an absorptivity factor for cocaine in the subject ranging from 0.640 h$^{-1}$ to 0.687 h$^{-1}$.

Another non-limiting aspect of the present disclosure is directed to a method of administering a topical anesthetic solution comprising cocaine hydrochloride to a subject to reduce sensation in a body region of the subject, the method comprising soaking absorbent articles with a solution comprising about 4%, by weight, cocaine hydrochloride, and contacting the absorbent articles with a nasal mucous membrane of the subject for at least about 20 minutes, wherein a urinary recovery of cocaine hydrochloride from the subject ranges from 38.9 µg to 289.5 µg over a period of 32 hours from the time of administration of the solution.

Another non-limiting aspect of the present disclosure is directed to a method of administering a topical anesthetic solution comprising cocaine hydrochloride to a subject to reduce sensation in a body region of the subject, wherein the method comprises soaking absorbent articles with a solution comprising about 4%, by weight, cocaine hydrochloride, and contacting the absorbent articles with a nasal mucous membrane of the subject for at least about 20 minutes, wherein the method achieves an ecgonine methyl ester $C_{max}$ in the subject ranging from 1.8 ng/mL to 13.2 ng/mL.

Yet another non-limiting aspect of the present disclosure is directed to a method of administering a topical anesthetic solution comprising cocaine hydrochloride to a subject to reduce sensation in a body region of the subject, wherein the method comprises soaking absorbent articles with a solution comprising about 4%, by weight, cocaine hydrochloride, and contacting the absorbent articles with a nasal mucous membrane of the subject for at least about 20 minutes, wherein the method achieves a benzoylecgonine $C_{max}$ in the subject ranging from 8.4 ng/mL to 103 ng/mL In certain non-limiting embodiments of the present disclosure, a method for inducing local anesthesia in a subject prior to performing a diagnostic, surgical, or post-operative procedure on or through the mucous membrane of the nasal cavities of a subject comprises soaking a cottonoid pledget with 1 mL of an aqueous solution comprising or consisting essentially of, by weight, about 4% cocaine hydrochloride, about 0.1% sodium benzoate, about 0.125% citric acid, optionally one or more colorants, and water, and contacting the soaked cottonoid pledget with the mucous membrane of the subject for at least about 20 minutes to reduce sensation in a body region of the subject. In another non-limiting embodiment of this method the 4% cocaine hydrochloride may be suspended in a colored aqueous solution.

In another non-limiting aspect of the present disclosure, a method of effectively anesthetizing a body region of a subject comprises immersing at least one absorbent article in an aqueous pharmaceutical composition comprising, by weight, about 3.6% to about 4.4% cocaine hydrochloride, about 0.07% to about 0.20% sodium benzoate, and about 0.125% citric acid, wherein the aqueous pharmaceutical composition has a pH between 2 and 4. The method further includes contacting the absorbent article and the aqueous pharmaceutical composition absorbed therein with a mucous membrane of the subject for a time period sufficient to reduce sensation in the body region proximate the mucous membrane. In certain non-limiting embodiments, the time period is sufficient to achieve a visual numeric rating score of 0 in the body region proximate the mucous membrane upon von Frey filament testing.

Certain other non-limiting aspects of the present disclosure are directed to a method of effectively anesthetizing a body region of a subject prior to performing a medical procedure on the subject. The method comprises immersing at least one absorbent article in an aqueous pharmaceutical composition comprising, by weight, about 3.6% to about 4.4% cocaine hydrochloride, about 0.07% to about 0.20% sodium benzoate, and about 0.125% citric acid, wherein the aqueous pharmaceutical composition has a pH between 2 and 4. The method further includes contacting the at least one absorbent article and the aqueous pharmaceutical composition absorbed therein with a mucous membrane of the subject for a time period, and obtaining a reduction in sensation in the body region proximate to the mucous membrane. In certain non-limiting embodiments, the reduction in sensation results in a visual numeric rating score of 0 upon von Frey filament testing the body region.

Another non-limiting aspect of the present disclosure is directed to a method of effectively anesthetizing a body region of a hepatically impaired subject. The method comprises immersing at least one absorbent article in an aqueous pharmaceutical composition comprising, by weight, about 3.6% to about 4.4% cocaine hydrochloride, about 0.07% to about 0.20% sodium benzoate, and about 0.125% citric acid, wherein the aqueous pharmaceutical composition has a pH between 2 and 4. The method further includes contacting the at least one absorbent article and the aqueous pharmaceutical composition absorbed therein with a mucous membrane of the subject for a time period sufficient to reduce sensation in a body region proximate the mucous membrane. The reduction in sensation results in a visual numeric rating score of 0 upon von Frey filament testing the body region. The method is not repeated on the hepatically impaired subject within 24 hours.

Another non-limiting aspect of the present disclosure is directed to a method of effectively anesthetizing a body region of a renally impaired subject. The method comprises immersing at least one absorbent article in an aqueous pharmaceutical composition comprising, by weight, about 3.6% to about 4.4% cocaine hydrochloride, about 0.07% to 0.20% sodium benzoate, and 0.125% citric acid, wherein the aqueous pharmaceutical composition has a pH between 2 and 4. The method further includes contacting the at least one absorbent article and the aqueous pharmaceutical composition absorbed therein with a mucous membrane of the subject for a time period sufficient to reduce sensation in a body region proximate the mucous membrane. The reduction in sensation results in a visual numeric rating score of 0 upon von Frey filament testing the body region.

BRIEF DESCRIPTION OF THE DRAWINGS

Various features and characteristics of non-limiting and non-exhaustive embodiments disclosed and described in this specification may be better understood by reference to the accompanying figures, in which:

FIGS. 16A-16C are views of a container closure system that can be used in conjunction with the container shown in FIGS. 15A and 15B, wherein FIG. 16A is an exterior elevational view of a ribbed, threaded closure cap, FIG. 16B is a side sectional view of the cap shown in FIG. 16A, and FIG. 16C is an exploded sectional view of the cap shown in FIG. 16B.

Figure 1:
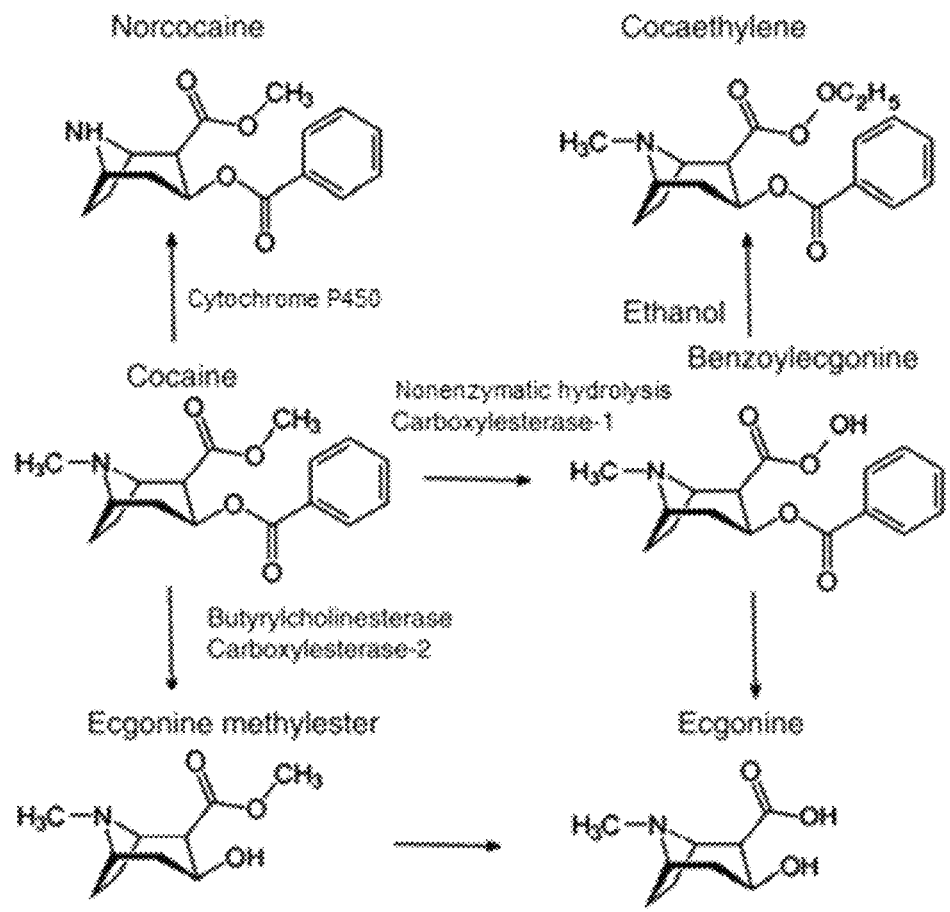
FIG. 1 is a schematic representation showing certain metabolic pathways of cocaine in humans.

The reader will appreciate the foregoing details, as well as others, upon considering the following detailed description of various non-limiting and non-exhaustive embodiments according to the present disclosure.

DETAILED DESCRIPTION

Various embodiments are described and illustrated in this specification to provide an overall understanding of the disclosed compositions and methods. It is understood that the various embodiments described and illustrated in this specification are non-limiting and non-exhaustive. Thus, the present invention is not limited by the description of the various non-limiting and non-exhaustive embodiments disclosed in this specification. Rather, the invention is defined solely by the claims. Certain features and characteristics illustrated and/or described in connection with various embodiments may be combined with the features and characteristics of other embodiments. Such modifications and variations are intended to be included within the scope of this specification. As such, the claims may be amended to recite any features or characteristics expressly or inherently described in, or otherwise expressly or inherently supported by, this specification. Further, Applicant reserves the right to amend the claims to affirmatively disclaim features or characteristics that may be found present in the prior art. The various embodiments disclosed and described in this specification can comprise, consist of, or consist essentially of the features and characteristics as variously described herein.

All percentages and ratios provided herein for a composition are weight percentages based on the total weight of the composition, unless otherwise indicated.

Any patent, publication, or other disclosure material that is said to be incorporated, in whole or in part, by reference herein is incorporated herein only to the extent that the incorporated material does not conflict with existing definitions, statements, or other disclosure material set forth in this disclosure. As such, and to the extent necessary, the disclosure as set forth herein supersedes any conflicting material incorporated herein by reference. Any material, or portion thereof, that is said to be incorporated by reference herein, but which conflicts with existing definitions, statements, or other disclosure material set forth herein is only incorporated to the extent that no conflict arises between that incorporated material and the existing disclosure material.

Any numerical ranges recited in this specification are intended to include all sub-ranges of the same numerical precision subsumed within the recited range. For example, a range of "1.0 to 10.0" is intended to include all sub-ranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited in this specification is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

The terms "mucosa" and "mucous membrane" as used herein refer to any naturally moist anatomical membrane or surface of a mammal, such as, for example, nasal, oral, aural, buccal, vaginal, rectal, and ophthalmic surfaces.

The terms "topical" and "topically" as used herein are used in a conventional sense, referring to direct contact with an anatomical site or surface area on a mammal, including, for example, skin and mucosa.

The term "$C_{max}$" as used herein refers to the maximum (i.e., peak) serum concentration.

The term "$C_{last}$" as used herein refers to the last observed quantifiable concentration.

The term "MRT" as used herein refers to the mean residence time, or the average amount of time that a single molecule of drug stays in the body.

The term "Cl/F" as used herein refers to the apparent total clearance of the drug from plasma.

The term "Vd/F" as used herein refers to the apparent volume of distribution after non-intravenous administration.

The term "AUC" as used herein refers to the integral of the concentration-time curve.

The term "$AUC_{last}$" and "$AUC_{0 \to t}$" as used herein refer to the area under a plasma concentration versus time curve from time 0 to the time of the last measured concentration of drug within the plasma.

The terms "$AUC_{inf}$" and "$AUC_{0 \to \infty}$" as used herein refer to the area under a plasma concentration versus time curve from time 0 to infinity.

The term "$T_{max}$" as used herein refers to the time after administration of a drug when the maximum plasma concentration is reached.

The term "$t_{1/2}$" as used herein refers to the half-life of an administered drug.

The term "$T_{last}$" as used herein refers to the time of the last observed quantifiable concentration of drug.

The term "% EXTRAP" as used herein refers to the percentage of area under the concentration-time curve (AUC) extrapolated after the last observed quantifiable concentration of drug ($T_{last}$).

The term "absorptivity factor" as used herein refers to the maximum concentration of drug absorbed into the blood plasma ($C_{max}$) divided by the area under the drug concentration-time curve from time 0 to infinity ($AUC_{inf}$).

The term "renal clearance" as used herein refers to the volume of plasma cleared of drug by the kidney per unit time.

The terms "subject" and "patient" are used interchangeably herein, and it is intended that both refer to a recipient on whom a method is conducted according to the present disclosure or another method, as the case may be.

The term "volume of distribution" as used herein refers to the apparent volume in which a drug is distributed (i.e., the parameter relating drug concentration to drug amount in the body).

The term "dose" as used herein refers to an amount of drug administered.

The term "efficacy" as used herein refers to the effectiveness of a topical pharmaceutical composition, measured by the degree of anesthetic effects that are observed after the topical pharmaceutical composition is administered to a subject.

The term "impurity" as used herein refers to an undesired substance in a composition. In some non-limiting embodiments, the amount of impurities may exist in the initial composition and/or may be formed after a certain period of time. In other non-limiting embodiments, impurities may be formed by the degradation of one or more components of the composition.

The phrase "ready to use" as used herein refers to a composition that is suitable for administration to a patient without dilution.

The phrase "below quantifiable limits" and "below quantitation" as used herein refers to an analyte present in quantities less than 0.1 ng/mL.

Prior investigators attempted to study certain attributes related to the application of cocaine, yet they did not use a ready to use, stable composition capable of producing the recited pharmacokinetic parameters. For example, Van Dyke et al., 1976, reports on a weight based administration of a 10% solution of cocaine hydrochloride on nasal mucosa. Administration of 1.5 mg/kg applied on the nasal mucosa produced a $C_{max}$ between 120 ng/mL and 474 ng/mL.

Patients also received diazepam and morphine sulfate 1 hour before receiving general anesthesia. Van Dyke 1976 did not report on standardized administration of a uniform amount of cocaine hydrochloride.

Van Dyke et al., 1978, compared pharmacokinetic values obtained via oral and intranasal administration of 2 mg/kg cocaine. The authors applied a 10% solution containing 115 mg to 246 mg topically on the nasal mucosa, or provided a gelatin capsule with the same amount of crystalline cocaine. The authors stated that the difference in peak plasma concentrations was not significant and that oral administration is at least as effective as the same dose given intranasally. The most substantial euphoric effects, i.e., the largest "high" rating obtained from intranasal application, corresponded to an average cocaine plasma level of 93 ng/mL to 160 ng/mL.

Wilkinson et al., 1980, described plasma cocaine levels after intranasal and oral administration of cocaine. Wilkinson administered various doses ranging between 0.19 mg/kg to 2.0 mg/kg via a 10% aqueous solution, or crystalline cocaine at 2.0 mg/kg and 3.0 mg/kg. Wilkinson reported similar relative bioavailability values for intranasal and oral routes of administration.

Bromley and Hayward, 1988, described and compared the use of cocaine and cocaine with adrenaline for nasal surgery. All patients received substantial premedication, which included papaveretum and hyoscine, induction with thiopentone, and suxamethonium. Patients also used a Magill breathing system with nitrous oxide and oxygen with halothane. The authors state that the primary use of cocaine is for its vasoconstriction activity and its local anesthetic effect makes a secondary contribution to the general anesthesia. The authors found that adrenaline lowers the absorption of cocaine, and did not significantly change pulse rate and blood pressure.

Greinwald and Holtel, 1996, described topical application of cocaine with cotton pledgets. Greinwald reported that no prior studies exist for absorption of cocaine from cottonoid pledgets, and serum levels of cocaine were rarely detectable in plasma samples. If cocaine detection occurred, the amount measured did not correlate with either the amount of nasal absorption or the time of mucosal contact. Greinwald also reported that approximately 37% of cocaine is absorbed from a cottonoid pledget.

Fattinger et al., 2000, studied cocaine in the systemic circulation after oral and nasal dosing. The authors note that only a small portion of the nasally administered cocaine is absorbed through the nose, and the majority is absorbed through the gastrointestinal tract.

Lannett Company, Inc. markets, and Roxane Laboratories, Inc. previously marketed topical cocaine hydrochloride solutions, but such products are not approved by the United States Food and Drug Administration as stable for the effective induction of local anesthesia when performing diagnostic procedures and surgeries on or through the mucous membranes of the nasal cavities in patients. There is a need for a stable topical cocaine hydrochloride solution, a method for applying that solution to create therapeutic levels of cocaine in patients, and a method for effectively and locally anesthetizing patients prior to performing diagnostic and surgical procedures.

Disclosed herein is a topically administered anesthetic pharmaceutical composition including cocaine hydrochloride. The composition may be used, for example, to anesthetize a body region of a subject prior to conducting a diagnostic, surgical, or post-operative procedure involving the body region. The pharmaceutical composition may be used in both outpatient and inpatient settings. Exemplary nasal procedures include nasal endoscopy, nasal endoscopy with debridement, laryngoscopy, nasal laryngoscopy, nasopharyngeal laryngoscopy, transnasal esophagoscopy, nasal stroboscopy, nasal endoscopy with polypectomy, nasal debridement, intraturbinate methylprednisolone acetate injection, turbinate reduction, sinuplasty, and nasal cauterization. Table 1 provides non-exhaustive examples of diagnostic and surgical procedures that may be conducted on the oral cavity and respiratory tract regions anesthetized using the pharmaceutical composition of the present disclosure.

TABLE 1

| Oral cavity procedures | Cleft palate evaluation, biopsy, and local tonsillectomy |
|---|---|
| Respiratory tract procedures | Indirect and direct laryngoscopy, laryngography, tracheoscopy, bronchoscopy, bronchography |

In a non-limiting embodiment according to the present disclosure, a pharmaceutical composition adapted for reducing sensation in a body region of a patient comprises about 4% cocaine hydrochloride, by weight, and a preservative, in an aqueous solution.

In various non-limiting embodiments, the pharmaceutical composition can include cocaine hydrochloride in a concentration, by weight percent, based on the total weight of the pharmaceutical composition, of about 3.6% to about 4.4%, by weight, or any range or specific percentage subsumed within that range.

In certain non-limiting embodiments, the pharmaceutical composition can include one or more preservative compounds to inhibit microbial growth and/or reduce the rate of metabolic deterioration of the cocaine hydrochloride in the composition, increasing composition stability. In certain non-limiting embodiments, the preservative may be one or more compounds selected from sodium benzoate, antimol, benzoic acid, carboxybenzene sodium salt, benzoan sodny, benzalkonium chloride, cetrimonium bromide, benzethonium chloride, alkyltrimethylammonium bromide, benzalkonium chloride/edetic acid, edetic acid, amino aryl acid esters, phenol, methylparaben, ethylparaben, propylparaben, butylparaben, chlorobutanol, phenylmercuric nitrate, sorbic acid, potassium sorbate, chlorocresol, glycerol, benzyl alcohol, cetyl alcohol, stearyl alcohol, sorbic acid, chloroactamide, trichlorocarban, thimerosal, imidurea, bronopol, chlorhexidine, 4-chlorocresol, 4-chloroxylenol, dichlorophene, and hexachlorophene.

In certain non-limiting embodiments, the pharmaceutical composition includes sodium benzoate as a preservative. In certain non-limiting embodiments the pharmaceutical composition includes about 0.1%, by weight, of sodium benzoate or another preservative. In certain non-limiting embodiments, the sodium benzoate concentration in the pharmaceutical composition is greater than 0 and less than 5%, by weight, or is present at any value or in any range subsumed therein, such as, for example, 4%, 3%, 2%, 1%, greater than 0 to less than 1%, 0.01% to 1%, 0.05% to 0.50%, or 0.07% to 0.20%.

In certain non-limiting embodiments, the pharmaceutical composition further includes one or more acidulants to inhibit disintegration of the cocaine hydrochloride into metabolites and to adjust the pH of the aqueous pharmaceutical composition. In certain non-limiting embodiments, the acidulant is one or more of citric acid, citric acid anhydrous, citric acid monohydrate, sodium citrate, L-malic acid, D-malic acid, lactic acid, L(+)-tartaric acid, fumaric acid, sodium lactate, calcium lactate, L-lactic acid, calcium citrate, magnesium citrate, ferrous lactate, tripotassium citrate, trisodium citrate, and tricalcium citrate.

In certain non-limiting embodiments, the aqueous pharmaceutical composition includes, by weight, about 0.125% citric acid. In certain non-limiting embodiments, the concentration, in weight percent, of citric acid or other acidulant in the pharmaceutical composition is greater than 0 to less than 5%, or has any value or is within range subsumed therein such as, for example, greater than 0 to less than 3%, greater than 0 to less than 1%, 0.1%, 0.150%, 0.130%, 0.120%, 0.110%, 0.2%, 0.3%, 0.4%, 0.5%, 0.01% to 1%, 0.01% to 0.85%, 0.05% to 0.50%, or 0.02% to 0.70%.

Certain non-limiting embodiments of the aqueous pharmaceutical composition herein include about 4% cocaine hydrochloride, by weight, a preservative, and an acidulant in an aqueous solution at a pH ranging from 1 to 6, or having a pH of any value or falling within any range subsumed therein, such as, for example, from 1.5 to 5.5, from 2 to 5, from 2.5 to 4.5, from 3 to 4, or from 3.5 to 3.9.

Certain non-limiting embodiments of the pharmaceutical composition of the present disclosure including about 4% cocaine hydrochloride result in a cocaine $AUC_{inf}$ ranging from 30.8 ng*h/mL to 79.0 ng*h/mL, following a topical application of the pharmaceutical composition to a body region of a subject for about 20 minutes. More generally, certain non-limiting embodiments of the pharmaceutical composition of the present disclosure including about 4% cocaine hydrochloride, by weight, result in a cocaine $AUC_{inf}$ selected from the following group following a topical application of the pharmaceutical composition to a body region of a subject for about 20 minutes: from 25.0 ng*h/mL to 370.0 ng*h/mL, from 30.0 ng*h/mL to 200 ng*h/mL, from 40.0 ng*h/mL to 150.0 ng*h/mL, from 34.1 ng*h/mL to 60.3 ng*h/mL, from 20.7 ng*h/mL to 68.1 ng*h/mL, from 30.8 ng*h/mL to 79.0 ng*h/mL, 40.6 ng*h/mL to 150.0 ng/mL, from 88.0 ng*h/mL to 366 ng*h/mL, from 124.8 ng*h/mL to 241.2 ng*h/mL, from 59.0 ng*h/mL to 111 ng*h/mL, from 61.2 ng*h/mL to 179.6 ng*h/mL, 44.4 ng*h/mL, 47.2 ng*h/mL, 54.9 ng*h/mL, 85.0 ng*h/mL, 95.3 ng*h/mL, 120.4 ng*h/mL, 183 ng*h/mL, and 227 ng*h/mL.

In certain non-limiting embodiments of methods of using the pharmaceutical composition according to the present disclosure, a volume of the pharmaceutical composition is contacted with a body region of a subject for about 20 minutes. More generally, in certain non-limiting embodiments of methods of using the pharmaceutical composition according to the present disclosure, a volume of the pharmaceutical composition is contacted with a body region of a subject for greater than 0 to less than 45 minutes, or any value or range subsumed therein, such as, for example, from 1 minute to 40 minutes, from 5 minutes to 30 minutes, from 8 minutes to 25 minutes, from 10 minutes to 20 minutes, 30 minutes, 25 minutes, 24 minutes, 23 minutes, 22 minutes, 21 minutes, 19 minutes, 18 minutes, 17 minutes, 16 minutes, 15 minutes, 10 minutes, 5 minutes, or 3 minutes. In various non-limiting embodiments of the method, the pharmaceutical composition is an aqueous solution comprising cocaine hydrochloride, a preservative, and an acidulant, in any of the concentrations as described and disclosed herein.

The pharmacokinetic parameter $C_{max}$ refers to the maximum (peak) serum concentration of a specific compound in the body of a subject after a pharmaceutical composition or compound has been administrated to the subject. One non-limiting embodiment herein is directed to a pharmaceutical composition for reducing sensation in a body region of a subject, wherein the composition is an aqueous solution including a preservative and about 4% cocaine hydrochloride by weight, and wherein the pharmaceutical composition results in a cocaine $C_{max}$ ranging from 19.7 ng/mL to 54.3 ng/mL in the subject following a topical application of the pharmaceutical composition to a body region of a subject for about 20 minutes. In certain non-limiting embodiments, the cocaine $C_{max}$ achieved following topical application of the pharmaceutical composition to a body region of a subject for about 20 minutes is within the range of from 10.0 ng/mL to 100.0 ng/mL, or has any value or falls within any range subsumed therein, such as, for example, from 20 ng/mL to 80 ng/mL, from 25 ng/mL to 70 ng/mL, from 30 ng/mL to 65 ng/mL, from 35 to 60 ng/mL, from 16.2 ng/mL to 85.2 ng/mL, from 20 ng/mL to 96 ng/mL, from 21.9 ng/mL to 93.7 ng/mL, from 29.6 ng/mL to 71.6 ng/mL, from 25.0 ng/mL to 51.2 ng/mL, from 19.7 ng/mL to 54.3 ng/mL, from 17.0 ng/mL to 52.2 ng/mL, from 21.8 ng/mL to 56.2 ng/mL, from 45.3 ng/mL to 89.3 ng/mL, 90 ng/mL, 85 ng/mL, 80 ng/mL, 75 ng/mL, 70 ng/mL, 67.3 ng/mL, 65 ng/mL, 60 ng/mL, 57.8 ng/mL, 55 ng/mL, 50 ng/mL, 50.7 ng/mL, 45 ng/mL, 40 ng/mL, 39 ng/mL, 38.1 ng/mL, 37 ng/mL, 34.6 ng/m, 35 ng/mL, 30.0 ng/mL, 25 ng/mL, 20 ng/mL, or 15 ng/mL.

The pharmacokinetic parameter $T_{max}$ for a pharmaceutical composition or compound is the time after administration to a subject at which the $C_{max}$ is observed in the subject. One non-limiting embodiment herein is directed to a pharmaceutical composition for reducing sensation in a body region of a subject, wherein the composition is an aqueous solution including a preservative and about 4% cocaine hydrochloride by weight, and wherein following a topical application of the pharmaceutical composition to the subject for about 20 minutes, a cocaine $T_{max}$ of 0.09 h to 0.77 h is observed in the subject. In various non-limiting embodiments, following the topical application of the pharmaceutical composition to a body region of a subject, the observed cocaine $T_{max}$ falls within the range from 0.01 h to 2 h, or has any value or falls within range subsumed therein, such as, for example, from 0.306 h to 1.87 h, from 0.205 h to 0.961 h, from 0.301 h to 0.595 h, from 0.435 h to 0.953 h, from 0.345 h to 0.517 h, from 0.095 h to 0.739 h, from 0.082 h to 0.739 h, from 0.092 h to 0.774 h, from 0.020 h to 1.00 h, from 0.030 h to 0.900 h, from 0.040 h to 0.800 h, from 0.030 h to 0.700 h, from 0.040 h to 0.600 h, 1.09 h, 1.20 h, 0.789 h, 0.583 h, 0.448 h, 0.433 h, 0.431 h, 0.417 h, or 0.694 h.

In a non-limiting embodiment herein, a pharmaceutical composition for reducing sensation in a body region of a subject includes about 4% cocaine hydrochloride, by weight, and a preservative, in an aqueous solution, wherein an absorptivity factor for cocaine ranging from 0.640 $h^{-1}$ to 0.687 $h^{-1}$ is achieved in the subject following a topical application of the pharmaceutical composition to the body region for about 20 minutes. In certain non-limiting embodiments, the absorptivity factor for cocaine resulting following the topical application of the pharmaceutical composition to the subject for about 20 minutes is in the range of from 0.100 $h^{-1}$ to 1.50 $h^{-1}$, or has any value or falls within any range subsumed therein, such as, for example, from 0.358 $h^{-1}$ to 0.522 $h^{-1}$, from 0.438 $h^{-1}$ to 0.466 $h^{-1}$, from 0.184 $h^{-1}$ to 0.233 $h^{-1}$, from 0.366 $h^{-1}$ to 0.372 $h^{-1}$, from 0.640 $h^{-1}$ to 0.687 $h^{-1}$, from 0.627 $h^{-1}$ to 0.690 $h^{-1}$, from 0.499 $h^{-1}$ to 0.866 $h^{-1}$, from 0.483 $h^{-1}$ to 0.789 $h^{-1}$, from 0.250 $h^{-1}$ to 1.0 $h^{-1}$, from 0.300 $h^{-1}$ to 0.900 $h^{-1}$, from 0.350 $h^{-1}$ to 0.800 $h^{-1}$, from 0.400 $h^{-1}$ to 0.700 $h^{-1}$, from 0.500 $h^{-1}$ to 0.600 $h^{-1}$, 0.227 $h^{-1}$, 0.370 $h^{-1}$, 0.456 $h^{-1}$, 0.487 $h^{-1}$, 0.545 $h^{-1}$, 0.878 $h^{-1}$, 0.964 $h^{-1}$, or 1.10 $h^{-1}$.

In a non-limiting embodiment herein, a pharmaceutical composition for reducing sensation in a body region of a subject includes about 4% cocaine hydrochloride, by weight, and a preservative, in an aqueous solution, and wherein topical administration of the pharmaceutical composition to the body region for about 20 minutes results in a urinary recovery of cocaine from the subject ranging from 49.9 μg to 184.1 μg over a period of 12 hours from the time of administration to the subject. In certain non-limiting embodiments, following the topical application of the pharmaceutical composition to the body region for about 20 minutes, a urinary recovery of cocaine from the subject is observed ranging from 20 μg to 350 μg, or having any value or falling within any range subsumed therein, over a period of 12 hours from the time of administration. Certain other non-limiting embodiments of the pharmaceutical composition result in a urinary recovery of cocaine from the subject in the range of from 49.9 μg to 184.1 μg, from 38.9 μg to 290 μg, from 38.3 μg to 166 μg, from 30 μg to 300 μg, from 35 μg to 250 μg, from 40 μg to 200 μg, or from 45 μg to 150 μg over a period of 12 hours from the time of topical administration of the composition to a body region of a subject.

The stability of the aqueous pharmaceutical composition comprising cocaine hydrochloride that is described herein can be evaluated by measuring the cocaine hydrochloride concentration remaining within the composition after the composition has been stored over a period of time at controlled temperatures and controlled relative humidity conditions. In a non-limiting embodiment herein, a ready to use pharmaceutical composition is provided originally including about 4% cocaine hydrochloride, by weight, and a preservative in an aqueous solution at a pH of 2 to 4, wherein the cocaine hydrochloride concentration remains at greater than 3%, by weight, after the composition is stored for 12 months at a temperature ranging from 23° C. to 27° C. and a relative humidity ranging from 55% to 65%. In various non-limiting embodiments, the cocaine hydrochloride concentration in the ready to use pharmaceutical composition after the composition is stored for 12 months at a temperature ranging from 23° C. to 27° C. and a relative humidity ranging from 55% to 65%, is greater than 3.1%, greater than 3.2%, greater than 3.3%, greater than 3.4%, greater than 3.5%, greater than 3.6%, greater than 3.7%, greater than 3.8%, greater than 3.9%, or greater than 3.95% cocaine hydrochloride.

In certain non-limiting embodiments herein, a ready to use pharmaceutical composition originally including about 4% cocaine hydrochloride, by weight, and a preservative, in an aqueous solution at a pH of 2 to 4, retains a cocaine hydrochloride concentration greater than 3.6%, by weight, after the composition is stored for 12 months at a temperature ranging from 23° C. to 27° C. and a relative humidity ranging from 55% to 65%.

In certain non-limiting embodiments herein, a ready to use pharmaceutical composition originally including about 4% cocaine hydrochloride, by weight, and a preservative, in an aqueous solution at a pH of 2 to 4, retains a cocaine hydrochloride concentration greater than 3.4%, by weight, after the composition has been stored for a time selected from 3 months, 6 months, 9 months, 12 months, 18 months, 20 months, 21 months, 24 months, 30 months, 36 months at a temperature ranging from 23° C. to 27° C. and a relative humidity ranging from 55% to 65%.

In certain non-limiting embodiments herein, a ready to use pharmaceutical composition originally including about 4% cocaine hydrochloride, by weight, and a preservative, in an aqueous solution at a pH of 2 to 4, retains a cocaine hydrochloride concentration greater than 3.4%, by weight, after the composition is stored for 6 months at a temperature ranging from 28° C. to 32° C., and a relative humidity ranging from 60% to 70%. In various non-limiting embodiments, the cocaine hydrochloride concentration in the ready to use pharmaceutical composition after the composition is stored for 6 months at a temperature ranging from 28° C. to 32° C., and a relative humidity ranging from 60% to 70%, is greater than 3.1%, greater than 3.2%, greater than 3.3%, greater than 3.4%, greater than 3.5%, greater than 3.6%, greater than 3.7%, greater than 3.8%, greater than 3.9%, or greater than 3.95%.

In certain non-limiting embodiments herein, a ready to use pharmaceutical composition originally including about 4% cocaine hydrochloride, by weight, and a preservative, in an aqueous solution at a pH of 2 to 4, retains a cocaine hydrochloride concentration greater than 3.4%, by weight, after the composition is stored for a time selected from 6 months, 9 months, 12 months, 18 months, 20 months, 24 months, 30 months, and 36 months, at a temperature ranging from 28° C. to 32° C., and a relative humidity ranging from 60% to 70%.

In certain non-limiting embodiments herein, a ready to use pharmaceutical composition originally including about 4% cocaine hydrochloride, by weight, and a preservative in an aqueous solution at a pH of 2 to 4, retains a cocaine hydrochloride concentration greater than 3.4%, by weight, after the composition is stored for at least 1 month at a temperature ranging from 38° C. to 42° C., and a relative humidity ranging from 70% to 80%. In various non-limiting embodiments, the cocaine hydrochloride concentration in the ready to use pharmaceutical composition after the composition is stored for a time selected from at least 1 month, 3 months, 6 months, 9 months, 12 months, 18 months, 20 months, 21 months, 24 months, 30 months, and 36 months at a temperature ranging from 38° C. to 42° C., and a relative humidity ranging from 70% to 80%, is greater than about 3.1%, greater than about 3.2%, greater than about 3.3%, greater than about 3.4%, greater than about 3.5%, greater than about 3.6%, greater than about 3.7%, greater than about 3.8%, greater than about 3.9%, or greater than about 3.95% cocaine hydrochloride.

In various non-limiting embodiments, a ready to use pharmaceutical composition is provided originally including about 4% cocaine hydrochloride, by weight, and a preservative in an aqueous solution at a pH of 2 to 4, wherein the cocaine hydrochloride concentration remains at greater than about 3.4%, by weight, after the composition is stored for a time selected from 1 month, 2 months, 3 months, 4 months, 5 months, 6 months, 7 months, and 8 months at a temperature ranging from 38° C. to 42° C. and a relative humidity ranging from 70% to 80%.

In a non-limiting embodiment, a ready to use pharmaceutical composition is provided originally including about 4% cocaine hydrochloride, by weight, and a preservative in an aqueous solution at a pH of 2 to 4, wherein the cocaine hydrochloride concentration remains at greater than about 3.4%, by weight, after the composition is stored for 3 months at a temperature ranging from 38° C. to 42° C. and a relative humidity ranging from 70% to 80%, wherein the pharmaceutical composition includes total impurities in a concentration no more than about 9%, or having any value or within any range subsumed therein, such as for example, no more than 8%, 7%, 6%, 5.75%, 5.5%, 5.2%, 4.5%, 4%, 3%, 2%, or 1%.

In various embodiments, after the ready to use pharmaceutical composition including about 4% cocaine hydrochloride, by weight, and a preservative in an aqueous solution at a pH of 2 to 4, has been stored for 3 months at a temperature ranging from 38° C. to 42° C. and a relative humidity ranging from 70% to 80%, the composition includes benzoylecgonine in a concentration no more than about 9% or having any value or within any range subsumed therein, such as for example, no more than 8%, 7%, 6%, 5.75%, 5.5%, 5.2%, 4.5%, 4%, 3%, 2%, or 1%.

In various embodiments, after the ready to use pharmaceutical composition including about 4% cocaine hydrochloride, by weight, and a preservative in an aqueous solution at a pH of 2 to 4, has been stored for 3 months at a temperature ranging from 38° C. to 42° C. and a relative humidity ranging from 70% to 80% the composition includes no more than about 400 ppm methanol per 4 mL pharmaceutical composition, or any value or within any range subsumed therein, such as for example, no more than 350 ppm/4 mL, 300 ppm/4 mL, 252 ppm/4 mL, 250 ppm/4 mL, 200 ppm/4 mL, 100 ppm/4 mL, or 50 ppm/4 mL.

In various embodiments, after the ready to use pharmaceutical composition including about 4% cocaine hydrochloride, by weight, and a preservative in an aqueous solution at a pH of 2 to 4, has been stored for 3 months at a temperature ranging from 38° C. to 42° C. and a relative humidity ranging from 70% to 80% the composition includes acetonitrile in concentrations below quantifiable limits, no more than about 500 ng/mL isopropanol, or any value subsumed therein such as for example, no more than 450 ng/mL, 400 ng/mL, 375 ng/mL, 372 ng/mL, 350 ng/mL, 300 ng/mL, or 200 ng/mL, and no more than about 2300 ng/mL trimethylsilanol, or any value or within any range subsumed therein, such as for example, no more than 2200 ng/mL, 2100 ng/mL, 2000 ng/mL, 1950 ng/mL, 1909 ng/mL, 1875 ng/mL, 1850 ng/mL, 1800 ng/mL, 1700 ng/mL, 1600 ng/mL, or 1550 ng/mL.

In various embodiments, after the ready to use pharmaceutical composition including about 4% cocaine hydrochloride, by weight, and a preservative in an aqueous solution at a pH of 2 to 4, has been stored for 6 months at a temperature ranging from 38° C. to 42° C. and a relative humidity ranging from 70% to 80% the composition includes no more than about 600 ng/mL chromium, or any value or within any range subsumed therein, such as for example, no more than 500 ng/mL, 450 ng/mL, 425 ng/mL, 408 ng/mL, 400 ng/mL, 300 ng/mL, or 200 ng/mL chromium, and no more than about 400 ng/mL nickel, or any value or within any range subsumed therein, such as for example, no more than 300 ng/mL, 250 ng/mL, 200 ng/mL, 188 ng/mL, 150 ng/mL, 100 ng/mL, 75 ng/mL, or 50 ng/mL nickel.

In a non-limiting embodiment, a ready to use pharmaceutical composition is provided originally including about 4% cocaine hydrochloride, by weight, and a preservative in an aqueous solution at a pH of 2 to 4, wherein the cocaine hydrochloride concentration remains at greater than about 3.4%, by weight, after the composition is stored for 6 months at a temperature ranging from 38° C. to 42° C. and a relative humidity ranging from 70% to 80%, and wherein the pharmaceutical composition includes an impurities concentration no more than about 12%, or having any value or within any range subsumed therein, such as for example, no more than 11%, 10%, 9.5%, 9.3%, 9%, 8%, 7%, or 6%.

In various embodiments, after the ready to use pharmaceutical composition including about 4% cocaine hydrochloride, by weight, and a preservative in an aqueous solution at a pH of 2 to 4, has been stored for 6 months at a temperature ranging from 38° C. to 42° C. and a relative humidity ranging from 70% to 80%, the composition includes no more than about 12% benzoylecgonine, or having any value or within any range subsumed therein, such as for example, no more than 11%, 10%, 9.5%, 9.3%, 9%, 8%, 7%, or 6%.

In various embodiments, after the ready to use pharmaceutical composition including about 4% cocaine hydrochloride, by weight, and a preservative in an aqueous solution at a pH of 2 to 4, has been stored for 6 months at a temperature ranging from 38° C. to 42° C. and a relative humidity ranging from 70% to 80%, the composition includes no more than about 600 ppm methanol per 4 mL pharmaceutical composition, or any value or within any range subsumed therein, such as for example, no more than 500 ppm/4 mL, 450 ppm/4 mL, 414 ppm/4 mL, 400 ppm/4 mL, 350 ppm/4 mL, 300 ppm/4 mL, 200 ppm/4 mL, 100 ppm/4 mL, or 50 ppm/4 mL.

In various embodiments, after the ready to use pharmaceutical composition including about 4% cocaine hydrochloride, by weight, and a preservative in an aqueous solution at a pH of 2 to 4, has been stored for 6 months at a temperature ranging from 38° C. to 42° C. and a relative humidity ranging from 70% to 80%, the composition includes acetonitrile in concentrations below quantifiable limits, no more than about 400 ng/mL isopropanol, or in any range or value subsumed therein such as, for example, no more than 350 ng/mL, 325 ng/mL, 313 ng/mL, 300 ng/mL, 250 ng/mL, or 200 ng/mL, and no more than about 500 ng/mL trimethylsilanol, or in any value or within any range subsumed therein, such as for example, no more than 400 ng/mL, 350 ng/mL, 319 ng/mL, 300 ng/mL, 250 ng/mL, 200 ng/mL, 100 ng/mL, 75 ng/mL, or 50 ng/mL.

In various embodiments, after the ready to use pharmaceutical composition including about 4% cocaine hydrochloride, by weight, and a preservative in an aqueous solution at a pH of 2 to 4, has been stored for 6 months at a temperature ranging from 38° C. to 42° C. and a relative humidity ranging from 70% to 80%, the composition includes no more than about 500 ng/mL chromium, or in any value or within any range subsumed therein, such as for example, no more than 400 ng/mL, 391 ng/mL, 350 ng/mL, 300 ng/mL, 200 ng/mL, 100 ng/mL, or 50 ng/mL chromium, and no more than about 300 ng/mL nickel, or in any value or within any range subsumed therein, such as for example, no more than 250 ng/mL, 200 ng/mL, 183 ng/mL, 150 ng/mL, 100 ng/mL, 75 ng/mL, or 50 ng/mL nickel.

In various non-limiting embodiments, a ready to use pharmaceutical composition is provided originally including about 4% cocaine hydrochloride, by weight, and a preservative in an aqueous solution at a pH of 2 to 4, wherein the cocaine hydrochloride concentration remains at greater than about 3.4%, by weight, after the composition is stored for a time selected from 1 month, 3 months, 6 months, 9 months, 12 months, 18 months, 20 months, 21 months, 24 months, 27 months, and 30 months at a temperature ranging from 3° C. to 7° C.

In various non-limiting embodiments, a ready to use pharmaceutical composition is provided originally including about 4% cocaine hydrochloride, by weight, and a preservative in an aqueous solution at a pH of 2 to 4, wherein the cocaine hydrochloride concentration remains at greater than about 3.6%, by weight, after the composition is stored for a time selected from 1 month, 3 months, 6 months, 9 months, 12 months, 18 months, 20 months, 21 months, 24 months, 27 months, and 30 months at a temperature ranging from 3° C. to 7° C.

In various non-limiting embodiments, a ready to use pharmaceutical composition is provided originally including about 8% cocaine hydrochloride, by weight, and a preservative in an aqueous solution at a pH of 2 to 4, wherein the cocaine hydrochloride concentration remains at greater than about 6.8%, by weight, or in any value or within any range subsumed therein, such as for example, greater than about 6%, 5%, 4%, 3.4%, 3%, or 2%, after the composition is stored for a time selected from 1 month, 3 months, 6 months, 9 months, 12 months, 18 months, 20 months, 21 months, 24 months, 27 months, and 30 months at a temperature ranging from 3° C. to 7° C.

Cocaine is predominantly metabolized in the human body, with little excreted in an unchanged form in the urine. In humans, cocaine is rapidly metabolized by hydrolytic pathways to form two major metabolites, benzoylecgonine (BE) and ecgonine methyl ester (EME), and by oxidative demethylation to form a minor metabolite, norcocaine, which has pharmacologic activity. FIG. 1 shows the metabolic pathways to form BE and EME. Ecgonine, a metabolite formed after sequential de-esterification steps, has also been observed. BE has been observed to be the major metabolite in the plasma after all routes of administration of cocaine.

The present inventors developed a highly storage stable pharmaceutical composition that inhibits the breakdown of cocaine hydrochloride in the pharmaceutical composition and provides a composition with a consistently therapeutically effective concentration of cocaine hydrochloride, including a limited concentration of impurities, over an extended time period. For example, one non-limiting embodiment of a storage stable pharmaceutical composition according to the present disclosure initially includes about 4% cocaine hydrochloride, by weight, and a preservative, in an aqueous solution at a pH of 2 to 4, wherein the composition comprises no more than 8% of total impurities, by weight, or in any value or within any range subsumed therein, such as for example, no more than 7%, no more than 6.5%, no more than 6%, no more than 5%, or no more than 4% total impurities, after the composition has been stored for 20 months at a temperature ranging from 23° C. to 27° C. and a relative humidity ranging from 55% to 65%. In various non-limiting embodiments, the storage stable pharmaceutical composition, after storage for 20 months at a temperature ranging from 23° C. to 27° C. and a relative humidity ranging from 55% to 65%, can comprise a benzoylecgonine concentration, by weight, of no more than 8%, or having any value or within any range subsumed therein, such as for example, no more than 7%, 6.5%, 6%, 5%, or 4%.

In various non-limiting embodiments, a storage stable pharmaceutical composition according to the present disclosure initially includes about 4% cocaine hydrochloride, by weight, and a preservative, in an aqueous solution at a pH of 2 to 4, wherein the composition comprises no more than 8% of total impurities, by weight, or having any value or within any range subsumed therein, such as for example, less than 7%, less than 6.1%, less than 6%, less than 5%, or less than 4% total impurities, after the composition has been stored for 18 months at a temperature ranging from 23° C. to 27° C. and a relative humidity ranging from 55% to 65%. In various non-limiting embodiments, the storage stable pharmaceutical composition, after storage for 18 months at a temperature ranging from 23° C. to 27° C. and a relative humidity ranging from 55% to 65%, can comprise a benzoylecgonine concentration, by weight, of no more than 8%, or having any value or within any range subsumed therein, such as for example, no more than 7%, 6.1%, 6%, 5%, or 4%.

In various non-limiting embodiments, a storage stable pharmaceutical composition according to the present disclosure initially includes about 4% cocaine hydrochloride, by weight, and a preservative, in an aqueous solution at a pH of 2 to 4, wherein the composition comprises no more than 7% of total impurities, by weight, or having any value or within any range subsumed therein, such as for example, less than 6%, less than 5%, less than 4.3%, less than 4%, or less than 3% total impurities, after the composition has been stored for 12 months at a temperature ranging from 23° C. to 27° C. and a relative humidity ranging from 55% to 65%. In various non-limiting embodiments, the storage stable pharmaceutical composition, after storage for 12 months at a temperature ranging from 23° C. to 27° C. and a relative humidity ranging from 55% to 65%, can comprise a benzoylecgonine concentration, by weight, of no more than 7% of benzoylecognine, or having any value or within any range subsumed therein, such as for example, less than 6%, less than 5%, less than 4.3%, less than 4%, or less than 3%.

In various non-limiting embodiments, a storage stable pharmaceutical composition according to the present disclosure initially includes about 4% cocaine hydrochloride, by weight, and a preservative, in an aqueous solution at a pH of 2 to 4, wherein the composition comprises no more than 5% of total impurities, by weight, or having any value or within any range subsumed therein, such as for example, no more than 4%, 3.75%, 3.5%, 3%, or 2% total impurities, after the composition has been stored for 9 months at a temperature ranging from 23° C. to 27° C. and a relative humidity ranging from 55% to 65%. In various non-limiting embodiments, the storage stable pharmaceutical composition, after storage for 9 months at a temperature ranging from 23° C. to 27° C. and a relative humidity ranging from 55% to 65%, can comprise a benzoylecgonine concentration of no more than 5% benzoylecgonine, by weight, or having any value or within any range subsumed therein, such as for example, no more than 4%, 3.75%, 3.5%, 3.25%, 3%, or 2%.

In various embodiments, after the storage stable pharmaceutical composition including about 4% cocaine hydrochloride, by weight, and a preservative in an aqueous solution at a pH of 2 to 4, has been stored for 9 months at a temperature ranging from 23° C. to 27° C. and a relative humidity ranging from 55% to 65%, the composition includes no more than about 500 ppm methanol per 4 mL pharmaceutical composition, or any value or within any range subsumed therein, such as for example, no more than 450 ppm/4 mL, 400 ppm/4 mL, 372 ppm/4 mL, 350 ppm/4 mL, 300 ppm/4 mL, 200 ppm/4 mL, 100 ppm/4 mL, 75 ppm/4 mL, or 50 ppm/4 mL.

In various embodiments, after the storage stable pharmaceutical composition including about 4% cocaine hydrochloride, by weight, and a preservative in an aqueous solution at a pH of 2 to 4, has been stored for 9 months at a temperature ranging from 23° C. to 27° C. and a relative humidity ranging from 55% to 65%, the composition includes acetonitrile in concentrations below quantifiable limits, no more than about 500 ng/mL isopropanol, or any value subsumed therein such as for example, no more than 450 ng/mL, 400 ng/mL, 375 ng/mL, 358 ng/mL, 350 ng/mL, 300 ng/mL, 250 ng/mL, or 200 ng/mL, and no more than about 900 ng/mL trimethylsilanol, or any value or within any range subsumed therein, such as for example, no more than 800 ng/mL, 750 ng/mL, 725 ng/mL, 706 ng/mL, 700 ng/mL, 600 ng/mL, 500 ng/mL, or 400 ng/mL.

In various embodiments, after the ready to use pharmaceutical composition including about 4% cocaine hydrochloride, by weight, and a preservative in an aqueous solution at a pH of 2 to 4, has been stored for 9 months at a temperature ranging from 23° C. to 27° C. and a relative humidity ranging from 55% to 65%, the composition includes no more than about 500 ng/mL chromium, or any value or within any range subsumed therein, such as for example, no more than 450 ng/mL, 425 ng/mL, 400 ng/mL, 385 ng/mL, 350 ng/mL, 300 ng/mL, 200 ng/mL, or 100 ng/mL chromium, and no more than about 300 ng/mL nickel, or any value or within any range subsumed therein, such as for example, no more than 250 ng/mL, 200 ng/mL, 176 ng/mL, 150 ng/mL, 100 ng/mL, or 75 ng/mL nickel.

In various non-limiting embodiments, a storage stable pharmaceutical composition according to the present disclosure initially includes about 4% cocaine hydrochloride, by weight, and a preservative, in an aqueous solution at a pH of 2 to 4, wherein the composition comprises no more than 6% of total impurities, by weight, or having any value or within any range subsumed therein, such as for example, no more than 7%, no more than 6%, no more than 5%, no more than 4%, no more than 3%, no more than 2.6%, no more than 2%, or no more than 1% total impurities, after the composition has been stored for 6 months at a temperature ranging from 23° C. to 27° C. and a relative humidity ranging from 55% to 65%. In various non-limiting embodiments, the storage stable pharmaceutical composition, after storage for 6 months at a temperature ranging from 23° C. to 27° C. and a relative humidity ranging from 55% to 65%, can comprise a benzoylecgonine concentration of no more than 5% of benzoylecgonine, by weight, or having any value or within any range subsumed therein, such as for example, less than 4%, less than 3%, less than 2.6%, less than 2%, or less than 1%.

In various non-limiting embodiments, a storage stable pharmaceutical composition according to the present disclosure initially includes about 4% cocaine hydrochloride, by weight, and a preservative, in an aqueous solution at a pH of 2 to 4, wherein the composition comprises no more than 4% of total impurities, by weight, or having any value or within any range subsumed therein, such as for example, less than 3.5%, less than 3%, less than 2.5%, less than 2%, less than 1.3%, or less than 1% total impurities after the composition has been stored for 3 months at a temperature ranging from 23° C. to 27° C. and a relative humidity ranging from 55% to 65%. In various non-limiting embodiments, the storage stable pharmaceutical composition, after storage for 3 months at a temperature ranging from 23° C. to 27° C. and a relative humidity ranging from 55% to 65%, can comprise a benzoylecgonine concentration, by weight, of no more than 4% of benzoylecgonine, by weight, or having any value or within any range subsumed therein, such as for example, less than 3.5%, less than 3%, less than 2.5%, less than 2%, less than 1.3%, or less than 1%.

In a non-limiting embodiment, a storage stable pharmaceutical composition initially comprises about 4% cocaine hydrochloride, by weight, and a preservative, in an aqueous solution at a pH of 2 to 4, and wherein the composition comprises no more than about 4%, about 5%, about 6%, about 7%, about 8%, about 9%, or about 10% of total impurities, by weight, after the composition has been stored for 12 months at a temperature ranging from 28° C. to 32° C. and a relative humidity ranging from 60% to 70%.

In various non-limiting embodiments, a storage stable pharmaceutical composition originally including about 4% cocaine hydrochloride, by weight, and a preservative in an aqueous solution at a pH of 2 to 4, comprises no more than 7.3% benzoylecgonine, by weight, after the composition is stored for 20 months at a temperature ranging from 23° C. to 27° C. and a relative humidity ranging from 55% to 65%.

In various non-limiting embodiments, the storage stable pharmaceutical composition originally including about 4% cocaine hydrochloride, by weight, and a preservative in an aqueous solution at a pH of 2 to 4, comprises no more than 5.9% benzoylecgonine, by weight, after the composition is stored for 4 months at a temperature ranging from 38° C. to 42° C. and a relative humidity ranging from 70% to 80%.

In various non-limiting embodiments, the storage stable pharmaceutical composition originally including about 4% cocaine hydrochloride, by weight, and a preservative in an aqueous solution at a pH of 2 to 4, comprises no more than 12% benzoylecgonine, by weight, or any value or within any range subsumed therein, such as for example, no more than 10%, 9.5%, 9.3%, 9%, 8%, 7%, 6%, or 5%, after the composition is stored for 6 months at a temperature ranging from 38° C. to 42° C. and a relative humidity ranging from 70% to 80%.

In a non-limiting embodiment, a storage stable pharmaceutical composition according to the present disclosure initially includes about 8% cocaine hydrochloride, by weight, and a preservative, in an aqueous solution at a pH of 2 to 4, wherein the composition comprises no more than 10% of total impurities, by weight, after the composition has been stored for 21 months at a temperature ranging from 23° C. to 27° C. and a relative humidity ranging from 55% to 65%. In an embodiment, the storage stable pharmaceutical composition initially includes about 8% cocaine hydrochloride, by weight, and a preservative, in an aqueous solution at a pH of 2 to 4, wherein the composition comprises no more than about 9%, about 8%, about 7%, or about 6.6% of total impurities, by weight, after the composition has been stored for 21 months at a temperature ranging from 23° C. to 27° C. and a relative humidity ranging from 55% to 65%. In an embodiment, the storage stable pharmaceutical composition initially includes about 8% cocaine hydrochloride, by weight, and a preservative, in an aqueous solution at a pH of 2 to 4, wherein the composition comprises no more than about 9%, about 8%, about 7%, or about 6.6% of benzoylecgonine, by weight, after the composition has been stored for 21 months at a temperature ranging from 23° C. to 27° C. and a relative humidity ranging from 55% to 65%.

In various embodiments, the storage stable pharmaceutical composition initially includes about 8% cocaine hydrochloride, by weight, and a preservative, in an aqueous solution at a pH of 2 to 4, wherein the composition comprises no more than about 9%, about 8%, about 7%, about 6%, or about 5.6% of total impurities, by weight, after the composition has been stored for 18 months at a temperature ranging from 23° C. to 27° C. and a relative humidity ranging from 55% to 65%. In various embodiments, the storage stable pharmaceutical composition initially includes about 8% cocaine hydrochloride, by weight, and a preservative, in an aqueous solution at a pH of 2 to 4, wherein the composition comprises no more than about 9%, about 8%, about 7%, about 6%, or about 5.6% of benzoylecgonine, by weight, after the composition has been stored for 18 months at a temperature ranging from 23° C. to 27° C. and a relative humidity ranging from 55% to 65%.

In various embodiments, the storage stable pharmaceutical composition initially includes about 8% cocaine hydrochloride, by weight, and a preservative, in an aqueous solution at a pH of 2 to 4, wherein the composition comprises no more than about 8%, about 7%, about 6%, about 5%, or about 4.7% of total impurities, by weight, after the composition has been stored for 15 months at a temperature ranging from 23° C. to 27° C. and a relative humidity ranging from 55% to 65%. In various embodiments, the storage stable pharmaceutical composition initially includes about 8% cocaine hydrochloride, by weight, and a preservative, in an aqueous solution at a pH of 2 to 4, wherein the composition comprises no more than about 8%, about 7%, about 6%, about 5%, or about 4.7% of benzoylecgonine, by weight, after the composition has been stored for 15 months at a temperature ranging from 23° C. to 27° C. and a relative humidity ranging from 55% to 65%.

In a non-limiting embodiment, a storage stable pharmaceutical composition initially including about 8% cocaine hydrochloride, by weight, and a preservative, in an aqueous solution at a pH of 2 to 4, comprises no more than about 7%, about 6%, about 5%, about 4%, or about 3.8% of total impurities, by weight, after the composition has been stored for 12 months at a temperature ranging from 23° C. to 27° C. and a relative humidity ranging from 55% to 65%. In various embodiments, the storage stable pharmaceutical composition initially including about 8% cocaine hydrochloride, by weight, and a preservative, in an aqueous solution at a pH of 2 to 4, comprises no more than about 7%, about 6%, about 5%, about 4%, or about 3.8% of benzoylecgonine, by weight, after the composition has been stored for 12 months at a temperature ranging from 23° C. to 27° C. and a relative humidity ranging from 55% to 65%.

In a non-limiting embodiment, the storage stable pharmaceutical composition initially including about 8% cocaine hydrochloride, by weight, and a preservative, in an aqueous solution at a pH of 2 to 4, comprises no more than about 6%, about 5%, about 4%, about 3%, or about 2.1% of total impurities, by weight, after the composition has been stored for 6 months at a temperature ranging from 23° C. to 27° C. and a relative humidity ranging from 55% to 65%. In various embodiments, the storage stable pharmaceutical composition initially including about 8% cocaine hydrochloride, by weight, and a preservative, in an aqueous solution at a pH of 2 to 4, comprises no more than about 6%, about 5%, about 4%, about 3%, or about 2.1% of benzoylecgonine, by weight, after the composition has been stored for 6 months at a temperature ranging from 23° C. to 27° C. and a relative humidity ranging from 55% to 65%.

In a non-limiting embodiment, a storage stable pharmaceutical composition initially including about 4% cocaine hydrochloride, by weight, and a preservative, in an aqueous solution at a pH of 2 to 4, comprises no more than 12% of total impurities, by weight, after the composition has been stored for 6 months at a temperature ranging from 38° C. to 42° C. and a relative humidity ranging from 70% to 80%. In various non-limiting embodiments, the storage stable pharmaceutical composition, after storage for 6 months at a temperature ranging from 38° C. to 42° C. and a relative humidity ranging from 70% to 80%, can comprise a total impurities concentration, by weight, of no more than 11%, or having any value or within any range subsumed therein, such as for example, no more than 10%, than 9.3%, than 9%, than 8%, than 7%, than 6%, than 5%, than 4%, or than 3%. In various non-limiting embodiments, the storage stable pharmaceutical composition, after storage for 6 months at a temperature ranging from 38° C. to 42° C. and a relative humidity ranging from 70% to 80%, can comprise a benzoylecgonine concentration, by weight, of no more than 12%, or having any value or within any range subsumed therein, such as for example, no more than 11%, than 10%, than 9.3%, than 9%, than 8%, than 7%, than 6%, than 5%, than 4%, or than 3%.

In various non-limiting embodiments, the storage stable pharmaceutical composition, after storage for 3 months at a temperature ranging from 38° C. to 42° C. and a relative humidity ranging from 70% to 80%, can comprise a total impurities concentration, by weight, of no more than 8%, or having any value or within any range subsumed therein, such as for example, no more than 7%, than 6%, than 5.5%, than 5.2%, than 5%, than 4%, than 3%, than 2%, or than 1%. In various non-limiting embodiments, the storage stable pharmaceutical composition, after storage for 3 months at a temperature ranging from 38° C. to 42° C. and a relative humidity ranging from 70% to 80%, can comprise a benzoylecgonine concentration, by weight, of no more than 8%, or having any value or within any range subsumed therein, such as for example, no more than 7%, than 6%, than 5.5%, than 5.2%, than 5%, than 4%, than 3%, than 2%, or than 1%.

In a non-limiting embodiment, a storage stable pharmaceutical composition initially including about 4% cocaine hydrochloride, by weight, and a preservative, in an aqueous solution at a pH of 2 to 4, comprises no more than 6% of total impurities, by weight, or having any value or within any range subsumed therein, such as for example, less than 5%, less than 4%, less than 3%, less than 2%, or less than 1% total impurities, after the composition has been stored for 24 months at a temperature ranging from 3° C. to 7° C. In various non-limiting embodiments, the storage stable pharmaceutical composition, after storage for 24 months at a temperature ranging from 3° C. to 7° C., can comprise a benzoylecgonine concentration, by weight, of no more than 6%, or having any value or within any range subsumed therein, such as for example, less than 5%, less than 4%, less than 3%, less than 2%, or less than 1% total impurities.

In a non-limiting embodiment, a storage stable pharmaceutical composition initially including about 4% cocaine hydrochloride, by weight, and a preservative, in an aqueous solution at a pH of 2 to 4, wherein the composition comprises no more than 5% of total impurities, by weight, or having any value or within any range subsumed therein, such as for example, less than 4%, less than 3%, less than 2.5%, less than 2%, or less than 1% total impurities, after the composition has been stored for 21 months at a temperature ranging from 3° C. to 7° C. In various non-limiting embodiments, the storage stable pharmaceutical composition, after storage for 21 months at a temperature ranging from 3° C. to 7° C., can comprise a benzoylecgonine concentration, by weight, of no more than 5% of total impurities, by weight, or having any value or within any range subsumed therein, such as for example, less than 4%, less than 3%, less than 2.5%, less than 2%, or less than 1%.

In a non-limiting embodiment, a storage stable pharmaceutical composition initially including about 4% cocaine hydrochloride, by weight, and a preservative, in an aqueous solution at a pH of 2 to 4, comprises no more than 4% of total impurities, by weight, or having any value or within any range subsumed therein, such as for example, less than 3%, less than 2%, or less than 1% total impurities, after the composition has been stored for 18 months at a temperature ranging from 3° C. to 7° C. In various non-limiting embodiments, the storage stable pharmaceutical composition, after storage for 18 months at a temperature ranging from 3° C. to 7° C., can comprise a benzoylecgonine concentration, by weight, of no more than 4%, or having any value or within any range subsumed therein, such as for example, less than 3%, less than 2%, or less than 1%.

In a non-limiting embodiment, a storage stable pharmaceutical composition initially including about 4% cocaine hydrochloride, by weight, and a preservative, in an aqueous solution at a pH of 2 to 4, comprises no more than 4% of total impurities, by weight, or having any value or within any range subsumed therein, such as for example, less than 3%, less than 2%, or less than 1% total impurities, after the composition has been stored for 12 months at a temperature ranging from 3° C. to 7° C. In various non-limiting embodiments, the storage stable pharmaceutical composition, after storage for 12 months at a temperature ranging from 3° C. to 7° C., can comprise a benzoylecgonine concentration, by weight, of no more than 4%, or having any value or within any range subsumed therein, such as for example, less than 3%, less than 2%, or less than 1%.

In a non-limiting embodiment, a storage stable pharmaceutical composition initially including about 4% cocaine hydrochloride, by weight, and a preservative, in an aqueous solution at a pH of 2 to 4, comprises no more than 4% of total impurities, by weight, or having any value or within any range subsumed therein, such as for example, less than 3%, less than 2%, or less than 1% total impurities, after the composition has been stored for 6 months at a temperature ranging from 3° C. to 7° C. In various non-limiting embodiments, the storage stable pharmaceutical composition, after storage for 6 months at a temperature ranging from 3° C. to 7° C., can comprise a benzoylecgonine concentration, by weight, of no more than 4%, or having any value or within any range subsumed therein, such as for example, less than 3%, less than 2%, or less than 1%.

The present disclosure also describes a ready to use pharmaceutical composition initially including about 4% cocaine hydrochloride, by weight, and a preservative in an aqueous solution at a pH of 2 to 4, wherein the cocaine hydrochloride concentration is greater than about 3.4%, by weight, after the composition has been stored for 3 months at a temperature ranging from 23° C. to 27° C. and a relative humidity ranging from 55% to 65%, wherein the composition includes no more than about 3% total impurities, or having any value or within any range subsumed therein, such as for example, no more than 2.5%, 2%, 1.5%, 1.3%, 1%, 0.8%, 0.5%, or 0.3%.

In various embodiments, after the ready to use pharmaceutical composition initially including about 4% cocaine hydrochloride, by weight, and a preservative in an aqueous solution at a pH of 2 to 4, has been stored for 3 months at a temperature ranging from 23° C. to 27° C. and a relative humidity ranging from 55% to 65%, the composition includes no more than about 3% benzoylecgonine, or any value or within any range subsumed therein, such as for example, no more than 2.5%, 2%, 1.5%, 1.3%, 1%, 0.8%, 0.5%, or 0.3%.

In various embodiments, after the ready to use pharmaceutical composition initially including about 4% cocaine hydrochloride, by weight, and a preservative in an aqueous solution at a pH of 2 to 4, has been stored for 3 months at a temperature ranging from 23° C. to 27° C. and a relative humidity ranging from 55% to 65%, the composition includes no more than about 200 ppm methanol per 4 mL pharmaceutical composition, or any value or within any range subsumed therein, such as for example, no more than 150 ppm/4 mL, 100 ppm/4 mL, 80 ppm/4 mL, 78 ppm/4 mL, 75 ppm/4 mL, 70 ppm/4 mL, 60 ppm/4 mL, or 50 ppm/4 mL.

In various embodiments, after the ready to use pharmaceutical composition initially including about 4% cocaine hydrochloride, by weight, and a preservative in an aqueous solution at a pH of 2 to 4, has been stored for 3 months at a temperature ranging from 23° C. to 27° C. and a relative humidity ranging from 55% to 65%, the composition includes isopropanol and acetonitrile in concentrations below quantifiable limits, and no more than about 2500 ng/mL trimethylsilanol, or any value or within any range subsumed therein, such as for example, no more than 2200 ng/mL, 1900 ng/mL, 1850 ng/mL, 1837 ng/mL, 1800 ng/mL, 1500 ng/mL, 1000 ng/mL, or 500 ng/mL.

In various embodiments, after the ready to use pharmaceutical composition initially including about 4% cocaine hydrochloride, by weight, and a preservative in an aqueous solution at a pH of 2 to 4, has been stored for 3 months at a temperature ranging from 23° C. to 27° C. and a relative humidity ranging from 55% to 65%, the composition includes no more than about 500 ng/mL chromium, or any value or within any range subsumed therein, such as for example, no more than 400 ng/mL, 414 ng/mL, 350 ng/mL, 300 ng/mL, 250 ng/mL, 200 ng/mL, or 100 ng/mL chromium, and no more than about 400 ng/mL nickel, or any value or within any range subsumed therein, such as for example, no more than 300 ng/mL, 275 ng/mL, 253 ng/mL, 250 ng/mL, 225 ng/mL, 200 ng/mL, or 100 ng/mL nickel.

In a non-limiting embodiment, a ready to use pharmaceutical composition initially includes about 4% cocaine hydrochloride, by weight, and a preservative in an aqueous solution at a pH of 2 to 4, wherein the cocaine hydrochloride concentration is greater than about 3.4%, by weight, after the composition has been stored for 6 months at a temperature ranging from 23° C. to 27° C. and a relative humidity ranging from 55% to 65%, and wherein the composition includes no more than about 12% total impurities, or having any value or within any range subsumed therein, such as for example, no more than 11%, 10%, 9.5%, 9.3%, 9%, 8.5%, 8%, 7%, 6%, or 5%.

In various embodiments, after the ready to use pharmaceutical composition initially including about 4% cocaine hydrochloride, by weight, and a preservative in an aqueous solution at a pH of 2 to 4, has been stored for 6 months at a temperature ranging from 23° C. to 27° C. and a relative humidity ranging from 55% to 65%, the composition includes no more than about 12% benzoylecgonine, or having any value or within any range subsumed therein, such as for example, no more than 11%, 10%, 9.5%, 9.3%, 9%, 8.5%, 8%, 7%, 6%, or 5%.

In various embodiments, after the ready to use pharmaceutical composition initially including about 4% cocaine hydrochloride, by weight, and a preservative in an aqueous solution at a pH of 2 to 4, has been stored for 6 months at a temperature ranging from 23° C. to 27° C. and a relative humidity ranging from 55% to 65%, the composition includes no more than about 600 ppm methanol per 4 mL pharmaceutical composition, or any value or within any range subsumed therein, such as for example, no more than 500 ppm/4 mL, 475 ppm/4 mL, 450 ppm/4 mL, 414 ppm/4 mL, 400 ppm/4 mL, 300 ppm/4 mL, 200 ppm/4 mL, or 100 ppm/4 mL.

In various embodiments, after the ready to use pharmaceutical composition initially including about 4% cocaine hydrochloride, by weight, and a preservative in an aqueous solution at a pH of 2 to 4, has been stored for 6 months at a temperature ranging from 23° C. to 27° C. and a relative humidity ranging from 55% to 65%, the composition includes acetonitrile in concentrations below quantifiable limits, no more than about 400 ng/mL isopropanol, or any value subsumed therein such as for example, no more than 300 ng/mL, 286 ng/mL, 275 ng/mL, 250 ng/mL, 200 ng/mL, or 100 ng/mL, and no more than about 500 ng/mL trimethylsilanol, or any value or within any range subsumed therein, such as for example, no more than 400 ng/mL, 375 ng/mL, 356 ng/mL, 325 ng/mL, 300 ng/mL, 200 ng/mL, or 100 ng/mL.

In various embodiments, after the ready to use pharmaceutical composition initially including about 4% cocaine hydrochloride, by weight, and a preservative in an aqueous solution at a pH of 2 to 4, has been stored for 6 months at a temperature ranging from 23° C. to 27° C. and a relative humidity ranging from 55% to 65%, the composition includes no more than about 500 ng/mL chromium, or any value or within any range subsumed therein, such as for example, no more than 400 ng/mL, 350 ng/mL, 325 ng/mL, 319 ng/mL, 300 ng/mL, 250 ng/mL, 200 ng/mL, or 100 ng/mL chromium, and no more than about 300 ng/mL nickel, or any value or within any range subsumed therein, such as for example, no more than 250 ng/mL, 200 ng/mL, 185 ng/mL, 175 ng/mL, 150 ng/mL, 100 ng/mL, or 75 ng/mL nickel.

In a non-limiting embodiment, a ready to use pharmaceutical composition initially including about 4% cocaine hydrochloride, by weight, and a preservative in an aqueous solution at a pH of 2 to 4, has a cocaine hydrochloride concentration greater than about 3.4%, by weight, after the composition has been stored for 9 months at a temperature ranging from 23° C. to 27° C. and a relative humidity ranging from 55% to 65%, wherein the composition includes no more than about 6% total impurities, or having any value or within any range subsumed therein, such as for example, no more than 5%, 4%, 3.5%, 3%, 2.5%, 2%, or 1%.

In various embodiments, after the ready to use pharmaceutical composition initially including about 4% cocaine hydrochloride, by weight, and a preservative in an aqueous solution at a pH of 2 to 4, has been stored for 9 months at a temperature ranging from 23° C. to 27° C. and a relative humidity ranging from 55% to 65%, the composition includes no more than about 6% benzoylecgonine, or having any value or within any range subsumed therein, such as for example, no more than 5%, 4%, 3.5%, 3%, 2.5%, 2%, or 1%.

In various embodiments, after the ready to use pharmaceutical composition initially including about 4% cocaine hydrochloride, by weight, and a preservative in an aqueous solution at a pH of 2 to 4, has been stored for 9 months at a temperature ranging from 23° C. to 27° C. and a relative humidity ranging from 55% to 65%, the composition includes no more than about 500 ppm methanol per 4 mL pharmaceutical composition, or any value or within any range subsumed therein, such as for example, no more than 400 ppm/4 mL, 375 ppm/4 mL, 372 ppm/4 mL, 350 ppm/4 mL, 300 ppm/4 mL, 200 ppm/4 mL, 100 ppm/4 mL, or 50 ppm/4 mL.

In various embodiments, after the ready to use pharmaceutical composition initially including about 4% cocaine hydrochloride, by weight, and a preservative in an aqueous solution at a pH of 2 to 4, has been stored for 9 months at a temperature ranging from 23° C. to 27° C. and a relative humidity ranging from 55% to 65%, the composition includes acetonitrile in concentrations below quantifiable limits, no more than about 500 ng/mL isopropanol, or any value subsumed therein such as for example, no more than 400 ng/mL, 375 ng/mL, 358 ng/mL, 300 ng/mL, or 200 ng/mL, and no more than about 800 ng/mL trimethylsilanol, or any value or within any range subsumed therein, such as for example, no more than 750 ng/mL, 725 ng/mL, 706 ng/mL, 650 ng/mL, 600 ng/mL, 500 ng/mL, or 400 ng/mL.

In various embodiments, after the ready to use pharmaceutical composition initially including about 4% cocaine hydrochloride, by weight, and a preservative in an aqueous solution at a pH of 2 to 4, has been stored for 9 months at a temperature ranging from 23° C. to 27° C. and a relative humidity ranging from 55% to 65%, the composition includes no more than about 500 ng/mL chromium, or any value or within any range subsumed therein, such as for example, no more than 400 ng/mL, 385 ng/mL, 350 ng/mL, 300 ng/mL, 250 ng/mL, 200 ng/mL, or 100 ng/mL chromium, and no more than about 300 ng/mL nickel, or any value or within any range subsumed therein, such as for example, no more than 250 ng/mL, 200 ng/mL, 185 ng/mL, 176 ng/mL, 150 ng/mL, 100 ng/mL, or 75 ng/mL nickel.

In a non-limiting embodiment, a ready to use pharmaceutical composition initially including about 4% cocaine hydrochloride, by weight, a preservative in an aqueous solution at a pH of 2 to 4, has a cocaine hydrochloride concentration that is greater than about 3.4%, by weight, after the composition has been stored for 12 months at a temperature ranging from 23° C. to 27° C. and a relative humidity ranging from 55% to 65%, wherein the composition includes no more than about 6% total impurities, or any value or within any range subsumed therein, such as for example, no more than 5%, 4.8%, 4.3%, 4%, 3.5%, 3%, 2%, or 1% total impurities.

In various embodiments, after the ready to use pharmaceutical composition initially including about 4% cocaine hydrochloride, by weight, and a preservative in an aqueous solution at a pH of 2 to 4, has been stored for 12 months at a temperature ranging from 23° C. to 27° C. and a relative humidity ranging from 55% to 65%, the composition includes no more than about 6% benzoylecgonine, or any value or within any range subsumed therein, such as for example, no more than 5%, 4.8%, 4.3%, 4%, 3.5%, 3%, 2%, or 1%.

In various embodiments, after the ready to use pharmaceutical composition initially including about 4% cocaine hydrochloride, by weight, and a preservative in an aqueous solution at a pH of 2 to 4, has been stored for 12 months at a temperature ranging from 23° C. to 27° C. and a relative humidity ranging from 55% to 65%, the composition includes no more than about 300 ppm methanol per 4 mL pharmaceutical composition, or any value or within any range subsumed therein, such as for example, no more than 250 ppm/4 mL, 200 ppm/4 mL, 192 ppm/4 mL, 150 ppm/4 mL, 100 ppm/4 mL, 80 ppm/4 mL, 70 ppm/4 mL, 60 ppm/4 mL, or 50 ppm/4 mL.

In various embodiments, after the ready to use pharmaceutical composition initially including about 4% cocaine hydrochloride, by weight, and a preservative in an aqueous solution at a pH of 2 to 4, has been stored for 12 months at a temperature ranging from 23° C. to 27° C. and a relative humidity ranging from 55% to 65%, the composition includes acetonitrile in concentrations below quantifiable limits, no more than about 400 ng/mL isopropanol, or any value subsumed therein such as for example, no more than 350 ng/mL, 325 ng/mL, 313 ng/mL, 300 ng/mL, 250 ng/mL, or 200 ng/mL, and no more than about 600 ng/mL trimethylsilanol, or any value or within any range subsumed therein, such as for example, no more than 500 ng/mL, 450 ng/mL, 439 ng/mL, 425 ng/mL, 400 ng/mL, 300 ng/mL, 200 ng/mL, or 100 ng/mL.

In various embodiments, after the ready to use pharmaceutical composition initially including about 4% cocaine hydrochloride, by weight, and a preservative in an aqueous solution at a pH of 2 to 4, has been stored for 12 months at a temperature ranging from 23° C. to 27° C. and a relative humidity ranging from 55% to 65%, the composition includes no more than about 500 ng/mL chromium, or any value or within any range subsumed therein, such as for example, no more than 400 ng/mL, 376 ng/mL, 350 ng/mL, 300 ng/mL, 200 ng/mL, 100 ng/mL, or 50 ng/mL chromium, and no more than about 400 ng/mL nickel, or any value or within any range subsumed therein, such as for example, no more than 350 ng/mL, 300 ng/mL, 250 ng/mL, 203 ng/mL, 150 ng/mL, 100 ng/mL, or 75 ng/mL nickel.

In a non-limiting embodiment, a ready to use pharmaceutical composition initially including about 4% cocaine hydrochloride, by weight, and a preservative in an aqueous solution at a pH of 2 to 4, has a cocaine hydrochloride concentration greater than about 3.4%, by weight, after the composition has been stored for 18 months at a temperature ranging from 23° C. to 27° C. and a relative humidity ranging from 55% to 65%, wherein the composition includes no more than about 10% total impurities, or having any value or within any range subsumed therein, such as for example, no more than 9%, 8%, 7%, 6.5%, 6.1%, 5.5%, 5%, 4%, 3%, or 2%.

In various embodiments, after the ready to use pharmaceutical composition initially including about 4% cocaine hydrochloride, by weight, and a preservative in an aqueous solution at a pH of 2 to 4, has been stored for 18 months at a temperature ranging from 23° C. to 27° C. and a relative humidity ranging from 55% to 65%, the composition includes no more than about 10% benzoylecgonine, or having any value or within any range subsumed therein, such as for example, no more than 9%, 8%, 7%, 6.5%, 6.1%, 5.5%, 5%, 4%, 3%, or 2%.

In various embodiments, after the ready to use pharmaceutical composition initially including about 4% cocaine hydrochloride, by weight, and a preservative in an aqueous solution at a pH of 2 to 4, has been stored for 18 months at a temperature ranging from 23° C. to 27° C. and a relative humidity ranging from 55% to 65%, the composition includes no more than about 400 ppm methanol per 4 mL pharmaceutical composition, or any value or within any range subsumed therein, such as for example, no more than 300 ppm/4 mL, 286 ppm/4 mL, 250 ppm/4 mL, 225 ppm/4 mL, 200 ppm/4 mL, 100 ppm/4 mL, 75 ppm/4 mL, or 50 ppm/4 mL.

In a non-limiting embodiment, a ready to use pharmaceutical composition initially including about 4% cocaine hydrochloride, by weight, and a preservative in an aqueous solution at a pH of 2 to 4, has a cocaine hydrochloride concentration greater than about 3.4%, by weight, after the composition has been stored for 20 months at a temperature ranging from 23° C. to 27° C. and a relative humidity ranging from 55% to 65%, wherein the composition includes no more than about 9% total impurities, or any value or within any range subsumed therein, such as for example, no more than 8%, 7%, 6.75%, 6.5%, 6%, 5.5%, 5%, 4%, 3%, or 2%.

In various embodiments, after the ready to use pharmaceutical composition initially including about 4% cocaine hydrochloride, by weight, and a preservative in an aqueous solution at a pH of 2 to 4, has been stored for 20 months at a temperature ranging from 23° C. to 27° C. and a relative humidity ranging from 55% to 65%, the composition includes no more than about 9% benzoylecgonine, or any value or within any range subsumed therein, such as for example, no more than 8%, 7%, 6.75%, 6.5%, 6%, 5.5%, 5%, 4%, 3%, or 2%.

In various embodiments, after the ready to use pharmaceutical composition initially including about 4% cocaine hydrochloride, by weight, and a preservative in an aqueous solution at a pH of 2 to 4, has been stored for 20 months at a temperature ranging from 23° C. to 27° C. and a relative humidity ranging from 55% to 65%, the composition includes no more than about 400 ppm methanol per 4 mL pharmaceutical composition, or any value or within any range subsumed therein, such as for example, no more than 350 ppm/4 mL, 307 ppm/4 mL, 300 ppm/4 mL, 250 ppm/4 mL, 200 ppm/4 mL, 150 ppm/4 mL, 100 ppm/4 mL, or 50 ppm/4 mL.

In various embodiments, after the ready to use pharmaceutical composition initially including about 4% cocaine hydrochloride, by weight, and a preservative in an aqueous solution at a pH of 2 to 4, has been stored for 20 months at a temperature ranging from 23° C. to 27° C. and a relative humidity ranging from 55% to 65%, the composition includes acetonitrile in concentrations below quantifiable limits, no more than about 500 ng/mL isopropanol, or any value or within any range subsumed therein such as for example, no more than 450 ng/mL, 428 ng/mL, 400 ng/mL, 350 ng/mL, 300 ng/mL, or 200 ng/mL, and no more than about 900 ng/mL trimethylsilanol, or any value or within any range subsumed therein, such as for example, no more than 800 ng/mL, 750 ng/mL, 740 ng/mL, 700 ng/mL, 650 ng/mL, 600 ng/mL, or 500 ng/mL.

In various embodiments, after the ready to use pharmaceutical composition initially including about 4% cocaine hydrochloride, by weight, and a preservative in an aqueous solution at a pH of 2 to 4, has been stored for 20 months at a temperature ranging from 23° C. to 27° C. and a relative humidity ranging from 55% to 65%, the composition includes no more than about 600 ng/mL chromium, or any value or within any range subsumed therein, such as for example, no more than 500 ng/mL, 425 ng/mL, 405 ng/mL, 400 ng/mL, 375 ng/mL, 300 ng/mL, or 200 ng/mL chromium, and no more than about 400 ng/mL nickel, or any value or within any range subsumed therein, such as for example, no more than 350 ng/mL, 300 ng/mL, 250 ng/mL, 202 ng/mL, 200 ng/mL, 150 ng/mL, or 100 ng/mL nickel.

The present disclosure also encompasses methods of using a pharmaceutical composition as an anesthetic prior to conducting a medical or diagnostic procedure on a subject. For example, in a non-limiting embodiment, a method of administering a topical anesthetic solution comprising cocaine hydrochloride to a subject to reduce sensation in a body region of the subject comprises soaking a number of (e.g., four) absorbent articles with the solution, and contacting the soaked absorbent articles with a nasal mucous membrane of the patient for at least about 20 minutes, wherein the method achieves a cocaine $AUC_{inf}$ in the subject ranging from 30.8 ng*h/mL to 79.0 ng*h/mL.

In various non-limiting embodiments of the method, the topical solution of the method is an aqueous solution comprising cocaine hydrochloride, a preservative, and an acidulant in any of the concentrations as described herein. In one non-limiting embodiment, the topical solution comprises about 4% by weight cocaine hydrochloride.

In various alternative non-limiting embodiments, the method can include contacting the soaked absorbent articles with the nasal mucous membrane of the subject for greater than 1 minute, or for any value or within any range subsumed therein, such as, for example, greater than 2 minutes, from 3 minutes to 50 minutes, from 4 minutes to 45 minutes, from 5 minutes to 30 minutes, from 6 minutes to 40 minutes, from 7 minutes to 35 minutes, from 8 minutes to 30 minutes, from 9 minutes to 25 minutes, from 10 minutes to 20 minutes, 5 minutes, 6 minutes, 7 minutes, 8 minutes, 9 minutes, 10 minutes, 11 minutes, 15 minutes, 20 minutes, greater than 5 minutes, greater than 10 minutes, greater than 15 minutes, or greater than 20 minutes.

In various non-limiting embodiments of the method wherein the topical solution comprises about 4% cocaine hydrochloride, any of the values previously described herein for cocaine $AUC_{inf}$, cocaine $C_{max}$, cocaine $T_{max}$, and cocaine urinary recovery are achieved following a topical application of 4% cocaine hydrochloride to a subject for 20 minutes.

In various non-limiting embodiments, the absorbent articles can comprise cottonoid pledgets. According to certain non-limiting embodiments, each cottonoid pledget can have a size and an absorbency sufficient to absorb up to about 1 mL of a pharmaceutical solution comprising cocaine hydrochloride according to the present disclosure. In various non-limiting embodiments, the cottonoid pledgets include height dimensions ranging from 0.75 cm to 3.0 cm in height, or any value or range subsumed therein, such as for example, from 1.0 cm to 2.5 cm, or from 1.3 cm to 2.0 cm. In various non-limiting embodiments, each of the cottonoid pledgets includes length dimensions ranging from 3.0 cm to 8.0 cm, or any value or range subsumed therein, such as for example, from 4.0 cm to 7.0 cm, or from 5.0 to 6.0 cm. In certain non-limiting embodiments, the cottonoid pledgets can exhibit dimensions of 1.3 cm by 4 cm.

In various non-limiting embodiments, a method according to the present disclosure can further include removing the absorbent article from contact with the mucous membrane, where following removal of the absorbent article from contact with the mucous membrane of the subject, the absorbent article retains up to 99% of the active agent absorbed therein. In certain non-limiting embodiments, the absorbent article retains up to 95%, up to 90%, up to 85%, up to 80%, up to 75%, up to 70%, up to 65%, up to 60%, up to 50%, 61%, 62%, 63%, 64%, 65%, or 66% of the original amount of active agent absorbed therein.

In a non-limiting embodiment, a method according to the present disclosure for administering a topical solution comprising about 4%, by weight, cocaine hydrochloride to a subject to reduce sensation in a body region of the subject comprises soaking a plurality of (e.g., four) absorbent articles with the solution, and contacting the absorbent articles with a nasal mucous membrane of the subject for at least about 20 minutes, wherein the method achieves a cocaine $T_{max}$ in the subject ranging from 0.09 h to 0.77 h. In various embodiments, the method achieves a cocaine $T_{max}$ in the subject ranging from about 0.02 h to about 1 h, from about 0.04 h to about 0.9 h, from about 0.07 h to about 0.8 h, or from about 0.09 h to about 0.77 h.

In certain embodiments, the method can include contacting the absorbent articles with the nasal mucous membrane of the patient for any of the time periods as previously described and disclosed in the methods herein.

In various embodiments of the method, the method can achieve a cocaine $C_{max}$ ranging from 19.7 ng/mL to 54.3 ng/mL, and an absorptivity factor for cocaine in the patient ranging from 0.640 $h^{-1}$ to 0.687 $h^{-1}$. In certain embodiments, the method achieves a $C_{max}$ ranging from about 15.0 ng/mL to about 95 ng/mL, from about 20 ng/mL to about 85 ng/mL, from about 25 ng/mL to about 51.2 ng/mL, from about 29.6 ng/mL to about 71.6 ng/mL, or from about 16.2 ng/mL to about 85.2 ng/mL.

In a non-limiting embodiment, a method according to the present disclosure for administering a topical anesthetic solution comprising about 4%, by weight, cocaine hydrochloride to a subject comprises soaking a plurality of (e.g., four) absorbent articles with the solution, and contacting the absorbent articles with a nasal mucous membrane of the subject for at least about 20 minutes, wherein a urinary recovery of cocaine ranges from 38.9 µg to 289.5 µg over a period of 32 hours from the time of administration. In various non-limiting embodiments, the method of administering the topical anesthetic solution to a patient can result in a urinary recovery of cocaine ranging from 5 µg to 400 µg, or any value or range subsumed therein, such as for example, from 7 µg to 300 µg, from 7.1 µg to 269.9 µg, from 18.3 µg to 389.7 µg, from 20 µg to 375 µg, from 30 µg to 200 µg, or from 38.34 µg to 166.16 µg, over a period of 32 hours from the time of administration of the anesthetic solution to a subject.

In various non-limiting embodiments, the method of administering the topical anesthetic solution comprising cocaine hydrochloride to a subject can result in a renal clearance of cocaine from the subject ranging from 0.01 L/h to 5.0 L/h, or having any value or range subsumed therein, such as for example, from 0.85 L/h to about 4.81 L/h, from 0.05 L/h to 4.0 L/h, from 0.15 L/h to 3.43 L/h, from 0.20 L/h to 3.60 L/h, or from 0.61 L/h to 3.39 L/h over a period of 32 hours from the time of administration.

In various non-limiting embodiments, the method of administering the topical anesthetic solution comprising cocaine hydrochloride to a subject can result in a urinary recovery of ecgonine methyl ester from the subject ranging from 321.5 µg to 1868.5 µg over a period of 32 hours from the time of administration of the solution. In certain non-limiting embodiments, the method of administering the topical anesthetic to a subject can result in a urinary recovery of ecgonine methyl ester from the subject ranging from 200 µg to 2500 µg, or any value or range subsumed therein, such as, for example, from 367.1 µg to 2482.9 µg, from 524.4 µg to 1571.65 µg, from 300 µg to 2000 µg, from 275 µg to 1500 µg, from 250 µg to 1000, or from 321.5 µg to 1868.5 µg over a period of 32 hours from the time of administration of the anesthetic solution.

In various non-limiting embodiments, the method of administering the topical anesthetic solution comprising cocaine hydrochloride to a subject can result in a urinary recovery of benzoylecgonine from the patient ranging from 400 µg to 7000 µg, or having any value or within any range subsumed therein, such as, for example, from 469 µg to 5059 µg, from 500 µg to 4500 µg, from 936 µg to 6540 µg, or from 1000 µg to 4000 µg over a period of 32 hours from the time of administration of the solution.

In a non-limiting embodiment, a method according to the present disclosure for administering a topical solution including cocaine hydrochloride to a subject to reduce sensation in a body region of the subject comprises soaking a plurality of (e.g., four) absorbent articles with an aqueous solution including about 4%, by weight, cocaine hydrochloride, and contacting the absorbent articles with a nasal mucous membrane of the patient for at least about 20 minutes, wherein the method achieves an ecgonine methyl ester $C_{max}$ ranging from 1.8 ng/mL to 13.2 ng/mL in the subject. In various non-limiting embodiments, the method can result in an ecgonine ethyl ester $C_{max}$ ranging from 1 ng/mL and 25 ng/mL, or having any value or within any subrange subsumed therein, such as for example, from 3.7 ng/mL to 16.3 ng/mL, from 1.8 ng/mL to 13.2 ng/mL, from 3 ng/mL to 15 ng/mL, from 6 to 17.8 ng/mL, from 8 ng/mL to 20 ng/mL in the subject.

In various non-limiting embodiments of the method, the method can result in a benzoylecgonine $C_{max}$ ranging from 8.4 ng/mL to 103 ng/mL. In certain non-limiting embodiments, the method can achieve a benzoylecgonine $C_{max}$ ranging from 5 ng/mL to 225 ng/mL, or having any value or within any subrange subsumed therein, such as for example, from 21.3 ng/mL to 219.5 ng/mL, from 8.4 ng/mL to 103 ng/mL, from 10 ng/mL to 90.0 ng/mL, from 12.3 ng/mL to 102.7 ng/mL, or from 15 ng/mL to 90 ng/mL in the subject.

Administration of the anesthetic solution comprising cocaine hydrochloride described herein to the nasal mucous membranes in the manner described herein reduces sensation in that body region. Reduction in sensation produced by local analgesia can be assessed using the von Frey filament test and a visual numeric rating scale (VNRS) by which the subject self-reports pain intensity (0=no pain and 10=worst possible pain). A clinician can perform a von Frey filament test to assess the level of efficacy of sensation reduction upon administering the anesthetic solution. Generally, the clinician can choose one or both nostrils for pre-procedural testing based upon the scheduled procedure. Each subject can be asked to close his/her eyes to prevent any visual clues. In this test, a large von Frey filament (6.10; 100 g) is initially applied to the nasal ala, vestibule, nasal hairs, and anterior septum to help the subject discriminate between these structures. The nasal ala are gently retracted laterally with a blunt-ended, single-pronged retractor to provide easy access to the nasal septum during measurements. The filament is pushed, at an approximately perpendicular angle, against the anterior nasal septum until it bends, so that a standardized force is applied to the anterior nasal septum, and the subject is asked to rate the pain (and not pressure) experienced using the VNRS.

In addition to utilizing a von Frey filament/VNRS protocol to assess efficacy, observed levels of cocaine and its metabolites in the blood can be equated with efficacy of pain reduction. Thus, for example, following administration of the anesthetic solution described herein to nasal mucous membranes in the manner described herein, the clinician can observe serum concentration levels of cocaine, ecgonine methyl ester, and benzoylecgonine in the subject and thereby assess corresponding sensation reduction. Those levels may be used to determine whether, for example, a secondary administration of a local anesthetic composition is necessary.

In certain embodiments of methods according to the present disclosure, the method includes administering a second anesthetic to the patient if the observed $C_{max}$ of cocaine metabolite ecgonine methyl ester is less than 1.8 ng/mL after administration of a pharmaceutical composition as described herein in a manner as described herein. In certain non-limiting embodiments, the method can comprise administering a second anesthetic if the ecgonine methyl ester $C_{max}$ is less than 7 ng/mL, or is any value or falls within any range subsumed therein, such as for example, less than 6 ng/mL, less than 5 ng/mL, less than 4 ng/mL, less than 3.7 ng/mL, less than 2 ng/mL, less than 1 ng/mL, or less than 0.5 ng/mL. In certain embodiments, the second anesthetic solution can be or include, for example, lidocaine, lidocaine hydrochloride, bupivacaine, dibucaine, tetracaine, and salts thereof, or the like, or another topical anesthetic solution.

In a non-limiting embodiment according to the present disclosure, a method of administering a topical solution comprising cocaine hydrochloride to a subject to reduce sensation in a body region of the subject comprises soaking a plurality of (e.g., four) absorbent articles with a solution comprising cocaine hydrochloride. The solution can include a cocaine hydrochloride concentration of about 4%, by weight. The method can further include contacting the absorbent articles with a nasal mucous membrane of the subject for at least about 20 minutes, whereby the method achieves a benzoylecgonine $C_{max}$ in the subject ranging from 8.4 ng/mL to 103 ng/mL. In certain non-limiting embodiments, the method can further comprise administering a second anesthetic solution to the subject if the benzoylecgonine Cmax is less than 25 ng/mL.

In another non-limiting embodiment according to the present disclosure, a method of administering a local anesthetic to a subject undergoing a diagnostic or surgical procedure includes soaking one or more pledgets in about 4 mL of a ready-to-use composition including about 32.0 mg/mL to 39.2 mg/mL of cocaine free-base or an equivalent amount of pharmaceutically acceptable salt of cocaine, about 0.07% to about 0.20%, by weight, sodium benzoate, about 0.125%, by weight, citric acid, optionally, at least one coloring additive, and water. The method further includes contacting each pledget on a mucous membrane of the subject for up to 20 minutes, removing each pledget, and monitoring the subject for seizures during the administration. In various embodiments, the method can further include monitoring the subject's vital signs prior to contacting each pledget on the subject's mucous membrane, wherein the vital signs may include at least one of blood pressure, heart rate, respiratory rate, and temperature. In certain embodiments the monitoring of the subject's vital signs may occur continuously during the placement of contacting each pledget on the subject's mucous membrane. In one embodiment of the method, four pledgets may be used to contact the subject's mucous membrane, wherein each of the four pledgets can comprise a cottonoid pledget including an absorbency sufficient to absorb up to about 1 mL of the ready to use composition. In certain embodiments of the method, upon removal, the one or more pledgets can retain at least about 90% of the ready to use composition.

In a non-limiting embodiment according to the present disclosure, a further method of administering a local anesthetic on a subject undergoing a diagnostic or surgical procedure, may include soaking one or more pledgets in about 4 mL of a ready-to-use composition. The ready to use composition can include about 32.0 mg/mL to 39.2 mg/mL of cocaine free-base or an equivalent amount of pharmaceutically acceptable salt of cocaine, about 0.07% to about 0.20% sodium benzoate, about 0.125% citric acid, optionally, at least one coloring additive, and water. The method further includes contacting each pledget on a mucous membrane of the subject for up to 20 minutes, removing each pledget, and monitoring the subject's benzoylecgonine $C_{max}$ for up to 30 minutes, 40 minutes, or 50 minutes. In various embodiments of the method, four cottonoid pledgets may be used to absorb up to about 1 mL of the ready to use composition.

In a non-limiting embodiment according to the present disclosure, a further method of administering a local anesthetic on a subject not concurrently receiving any other vasoconstrictor agent, can include soaking one or more pledgets in about 4 mL of a ready-to-use composition. The ready to use composition can include about 32.0 mg/mL to 39.2 mg/mL of cocaine free-base or an equivalent amount of pharmaceutically acceptable salt of cocaine, about 0.07% to about 0.20% sodium benzoate, about 0.125% citric acid, optionally, at least one coloring additive, and water. The method further includes contacting each pledget on a mucous membrane of the subject for up to 20 minutes, and removing each pledget. In certain non-limiting embodiments, once removed from the subject's mucous membrane, the pledgets may retain at least about 90% of the ready to use composition.

In a non-limiting embodiment according to the present disclosure, a method of administering a local anesthetic to a subject can include soaking one or more pledgets in about 4 mL of a composition comprising about 3.8% to about 4.2% cocaine hydrochloride, by weight, and contacting each of the one or more pledgets on a mucous membrane of a subject for about 20 minutes. The pledgets are subsequently removed from the mucous membrane, while monitoring the subject's heart rate. The subject's heart rate is monitored for changes from the subject's baseline heart rate for about 30 minutes, about 40 minutes, about 50 minutes, about 60 minutes, about 75 minutes, about 80 minutes, or about 90 minutes following the removal of the pledgets. A change in the subject's baseline heart rate after about 60 minutes following administration of the local anesthetic composition can range from about 2 beats per minute to about 10 beats per minute, about 3 beats per minute to about 9 beats per minute, or about 4 beats per minute to about 8 beats per minute. Following removal of the pledgets, an electrocardiogram (ECG) of the subject can be monitored for about 75 minutes to observe any change in the subject's baseline QTcF. After about 60 minutes following administration of the local anesthetic composition a change in the subject's baseline QTcF can range from about 0.5 ms to about 3 ms, about 0.75 ms to about 5 ms, about 1 ms to about 5 ms, about 1.5 ms to about 6 ms, or about 2 ms to about 7 ms. In certain embodiments, the method of administering a local anesthetic to a subject, can include soaking the pledgets in a composition comprising about 3.6% to about 4.4%, about 3.8% to about 4.2%, or about 3.9% to about 4.1% cocaine hydrochloride, by weight.

In another non-limiting embodiment, a method of effectively anesthetizing a body region of a patient including immersing at least one absorbent article in an aqueous pharmaceutical composition, the aqueous pharmaceutical composition including, by weight, about 32.0 mg/mL to 39.2 mg/mL of cocaine free-base or an equivalent amount of pharmaceutically acceptable salt of cocaine, and about 0.07% to about 0.20% sodium benzoate, wherein the aqueous pharmaceutical composition has a pH between 2 and 4. The method further includes contacting the at least one absorbent article and the aqueous pharmaceutical composition absorbed therein with a mucous membrane of the patient for a time period such that the total dose to the patient does not exceed 3 mg/kg of body weight, and thereby obtaining a visual numeric rating score of 0 in the body region proximate to the mucous membrane upon von Frey filament testing. In certain embodiments, the at least one absorbent article comprises at least one cottonoid pledget. In certain embodiments, the method can result in a total dose of cocaine free-base composition to the patient that does not exceed 5 mg/kg of body weight, 4 mg/kg of body weight, 3 mg/kg of body weight, 2 mg/kg of body weight, or 1 mg/kg of body weight of the patient.

In various embodiments, the pharmaceutical compositions comprising cocaine hydrochloride that are described herein can include coloring additives (colorants) to provide the solution with a specific desired color. Those having ordinary skill will be able to readily identify and procure suitable coloring additives for the compositions herein.

According to aspects of the present disclosure, local anesthesia can be achieved prior to performing diagnostic, surgical, or post-operative procedures on or through a mucous membrane of the nasal cavities of a subject by soaking one or more cottonoid pledgets or other absorbent articles with about 1 mL of an anesthetic aqueous solution per article, wherein the solution includes, by weight, about 4% cocaine hydrochloride, about 0.1% sodium benzoate, about 0.125% citric acid, and optionally a coloring additive. The method also includes contacting the soaked absorbent articles with a nasal mucous membrane of the patient for at least about 20 minutes. The diagnostic, surgical, or post-operative procedure can then be conducted.

The present disclosure also encompasses a method for effectively anesthetizing a body region of a subject comprising immersing at least one absorbent article in an aqueous pharmaceutical composition including about 3.6% to about 4.4% cocaine hydrochloride, about 0.07% to about 0.20% sodium benzoate, and about 0.125% citric acid, wherein the aqueous pharmaceutical composition of the method has a pH between 2 and 4. The at least one absorbent article and the aqueous pharmaceutical composition absorbed therein is contacted with a mucous membrane of the patient for a time period so as to reduce sensation and achieve a visual numeric rating score of 0 in the body region proximate to the mucous membrane upon filament testing.

In certain non-limiting embodiments of the method, the absorbent article that is contacted with the aqueous pharmaceutical composition is a cottonoid pledget with absorbency sufficient to absorb at least about 1 mL of the aqueous pharmaceutical composition. In certain non-limiting embodiments, the cottonoid pledget retains up to 90% of the solution when removed from contact with the patient.

The pharmaceutical composition described herein may be used as a topical anesthetic to anesthetize a body region of hepatically impaired and renally impaired subjects. For example, a method according to the present disclosure for effectively anesthetizing a body region of a hepatically or renally impaired subject includes immersing an absorbent article in an aqueous pharmaceutical composition comprising about 3.6% to about 4.4% cocaine hydrochloride, about 0.07% to about 0.20% sodium benzoate, and about 0.125% citric acid, wherein the aqueous pharmaceutical composition has a pH between 2 and 4. The absorbent article and the aqueous pharmaceutical composition absorbed therein are contacted with a mucous membrane of the subject for a time period sufficient to anesthetize the body region. For example, the time period may be sufficient to achieve a visual numeric rating score of 0 in the body region proximate to the mucous membrane upon filament testing. With regard to hepatically impaired patients, the step of contacting an absorbent article containing the aqueous pharmaceutical composition with the mucous membrane is not repeated within 24 hours from the time of initial administration.

By monitoring the levels of the pharmacokinetic parameters, the methods and pharmaceutical compositions described herein can be applied to achieve successful analgesia (indicating a VNRS score of 0=no pain) before a medical procedure is initiated.

For example, in renally impaired subjects, pharmacokinetic parameters confirmed that successful analgesia (indicating a VNRS score of 0=no pain) can be achieved in patients using the methods and compositions herein, and without harming those subjects. For example, the following pharmacokinetic values were observed in renally impaired patients administered pharmaceutical compositions as described by methods described herein involving contacting soaked absorbent articles with nasal mucous membranes of the subjects, and without harm to the subjects: cocaine $C_{max}$ ranging from 21.9 ng/mL to 93.7 ng/mL; $T_{max}$ value for cocaine ranging from 0.301 h to 0.595 h; $AUC_{inf}$ for cocaine ranging from 61.2 ng*h/mL to 179.6 ng*h/mL; apparent clearance of cocaine ranging from 645 L/h to 2389 L/h; absorptivity factor for cocaine ranging from 0.358 h$^{-1}$ to 0.522 h$^{-1}$; urinary recovery of cocaine ranging from 7.1 µg to 269.9 µg, and renal clearance for cocaine ranging from 0.528 L/h to 1.912 L/h over a period of 32 hours from the time of the administration. In certain embodiments of methods herein, one may compare the measured value for one or more of these parameters with these ranges to assess efficacy of anesthetization. Also, where one or more of the pharmacokinetic parameters falls outside of the known parameter range for sufficient and safe anesthetization of the region (successful analgesia), such as for example, where a $C_{max}$ of ecgonine methyl ester in the patient falls below 6 ng/mL and/or if the $C_{max}$ of benzoylecgonine in the patient falls below 21.3 ng/mL, the method can further include administering a second anesthetic composition to the subject.

Similarly, in hepatically impaired subjects, pharmacokinetic parameters confirmed that successful analgesia (indicating a VNRS score of 0=no pain) can be achieved in patients using the methods and compositions herein, and without harming those subjects. For example, the following pharmacokinetic values were observed in hepatically impaired patients administered pharmaceutical compositions as described by methods described herein involving contacting soaked absorbent articles with nasal mucous membranes of the subjects, and without harm to the subjects: cocaine $C_{max}$ ranging from 16.2 ng/mL to 85.2 ng/mL; $T_{max}$ value for cocaine ranging from 0.306 h to 1.874 h; $AUC_{inf}$ for cocaine ranging from 88 ng*h/mL to 366 ng*h/mL; apparent clearance of cocaine ranging from 390 L/h to 1344 L/h; absorptivity factor for cocaine ranging from 0.184 h$^{-1}$ to 0.233 h$^{-1}$; and renal clearance for cocaine that ranges from 0.076 L/h to 1.918 L/h over a period of 32 hours from the time of the administration. In certain embodiments of methods herein, one may compare the measured value for one or more of these parameters with these ranges to assess efficacy of anesthetization. Also, where one or more of the pharmacokinetic parameters falls outside of the known parameter range for sufficient and safe anesthetization of the region (successful analgesia), the method can further include administering a second anesthetic composition to the subject.

The examples that follow are intended to further describe certain non-limiting embodiments, without restricting the scope of the present invention. Persons having ordinary skill in the art will appreciate that variations of the following examples are possible within the scope of the invention, which is defined solely by the claims.

Example 1

Single-dose plasma and urinary pharmacokinetics of the pharmaceutical composition following intranasal administration was characterized in this study. This was a single-dose study in 30 healthy volunteers. The objective of the study was to examine the systemic pharmacokinetics of the pharmaceutical composition following acute, topical intranasal administration.

Materials and Methods

A single dose of a pharmaceutical composition was administered to both nostrils using cottonoid pledgets. The composition was an aqueous solution including 40 mg/mL cocaine hydrochloride, 1.25 mg/mL citric acid, 1.00 mg/mL sodium benzoate, a colorant (0.02 mg/mL D&C Yellow No. 10, 0.02 mg/mL FD&C Green No. 3), and 957.7 mg/mL water. Four mL of the pharmaceutical composition was poured into a standard medicine cup and four cottonoid pledgets (approximately 1.3 cm×4 cm) were added to this solution and allowed to soak for 10 minutes. Each pledget absorbed approximately 1 mL of pharmaceutical composition (i.e., 40 mg cocaine hydrochloride). Two soaked pledgets were placed into each nasal cavity of the subject and against the anterior septum for 20 minutes; thus, a total dose of 160 mg of cocaine hydrochloride was administered.

Blood samples were collected pre-dose (30 minutes before pledget insertion), and 7.5, 15, 20, 30, 45, 60, 75, 90, and 105 minutes and 2, 3, 4, 6, 8, 10, and 12 hours from the start of application of the pharmaceutical composition. Plasma concentrations of cocaine, BE, and EME were determined using a validated liquid chromatography-tandem mass spectrometry (LC-MS/MS) method with a lower limit of quantification (LLOQ) of 5 ng/mL for cocaine, 100 ng/mL for BE, and 50 ng/mL for EME. A 25-µL aliquot of each stabilized plasma sample was processed by liquid-liquid extraction. The compounds were detected and quantified by LC-MS/MS in positive ion mode on an MDS Sciex API 4000 equipped with a TURBOIONSPRAY® interface. Calibration curves were obtained by performing a linear regression (weighted 1/x$^2$) on the calibration standards.

Plasma pharmacokinetic parameters were analyzed using noncompartmental methods. The effect of gender on $C_{max}$, $T_{max}$, $AUC_{last}$, $AUC_{inf}$, and $t_{1/2}$ was determined. The effects of age, body weight, and BMI on $AUC_{last}$ were determined.

Urine samples were collected pre-dose and at the following intervals from the start of intranasal application of the pharmaceutical composition: 0-2 hours, 2-4 hours, 4-8 hours, and 8-12 hours. Urine concentrations of cocaine, BE, and EME were determined using a validated LC-MS/MS method with an LLOQ of 5 ng/mL for cocaine, 100 ng/mL for BE, and 50 ng/mL for EME. A 25-µL aliquot of each urine sample was processed by liquid-liquid extraction. The compounds were detected and quantified by LC-MS/MS in positive ion mode on an MDS Sciex API 4000 equipped with a TURBOIONSPRAY® interface. Calibration curves were obtained by performing a linear regression (weighted 1/x$^2$) on the calibration standards.

Urinary pharmacokinetic parameters were analyzed using noncompartmental methods. Urinary pharmacokinetic parameters included total urinary recovery (µg), urinary recovery as a percentage of dose, and renal clearance (CLr; cocaine only).

Results

A total of 30 subjects (14 males and 16 females) with a mean age of 46.1 years (range, 22 to 78 years) and mean BMI of 25.5 kg/m$^2$ (range, 19.6 kg/m$^2$ to 31.6 kg/m$^2$) were enrolled; most subjects (96.7%) were white.

Figure 2:
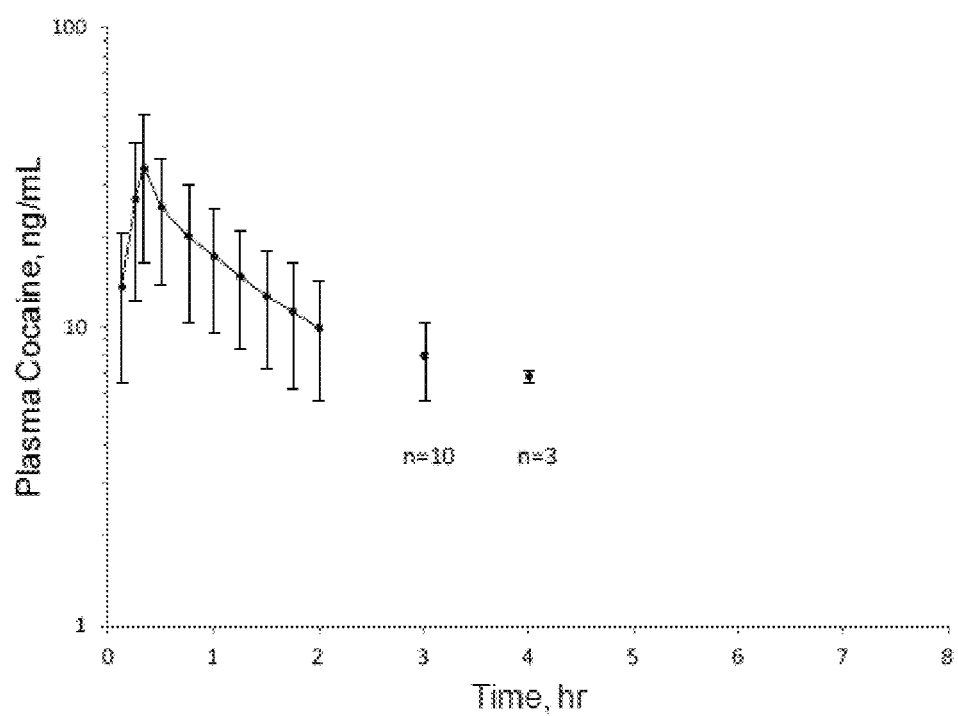
FIG. 2 is a plot of plasma concentration of cocaine as a function of time following administration of an intranasal dose of a pharmaceutical composition including cocaine hydrochloride in a concentration of 40 mg/mL.

Cocaine was rapidly absorbed during the pharmaceutical composition exposure period. $C_{max}$ ranged from 7.93 ng/mL to 70.3 ng/mL with mean $C_{max}$ (37.0±17.3 ng/mL) observed shortly after the time of pledget removal ($T_{max}$ of 0.43±0.34 hours) (see FIG. 2 and Table 2 below). Plasma concentrations then fell rapidly, with a mean $t_{1/2}$ of 1.04±0.35 h. Cocaine concentrations fell below the LLOQ (5 ng/mL) between 1.5 h and 4 h after dosing.

TABLE 2

Cocaine plasma pharmacokinetic parameters after an intranasal dose of pharmaceutical composition.

| Parameter | Units | n | Mean | SD | CV | Geo-metric Mean | Geo-metric SD |
|---|---|---|---|---|---|---|---|
| $C_{max}$ | ng/mL | 30 | 37.0 | 17.3 | 46.7 | 32.8 | 1.69 |
| $T_{max}$ | h | 30 | 0.433 | 0.341 | 78.6 | 0.374 | 1.59 |

TABLE 2-continued

Cocaine plasma pharmacokinetic parameters after an intranasal dose of pharmaceutical composition.

| Parameter | Units | n | Mean | SD | CV | Geometric Mean | Geometric SD |
|---|---|---|---|---|---|---|---|
| $C_{last}$ | ng/mL | 30 | 7.18 | 1.40 | 19.5 | 7.05 | 1.21 |
| $T_{last}$ | h | 30 | 2.40 | 0.709 | 29.5 | 2.31 | 1.31 |
| $AUC_{last}$ | ng h/mL | 30 | 38.4 | 20.2 | 52.5 | 34.2 | 1.61 |
| $AUC_{inf}$ | ng h/mL | 19 | 54.9 | 24.1 | 43.8 | 50.3 | 1.54 |
| $t_{1/2}$ | h | 25 | 1.04 | 0.349 | 33.7 | 0.975 | 1.44 |
| MRT | h | 19 | 1.56 | 0.45 | 28.9 | 1.50 | 1.34 |
| CL/F | L/h | 19 | 3096 | 1276 | 41.2 | 2843 | 1.54 |
| CL/F | mL/min | 19 | 51601 | 21264 | 41.2 | 47375 | 1.54 |
| Vd/F | L | 19 | 3877 | 1266 | 32.6 | 3680 | 1.40 |
| % EXTRAP | % | 19 | 18.7 | 5.90 | 31.6 | 17.7 | 1.41 |

% EXTRAP = area under the concentration-time curve extrapolated after the time of last observed quantifiable concentration; $AUC_{inf}$ = area under the concentration-time curve from time 0 to infinity; $AUC_{last}$ = area under the concentration-time curve from time 0 to the time of the last measurable concentration; $C_{last}$ = last observed quantifiable concentration; CL/F = apparent clearance; $C_{max}$ = maximum concentration; CV = coefficient of variation; MRT = mean residence time; SD = standard deviation; $t_{1/2}$ = half-life; $T_{last}$ = time of last observed quantifiable concentration; $T_{max}$ = time of maximum concentration; Vd/F = apparent volume of distribution Apparent clearance (CL/F) was 3,096 L/hr. A comparison of CL/UF to the systemic clearance (CL) of intravenous cocaine (32 mL/min/kg or approximately 134 L/h) suggests a rough estimate that only 4% of the 160 mg dose of the pharmaceutical composition was absorbed intact during the 20-minute exposure period.

Figure 3:
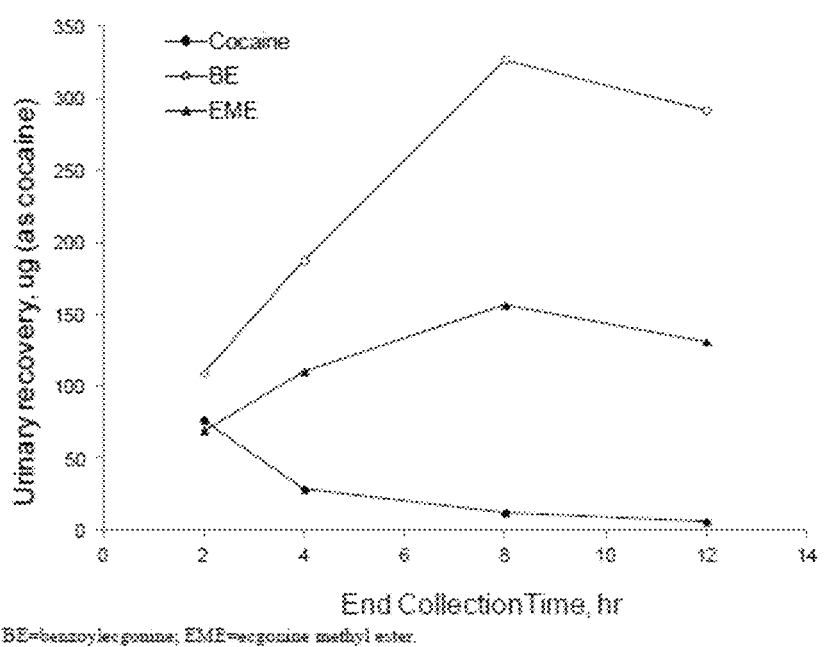
FIG. 3 is a plot of urinary recovery of cocaine, benzoylecgonine (BE), and ecgonine methylester (EME) as a function of time following administration of an intranasal dose of a pharmaceutical composition including cocaine hydrochloride in a concentration of 40 mg/mL.

Urine pharmacokinetic parameters for cocaine are summarized in Table 3 below. Cocaine was recovered in urine with a time course similar to that in plasma (FIG. 3). The majority of excreted cocaine was recovered in the 0-2 h collection interval. Although not detectable in plasma, BE and EME were recovered in urine during the 0-12 h collection period. Urinary excretion of BE and EME increased over time, with the highest amounts of both metabolites recovered in the 4-8 h collection interval. Urinary recovery of the metabolites continued at 8-12 h, suggesting that additional amounts of BE and EME were excreted at time points beyond the last collection. Although neither metabolite was detectable in the plasma, these data suggest that both BE and EME were present in the plasma for an extended (>12 h) time after dosing, but at levels that did not exceed 100 ng/mL and 50 ng/mL, respectively.

TABLE 3

Urine pharmacokinetic parameters after an intranasal dose of the pharmaceutical composition.

Total Urinary Recovery, µg[a]

| | Cocaine | BE | EME |
|---|---|---|---|
| n | 30 | 30 | 30 |
| Mean | 117 | 816 | 275 |
| SD | 67.1 | 440 | 113 |
| Median | 114 | 769 | 276 |
| Geometric mean | 96.5 | 713 | 252 |

Urinary Recovery, % dose[a]

| | Cocaine | BE | EME | Total |
|---|---|---|---|---|
| n | 30 | 30 | 30 | 30 |
| Mean | 0.0729 | 0.534 | 0.262 | 0.869 |
| SD | 0.0419 | 0.288 | 0.108 | 0.362 |
| Median | 0.0714 | 0.504 | 0.263 | 0.804 |
| Geometric mean | 0.0603 | 0.467 | 0.240 | 0.801 |

Renal Clearance of Cocaine

| | L/h | mL/min |
|---|---|---|
| n | 25 | 25 |
| Mean | 2.83 | 47.2 |
| SD | 1.98 | 33.0 |
| Median | 2.56 | 42.7 |
| Geometric mean | 2.23 | 37.2 |

[a]Metabolite recovery is expressed as cocaine equivalents
BE—benzoylecgonine;
EME—ecgonine methyl ester;
SD—standard deviation.

Effect of Intrinsic Factors on Pharmacokinetics

The effect of intrinsic factors (i.e., age, gender, body weight, and BMI) on the pharmacokinetic parameters of cocaine following topical nasal administration of the pharmaceutical composition was examined in Example 1.

Subject Gender

Figure 4:
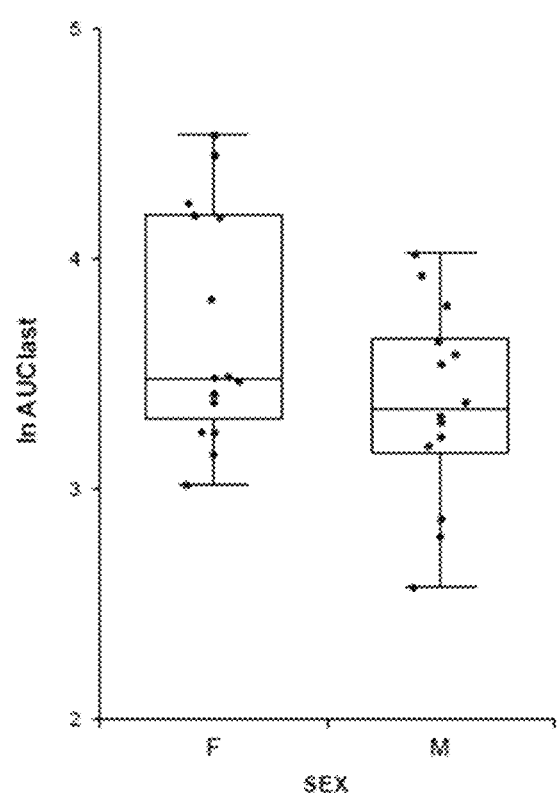
FIG. 4 is box and dot plot of the natural log of cocaine $AUC_{last}$ by subject gender following administration of an intranasal dose of a pharmaceutical composition including cocaine hydrochloride in a concentration of 40 mg/mL.

Cocaine exposure (i.e., $C_{max}$, $AUC_{last}$, and $AUC_{inf}$) was slightly higher in females than males whereas $T_{max}$ and $t_{1/2}$ were similar in males and females (Table 4). A higher range of cocaine exposure (i.e., $AUC_{last}$) was seen in females compared to males (FIG. 4).

TABLE 4

Cocaine pharmacokinetic parameters by gender in Example 1.

| | $C_{max}$ (ng/mL) | | $T_{max}$ (h) | | $AUC_{last}$ (ng h/mL) | | $AUC_{inf}$ (ng h/mL) | | $t_{1/2}$ (h) | |
|---|---|---|---|---|---|---|---|---|---|---|
| | Male | Female | Male | Female | Male | Female | Male | Female | Male | Female |
| n | 14 | 16 | 14 | 16 | 14 | 16 | 8 | 11 | 12 | 13 |
| Mean | 34.6 | 39.0 | 0.417 | 0.448 | 31.5 | 44.4 | 47.2 | 60.6 | 1.06 | 1.01 |
| SD | 17.6 | 17.2 | 0.322 | 0.366 | 12.7 | 23.7 | 13.1 | 29.0 | 0.346 | 0.365 |
| CV | 50.9 | 44.1 | 77.3 | 81.8 | 40.4 | 53.5 | 27.7 | 47.9 | 32.6 | 36.1 |
| Median | 31.6 | 37.0 | 0.333 | 0.333 | 28.5 | 32.4 | 46.2 | 57.6 | 0.966 | 1.01 |
| Geometric mean | 30.0 | 35.5 | 0.362 | 0.385 | 29.1 | 39.4 | 45.7 | 53.9 | 1.01 | 0.941 |

$AUC_{inf}$: area under the concentration-time curve from time 0 to infinity; $AUC_{last}$: area under the concentration-time curve from time 0 to the time of the last measurable concentration; $C_{max}$: maximum concentration; CV: coefficient of variation; SD: standard deviation; $t_{1/2}$: half-life; $T_{max}$: time of maximum concentration.

Figure 5:
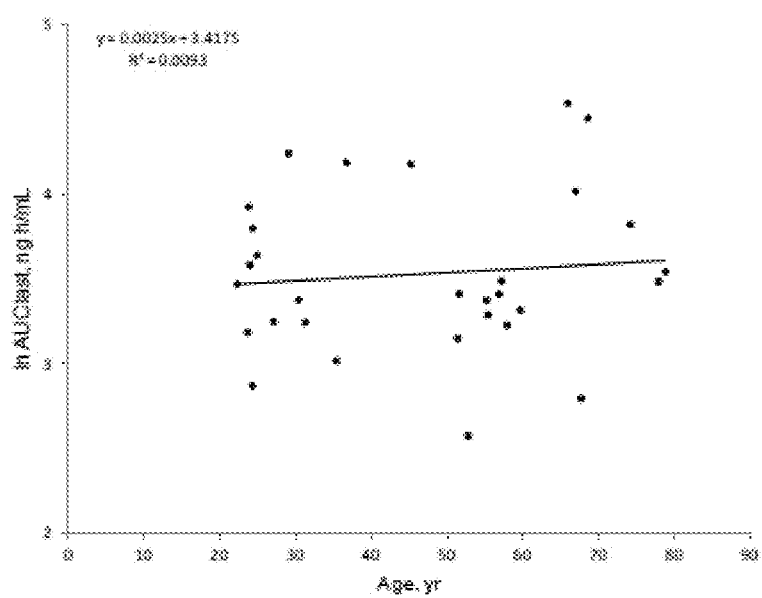
FIG. 5 is a plot of the natural log of cocaine $AUC_{last}$ as a function of subject age following administration of an intranasal dose of a pharmaceutical composition including cocaine hydrochloride in a concentration of 40 mg/mL.

Subject Age $AUC_{last}$ for cocaine was similar across the subject age range (22 years to 79 years) in Example 1 (see FIG. 5).

Subject Body Weight

Figure 6:
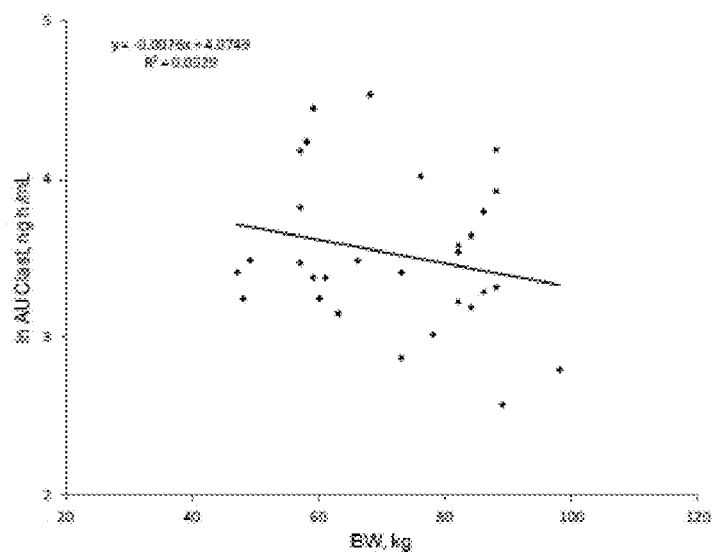
FIG. 6 is a plot of the natural log of cocaine $AUC_{last}$ as a function of subject body weight following administration of an intranasal dose of a pharmaceutical composition including cocaine hydrochloride in a concentration of 40 mg/mL.

There was a downward trend in $AUC_{last}$ for cocaine with increasing body weight, the correlation ($R^2$=0.0529) was not strong in Example 1 (see FIG. 6).

Subject BMI

Figure 7:
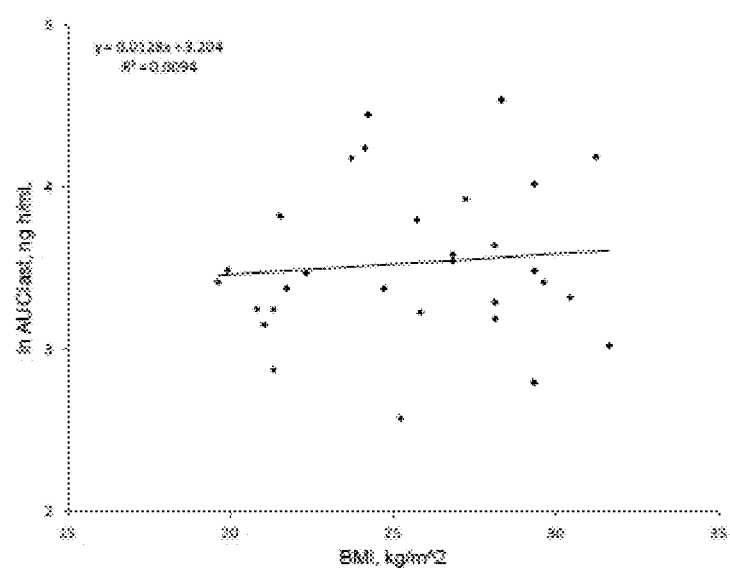
FIG. 7 is a plot of the natural log of cocaine $AUC_{last}$ as a function of subject body mass index (BMI) following administration of an intranasal dose of a pharmaceutical composition including cocaine hydrochloride in a concentration of 40 mg/mL.

There was no evidence for a change in $AUC_{last}$ for cocaine with BMI (see FIG. 7).

Example 2

The primary objective of Example 2 was to evaluate the potential effect of renal impairment on the systemic pharmacokinetic parameters of acute intranasal treatment with the pharmaceutical composition. The secondary objective was to evaluate the safety and tolerability of acute intranasal treatment with the pharmaceutical composition in subjects with normal renal function and severe renal impairment.

One way to determine renal impairment is to determine an estimated Glomerular Filtration Rate (eGFR) for a subject. The eGFR is mathematically derived from a subject's serum creatinine level, age, sex, and race. A subject with an eGFR less than 60 ml/min/1.73 $m^2$, measured in two tests conducted at least 90 days apart, has mild chronic kidney disease. Subjects with an eGFR of 45-59 ml/min/1.73 $m^2$ have a mild to moderate loss of kidney function. Subjects with an eGFR of 30-44 mL/min/1.73 $m^2$ have moderate to severe loss of kidney function. Subjects with an eGFR of 15-29 ml/min/1.73 $m^2$ have severe loss of kidney function. Subjects with an eGFR of under 15 ml/min/1.73 $m^2$ have kidney failure.

Materials and Methods

Male and female subjects≥18 years of age with either severe renal impairment (n=8), defined as an estimated glomerular filtration rate (eGFR) of 15-29 mL/min/1.73 $m^2$ or normal renal function (n=8), defined as an eGFR of ≥60 mL/min/1.73 $m^2$, and without a known allergy to ester-based anesthetics were enrolled in the study. Subjects were administered a pharmaceutical composition in the form of an aqueous solution comprising: 40 mg/mL cocaine hydrochloride, 1.25 mg/mL citric acid, 1.00 mg/mL sodium benzoate, a colorant (0.02 mg/mL D&C Yellow No. 10, 0.02 mg/mL FD&C Green No. 3), and 957.7 mg/mL water. The subjects were dosed with the pharmaceutical composition as follows: 4 mL of the pharmaceutical composition were poured into a standard medicine cup. Four (4) cottonoid pledgets (approximately 1.3 cm×4 cm) were placed in the 4 mL of the pharmaceutical composition for 10 minutes and allowed to soak. Each pledget absorbed approximately 1 mL of solution. The drug-soaked pledgets were placed into the nasal cavity (2 per side) and up against the septum at time 0 and removed after 20 minutes.

Pharmacokinetic parameter blood samples were drawn at 0 hour (pre-dose), and post dose at: 7, 15, 20 (immediately after pledget removal), 30, 45, 60, 75, 90, and 105 min, and 2, 3, 4, 6, 8, 10, 12, 24, 28 and 32 h, based upon the beginning of dose application. Plasma was separated and stabilizer was added to prevent continued ester hydrolysis of cocaine in the samples. Total concentrations of cocaine and its major metabolites, BE and EME, and the active metabolite, norcocaine, were determined in all plasma samples using a validated LC-MS/MS method with an LLOQ of 0.1 ng/mL for cocaine and norcocaine, and 1.0 ng/mL for BE and EME. A 50-μL aliquot of each stabilized plasma sample was processed by liquid-liquid extraction. The compounds were detected and quantified by LC-MS/MS in positive ion mode on an MDS Sciex API 4000 equipped with a TURBOIONSPRAY® interface. Calibration curves were obtained by performing a linear regression (weighted $1/x^2$) on the calibration standards. Plasma pharmacokinetic parameters were analyzed using noncompartmental methods. Plasma pharmacokinetic parameters included $AUC_{last}$, $AUC_{inf}$, $C_{max}$, $T_{max}$, $C_{last}$, $T_{last}$, $t_{1/2}$, CL/F (cocaine only), and % EXTRAP.

Plasma samples were analyzed for cocaine (LOQ, 0.1 ng/mL), benzoylecgonine (BE, LOQ, 1.0 ng/mL), ecgonine methyl ester (EME, LOQ, 1.0 ng/mL) and norcocaine (LOQ, 0.1 ng/mL) using the inVentiv Health Clinical Lab, Inc. Method™ 1668. Urine samples were analyzed for cocaine (LOQ, 0.1 ng/mL), benzoylecgonine (BE, LOQ, 1.0 ng/mL), and ecgonine methyl ester (EME, LOQ, 1.0 ng/mL).

Plasma and urine pharmacokinetic parameters for cocaine, BE, and EME were derived using non-compartmental methods. The specified PK parameters were not determined for norcocaine because plasma concentrations were below quantitation (<0.1 ng/mL) at all time points in most subjects. For the plasma analysis, $C_{max}$, $T_{max}$, $C_{last}$, and $T_{last}$ were determined by inspection. Concentrations reported as BQ (below quantitation) were assigned a value of zero if they were prior to $T_{max}$, and were otherwise ignored. The area under the plasma concentration-time curve from time zero to $T_{last}$ ($AUC_{last}$) was determined by trapezoidal integration. The AUC was extrapolated to infinity as: $AUC_{inf} = AUC_{last} + (C_{last}/k)$, where k, the elimination rate constant, was determined from the terminal log-linear concentration data using at least 3 time points. The half-life was calculated as $t_{1/2}$=ln 2/k. The CL/F for cocaine was determined as Dose/$AUC_{inf}$. Values of $AUC_{inf}$ for which the extrapolated portion of the AUC (% Extrap) was >30% were not used in the clearance calculations or summarized.

For the urine analysis of cocaine, BE, and EME, individual urinary recoveries for each analyte were determined over each collection interval as the product of the urine concentration times the urine volume. The total recoveries were determined as the sum of the recoveries over all the intervals. Total urinary recoveries were also expressed as the percentage of the administered dose, after correction for the molecular weight of each analyte. The renal clearances of cocaine, BE, and EME were determined as the urinary recovery (in μg) divided by the plasma AUC over the same time interval (the longest period for which both plasma and urine measurements were available).

Urine was collected prior to dosing and from 0-2, 2-4, 4-8, 8-12, 12-24, and 24-32 hours after the beginning of dose application. Urine concentrations of cocaine, BE, and EME were determined using a LC-MS/MS method with an LLOQ of 0.1 ng/mL for cocaine and 1.0 ng/mL for BE and EME. Testing methods used were consistent with those used by inVentiv Health Clinical Lab, Inc., Miami, Fla., U.S.A. Urinary pharmacokinetic parameters included total urinary recovery (μg), urinary recovery as a percentage of dose, and CLr.

Safety assessments, including monitoring adverse events (AEs), vital sign measurements, and laboratory tests were performed. A nasal exam was visually conducted pre-dose and at the end of the procedure to determine if irritation was present at the prospective application site.

A total of 8 subjects with normal renal function and 8 subjects with severe renal impairment were enrolled, and received the protocol-specified treatment with the pharmaceutical composition. All 16 subjects provided pharmacokinetic data. Pharmacokinetic parameters were compared between groups using analysis of variance (ANOVA) with renal status as a fixed effect. Geometric mean ratios with 90% confidence intervals (CI) were calculated to compare $C_{max}$, $AUC_{last}$, CLr, and CL/F for cocaine, and $C_{max}$, $AUC_{last}$, and CLr for each metabolite between subjects with normal renal function and for subjects with severe renal impairment.

Results

Demographic and baseline characteristics were similar in the normal renal function and severe renal impairment groups, except for eGFR. All of the subjects in the study were healthy adult male (75.0%) and female (25.0%) volunteers. The subjects ranged in age from 41 to 75 years (mean ages were 57.6 and 62.5 years in the normal renal function and severe renal impairment groups, respectively) and were black or white (87.5% and 12.5%, respectively). Mean eGFR was 85.25 mL/min/1.73 m² for the normal renal function group and 23.85 mL/min/1.73 m² for the severe renal impairment group. Mean body weight was 94.65 kg for the normal renal function group and 99.5 kg for the severe renal impairment group.

The pharmaceutical composition was safe and well tolerated in both subjects with normal renal function and subjects with severe renal impairment.

In subjects with normal renal function, cocaine appeared rapidly in the plasma following intranasal application of the pharmaceutical composition, with measurable levels in all subjects at the first time exponential manner after $T_{max}$ throughout the remainder of the 32-hour study.

Figure 8:
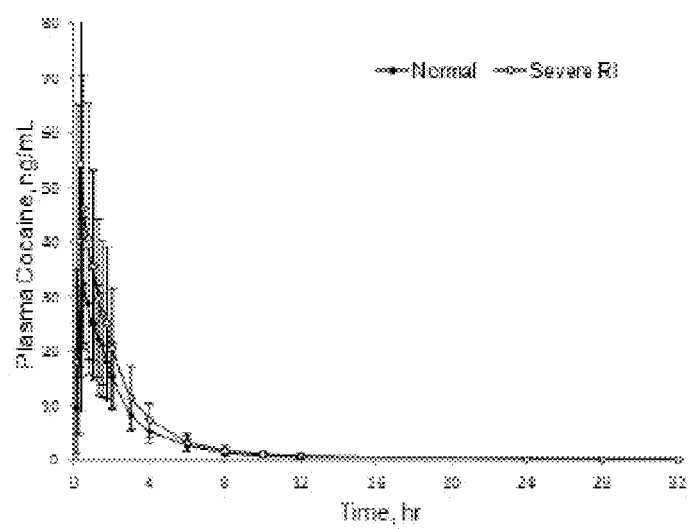
FIG. 8 is a linear plot of mean plasma cocaine concentration (including standard deviations) as a function of time following administration of an intranasal dose of a pharmaceutical composition including cocaine hydrochloride in a concentration of 40 mg/mL to subjects with normal renal function and subjects with severe renal impairment.
Figure 9:
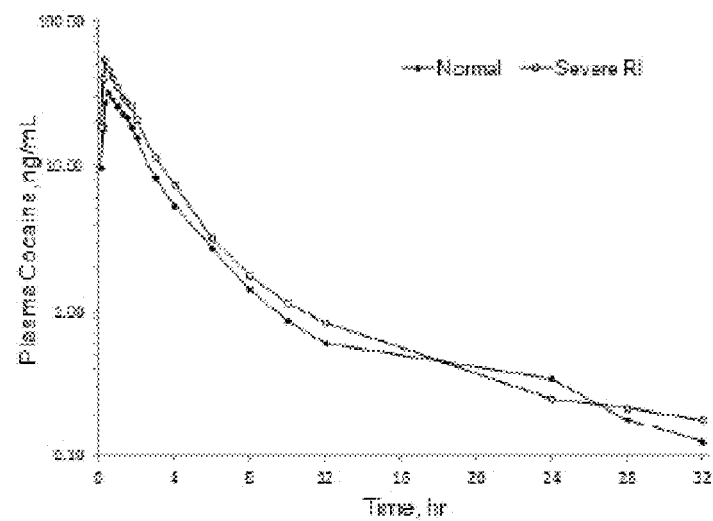
FIG. 9 is a logarithmic plot of plasma cocaine concentration as a function of time following administration of an intranasal dose of a pharmaceutical composition including cocaine hydrochloride in a concentration of 40 mg/mL to subjects with normal renal function and subjects with severe renal impairment.

Following administration of the same pharmaceutical composition dose to subjects with severe renal impairment, a similar time course was observed, with rapid absorption followed by an apparently bi-exponential decline after $T_{max}$. Plasma exposures in the severe renal impairment group were about 33% to 34% higher than those in normal subjects (see FIGS. 8 and 9).

In normal subjects, plasma concentrations of the metabolites, BE and EME, rose rapidly over the first few hours post-dose, then declined slowly over the remainder of the 32-hour sampling interval. Following administration of the same pharmaceutical composition dose to subjects with severe renal impairment, a similar pattern of rising BE and EME concentrations was observed during the first few hours after dosing. However, peak concentrations were generally at least 2-fold higher than those in normal subjects, and concentrations declined more slowly in subjects with severe renal impairment. Plasma concentrations of the active metabolite, norcocaine, were below the LLOQ (0.1 ng/mL) in all samples in all individuals, except for four samples in one subject in the renal impairment group, in which concentrations were barely above the LLOQ (0.101 to 0.115 ng/mL).

In subjects with normal renal function, cocaine appeared rapidly in the plasma following intranasal application of the pharmaceutical composition, with measurable levels in all subjects at the first time point, 7 minutes after the start of treatment. Plasma concentrations rose to reach a geometric mean $C_{max}$ of 35.9 ng/mL at a median $T_{max}$ of 30 minutes (10 minutes after pledget removal), and then declined in an apparently bi-exponential manner over the remainder of the 32-hour study. The apparent half-life of the terminal phase was 4.12 h, the $AUC_{inf}$ was 80.5 ng*h/mL, and the apparent clearance (CL/F) was 1774 L/h (geometric means). Following administration of the same pharmaceutical composition dose to subjects with severe renal impairment, a similar time course was observed, with rapid absorption followed by an apparently bi-exponential decline after $T_{max}$. Plasma exposures in the severe renal impairment group were about 33% higher than those in normal subjects, with geometric mean $C_{max}$ of 47.9 ng/mL and $AUC_{inf}$ of 107.2 ng*h/mL. This was accompanied by a corresponding increase in the geometric mean half-life from 4.12 h in normal subjects to 5.42 h in severe renal impairment.

Cocaine plasma pharmacokinetic parameters in subjects with normal renal function and those with severe renal impairment are summarized below in Tables 5 and 6. The results of ANOVA (analysis of variance) of the pharmacokinetic parameters are presented in Table 7.

TABLE 5

Summary of cocaine pharmacokinetic parameters in subjects with normal renal function after a single intranasal dose of the pharmaceutical composition.

| Parameter | unit | n | Mean | SD | CV | Geometric mean | Min | Max | Median |
|---|---|---|---|---|---|---|---|---|---|
| $C_{max}$ | ng/mL | 8 | 38.1 | 13.1 | 34.4 | 35.9 | 16.7 | 62.7 | 37.0 |
| $T_{max}$ | h | 8 | 0.583 | 0.378 | 64.8 | 0.518 | 0.333 | 1.500 | 0.500 |
| $C_{last}$ | ng/mL | 8 | 0.263 | 0.21 | 79.4 | 0.209 | 0.114 | 0.626 | 0.154 |
| $T_{last}$ | h | 8 | 22.5 | 9.304 | 41.4 | 20.6 | 12.0 | 32.0 | 24.0 |
| $AUC_{0 \to t}$ | ng h/mL | 8 | 83.5 | 26.4 | 31.7 | 78.7 | 34.29 | 109.9 | 91.6 |
| $AUC_{0 \to \infty}$ | ng h/mL | 8 | 85.0 | 26.0 | 30.6 | 80.5 | 37.67 | 110.3 | 92.9 |
| $t_{1/2}$ | h | 8 | 5.00 | 3.301 | 66.0 | 4.12 | 2.06 | 10.67 | 3.89 |
| CL/F | L/h | 8 | 1902 | 859 | 45.2 | 1774 | 1295 | 3793 | 1542 |
| CL/F | mL/min | 8 | 31696 | 14325 | 45.2 | 29564 | 21584 | 63210 | 25697 |

$C_{max}$, maximum concentration in plasma;

$T_{max}$, time at which $C_{max}$ was observed;

$C_{last}$, last measurable concentration;

$T_{last}$, time at which $C_{last}$ was observed;

$AUC_{0 \to t}$, Area under the concentration-time curve from time zero to $T_{last}$;

$AUC_{0 \to \infty}$, Area under the concentration-time curve from time zero to infinity;

$t_{1/2}$, half-life;

CL/F, apparent clearance.

TABLE 6

Summary of cocaine pharmacokinetic parameters in subjects with severe
renal impairment after a single intranasal dose of the pharmaceutical composition.

| Parameter | unit | n | Mean | SD | CV | Geometric mean | Min | Max | Median |
|---|---|---|---|---|---|---|---|---|---|
| $C_{max}$ | ng/mL | 8 | 57.8 | 35.9 | 62.0 | 47.9 | 14.1 | 131.0 | 55.4 |
| $T_{max}$ | h | 8 | 0.448 | 0.147 | 32.9 | 0.429 | 0.333 | 0.750 | 0.417 |
| $C_{last}$ | ng/mL | 8 | 0.186 | 0.125 | 67.2 | 0.159 | 0.102 | 0.432 | 0.131 |
| $T_{last}$ | h | 8 | 28.0 | 7.09 | 25.3 | 26.9 | 12.0 | 32.0 | 32.0 |
| $AUC_{0 \to t}$ | ng·h/mL | 8 | 118.8 | 58.1 | 48.9 | 105.8 | 43.0 | 221 | 109 |
| $AUC_{0 \to \infty}$ | ng·h/mL | 8 | 120.4 | 59.2 | 49.1 | 107.2 | 44.2 | 227 | 110 |
| $t_{1/2}$ | h | 8 | 6.02 | 2.30 | 38.3 | 5.42 | 1.53 | 8.65 | 6.39 |
| CL/F | L/h | 8 | 1517 | 872 | 57.5 | 1333 | 630 | 3234 | 1304 |
| CL/F | mL/min | 8 | 25291 | 14531 | 57.5 | 22211 | 10506 | 53905 | 21732 |

$C_{max}$, maximum concentration in plasma;
$T_{max}$, time at which $C_{max}$ was observed;
$C_{last}$, last measurable concentration;
$T_{last}$, time at which $C_{last}$ was observed;
$AUC_{0 \to t}$, Area under the concentration-time curve from time zero to $T_{last}$;
$AUC_{0 \to \infty}$, Area under the concentration-time curve from time zero to infinity;
$t_{1/2}$, half-life;
CL/F, apparent clearance.

TABLE 7

Summary of ANOVA comparing cocaine pharmacokinetic
parameters in subjects with normal renal function and those
with severe renal impairment after a single intranasal dose of
the pharmaceutical composition.

| PK parameter | Renal Function | n | Geometric Least Squares Mean | Test/ Reference | Comparison Ratio (%) | 90% CI |
|---|---|---|---|---|---|---|
| $C_{max}$ | Normal | 8 | 35.9 | Impaired/ | 133.28 | (81.39, |
| (ng/mL) | Impaired | 8 | 47.9 | Normal | | 218.24) |
| $AUC_{last}$ | Normal | 8 | 78.7 | Impaired/ | 134.46 | (88.62, |
| (ng·h/mL) | Impaired | 8 | 106 | Normal | | 204.00) |
| CL/F | Normal | 8 | 1774 | Impaired/ | 75.13 | (50.02, |
| (L/h) | Impaired | 8 | 1333 | Normal | | 112.85) |
| CLr | Normal | 8 | 1.61 | Impaired/ | 64.33 | (32.67, |
| (L/h) | Impaired | 7 | 1.04 | Normal | | 126.67) |

$AUC_{last}$: area under the plasma concentration-time curve from time 0 to the time of the last measurable concentration;
CI: confidence interval;
CL/F: apparent clearance;
CLr: renal clearance;
$C_{max}$: maximum plasma concentration.

Cocaine plasma exposure, as indicated by geometric mean $C_{max}$, $AUC_{last}$, and $AUC_{inf}$ values, was approximately 33% higher in subjects with renal impairment. CL/F was approximately 25% lower and CLr was approximately 36% lower in subjects with renal impairment than in normal subjects. Mean $T_{max}$ and $t_{1/2}$ values were similar in the two groups.

Plasma exposures of the metabolites, BE and EME, were higher in subjects with severe renal impairment than in those with normal renal function. Geometric mean $C_{max}$ and $AUC_{inf}$ values in the renal impairment group were approximately 2 times and 3 to 4 times higher, respectively, than those in subjects with normal renal function. Severe renal impairment resulted in a reduction in CLr for both BE and EME of approximately 76%.

In normal subjects, BE concentrations in plasma rose rapidly over the first few hours to reach a geometric mean $C_{max}$ of 40.9 ng/mL at a median $T_{max}$ of 2.5 h. Plasma BE then declined slowly over the remainder of the 32-hour study, with a half-life (8.429 h) that was approximately 2-fold longer than that of the parent drug. The geometric mean $AUC_{inf}$ for BE was 639.2 ng*h/mL, nearly 8-fold higher than that of parent drug. Following administration of the same pharmaceutical composition dose to subjects with severe renal impairment a similar pattern of rising BE concentrations was observed during the first few hours after dosing. However, peak concentrations were more than 2-fold higher (geometric mean $C_{max}$, 90.5 ng/mL) than those patients with normal renal function and median $T_{max}$ was delayed until 6.0 h after dosing. Plasma BE declined slowly over the rest of the study, with 32-hour levels remaining at 41.3 ng/mL, compared to the 4 ng/mL observed in normal subjects. Valid assessment of $AUC_{inf}$ values for BE could not be made, because % EXTRAP was greater than 30% in all renally-impaired subjects. The exposure to BE in severe renally impaired subjects (geometric mean $AUC_{last}$, 2091 ng*h/mL) was more than 3.5-fold higher than in normal subjects (geometric mean $AUC_{last}$, 589.5 ng*h/mL), while the half-life in severe renally impaired subjects (24.65 h) was increased nearly 3-fold compared to the half-life in normal subjects (8.429 h). These data suggest that the elimination of the BE metabolite of cocaine was notably decreased in severe renal impairment.

In normal subjects, EME concentrations in plasma rose over the first few hours to reach a geometric mean $C_{max}$ of 5.8 ng/mL at a median $T_{max}$ of 3.0 h, and then declined slowly over the remainder of the 32-hour study, with a half-life (5.02 h) slightly longer than that of the parent drug. The geometric mean $AUC_{inf}$ for EME was 79.3 ng*h/mL, nearly identical to that of the parent drug.

Following administration of the same pharmaceutical composition dose to subjects with severe renal impairment, a similar pattern of rising EME concentrations was observed during the first few hours after dosing. However, peak concentrations were nearly 2-fold higher (geometric mean $C_{max}$, 10.3 ng/mL) than those in normal subjects. The geometric mean half-life of EME in severe renal impairment (13.16 h) was more than twice that observed in normal subjects (5.02 h), and the geometric mean $AUC_{inf}$ (244.5 ng*h/mL) was approximately 3-fold higher than in normal subjects (79.3 ng*h/mL). These data suggest that severe renal impairment resulted in increased exposures to the EME metabolite of cocaine.

The cocaine metabolite BE plasma pharmacokinetic parameters in subjects with normal renal function and those with severe renal impairment are summarized below in Tables 8 and 9.

TABLE 8

Summary of BE pharmacokinetic parameters in subjects with normal renal function after a single intranasal dose of the pharmaceutical composition.

| Parameter | unit | n | Mean | SD | CV | Geometric mean | Min | Max | Median |
|---|---|---|---|---|---|---|---|---|---|
| $C_{max}$ | ng/mL | 8 | 55.7 | 47.3 | 84.8 | 40.9 | 9.0 | 158.0 | 42.1 |
| $T_{max}$ | h | 8 | 3.22 | 1.92 | 59.7 | 2.75 | 1.25 | 6.00 | 2.50 |
| $C_{last}$ | ng/mL | 8 | 5.08 | 3.94 | 77.6 | 3.96 | 1.32 | 13.60 | 4.34 |
| $T_{last}$ | h | 8 | 32.0 | 0.00 | 0.00 | 32.0 | 32.0 | 32.0 | 32.0 |
| $AUC_{0 \to t}$ | ng h/mL | 8 | 762.1 | 614.5 | 80.6 | 589.5 | 167.4 | 2126 | 616 |
| $AUC_{0 \to \infty}$ | ng h/mL | 8 | 823.8 | 658.8 | 80.0 | 639.2 | 166.1 | 2284 | 676 |
| $t_{1/2}$ | h | 8 | 8.47 | 0.900 | 10.6 | 8.429 | 7.37 | 9.79 | 8.32 |

$C_{max}$, maximum concentration in plasma;
$T_{max}$, time at which $C_{max}$ was observed;
$C_{last}$, last measurable concentration;
$T_{last}$, time at which $C_{last}$ was observed;
$AUC_{0 \to t}$, Area under the concentration-time curve from time zero to $T_{last}$;
$AUC_{0 \to \infty}$, Area under the concentration-time curve from time zero to infinity;
$t_{1/2}$, half-life;
$^a AUC_{0 \to \infty}$ not summarized, the extrapolated AUC exceeded 30% of the total AUC for all subjects in this group.

TABLE 9

Summary of BE pharmacokinetic parameters in subjects with severe renal impairment after a single intranasal dose of the pharmaceutical composition.

| Parameter | unit | n | Mean | SD | CV | Geometric mean | Min | Max | Median |
|---|---|---|---|---|---|---|---|---|---|
| $C_{max}$ | ng/mL | 8 | 120.4 | 99.1 | 82.3 | 90.5 | 23.7 | 290.0 | 75.8 |
| $T_{max}$ | h | 8 | 6.625 | 2.774 | 41.9 | 6.13 | 3.00 | 12.0 | 6.00 |
| $C_{last}$ | ng/mL | 8 | 54.36 | 44.78 | 82.4 | 41.3 | 14.50 | 133.0 | 35.7 |
| $T_{last}$ | h | 8 | 32.0 | 0.00 | 0.00 | 32.0 | 32.0 | 32.0 | 32.0 |
| $AUC_{0 \to t}$ | ng h/mL | 8 | 2733.6 | 2190.7 | 80.1 | 2091 | 605.7 | 6242 | 1758 |
| $AUC_{0 \to \infty}$ | ng h/mL | $0^a$ | nd | nd | nd | nd | nd | nd | nd |
| $t_{1/2}$ | h | 8 | 24.97 | 4.355 | 17.4 | 24.65 | 19.85 | 31.62 | 24.0 |

$C_{max}$, maximum concentration in plasma;
$T_{max}$, time at which $C_{max}$ was observed;
$C_{last}$, last measurable concentration;
$T_{last}$, time at which $C_{last}$ was observed;
$AUC_{0 \to t}$, Area under the concentration-time curve from time zero to $T_{last}$;
$AUC_{0 \to \infty}$, Area under the concentration-time curve from time zero to infinity;
$t_{1/2}$, half-life;
$^a AUC_{0 \to \infty}$ not summarized, the extrapolated AUC exceeded 30% of the total AUC for all subjects in this group.

The cocaine metabolite EME plasma pharmacokinetic parameters in subjects with normal renal function and those with severe renal impairment are summarized below in Tables 10 and 11.

TABLE 10

Summary of EME pharmacokinetic parameters in subjects with normal renal function after a single intranasal dose of the pharmaceutical composition.

| Parameter | unit | n | Mean | SD | CV | Geometric mean | Min | Max | Median |
|---|---|---|---|---|---|---|---|---|---|
| $C_{max}$ | ng/mL | 8 | 7.5 | 5.7 | 75.7 | 5.8 | 1.8 | 19.2 | 5.8 |
| $T_{max}$ | h | 8 | 2.698 | 1.279 | 47.4 | 2.196 | 0.333 | 4.00 | 3.00 |
| $C_{last}$ | ng/mL | 8 | 1.583 | 0.552 | 34.9 | 1.505 | 1.070 | 2.58 | 1.42 |
| $T_{last}$ | h | 8 | 13.5 | 7.69 | 57.0 | 12.3 | 8.0 | 32.0 | 12.0 |
| $AUC_{0 \to t}$ | ng h/mL | 8 | 64.0 | 70.6 | 110.3 | 41.8 | 9.3 | 231 | 46.3 |
| $AUC_{0 \to \infty}$ | ng h/mL | $6^a$ | 94.5 | 73.3 | 77.6 | 79.3 | 44.4 | 241 | 66.8 |
| $t_{1/2}$ | h | 7 | 5.12 | 1.076 | 21.0 | 5.02 | 3.62 | 6.67 | 5.53 |

$C_{max}$, maximum concentration in plasma;
$T_{max}$, time at which Cmax was observed;
$C_{last}$, last measurable concentration;
$T_{last}$, time at which Clast was observed;
$AUC_{0 \to t}$, Area under the concentration-time curve from time zero to $T_{last}$;
$AUC_{0 \to \infty}$, Area under the concentration-time curve from time zero to infinity;
$t_{1/2}$, half-life.
$^a AUC_{0 \to \infty}$ not summarized for one subject whose extrapolated AUC exceeded 30% of the total AUC.

TABLE 11

Summary of EME pharmacokinetic parameters in subjects with severe renal impairment after a single intranasal dose of the pharmaceutical composition.

| Parameter | unit | n | Mean | SD | CV | Geometric mean | Min | Max | Median |
|---|---|---|---|---|---|---|---|---|---|
| $C_{max}$ | ng/mL | 8 | 11.9 | 5.9 | 49.9 | 10.3 | 3.2 | 20.5 | 11.5 |
| $T_{max}$ | h | 8 | 4.53 | 3.34 | 73.7 | 3.715 | 1.50 | 12.00 | 4.00 |
| $C_{last}$ | ng/mL | 8 | 2.46 | 1.440 | 58.5 | 2.218 | 1.51 | 5.85 | 1.93 |
| $T_{last}$ | h | 8 | 31.5 | 1.41 | 4.5 | 31.5 | 28.0 | 32.0 | 32.0 |
| $AUC_{0 \to t}$ | ng h/mL | 8 | 201.1 | 98.2 | 48.8 | 180.2 | 61.0 | 382 | 196 |
| $AUC_{0 \to \infty}$ | ng h/mL | 7[a] | 267.5 | 130.0 | 48.6 | 244.5 | 143.9 | 527 | 242 |
| $t_{1/2}$ | h | 8 | 13.97 | 5.53 | 39.6 | 13.16 | 8.13 | 25.70 | 12.27 |

$C_{max}$, maximum concentration in plasma;
$T_{max}$, time at which $C_{max}$ was observed;
$C_{last}$, last measurable concentration;
$T_{last}$, time at which Clast was observed;
$AUC_{0 \to t}$, Area under the concentration-time curve from time zero to $T_{last}$;
$AUC_{0 \to \infty}$, Area under the concentration-time curve from time zero to infinity;
$t_{1/2}$, half-life.
[a]$AUC_{0 \to \infty}$ not summarized for one subject whose extrapolated AUC exceeded 30% of the total AUC.

The parent drug, cocaine, and its primary metabolites, BE and EME, were all present in the urine following intranasal administration of pharmaceutical composition. The time course of cocaine recovery in the urine showed that the rate of urinary excretion was highest immediately after dosing, and then fell to lower levels beyond 12 hours. Urinary recovery curves were similar for normal and renally impaired subjects after 4 hours, but more cocaine was recovered in normal subjects during the first (0-2 h) collection period, suggesting a delay in excretion associated with renal impairment.

Urinary recovery of BE generally increased during the first 24 hours of the study, as expected from the longer residence of this metabolite in the body. In the severe renally impaired subjects, there was a tendency for lower BE recovery at earlier (2-12 h) time points and higher BE recovery at later (24-32 h) time points. This delay in excretion is consistent with the observation that severe renal impairment increased both plasma $t_{1/2}$ and $T_{max}$ of this metabolite.

The pattern of urinary recovery observed for the minor metabolite EME was similar for normal and severe renally impaired subjects. However, as observed for BE, the excretion of EME appeared to be delayed in the severe renal impairment group, with lower recoveries in the 2-12 h time frame, and higher recoveries in the 24-32 h time frame compared to normal subjects. Again, this delay is consistent with the increased plasma exposures observed for this metabolite.

In terms of 0-32 h urinary recoveries as a percent of the administered dose, the recovery of cocaine was, as expected, only a small fraction of the administered dose due to low topical bioavailability and systemic metabolism. The recovery of unchanged drug was 0.115% in normal subjects and 0.097% in severe renal impairment. The 0-32 h urinary recoveries for the two metabolites did not appear to differ between the two groups. (Table 12). Total (drug+metabolites) urinary recoveries were only slightly higher in severe renally impaired subjects (4.36±2.30%) compared to normal subjects (3.31±2.53%).

TABLE 12

Summary of urinary recovery showing 0 to 32 hour urinary recovery as % of administered dose of the pharmaceutical composition.

| | Cocaine | | Benzoylecgonine | | Ecgonine Methyl Ester | | Total Urinary Recovery | |
|---|---|---|---|---|---|---|---|---|
| | Normal | Severe RI | Normal | Severe RI | Normal | Severe RI | Normal | Severe RI |
| n | 7 | 4 | 7 | 4 | 7 | 4 | 7 | 4 |
| mean | 0.115 | 0.097 | 2.029 | 2.744 | 1.167 | 1.519 | 3.31 | 4.36 |
| SD | 0.088 | 0.092 | 1.684 | 2.056 | 0.824 | 1.128 | 2.53 | 2.298 |
| CV | 76.27 | 94.90 | 83.03 | 74.94 | 70.65 | 74.21 | 76.4 | 52.7 |
| median | 0.089 | 0.063 | 1.089 | 1.988 | 0.952 | 1.177 | 2.20 | 4.00 |
| geometric mean | 0.086 | 0.072 | 1.546 | 2.294 | 0.954 | 1.255 | 2.625 | 3.899 |

Metabolite recoveries expressed as cocaine equivalents

Severe renal impairment appears to have reduced the renal clearances of all three analytes to some extent. For cocaine this effect was modest, with geometric mean clearance falling from 1.61 L/h (normal) to 1.04 L/h (renal impairment). The urinary clearance of BE fell from 3.61 L/h in normal subjects to 0.854 L/h in severe renally impaired subjects, while the renal clearance of EME fell from 18.1 L/h in normal subjects to 4.23 L/h in severe renally impaired subjects. These 4-fold reductions in renal clearance of the primary cocaine metabolites are consistent with the increases in plasma exposures and half-lives observed in this study, and support the conclusion that severe renal impairment is associated with substantial increases in exposure to the primary metabolites of cocaine observed after intranasal dosing.

TABLE 13

Summary of cocaine, BE, and EME urinary pharmacokinetic parameters in subjects with normal renal function and those with severe renal impairment after a single intranasal dose of the pharmaceutical composition.

| Renal Function | Statistic | Cocaine | BE | EME | Total |
|---|---|---|---|---|---|
| | | Urine Recovery as % of Dose[a,b] | | | |
| Normal | Mean | 0.115 | 2.03 | 1.17 | 3.31 |
| | SD | 0.088 | 1.68 | 0.824 | 2.53 |
| | CV % | 76.3 | 83.0 | 70.7 | 76.4 |
| | Geomean | 0.086 | 1.55 | 0.954 | 2.63 |
| Impaired | Mean | 0.097 | 2.74 | 1.52 | 4.36 |
| | SD | 0.092 | 2.06 | 1.13 | 2.30 |
| | CV % | 94.9 | 74.9 | 74.2 | 52.7 |
| | Geomean | 0.072 | 2.29 | 1.26 | 3.90 |
| | | CLr (L/h)[c] | | | |
| Normal | Mean | 2.00 | 3.77 | 19.1 | NA |
| | SD | 1.39 | 1.09 | 6.04 | |
| | CV % | 69.4 | 28.9 | 31.7 | |
| | Geomean | 1.61 | 3.61 | 18.1 | |
| Impaired | Mean | 1.22 | 0.919 | 4.95 | NA |
| | SD | 0.692 | 0.363 | 3.16 | |
| | CV % | 56.6 | 39.5 | 63.8 | |
| | Geomean | 1.04 | 0.854 | 4.23 | |

[a] Includes subjects with complete urine collections over 32 h; metabolite recovery expressed as cocaine equivalents
[b] n = 7 for normal renal function and n = 4 for severe renal impairment
[c] n = 8 for normal renal function and n = 6 for severe renal impairment
BE: benzoylecgonine;
CLr: renal clearance;
CV: coefficient of variation;
EME: ecgonine methyl ester;
Geomean: geometric mean;
NA: not applicable;
SD: standard deviation.

TABLE 14

Summary of urinary recovery for subjects with normal renal function over a period of 32 hours post administration of the pharmaceutical composition.
0-32 h Urinary Recovery (μg)

| | Cocaine | BE | EME |
|---|---|---|---|
| mean | 164.2 | 2764 | 1095 |
| SD | 125.3 | 2295 | 773.5 |
| CV | 76.27 | 83.03 | 70.65 |
| median | 126.6 | 1483 | 892.8 |
| geometric mean | 122.8 | 2106 | 894.9 |

TABLE 15

Summary of urinary recovery for subjects with severe renal impairment over a period of 32 hours post administration of the pharmaceutical composition.
0-32 h Urinary Recovery (μg)

| | Cocaine | BE | EME |
|---|---|---|---|
| mean | 138.5 | 3738 | 1425 |
| SD | 131.4 | 2802 | 1057.9 |
| CV | 94.90 | 74.94 | 74.21 |
| median | 89.8 | 2709 | 1104 |
| geometric mean | 102.7 | 3126 | 1177.8 |

TABLE 16

Summary of renal clearance for subjects with normal renal function post administration of the pharmaceutical composition.

| | Cocaine | BE | EME |
|---|---|---|---|
| | Renal Clearance (L/h) | | |
| mean | 2.00 | 3.77 | 19.1 |
| SD | 1.39 | 1.09 | 6.04 |
| CV | 69.4 | 28.9 | 31.7 |
| median | 2.02 | 4.01 | 21.4 |
| geometric mean | 1.61 | 3.61 | 18.1 |
| | Renal Clearance (mL/min) | | |
| mean | 33.33 | 62.78 | 317.8 |
| SD | 23.1 | 18.16 | 100.6 |
| CV | 69.4 | 28.92 | 31.66 |
| median | 33.65 | 66.86 | 356.1 |
| geometric mean | 26.86 | 60.14 | 302.2 |

TABLE 17

Summary of renal clearance for subjects with severe renal impairment post administration of the pharmaceutical composition.

| | Cocaine | BE | EME |
|---|---|---|---|
| | Renal Clearance (L/h) | | |
| mean | 1.22 | 0.919 | 4.95 |
| SD | 0.692 | 0.363 | 3.16 |
| CV | 56.6 | 39.5 | 63.8 |
| median | 1.18 | 0.824 | 4.05 |
| geometric mean | 1.04 | 0.854 | 4.23 |
| | Renal Clearance (mL/min) | | |
| mean | 20.37 | 15.3 | 82.5 |
| SD | 11.5 | 6.05 | 52.7 |
| CV | 56.62 | 39.5 | 63.8 |
| median | 19.59 | 13.7 | 67.6 |
| geometric mean | 17.28 | 14.2 | 70.6 |

Effect of Renal Impairment

Cocaine and its principal metabolites, BE and EME, were observed in both plasma and urine after a single intranasal exposure to the pharmaceutical composition, equivalent to 160 mg of cocaine hydrochloride, in subjects with normal renal function (eGFR≥60 mL/min/1.73 m$^2$) and severe renal impairment (eGFR 15-29 mL/min/1.73 m$^2$). Norcocaine was not measurable in the plasma of most subjects. Severe renal impairment was associated with a 76% decrease in renal clearance of BE and EME, resulting in notable increases in plasma exposure ($C_{max}$ and AUC) to these metabolites compared to normal subjects.

In humans, cocaine is eliminated predominantly by metabolism, with little excreted unchanged in the urine.

Only 1% to 10% of a dose of cocaine is eliminated unmetabolized in urine. Consistent with this low urinary recovery, cocaine CLr is less than 2% of CL. CLr values are less than 40% of human glomerular filtration rate ("GFR") (125 mL/min).

Intranasal administration of the pharmaceutical composition was safe and well tolerated in both subjects with normal renal function and subjects with severe renal impairment. The geometric mean cocaine $C_{max}$ value in subjects with severe renal impairment (47.9 ng/mL) was well below these values, indicating that the risk of cardiac repolarization effects would be negligible in renally impaired individuals. The minimal effect of renal impairment on exposure of the active parent drug, cocaine, coupled with the low risk of cardiac effects expected in this group, suggests that dose adjustment of the pharmaceutical composition should not be required in subjects with reduced renal function.

Example 3

The primary objective of Example 3 was to evaluate the potential effect of hepatic impairment on the systemic pharmacokinetic parameters of the pharmaceutical composition after single dose intranasal administration. The secondary objective was to evaluate the safety and tolerability of the pharmaceutical composition in subjects with normal hepatic function and hepatic impairment.

One way to measure hepatic impairment is to determine a Child-Pugh score for a subject. A Child-Pugh score relies on five clinical measures of liver disease: total bilirubin, serum albumin, prothrombin time, presence of ascites, and presence of hepatic encephalopathy. Each clinical measure is assigned a value on a scale from 1-3 depending on its severity or degree of abnormality. The sum of the individual values is used to assign a Child-Pugh grade of A, B, or C where grade C is worse than grade B, and grade B is worse than grade A.

Another way to measure hepatic impairment is to determine a the Model for End-Stage Liver Disease ("MELD") Score for a subject. A MELD score uses a subject's values for serum bilirubin, serum creatinine, and international normalized ratio for prothrombin time. The values are used in a formula to generate a numerical output that corresponds to disease severity and survival.

Materials and Methods

Twelve male and female subjects≥18 years of age with either Child-Pugh Grade B (n=9) or Grade C (n=3) hepatic impairment or normal hepatic function (n=12), and without a known allergy to ester-based anesthetics were enrolled in the study. Subjects were dosed with pharmaceutical composition in the form of an aqueous solution comprising 40 mg/mL cocaine hydrochloride, 1.25 mg/mL citric acid, 1.00 mg/mL sodium benzoate, a colorant (0.02 mg/mL D&C Yellow No. 10, 0.02 mg/mL FD&C Green No. 3), and 957.7 mg/mL water. The subjects were dosed as follows: four mL (4 mL) of the pharmaceutical composition (containing approximately 160 mg of cocaine hydrochloride) were poured into a standard medicine cup. Four (4) cottonoid pledgets (approximately 1.3 cm×4 cm) were soaked in the 4 mL of the solution for 10 minutes and allowed to soak. Each pledget absorbed approximately 1 mL of solution. The drug-soaked pledgets were placed into the nasal cavity (2 per side) and against the septum of each subject at time 0 and removed after 20 minutes.

Pharmacokinetic blood samples were drawn at 0 hour (pre-dose), and post dose at: 7, 15, 20 (immediately after pledget removal), 30, 45, 60, 75, 90, and 105 min, and 2, 3, 4, 6, 8, 10, 12, 24, 28, and 32 h, based upon the beginning of dose application. Plasma was separated and stabilizer was added to prevent continued ester hydrolysis of cocaine in the samples. Total concentrations of cocaine and its major metabolites, BE and EME, and the active metabolite, norcocaine, were determined in all plasma samples using a validated LC-MS/MS method with an LLOQ of 0.1 ng/mL for cocaine and norcocaine, and 1.0 ng/mL for BE and EME. A 50-µL aliquot of each stabilized plasma sample was processed by liquid-liquid extraction. The compounds were detected and quantified by LC-MS/MS in positive ion mode on an MDS Sciex API 4000 equipped with a TURBOIONSPRAY® interface. Calibration curves were obtained by performing a linear regression (weighted $1/x^2$) on the calibration standards. Plasma pharmacokinetic parameters were analyzed using noncompartmental methods. Plasma pharmacokinetic parameters included $AUC_{last}$, $AUC_{inf}$, $C_{max}$, $T_{max}$, $C_{last}$, $T_{last}$, $t_{1/2}$, CL/F (cocaine only), and % EXTRAP.

Urine was collected prior to dosing and from 0-2, 2-4, 4-8, 8-12, 12-24, and 24-32 hours after beginning of dose application. Urine concentrations of cocaine, BE, and EME were determined using a validated LC-MS/MS method with an LLOQ of 0.1 ng/mL for cocaine and 1.0 ng/mL for BE and EME. Urinary pharmacokinetic parameters included total urinary recovery (µg), urinary recovery as a percentage of dose, and CLr.

Safety assessments, including monitoring AEs, vital sign measurements, and laboratory tests were performed. A nasal exam was visually conducted pre-dose and at the end of the study to determine if irritation was present at the prospective application site.

Pharmacokinetic parameters were compared between groups using ANOVA with hepatic function (Grade B or Grade C impaired vs. normal) as a fixed effect. Geometric mean ratios with 90% confidence intervals were calculated to compare $C_{max}$, $AUC_{last}$, and CL/F for cocaine, and $C_{max}$ and $AUC_{last}$ for each metabolite between subjects with normal hepatic function and subjects with hepatic impairment.

Results

Demographic and baseline characteristics were similar in the normal hepatic function, Grade B hepatic impairment, and Grade C hepatic impairment groups. All of the subjects in the study were healthy adult male (83.3%) and female (16.7%) volunteers. The subjects ranged in age from 27 to 74 years (overall mean, 51.7 years), were white or black (83.3% and 16.7%, respectively), and had an overall mean body weight of 91.25 kg.

The pharmaceutical composition was observed as safe and well tolerated in subjects with normal hepatic function, as well as subjects with Grade B and Grade C hepatic impairment.

In subjects with normal hepatic function, cocaine appeared rapidly in the plasma following intranasal application of the pharmaceutical composition, (reaching $T_{max}$ at approximately 0.5 hours) with measurable levels in all subjects at the first time point (7 min) after the start of treatment. Plasma concentrations declined in an apparently bi-exponential manner after $T_{max}$ throughout the remainder of the 32-hour study.

Figure 10:
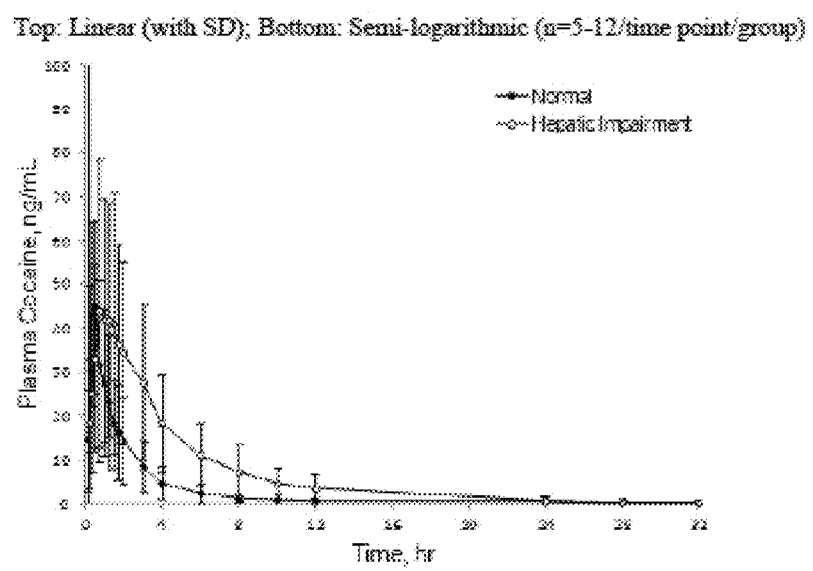
FIG. 10 is a linear plot of mean cocaine plasma concentration (including standard deviations) as a function of time following administration of an intranasal dose of a pharmaceutical composition including cocaine hydrochloride in a concentration of 40 mg/mL to subjects with normal hepatic function and subjects with hepatic impairment.
Figure 11:
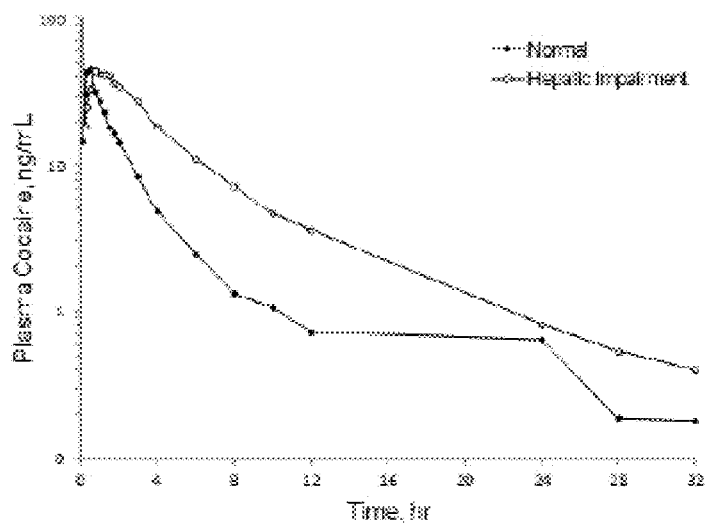
FIG. 11 is a logarithmic plot of plasma cocaine concentration as a function of time following administration of an intranasal dose of a pharmaceutical composition including cocaine hydrochloride in a concentration of 40 mg/mL to subjects with normal hepatic function and subjects with hepatic impairment.

Following administration of the same pharmaceutical composition dose to subjects with hepatic impairment, the time course of plasma cocaine appeared somewhat delayed compared to normal subjects, with a later $T_{max}$, a broader peak, and slower decline during the initial 12 hours after dosing. After $T_{max}$, plasma cocaine exposures in the hepatic impairment group were about 2.5 times higher than those patients with normal hepatic function (FIGS. 10 and 11).

In normal subjects, plasma concentrations of the metabolites BE and EME rose rapidly over the first few hours post-dose, then declined slowly over the remainder of the 32-hour sampling interval. Following administration of the same pharmaceutical composition dose to subjects with hepatic impairment, BE and EME concentrations rose more slowly, with a delayed $T_{max}$, and exhibited a broader peak than observed in subjects with normal hepatic function. Peak concentrations were 1.5 to 2 times higher than those in normal subjects, and concentrations declined at a similar rate (EME) or more slowly (BE) in subjects with hepatic impairment. Plasma concentrations of the active metabolite, norcocaine, were not measurable (LLOQ=0.1 ng/mL) in plasma after pharmaceutical composition dosing in any of the subjects with normal hepatic function, or in 8 of the 12 subjects with hepatic impairment. Norcocaine was detected at low levels (≤0.31 ng/mL), within 3 times the LLOQ, at multiple time points in three Grade B impaired subjects, and at a single time point in one Grade B subject (0.354 ng/mL at 7 min).

Hepatic impairment had little to no effect on the $C_{max}$ of cocaine; geometric means were 5% higher (56% higher with the outlier included) and 32% lower in Grade B and Grade C hepatic impairment, respectively, and 90% confidence intervals (CI) on geometric mean ratios (GMR) encompassed 100% for both hepatic impairment groups. The geometric mean $C_{max}$ value across all hepatically impaired individuals was 7% lower (27% higher with the outlier included) than that in subjects with normal hepatic function. The apparent clearance of cocaine was correspondingly reduced in hepatically impaired subjects, with GMR (90% CI) of 36.25% (22.78-57.68%) for Grade B and 55.28% (28.80-106.12%) for Grade C impairment. The geometric mean half-life for cocaine was 6.62 h in normal subjects and 4.99 h in hepatic impairment.

Cocaine plasma pharmacokinetic parameters in subjects with normal hepatic function and those with hepatic impairment are summarized in Tables 18 and 19. The results of ANOVA are presented in Table 20.

TABLE 18

Summary of cocaine pharmacokinetic parameters in subjects with normal hepatic function after administration of a single intranasal dose of the pharmaceutical composition.

| Parameter | unit | n | Mean | SD | CV | Geometric mean | Min | Max | Median |
|---|---|---|---|---|---|---|---|---|---|
| Cmax | ng/mL | 12 | 50.6 | 21.0 | 41.5 | 44.2 | 7.64 | 75.2 | 53.6 |
| Tmax | h | 12 | 0.431 | 0.0858 | 19.9 | 0.422 | 0.333 | 0.500 | 0.500 |
| Clast | ng/mL | 12 | 0.210 | 0.107 | 51.0 | 0.188 | 0.102 | 0.405 | 0.160 |
| Tlast | h | 12 | 26.0 | 7.34 | 28.2 | 24.7 | 12.0 | 32.0 | 28.0 |
| $AUC_{0 \to t}$ | ng h/mL | 12 | 92.8 | 55.3 | 59.5 | 79.2 | 20.0 | 235 | 82.4 |
| $AUC_{0 \to \infty}$ | ng h/mL | 12 | 95.3 | 54.7 | 57.4 | 82.4 | 21.7 | 237 | 83.3 |
| $t_{1/2}$ | h | 12 | 8.11 | 5.55 | 68.4 | 6.62 | 1.84 | 22.5 | 6.93 |
| CL/F | L/h | 12 | 2066 | 1538 | 74.4 | 1735 | 604 | 6588 | 1744 |
| CL/F | mL/min | 12 | 34438 | 25637 | 74.4 | 28911 | 10064 | 109805 | 29065 |

TABLE 19

Summary of cocaine pharmacokinetic parameters in subjects with hepatic impairment after a single intranasal dose of the pharmaceutical composition.

| Parameter | unit | n | Mean | SD | CV | Geometric mean | Min | Max | Median |
|---|---|---|---|---|---|---|---|---|---|
| Cmax | ng/mL | 11 | 50.7 | 34.5 | 68.0 | 41.2 | 17.1 | 119 | 42.6 |
| Tmax | h | 11 | 1.09 | 0.784 | 72.1 | 0.828 | 0.117 | 3.00 | 0.750 |
| Clast | ng/mL | 11 | 0.393 | 0.469 | 119 | 0.270 | 0.115 | 1.73 | 0.211 |
| Tlast | h | 11 | 31.6 | 1.21 | 3.81 | 31.6 | 28.0 | 32.0 | 32.0 |
| $AUC_{0 \to t}$ | ng h/mL | 11 | 223 | 138 | 61.8 | 189 | 89.5 | 523 | 176 |
| $AUC_{0 \to \infty}$ | ng h/mL | 11 | 227 | 139 | 61.1 | 192 | 90.9 | 528 | 177 |
| $t_{1/2}$ | h | 11 | 5.42 | 2.17 | 40.0 | 4.94 | 1.46 | 9.86 | 5.63 |
| CL/F | L/h | 11 | 867 | 477 | 55.0 | 743 | 271 | 1571 | 808 |
| CL/F | mL/min | 11 | 14446 | 7948 | 55.0 | 12377 | 4512 | 26182 | 13468 |

The geometric mean $C_{max}$ value across all hepatically impaired individuals was 7% lower (27% higher with the outlier included) than that in subjects with normal hepatic function (Table 20). Overall exposure of cocaine was elevated somewhat in hepatic impairment. Plasma cocaine $AUC_{last}$ was 2.8 times higher in Grade B impaired subjects and 1.8 times higher in Grade C impaired subjects compared to normal subjects. Cocaine Cl/F was correspondingly reduced, by 64% and 45% in subjects with Grade B and Grade C hepatic impairment, respectively.

A statistical analysis was conducted to evaluate the potential effects of hepatic impairment on the primary pharmacokinetic endpoints of Example 3. Analysis of Variance (ANOVA) on hepatic function was carried out on the following natural log-transformed PK parameters:

$AUC_{last}$ and $C_{max}$ for cocaine, BE, and EME using hepatic status as a fixed effect CL/F for cocaine using hepatic status as a fixed effect.

GMR with 90% confidence intervals were calculated comparing each of the above PK parameters between hepatically impaired subjects (Grade B or C) and normal subjects, based on these ANOVA models.

TABLE 20

Summary of ANOVA comparing cocaine pharmacokinetic parameters in subjects with normal hepatic function and those with Grade B or Grade C hepatic impairment after a single intranasal dose of the pharmaceutical composition.

| PK parameter | Hepatic Function | n | Geometric Least Squares Mean | Comparison Test/Reference | Ratio (%) | 90% CI |
|---|---|---|---|---|---|---|
| $C_{max}$ | Normal | 12 | 44.2 | — | — | — |
| (ng/mL) | Grade B[a] | 8 | 46.4 | Grade B/Normal | 104.89 | (61.07, 180.17) |
|  | Grade C | 3 | 30.1 | Grade C/Normal | 68.13 | (34.30, 135.33) |
| $AUC_{last}$ | Normal | 12 | 79.2 | — | — | — |
| (ng · h/mL) | Grade B | 9 | 225 | Grade B/Normal | 284.54 | (176.53, 458.63) |
|  | Grade C | 3 | 142 | Grade C/Normal | 179.88 | (91.85, 352.27) |
| CL/F | Normal | 12 | 1735 | — | — | — |
| (L/h) | Grade B | 9 | 629 | Grade B/Normal | 36.25 | (22.78, 57.68) |
|  | Grade C | 3 | 959 | Grade C/Normal | 55.28 | (28.80, 106.12) |

[a]Excludes one subject with anomalous concentration value at 7 minutes;
$AUC_{last}$: area under the plasma concentration-time curve from time 0 to the time of the last measurable concentration;
CI: confidence interval;
CL/F: apparent clearance;
$C_{max}$: maximum concentration.

Overall plasma exposures of the metabolites BE and EME were higher in subjects with hepatic impairment than in those with normal hepatic function. In subjects with Grade B hepatic impairment, geometric mean $C_{max}$ values for the metabolites were less than 2 times higher, and $AUC_{last}$ values were approximately 2.4 times higher, than in subjects with normal hepatic function. In the 3 Grade C hepatic impairment subjects, $AUC_{last}$ values were 2.2 times higher (EME) or not appreciably changed (BE; 12% increased) compared to subjects with normal hepatic function. There was no appreciable change (12 to 18% reduction) in BE or EME $C_{max}$ in Grade C hepatic impairment compared to normal subjects.

The cocaine metabolite BE plasma pharmacokinetic parameters in subjects with normal renal function and those with severe renal impairment are summarized below in Tables 21 and 22.

TABLE 21

Summary of BE pharmacokinetic parameters in subjects with normal hepatic function after administration of a single intranasal dose of the pharmaceutical composition.

| Parameter | unit | n | Mean | SD | CV | Geometric mean | Min | Max | Median |
|---|---|---|---|---|---|---|---|---|---|
| Cmax | ng/mL | 12 | 57.5 | 45.2 | 78.7 | 43.7 | 7.03 | 171 | 35.5 |
| Tmax | h | 12 | 2.38 | 1.92 | 81.0 | 1.96 | 1.00 | 8.00 | 1.63 |
| Clast | ng/mL | 12 | 6.17 | 8.13 | 132 | 4.33 | 2.02 | 31.6 | 3.71 |
| Tlast | h | 12 | 32.0 | 0.00 | 0.00 | 32.0 | 32.0 | 32.0 | 32.0 |
| $AUC_{0 \to t}$ | ng h/mL | 12 | 784 | 736 | 94.0 | 603 | 144 | 2969 | 523 |

TABLE 21-continued

Summary of BE pharmacokinetic parameters in subjects with normal hepatic function after administration of a single intranasal dose of the pharmaceutical composition.

| Parameter | unit | n | Mean | SD | CV | Geometric mean | Min | Max | Median |
|---|---|---|---|---|---|---|---|---|---|
| $AUC_{0 \to \infty}$ | ng h/mL | 12 | 869 | 855 | 98.3 | 667 | 182 | 3446 | 568 |
| $t_{1/2}$ | h | 12 | 9.16 | 1.86 | 20.3 | 9.00 | 6.64 | 13.1 | 8.91 |

TABLE 22

Summary of BE pharmacokinetic parameters in subjects with hepatic impairment after administration of a single intranasal dose of the pharmaceutical composition.

| Parameter | unit | n | Mean | SD | CV | Geometric mean | Min | Max | Median |
|---|---|---|---|---|---|---|---|---|---|
| Cmax | ng/mL | 12 | 81.2 | 61.7 | 75.9 | 67.1 | 27.4 | 248 | 67.8 |
| Tmax | h | 12 | 7.50 | 2.97 | 39.6 | 6.95 | 4.00 | 12.0 | 7.00 |
| Clast | ng/mL | 12 | 17.6 | 10.8 | 61.6 | 14.3 | 3.33 | 42.6 | 16.6 |
| Tlast | h | 12 | 32.0 | 0.00 | 0.00 | 32.0 | 32.0 | 32.0 | 32.0 |
| $AUC_{0 \to t}$ | ng h/mL | 12 | 1402 | 790 | 56.3 | 1235 | 606 | 3356 | 1190 |
| $AUC_{0 \to \infty}$ | ng h/mL | 8 | 1724 | 945 | 54.8 | 1513 | 647 | 3532 | 1448 |
| $t_{1/2}$ | h | 12 | 14.0 | 7.60 | 54.2 | 12.3 | 6.65 | 31.0 | 12.1 |

EME plasma pharmacokinetic parameters in subjects with normal hepatic function and those with severe hepatic impairment are summarized below in Tables 23 and 24.

TABLE 23

Summary of EME pharmacokinetic parameters in subjects with normal hepatic function after administration of a single intranasal dose of the pharmaceutical composition.

| Parameter | unit | n | Mean | SD | CV | Geometric mean | Min | Max | Median |
|---|---|---|---|---|---|---|---|---|---|
| Cmax | ng/mL | 11 | 10.0 | 6.30 | 62.9 | 8.75 | 3.83 | 26.8 | 7.81 |
| Tmax | h | 11 | 1.45 | 0.650 | 44.7 | 1.33 | 0.500 | 3.00 | 1.25 |
| Clast | ng/mL | 11 | 1.85 | 0.904 | 49.0 | 1.67 | 1.00 | 3.72 | 1.60 |
| Tlast | h | 11 | 16.5 | 6.82 | 41.2 | 15.4 | 10.0 | 28.0 | 12.0 |
| $AUC_{0 \to t}$ | ng h/mL | 11 | 72.9 | 50.0 | 68.5 | 61.2 | 24.5 | 198 | 59.1 |
| $AUC_{0 \to \infty}$ | ng h/mL | 9 | 89.6 | 56.6 | 63.2 | 76.1 | 31.5 | 212 | 72.9 |
| $t_{1/2}$ | h | 11 | 6.27 | 2.03 | 32.4 | 5.99 | 4.16 | 9.97 | 5.69 |

TABLE 24

Summary of EME pharmacokinetic parameters in subjects with hepatic impairment after administration of a single intranasal dose of the pharmaceutical composition.

| Parameter | unit | n | Mean | SD | CV | Geometric mean | Min | Max | Median |
|---|---|---|---|---|---|---|---|---|---|
| Cmax | ng/mL | 12 | 16.1 | 14.9 | 92.5 | 11.3 | 2.57 | 52.7 | 9.11 |
| Tmax | h | 12 | 3.84 | 1.93 | 50.1 | 2.90 | 0.117 | 6.00 | 4.00 |
| Clast | ng/mL | 12 | 1.65 | 0.542 | 32.9 | 1.57 | 1.02 | 2.97 | 1.67 |
| Tlast | h | 12 | 27.7 | 7.52 | 27.2 | 26.3 | 12.0 | 32.0 | 32.0 |
| $AUC_{0 \to t}$ | ng h/mL | 12 | 185 | 130 | 70.3 | 146 | 25.6 | 505 | 140 |
| $AUC_{0 \to \infty}$ | ng h/mL | 10 | 233 | 118 | 50.8 | 212 | 127 | 517 | 185 |
| $t_{1/2}$ | h | 10 | 9.26 | 3.64 | 39.3 | 8.67 | 5.44 | 15.7 | 8.3 |

Norcocaine plasma pharmacokinetic parameters in subjects with normal hepatic function could not be determined because the concentrations of norcocaine were below the limit of quantitation (0.1 ng/mL) in all subjects with normal hepatic function at all study time points. Norcocaine plasma pharmacokinetic parameters in subjects with severe hepatic impairment are summarized below in Table 25.

TABLE 25

Summary of norcocaine pharmacokinetic parameters in subjects with hepatic impairment after administration of a single intranasal dose of the pharmaceutical composition.

| Parameter | unit | n | Mean | SD | CV | Geometric mean | Min | Max | Median |
|---|---|---|---|---|---|---|---|---|---|
| Cmax | ng/mL | 3 | 0.227 | 0.0751 | 33.1 | 0.219 | 0.160 | 0.308 | 0.212 |
| Tmax | h | 3 | 1.50 | 0.00 | 0.00 | 1.50 | 1.50 | 1.50 | 1.50 |
| Clast | ng/mL | 3 | 0.127 | 0.0225 | 17.7 | 0.126 | 0.105 | 0.150 | 0.126 |
| Tlast | h | 3 | 6.33 | 4.93 | 77.9 | 5.24 | 3.00 | 12.0 | 4.00 |
| $AUC_{0 \to t}$ | ng h/mL | 3 | 0.950 | 0.735 | 77.4 | 0.753 | 0.309 | 1.75 | 0.788 |
| $AUC_{0 \to \infty}$ | ng h/mL | 0 | nd | nd | nd | nd | nd | nd | nd |
| $t_{1/2}$ | h | 2 | 6.23 | 5.12 | 82.2 | 5.07 | 2.61 | 9.85 | 6.23 | nd - could not be determined; plasma norcocaine concentrations were below the limit of quantitation (0.1 ng/mL) at all time points in 8 of the 12 subjects with hepatic impairment.

Cocaine, BE, and EME were all excreted into urine following intranasal administration of pharmaceutical composition. Hepatic impairment increased the geometric mean urinary recovery of the BE and EME metabolites by approximately 2-fold compared to normal subjects, but had little effect on geometric mean cocaine recovery. These increased recoveries were not accompanied by a proportional increase in CLr of the metabolites; geometric mean CLr values for BE and EME were in fact slightly lower in hepatic impairment and were highly variable in both groups.

The parent drug, cocaine, and its primary metabolites, BE and EME, were all present in the urine following intranasal administration of the pharmaceutical composition. The time course of cocaine recovery in the urine of normal subjects showed that the rate of urinary excretion was highest immediately after dosing, and then fell at later time points. In hepatically impaired subjects, cocaine urinary recovery rose over the first 8 hours, and then fell to levels similar to those in normal subjects from 12 to 32 hours, suggesting a delay in cocaine excretion associated with hepatic impairment.

Urinary recovery of BE generally increased during the first 24 hours of the study, as expected from the longer residence of this metabolite in the body. In the hepatic impairment subjects, higher BE recovery was observed, especially in the 12 and 24 h collections. This pattern resulted in an approximately 2-fold increase in urinary recovery of BE in the hepatically impaired subjects.

The pattern of urinary recovery observed for EME demonstrated greater urinary recovery of EME in the 8 to 32 h collections in subjects with hepatic impairment compared to normal subjects. This resulted in a 2.2-fold increase in urinary recovery of EME in the hepatically impaired subjects.

In terms of 0-32 h urinary recoveries as a percent of the administered dose, the recovery of cocaine was, as expected, only a small fraction of the administered dose due to low topical bioavailability and systemic metabolism. The recovery of unchanged drug was 0.057% in normal subjects and 0.071% in hepatic impairment. The 0-32 h urinary recoveries increased by about 2-fold for BE, and 2.5-fold for EME in the hepatic impairment group compared to normal subjects. Total (drug+metabolites) urinary recoveries were 2.92±1.54% in normal subjects and 6.96±5.77% in hepatic impairment subjects, an increase of more than 2-fold resulting from hepatic impairment.

Hepatic impairment had little to no effect on cocaine recovery, but increased the urinary recoveries of the BE and EME metabolites by roughly 2-fold. These increased recoveries were not accompanied by a proportional increase in renal clearance. Rather, renal clearance for the metabolites was slightly lower (less than 40%) in hepatic impairment and was highly variable in both groups, with individual values overlapping considerably between subjects with normal or impaired hepatic function. The increased urinary metabolite recoveries were accompanied by increased plasma exposures in hepatic impairment. These changes suggest that increased exposures to BE and EME were mainly due to a reduction in hepatic elimination pathways for these metabolites in subjects with hepatic impairment.

Although urinary recovery of cocaine was nearly unchanged, both the renal and apparent plasma clearances were reduced in the presence of hepatic impairment, leading to increased systemic exposures to the parent drug. It is notable that the plasma half-life of cocaine was not increased in subjects with hepatic impairment.

TABLE 26

Summary of cocaine, BE, and EME urinary pharmacokinetic parameters in subjects with normal hepatic function and those with hepatic impairment after administration of a single intranasal dose of the pharmaceutical composition.

| Hepatic Function | Statistic | Cocaine | BE | EME | Total |
|---|---|---|---|---|---|
| Urine Recovery as % of Dose[a,b] | | | | | |
| Normal | Mean | 0.072 | 1.73 | 1.12 | 2.92 |
|  | SD | 0.045 | 1.00 | 0.558 | 1.54 |
|  | CV % | 62.5 | 57.7 | 49.9 | 52.6 |
|  | Geomean | 0.057 | 1.42 | 0.93 | 2.46 |
| Impaired | Mean | 0.143 | 3.30 | 3.51 | 6.96 |
|  | SD | 0.130 | 2.14 | 3.67 | 5.77 |
|  | CV % | 91.1 | 64.8 | 105 | 8.29 |
|  | Geomean | 0.071 | 2.74 | 2.43 | 5.40 |
| CLr (L/h)[c] | | | | | |
| Normal | Mean | 1.79 | 4.30 | 17.2[d] | NA |
|  | SD | 1.64 | 2.07 | 11.5 |  |
|  | CV % | 91.9 | 48.3 | 66.8 |  |
|  | Geomean | 1.17 | 3.96 | 14.6 |  |
| Impaired | Mean | 0.997 | 2.90 | 10.9 | NA |
|  | SD | 92.3 | 47.9 | 41.1 |  |
|  | CV % | 0.921 | 1.39 | 4.47 |  |
|  | Geomean | 0.468 | 2.59 | 10.2 |  |

TABLE 27

Summary of urinary recovery for subjects with normal hepatic function over a period of 32 hours post administration of the pharmaceutical composition.
0-32 h Urinary Recovery (μg)

|  | Cocaine | BE | EME |
|---|---|---|---|
| mean | 102.25 | 2359.75 | 1048.23 |
| SD | 63.91 | 1360.71 | 523.42 |
| CV | 62.51 | 57.66 | 49.93 |
| median | 108.1 | 2098.9 | 1164.3 |
| geometric mean | 81.5 | 1928.3 | 875.2 |

TABLE 28

Summary of urinary recovery for subjects with hepatic impairment over a period of 32 hours post administration of the pharmaceutical composition.
0-32 h Urinary Recovery (μg)

|  | Cocaine | BE | EME |
|---|---|---|---|
| mean | 204 | 4500 | 3294 |
| SD | 185.7 | 2916 | 3442 |
| CV | 91.14 | 64.81 | 104.48 |
| median | 193.5 | 3283.7 | 2249.7 |
| geometric mean | 101.4 | 3735.6 | 2278.1 |

TABLE 29

Summary of renal clearance for subjects with normal hepatic function post administration of the pharmaceutical composition.

|  | Cocaine | BE | EME |
|---|---|---|---|
| Renal Clearance (L/h) | | | |
| mean | 1.790 | 4.2951 | 71.585 |
| SD | 1.644 | 2.073 | 34.550 |
| CV | 91.87 | 48.26 | 48.26 |
| median | 1.322 | 3.494 | 58.237 |
| geometric mean | 1.172 | 3.957 | 65.948 |
| Renal Clearance (mL/min) | | | |
| mean | 29.827 | 71.585 | 286.128 |
| SD | 27.403 | 34.550 | 191.157 |
| CV | 91.87 | 48.26 | 66.81 |
| median | 22.027 | 58.237 | 219.782 |
| geometric mean | 19.530 | 65.948 | 243.011 |

TABLE 30

Summary of renal clearance for subjects with hepatic impairment post administration of the pharmaceutical composition.

|  | Cocaine | BE | EME |
|---|---|---|---|
| Renal Clearance (L/h) | | | |
| mean | 0.9970 | 2.8964 | 10.8740 |
| SD | 0.9207 | 1.3875 | 4.4662 |
| CV | 92.3 | 47.9 | 41.1 |
| median | 0.9360 | 2.8680 | 9.6551 |
| geometric mean | 0.4676 | 2.5866 | 10.1852 |
| Renal Clearance (mL/min) | | | |
| mean | 16.62 | 48.27 | 181.23 |
| SD | 15.34 | 23.12 | 74.44 |
| CV | 92.3 | 47.9 | 41.1 |
| median | 15.60 | 47.80 | 160.92 |
| geometric mean | 7.79 | 43.11 | 169.75 |

Effects of Hepatic Impairment

Cocaine and its principal metabolites, BE and EME, were observed in both plasma and urine after a single intranasal exposure to the pharmaceutical composition, equivalent to 160 mg of cocaine hydrochloride, in subjects with normal hepatic function and hepatic impairment (Child-Pugh Grades B and C). Norcocaine was not measurable in the plasma of normal subjects or in 8 of 12 hepatically impaired subjects. Hepatic impairment had a minimal effect on the $C_{max}$ of cocaine. Compared to subjects with normal hepatic function, a less than 2-fold increase in geometric mean $C_{max}$ was observed for BE and EME in Grade B hepatic impairment, with no appreciable change in BE and EME $C_{max}$ observed in Grade C hepatic impairment. In subjects with Grade B hepatic impairment, AUC values for cocaine, BE, and EME were 2.4 to 2.8 times higher than in subjects with normal hepatic function. The effects of hepatic impairment on cocaine, BE, and EME were less marked in the 3 subjects with Grade C impairment than in the 9 subjects with Grade B hepatic impairment. Increased overall plasma exposures of cocaine (AUC) were consistent with observed decreases in both CL/F and CLr.

There was a minimal effect of hepatic impairment on cocaine $C_{max}$ and an increase in AUC. This is consistent with the fact that early systemic concentrations are driven by rapid uptake via the nasal mucosa, which completely bypasses the liver, while prolonged elevations in cocaine plasma concentrations after $T_{max}$ may be due to reduced hepatic elimination of drug circulating in plasma. In addition, the increases in plasma exposure of BE and EME observed in subjects with hepatic impairment were accompanied by elevated urinary recovery of the metabolites, resulting in a minimal change in CLr for these compounds. This suggests that the enhanced systemic levels of the metabolites may be due to reduced liver elimination in subjects with hepatic impairment, and is consistent with observations that BE and EME are formed in part by hepatic carboxylesterases.

The minimal effect of hepatic impairment on cocaine $C_{max}$, coupled with the low risk of cardiac effects expected in this group, suggests that dose adjustment of pharmaceutical composition should not be required in subjects with reduced hepatic function. However, based on the sustained higher exposure of cocaine in the post-absorptive phase and the potential for a cumulative increase in systemic concentrations, a second dose of pharmaceutical composition should not be administered to subjects with hepatic impairment within 24 hours of the initial dose.

Example 4

The objective of Example 4 was to assess the efficacy of the pharmaceutical composition after topical intranasal administration of a single dose in adult patients undergoing intranasal procedures.

Example 4 was a randomized, double-blind, multicenter, placebo- and dose-controlled, single-dose study in 648 adult patients undergoing a diagnostic or surgical procedure on or through the mucous membranes of one or both of the nasal cavities.

Efficacy was evaluated using pharmaceutical compositions in the form of topical aqueous solutions including, by weight, 4% and 8% cocaine hydrochloride as anesthetics for diagnostic procedures and surgeries on or through the mucous membranes of the nasal cavities (e.g., nasal/sinus endoscopy, sinusotomy, fracture nasal turbinate[s], lysis intranasal synechia, insertion of nasal septal prosthesis, biopsy intranasal, excision of nasal polyps, excision turbinate[s], removal of foreign body intranasal, septoplasty, and sinus debridement). The topical aqueous solutions used in this example included: 40 mg/mL cocaine hydrochloride, 1.25 mg/mL citric acid, 1.00 mg/mL sodium benzoate, a colorant (0.02 mg/mL D&C Yellow No. 10, 0.02 mg/mL FD&C Green No. 3), and 957.7 mg/mL water (herein referred to as "4% pharmaceutical composition"); or 80 mg/mL cocaine hydrochloride, 1.25 mg/mL citric acid, 1.00 mg/mL sodium benzoate, a colorant (0.02 mg/mL D&C Yellow No. 10, 0.02 mg/mL FD&C Green No. 3), and 917.7 mg/mL water (herein referred to as "8% pharmaceutical composition").

Example 4 consisted of a screening period performed within 14 days of a 1-day diagnostic procedure or surgery, a treatment period performed on the day of the diagnostic procedure or surgery (Day 1), and a follow-up visit (Day 8). Male and female patients≥18 years of age with the need for a diagnostic procedure or surgery on or through the nasal mucous membranes of either one or both nostrils, and who had the ability to feel pain in the anterior nasal septum and to clearly communicate the pain sensation, were enrolled in this study. Patients were randomized in a 1:3:3 ratio to placebo, 4% pharmaceutical composition (40 mg/mL cocaine hydrochloride), or 8% pharmaceutical composition (80 mg/mL cocaine hydrochloride), respectively. Patients did not receive general anesthesia.

Figure 12:
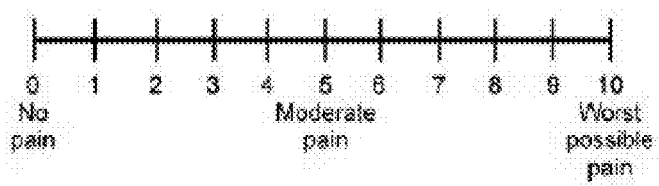
FIG. 12 shows a visual numeric rating scale for assessment of pain as used to determine analgesic success.

Immediately following drug treatment, the nasal mucous membranes were assessed for local analgesia using the Von Frey Filament Test and a Visual Numeric Rating Scale (VNRS) for patient self-reporting of pain intensity (0=no pain and 10=worst possible pain) (FIG. 12). Von Frey Filaments are a set of nylon monofilaments of increasing diameter and lengths that are attached to rods at right angles. These filaments are used to provide controlled gradients of force to assess whether or not a subject can detect pain, touch, and/or pressure at various physical locations. The range of filament sizes is designed to provide increased force and pressure in an exponential relationship.

The investigator chose the nostril for pre-procedural testing based upon the scheduled procedure. Each patient was asked to close his/her eyes to prevent any visual clues. A large Von Frey Filament (6.10; 100 g) was applied to the nasal ala, vestibule, nasal hairs, and anterior septum to help the patient discriminate between these structures. The nasal ala was gently retracted laterally with a blunt-ended, single-pronged retractor to provide easy access to the nasal septum during measurements. The filament (6.10; 100 g) was pushed, at a perpendicular angle, against the anterior nasal septum until it bent, at which time a standardized force was applied to the anterior nasal septum. The patient was then asked to rate the pain experienced using the VNRS. The investigator counseled the patient that pain and not pressure was being measured and that pressure was not to be reported as pain.

Unblinding

After the Visual Numeric Rating Scale (VNRS) pain evaluation, the study blind was broken for placebo versus pharmaceutical composition to ensure that placebo-treated patients with a VNRS score of 0 did not undergo the diagnostic or surgical procedure without anesthesia. If the placebo patients were not identified, then the procedure would have started without the opportunity for analgesia and the placebo patients would have potentially experienced significant pain that may have stalled or stopped the intended procedure or caused harm to the patient. The study blind was maintained for patients who were administered the pharmaceutical composition (4% or 8% cocaine hydrochloride). Evaluation of procedural medications confirmed that, for almost all patients, the pain control attained with the pharmaceutical composition allowed for completion of the surgical procedures without additional medication.

Efficacy Endpoints and Analyses

The primary efficacy endpoint was analgesic success. A patient was considered an analgesic success if both of the following criteria were met:

Had a score of 0 on the VNRS based on the Von Frey Filament test prior to the diagnostic procedure or surgery.

Had no need for further medication (with the exception of antibiotics or cardiac medications) during the diagnostic procedure or surgery.

Patients who had a VNRS score>0 immediately following pharmaceutical composition treatment or who needed additional medication (with the exception of antibiotics or cardiac medications) during the procedure were considered treatment failures. The percentage of patients who achieved analgesic success in the intent-to-treat (ITT) population, defined as all patients who were randomized and received pharmaceutical composition treatment, was compared between the placebo and the pharmaceutical composition test groups using a two-tailed Fisher's Exact Test at an alpha 0.05 level of significance. The primary comparison for analgesic success was between the 4% pharmaceutical composition and placebo groups. The proportion of analgesic success was also tested for the 8% pharmaceutical composition versus placebo.

To further address the potential for the impact of unblinding on the assessment of efficacy, the following additional sensitivity analyses were also conducted:

An analysis of analgesic success that only evaluated the fully blinded first component of the primary endpoint, i.e., analyzing only the patient's pain assessment using the VNRS. Success was defined as a pain score of 0. The second component of the primary endpoint was not considered in this analysis.

An analysis that included both components of the primary endpoint (VNRS and additional medication during the procedure with the exception of antibiotics or cardiac medications), but counting any patients in the pharmaceutical composition test group who received additional medication during the procedure as failures. For patients in the placebo group, the VNRS pain score of 0 was carried forward as a success regardless of whether the patient received any medication during the procedure.

To determine whether analgesic success was consistent across subgroups, the following subgroups were evaluated:

Sex (male and female)

Race (white, black, and all other races pooled)

Age (≥44 years [median] and <44 years)

Weight (≥80 kg [median] and <80 kg; <50 kg and <60 kg)

Type of procedure (nasal endoscope alone and other procedures).

All subgroup analyses were performed using the ITT population defined as all patients who were considered an analgesic success in that they achieved a VNRS score of 0=no pain, and had no need for further medication (with the exception of antibiotics or cardiac medications) during the diagnostic procedure or surgery as determined by the investigator/physician based upon his/her clinical impressions of the presence of pain or excessive bleeding.

Demographics and Baseline Characteristics

The placebo, 4% pharmaceutical composition, and 8% pharmaceutical composition treatment groups were similar with respect to age, sex, race, height, and weight (Table 31). Most of the patients were female (60.5%) and white (78.9%) with a mean age of 44.1 years (range, 17 to 86 years).

TABLE 31

Demographics and baseline characteristics of subjects that participated in Example 4.

| Characteristic | Placebo (N = 95) n (%) | 4% RX0041-002 (N = 278) n (%) | 8% RX0041-002 (N = 275) n (%) | Overall (N = 648) n (%) |
|---|---|---|---|---|
| Age (Yrs) | | | | |
| Mean | 44.9 | 42.7 | 45.3 | 44.1 |
| SD | 16.9 | 16.6 | 15.3 | 16.1 |
| Median | 46 | 42 | 45 | 44 |
| Minimum, Maximum | 18, 80 | 18, 86 | 17, 83 | 17, 86 |
| Sex | | | | |
| Female | 55 (57.9%) | 170 (61.2%) | 167 (60.7%) | 392 (60.5%) |
| Male | 40 (42.1%) | 108 (38.8%) | 108 (39.3%) | 256 (39.5%) |
| Ethnicity | | | | |
| Hispanic or Latino | 10 (10.5%) | 23 (8.3%) | 12 (4.4%) | 45 (6.9%) |
| Not Hispanic or Latino | 85 (89.5%) | 254 (91.4%) | 263 (95.6%) | 607 (92.9%) |
| Race | | | | |
| American Indian or Alaska | 0 (0.0%) | 0 (0.0%) | 1 (0.4%) | 1 (0.2%) |
| Asian | 1 (1.1%) | 1 (0.4%) | 3 (1.1%) | 5 (0.8%) |
| Black or African American | 16 (16.8%) | 49 (17.6%) | 51 (18.5%) | 116 (17.9%) |
| Other | 3 (3.2%) | 7 (2.5%) | 4 (1.5%) | 14 (2.2%) |
| White | 75 (78.9%) | 220 (79.1%) | 216 (78.5%) | 511 (78.9%) |
| Height (cm) | | | | |
| Mean | 168.73 | 167.89 | 168.47 | 168.26 |
| SD | 9.77 | 10.93 | 10.56 | 10.6 |
| Median | 170 | 167.6 | 168 | 168 |
| Minimum, Maximum | 144.7, 195.5 | 139.0, 213.3 | 132.1, 198.1 | 132.1, 213.3 |
| Weight (kg) | | | | |
| Mean | 83.69 | 81.57 | 83.94 | 82.88 |
| SD | 22.91 | 21.45 | 22.99 | 22.32 |
| Median | 81 | 79.8 | 80 | 80 |
| Minimum, Maximum | 46.0, 175.0 | 40.4, 189.0 | 45.0, 183.3 | 40.4, 189.0 |
| BMI (kg/m$^2$) | | | | |
| Mean | 29.24 | 28.92 | 29.58 | 29.25 |
| SD | 6.91 | 7.11 | 7.79 | 7.37 |
| Median | 28.40 | 27.15 | 28.10 | 27.80 |
| Minimum, Maximum | 15.5, 57.0 | 17.2, 64.5 | 16.6, 70.1 | 15.5, 70.1 |

Prior Medical History

The percentage of patients with a previous medical condition was 94.7% in the placebo group and 92.4% and 94.2% in the 4% and 8% pharmaceutical composition treatment groups, respectively. The most common previous medical conditions were allergic rhinitis (42.1%, 36.7%, and 34.8% in the placebo, 4%, and 8% pharmaceutical composition treatment groups, respectively), sinusitis (23.2%, 23.7%, and 23.0% in the placebo, 4% and 8% pharmaceutical composition treatment groups, respectively), and nasal septum deviation (20.0%, 19.8%, and 24.0% in the placebo, 4%, and 8% pharmaceutical composition treatment groups, respectively).

Prior and Concomitant Medications

Prior medications were taken by 14.7% of the placebo group, 24.0% of the 4% pharmaceutical composition treatment group, and 24.5% of the 8% pharmaceutical composition treatment group. The most common prior medication varied across the groups. Ibuprofen/Motrin (3.2%, 4.7%, and 2.5% in the placebo, 4%, and 8% pharmaceutical composition treatment groups, respectively) was the most common medication in the placebo and 4% pharmaceutical composition treatment groups. Acetaminophen with oxycodone (no patients, 1.1%, and 3.6% in the placebo, 4%, and 8% pharmaceutical composition treatment groups, respectively) was the most common prior medication in the 8% pharmaceutical composition treatment group.

Types of Intranasal Procedures

The types of intranasal procedures were well balanced across the placebo, 4% pharmaceutical composition, and 8% pharmaceutical composition treatment groups (see Table 32). The most common diagnostic or surgical procedure in each of the groups was nasal endoscopy (54.7%, 59.6%, and 60.8% in the placebo, 4% pharmaceutical composition, and 8% pharmaceutical composition groups, respectively). Other procedures performed in more than 1 patient in either the placebo or pharmaceutical composition groups included nasal laryngoscopy, nasopharyngeal laryngoscopy, nasal debridement, nasal endoscopy with debridement, intraturbinate DepoMedrol injection, laryngoscopy, transnasal esophagoscopy, turbinate reduction, nasal endoscopy with polypectomy, and sinuplasty.

TABLE 32

Diagnostic or surgical procedures.

| Procedure | Placebo (N = 95) n (%) | 4% RX0041-002 (N = 278) n (%) | 8% RX0041-002 (N = 275) n (%) |
|---|---|---|---|
| Nasal Endoscope Alone | | | |
| Nasal Endoscopy | 52 (54.7) | 169 (60.8) | 164 (59.6) |
| Other Procedures | | | |
| Nasal Laryngoscopy | 14 (14.7) | 43 (15.5) | 33 (12.0) |
| Nasopharyngeal Laryngoscopy | 12 (12.6) | 18 (6.5) | 23 (8.4) |
| Nasal Debridement | 3 (3.2) | 15 (5.4) | 19 (6.9) |
| Nasal Endoscopy with Debridement | 0 (0.0) | 9 (3.2) | 11 (4.0) |
| Intraturbinate DepoMedrol Injection | 5 (5.3) | 7 (2.5) | 7 (2.5) |
| Laryngoscopy | 3 (3.2) | 6 (2.2) | 5 (1.8) |
| Transnasal Esophagoscopy | 2 (2.1) | 2 (0.7) | 1 (0.4) |
| Turbinate Reduction | 1 (1.1) | 2 (0.7) | 3 (1.1) |
| Nasal Endoscopy with Polypectomy | 0 (0.0) | 2 (0.7) | 2 (0.7) |
| Sinuplasty | 0 (0.0) | 0 (0.0) | 2 (0.7) |
| Nasal Endoscopy and Stroboscopy | 0 (0.0) | 0 (0.0) | 1 (0.4) |
| Nasal Cauterization | 0 (0.0) | 0 (0.0) | 1 (0.4) |
| Nasal Endoscopy and Nasal Laryngoscopy | 0 (0.0) | 1 (0.4) | 0 (0.0) |
| Nasal Stroboscopy | 1 (1.1) | 0 (0.0) | 0 (0.0) |

Efficacy Results

Pain at Baseline

Pain scores at baseline were >0 in all patients in the placebo and pharmaceutical composition treatment groups, with the exception of 1 patient in the 4% pharmaceutical composition group. Additionally, the most commonly reported baseline scores were between 3 and 5, ranging up to the maximum pain score of 10 (see Table 33).

TABLE 33

Frequency Distribution of Visual Numeric Rating Scores at Baseline.

| Visual Numeric Rating Score[a] | Placebo (N = 95) n (%) | 4% RX0041-002 (N = 278) n (%) | 8% RX0041-002 (N = 275) n (%) |
|---|---|---|---|
| 0 | 0 (0.0) | 1 (0.4) | 0 (0.0) |
| 1 | 3 (3.2) | 15 (5.4) | 17 (6.2) |
| 2 | 9 (9.5) | 33 (11.9) | 40 (14.5) |
| 3 | 23 (24.2) | 62 (22.3) | 48 (17.5) |
| 4 | 10 (10.5) | 49 (17.6) | 46 (16.7) |
| 5 | 26 (27.4) | 46 (16.5) | 45 (16.4) |
| 6 | 9 (9.5) | 31 (11.2) | 29 (10.5) |
| 7 | 5 (5.3) | 22 (7.9) | 20 (7.3) |
| 8 | 8 (8.4) | 12 (4.3) | 15 (5.5) |
| 9 | 2 (2.1) | 4 (1.4) | 7 (2.5) |
| 9.5 | 0 (0.0) | 0 (0.0) | 1 (0.4) |
| 10 | 0 (0.0) | 3 (1.1) | 7 (2.5) |

[a] 0 = no pain; 5 = moderate pain; 10 = worst possible pain.

This demonstrates that the 6.10 Von Frey Filament did provide a painful stimulus and thus, was an appropriate method for assessing local anesthetic effect.

Primary Efficacy Endpoint

The primary efficacy endpoint, analgesic success in the 4% pharmaceutical composition test group was met (see Table 34). A 4% pharmaceutical composition dose significantly increased (77.3%; p<0.0001) the percentage of patients who achieved analgesic success compared with the placebo group (9.5%).

The exploratory efficacy endpoint, analgesic success in the 8% pharmaceutical composition test group, was also met. An 8% pharmaceutical composition dose increased (81.1%; p<0.0001) the percentage of patients who achieved analgesic success compared with the placebo group (9.5%). A dose response for analgesic success was observed in patients who achieved analgesic success when the pharmaceutical composition dose was increased from 4% to 8% (77.3% and 81.1%, respectively).

TABLE 34

Analgesic success rates.

| Event | Placebo (N = 95) n (%) | 4% RX0041-002 (N = 278) n (%) | 8% RX0041-002 (N = 275) n (%) |
|---|---|---|---|
| Success | 9 (9.5%) | 215 (77.3%) | 223 (81.1%) |
| Failure | 86 (90.5%) | 63 (22.7%) | 52 (18.9%) |
| P-value* | | <0.0001 | <0.0001 |

*Fisher's Exact Test. Pairwise comparison on active drug to placebo.

The higher success rates in the 8% group compared to the 4% pharmaceutical composition group were attributable to the number of patients with non-zero pain scores (62 patients in the 4% and 51 patients in 8% pharmaceutical composition treatment groups) and the number of patients who received additional medication during the procedure (4 patients in the 4% and 1 patient in the 8% pharmaceutical composition treatment groups) (see Table 35). All medications administered during the procedure were topical nasal medications. Among the 5 pharmaceutical composition treated patients who received additional procedural medications, the procedures they had were: 2 nasal endoscopy, 1 turbinate reduction, and 1 procedure unspecified in the 4% pharmaceutical composition treatment group, and 1 nasal debridement in the 8% pharmaceutical composition treatment group.

TABLE 35

Reasons for analgesic failure in the pharmaceutical composition test groups.

| | 4% RX0041-002 (N = 63) | 8% RX0041-002 (N = 52) |
|---|---|---|
| VNRS >0 immediately after study drug treatment | 62 (93.6%) | 51 (98.0%) |
| Required additional medication during the procedure[1] | 4 (6.4%) | 1 (2.0%) |

Note:
Patients could be in both categories of failure. The percentages are based on the total number of failures in each group.
[1] All medications administered during the procedure were topical nasal medications.
VNRS = visual numeric rating scale.

Figure 13:
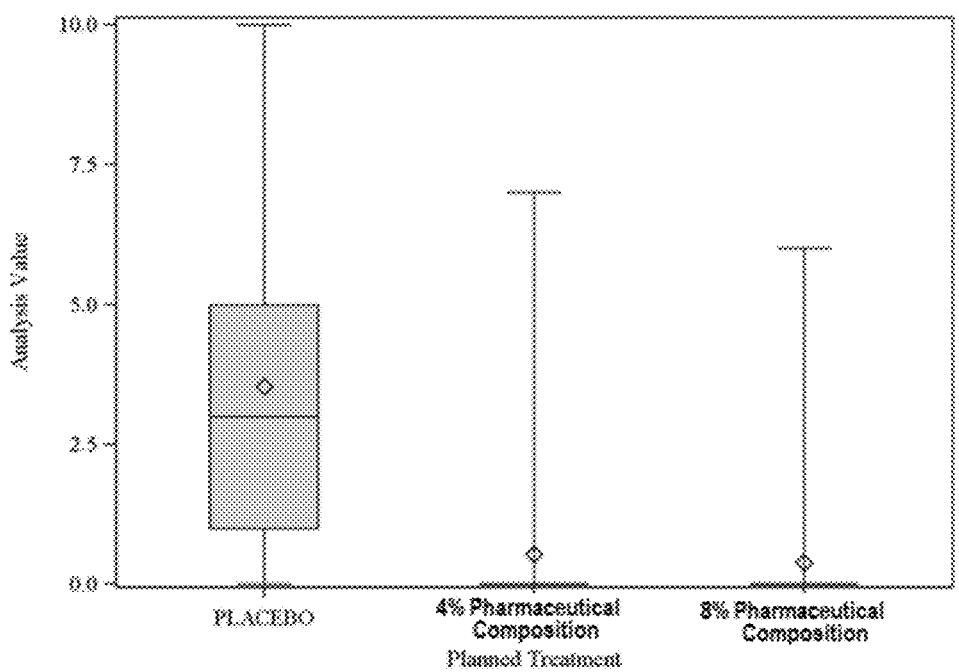
FIG. 13 is a box-and-whisker plot of analgesia data results of a Von Frey Filament Test performed on patient groups administered 4% or 8% pharmaceutical composition (40 mg/mL cocaine hydrochloride or 80 mg/mL cocaine hydrochloride, respectively) 20 minutes following pharmaceutical composition administration. The data results show the achievement of complete analgesia as measured by the Von Frey Filament Test for both patient treatment groups administered 4% or 8% pharmaceutical composition as compared to a placebo.
Figure 14:
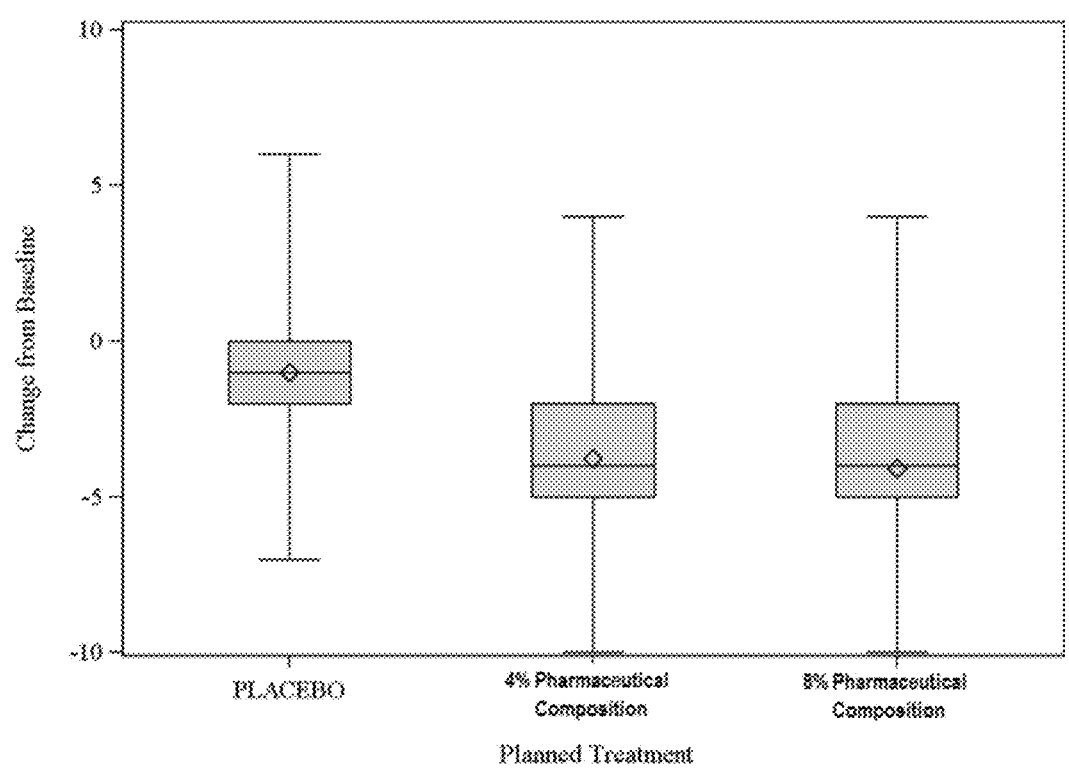
FIG. 14 is a box-and-whisker plot of change in Visual Numeric Rating Scale (VNRS) data results of the Von Frey Filament Test of FIG. 13. The data results of FIG. 14 show the change from baseline in pain score assessed using the VNRS of patient groups administered either the 4% or 8% pharmaceutical composition as compared to a placebo.

FIG. 13 shows the achievement of complete analgesia on the Von Frey Filament Test for the two pharmaceutical composition treatment groups 20 minutes after pharmaceutical composition administration. FIG. 14 shows the mean reduction in pain score and Table 36 shows the distribution of mean changes in pain scores. These data support the dose response between groups as the pharmaceutical composition dose was increased from 4% to 8%. The majority of patients in the pharmaceutical composition treatment groups had reductions in pain score (94.2% in the 4% pharmaceutical composition treatment group; and 96.0% in the 8% pharmaceutical composition treatment group; see Table 36). In both of the pharmaceutical composition treatment groups, the most common pain score reductions were −2, −3, −4 or −5. Four patients in each pharmaceutical composition treatment group had increases in pain score and 19 patients (12 and 7 patients in the 4% and 8% pharmaceutical composition treatment groups, respectively) had no change in pain score. In the placebo group, the majority of patients had little or no change in pain score from baseline.

TABLE 36

Change from baseline (screening) frequency distribution of Visual Numeric Rating Scores 20 minutes after pharmaceutical composition or placebo administration

| Visual Numeric Rating Score[a] | Placebo (N = 95) n (%) | 4% RX0041-002 (N = 278) n (%) | 8% RX0041-002 (N = 275) n (%) |
|---|---|---|---|
| −10 | 0 (0) | 3 (1.1) | 5 (1.8) |
| −9.5 | 0 (0) | 0 (0.0) | 1 (0.4) |
| −9 | 0 (0) | 3 (1.1) | 7 (2.5) |
| −8 | 0 (0) | 12 (4.3) | 13 (4.7) |
| −7 | 2 (2.1) | 15 (5.4) | 17 (6.2) |
| −6.5 | 0 (0) | 1 (0.4) | 0 (0) |
| −6 | 0 (0) | 20 (7.2) | 25 (9.1) |
| −5 | 5 (5.3) | 44 (15.8) | 42 (15.3) |
| −4 | 6 (6.3) | 43 (15.5) | 47 (17.1) |
| −3 | 10 (10.5) | 64 (23.0) | 48 (17.5) |
| −2 | 15 (15.8) | 32 (11.5) | 35 (12.7) |
| −1 | 14 (14.7) | 25 (9.0) | 24 (8.7) |
| 0 | 22 (23.2) | 12 (4.3) | 7 (2.5) |
| 1 | 11 (11.6) | 2 (0.7) | 1 (0.4) |
| 2 | 4 (4.2) | 1 (0.4) | 1 (0.4) |
| 3 | 3 (3.2) | 0 (0.0) | 1 (0.4) |
| 4 | 2 (2.1) | 1 (0.4) | 1 (0.4) |
| 6 | 1 (1.1) | 0 (0.0) | 0 (0) |

[a] 0 = no pain; 5 = moderate pain; 10 = worst possible pain.

Sensitivity Analyses

The 4% and 8% pharmaceutical composition doses also significantly increased the percentage of patients who achieved analgesic success in a sensitivity analysis that evaluated VNRS scores only (Table 37). These results are highly consistent with those shown in Table 34 and demonstrate that failure in the placebo group was largely due to persistent pain as measured with the VNRS during the fully blinded portion of the study.

TABLE 37

Sensitivity Analysis of Analgesic Success Rates (VNRS = 0 Only)

|  | Placebo (N = 95) n (%) | 4% RX0041-002 (N = 278) n (%) | 8% RX0041-002 (N = 275) n (%) |
|---|---|---|---|
| Success | 14 (14.7) | 216 (77.7) | 224 (81.5) |
| Failure | 81 (85.3) | 62 (22.3) | 51 (18.5) |
| P-value* |  | <0.0001 | <0.0001 |

*Fisher's Exact Test. Pairwise comparison on active drug to placebo.

A sensitivity analysis in which the need for additional medication following the pain assessment (Von Frey Filament) was not assessed as a failure in the placebo group, but was assessed as a failure in the pharmaceutical composition treatment groups shows that, even when biasing the analysis against the pharmaceutical composition, that the pharmaceutical composition was significantly more effective than placebo for analgesic efficacy (see Table 38).

TABLE 38

Sensitivity Analysis of Analgesic Success Rates (VNRS = 0 Only [Placebo Only])

|  | Placebo (N = 95) n (%) | 4% RX0041-002 (N = 278) n (%) | 8% RX0041-002 (N = 275) n (%) |
|---|---|---|---|
| Success | 14 (14.7) | 215 (77.3) | 223 (81.1) |
| Failure | 81 (85.3) | 63 (22.7) | 52 (18.9) |
| P-value* |  | <0.0001 | <0.0001 |

*Fisher's Exact Test. Pairwise comparison on active drug to placebo.
VNRS = visual numeric rating scale.

Subgroup Analyses

The significant analgesic success seen with 4% pharmaceutical composition versus placebo in the overall population was maintained for all subgroups (p<0.001), including males and females; Whites and Blacks; patients at least 44 years of age and less than 44 years of age; patients weighing at least 80 kg, patients weighing less than 80 kg, patients weighing less than 60 kg; and patients undergoing nasal endoscopy alone and other types of procedures (see Table 39). The two exceptions were other races (pooled) and one of the low body weight subgroups (<50 kg).

For other races pooled and patients weighing less than 50 kg, the analgesic success rates were also higher with 4% pharmaceutical composition compared with placebo, but these differences were not statistically significant because of the small number of patients in these subgroups.

The significant analgesic success seen with 8% pharmaceutical composition versus placebo in the overall population was also maintained for all of the subgroups (p<0.001), with the exception of other races pooled and patients weighing less than 50 kg.

Additionally, a dose response for analgesic success was seen in all subgroups when the pharmaceutical composition dose was increased from 4% to 8%, except for other races pooled and low body weight patients (<50 kg and <60 kg).

TABLE 39

Analgesic success rates in subgroups

|  | Placebo n/N (%) | 4% RX0041-002 n/N (%) | 8% RX0041-002 n/N (%) |
|---|---|---|---|
| Sex |  |  |  |
| Males | 3/40 (7.5) | 88/108 (81.5) | 89/108 (82.4) |
| p-value |  | <0.0001 | <0.0001 |
| Females | 6/54 (10.9) | 127/170 (74.7) | 134/167 (81.1) |
| p-value |  | <0.0001 | <0.0001 |
| Race |  |  |  |
| White | 7/75 (9.3) | 166/220 (75.5) | 175/216 (81.0) |
| p-value |  | <0.0001 | <0.0001 |
| Black | 2/16 (12.5) | 40/49 (81.6) | 43/51 (84.3) |
| p-value |  | <0.0001 | <0.0001 |
| Other races pooled | 0/4 (0) | 9/9 (100.0) | 5/8 (62.5) |
| p-value |  | 0.0014 | 0.0808 |
| Age |  |  |  |
| ≥44 years | 7/53 (13.2) | 99/134 (73.9) | 121/149 (81.2) |
| p-value |  | <0.0001 | <0.0001 |
| <44 years | 2/42 (4.8) | 116/144 (80.6) | 102/126 (81.0) |
| p-value |  | <0.0001 | <0.0001 |
| Weight |  |  |  |
| ≥80 kg | 1/49 (2.0) | 109/138 (79.0) | 112/138 (81.2) |
| p-value |  | <0.0001 | <0.0001 |
| <80 kg | 8/46 (17.4) | 106/140 (75.7) | 110/136 (80.9) |
| p-value |  | <0.0001 | <0.0001 |
| <50 kg | 1/3 (33.3) | 6/8 (75.0) | 7/9 (77.8) |
| p-value |  | 0.4909 | 0.2364 |
| <60 kg | 3/14 (21.4) | 32/40 (80.0) | 26/33 (78.8) |
| p-value |  | 0.0002 | 0.0006 |
| Type of procedure |  |  |  |
| Nasal endoscope alone | 5/52 (9.6) | 124/169 (73.4) | 129/164 (78.7) |
| p-value |  | <0.0001 | <0.0001 |
| Other procedures | 4/43 (9.3) | 91/109 (83.5)[a] | 94/111 (84.7) |
| p-value |  | <0.0001 | <0.0001 |

Summary of Example 4 Results

Example 4 was conducted at 9 study sites with 648 patients. The number of patients randomized per study site ranged from 5 to 112, which equates to 0.8% and 17.3% of the patient population, respectively. Thus, Example 4 is a large, multicenter study in which no single study site provided a large fraction of the patients. Example 4 showed consistent analgesic success rates for two doses of pharmaceutical composition versus placebo both in the overall population and across subgroups defined by sex, race, age, and weight. Thus, the efficacy findings for the pharmaceutical composition are internally consistent and generalizable.

The p values for the comparison of analgesic success in the 4% pharmaceutical composition versus placebo group were low (p<0.0001 using two-tailed Fisher's exact test at $\alpha=0.05$). This p value is highly inconsistent with the null hypothesis of no treatment effect for the pharmaceutical composition.

Analysis of Clinical Information Relevant to Dosing Recommendations

The minimum effective dose of the two pharmaceutical composition doses in Example 4 for topical nasal anesthesia during diagnostic procedures on or through the mucous membranes of the nasal cavities is 4%. This is supported by the following evidence in Example 4:

Statistically significant and clinically meaningful increases in the percentage of patients who achieved analgesic success (the primary efficacy endpoint) were provided by a topical nasal dose of 4% pharmaceutical composition compared to placebo.

Consistent and reproducible results were shown for 4% pharmaceutical composition across all subgroups, including groups defined by sex, race, age, and weight.

A dose response in the percentage of patients, both overall and in the subgroups, who achieved analgesic success was seen when the pharmaceutical composition dose was increased from 4% to 8%.

Persistence of Efficacy

The pharmaceutical composition provided persistent local nasal anesthesia with essentially no need for additional analgesic medication during diagnostic and surgical procedures on or through the mucous membranes of the nasal cavities. The pharmaceutical composition has a half-life of approximately 1 hour.

Efficacy Conclusions

Results from Example 4 show that the pharmaceutical composition is effective for the induction of local anesthesia across a wide range of diagnostic procedures and surgeries on or through the mucous membranes of the nasal cavities. Example 4 included patients undergoing a wide range of procedures and thus, provides an adequate representation of the rhinologic procedures which may require nasal topical anesthetics to alleviate pain.

The efficacy endpoint in Example 4, analgesic success, was met. Topical nasal doses of 4% pharmaceutical composition (40 mg/mL cocaine hydrochloride) provided statistically significant and clinically meaningful increases in the percentage of patients who achieved analgesic success. The sensitivity analyses supported the findings for efficacy. Additionally, consistent and reproducible results were shown for the 4% pharmaceutical composition across subgroups, including groups defined by sex, race, age, and weight. Topical nasal doses of 8% pharmaceutical composition (80 mg/mL cocaine hydrochloride) also provided statistically significant and clinically meaningful increases in the percentage of patients who achieved analgesic success. A dose response was seen for analgesic success between groups when the dose was increased from 4% to 8% pharmaceutical composition; this dose response was seen in the overall population, the sensitivity analyses, and across most subgroups, except for those with a small number of patients.

Example 4 is adequate to support the effectiveness of the pharmaceutical composition because it was a large multi-center study, the efficacy findings in the study are internally consistent and generalizable, a dose-response was shown, and the low p values (p<0.0001) in favor of the pharmaceutical composition for analgesic success are highly inconsistent with the null hypothesis of no treatment effect.

Example 5

Figure 15A:
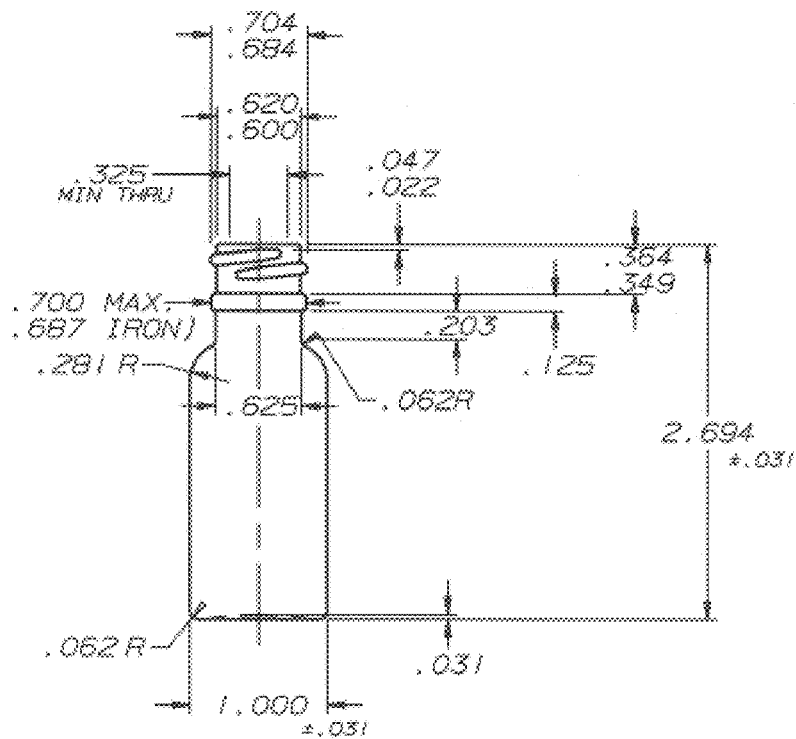
FIGS. 15A and 15B, respectively, are side and sectional views of a 0.5 oz. amber glass container used to contain a pharmaceutical composition, as described herein.
Figure 15B:
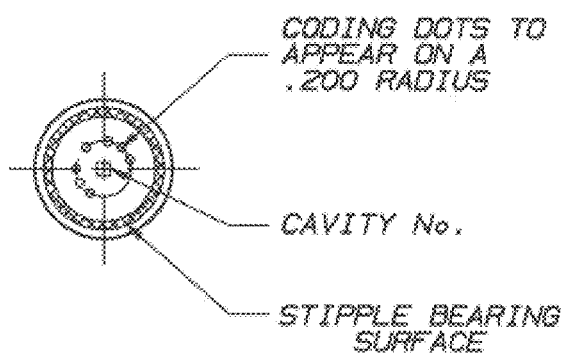
Figure 16A:
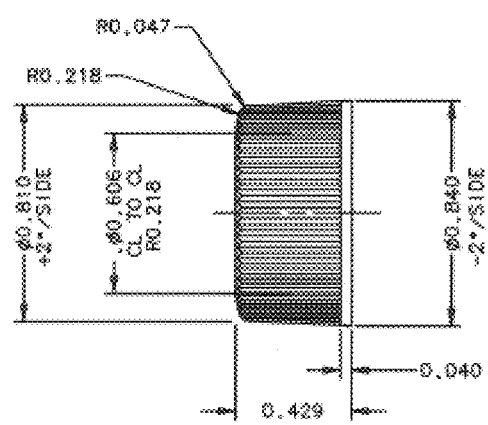
Figure 16B:
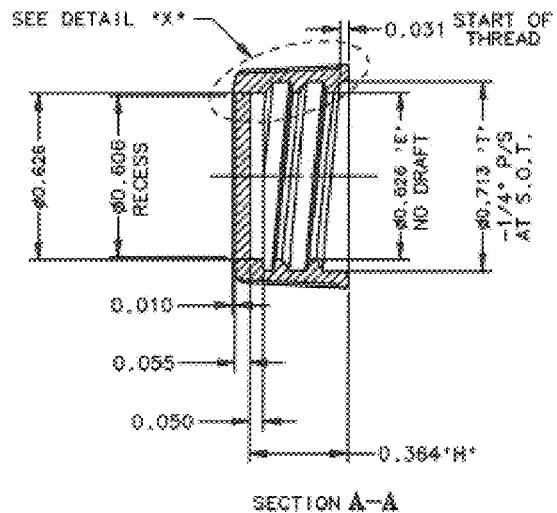
Figure 16C:
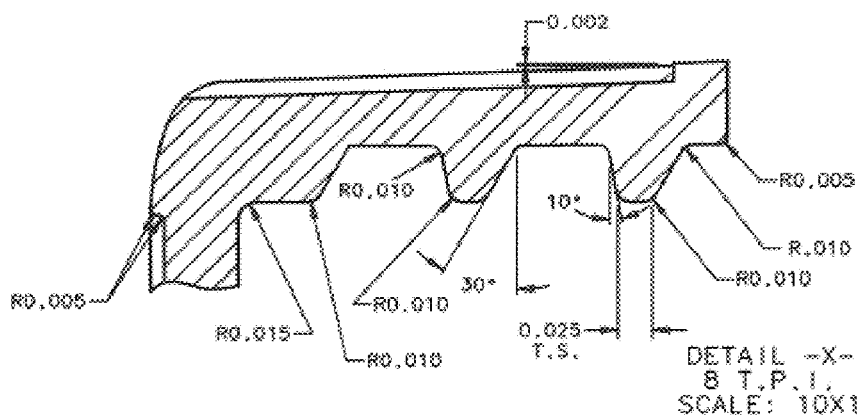

Stability studies were conducted on pharmaceutical compositions in a container closure system. The pharmaceutical compositions were aqueous solutions having the composition of the 4% and 8% cocaine hydrochloride solutions described in Example 4. The container closure system used to contain the 4% cocaine hydrochloride pharmaceutical composition consisted of a 0.5 oz. amber glass bottle (depicted in FIGS. 15A and 15B) with a ribbed closure (depicted in FIGS. 16A-16C) containing a foam liner. Aspects of the container closure system are presented in Table 40.

TABLE 40

Container closure system for pharmaceutical composition containing 4% cocaine hydrochloride.

| Container Closure | Manufacturer |
| --- | --- |
| Bottle: 0.5 oz boston round, amber glass bottle | Gerresheimer Essenr GmbH Primary Packaging Glass |
| Closure: 18-mm/400 ribbed closure | Amcor Rigid Plastics USA, Inc. |
| Liner: F-217 foam Liner | Tri-Seal International, Inc. |

The amber glass bottle used was a 0.5 oz. boston round, amber glass bottle, made of amber, Type III molded glass. The observed spectral transmission for the glass bottle did not exceed 10% at any wavelength in the range of 290 nm to 450 nm.

The ribbed closure (FIGS. 16A-16C) was made of white polypropylene. The foam liner of was made of three-ply coextruded material including a foamed low density polyethylene core between two solid layers of low density polyethylene. The foam liner was manufactured by Tri-Seal, International, Inc., Blauvel, NY, U.S.A.

Three stability studies were conducted on the stability of the 4% cocaine hydrochloride pharmaceutical compositions. The stability studies involved the following testing periods and conditions:

20 months under long term conditions (25° C.±2° C. and 60%±5% relative humidity).

6 months under accelerated conditions (40° C.±2° C. and 75%±5% relative humidity).

12 months under intermediate conditions (30° C.±2° C. and 65%±5% relative humidity).

A long-term stability study of the pharmaceutical composition contained in the closure system was conducted over a period of 20 months to determine the rate of physical or chemical degradation of the pharmaceutical composition including 4% cocaine hydrochloride.

All long-term stability samples (each sample containing 4 mL of the pharmaceutical composition including 40 mg/mL cocaine hydrochloride, batch lot S35900113) were placed upright or inverted in an environmental chamber and maintained in an upright or inverted position during the stability study. All of the containers were maintained at 25° C.±2° C. and 60%±5% relative humidity conditions, uninterrupted, (except for the adding or withdrawal of test samples) for a period of twenty months. Samples were removed from conditions at the specified time point and tested for pH, preservative content, related substances, methanol content, microbial limits at the required time point, and cocaine hydrochloride content. Storage of the stability samples was completed using a calibrated environmental chamber. Testing of the stability samples was completed using High Pressure Liquid Chromatography.

Shelf life of the 4% cocaine hydrochloride pharmaceutical composition was estimated to be at least 20 months at ambient conditions, based upon the long term (20 months) stability assay results shown in Table 41 and FIGS. 17 and 18, which are described below. One batch lot of 4% pharmaceutical composition (4 mL containing 40 mg/mL cocaine hydrochloride, batch lot S35900113) was tested in both upright and inverted container orientations over the long term stability conditions of 25±2° C. and 60±5% relative humidity for a period of 20 months. Both assays showed that greater than 90 percent of the cocaine hydrochloride was retained in the pharmaceutical composition over the course of the long term 20 month stability assay.

Figure 17:
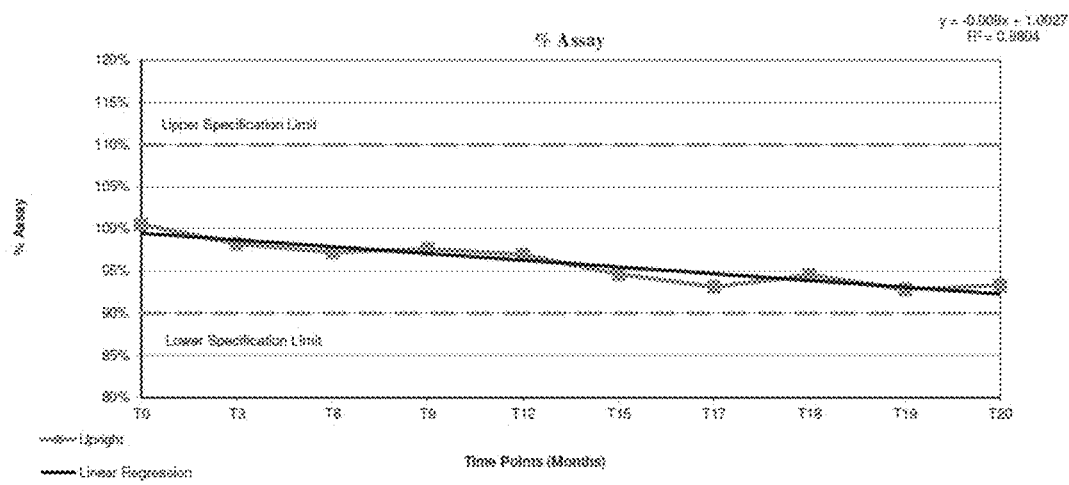
FIG. 17 is a plot of the cocaine hydrochloride assay percentage as a function of time for a pharmaceutical composition (batch lot S35900113) stored in an upright container over a 20-month period at 25° C.±2° C. and 60%±5% relative humidity, thereby providing an assessment of the shelf life stability of the pharmaceutical composition.

FIG. 17 is a plot of the percent detectable cocaine hydrochloride versus time for the 4 mL filled upright container of the 4% cocaine hydrochloride pharmaceutical composition (40 mg/mL cocaine hydrochloride), stored under the long term stability conditions of 25±2° C. and 60±5% relative humidity over 20 months.

Figure 18:
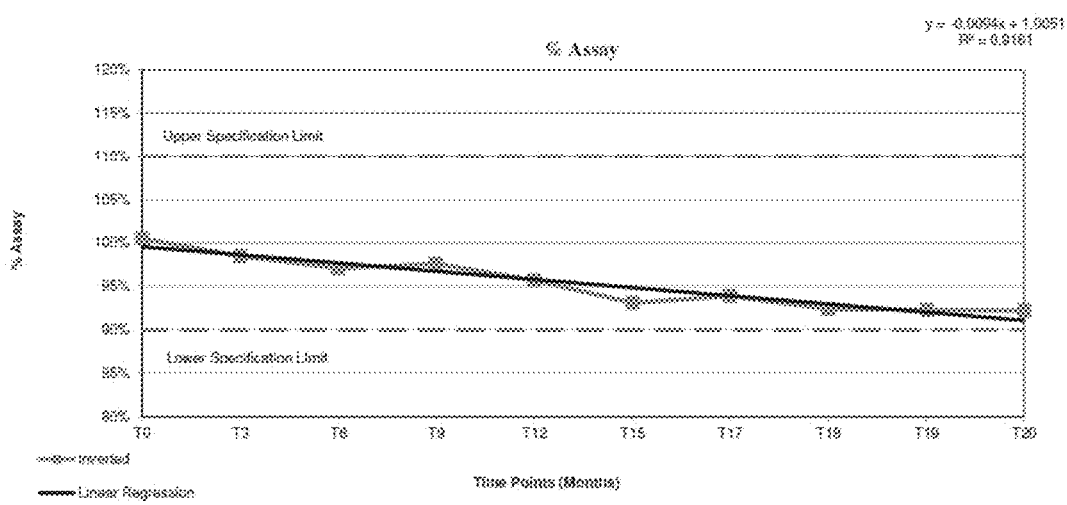
FIG. 18 is a plot of the cocaine hydrochloride assay percentage as a function of time for a pharmaceutical composition (batch lot S35900113) stored in an inverted container over a 20-month period at 25° C.±2° C. and 60%±5% relative humidity, thereby providing an assessment of the shelf life stability of the pharmaceutical composition.

FIG. 18 is a plot of the percent detectable cocaine hydrochloride versus time for the 4 mL filled inverted container of the 4% cocaine hydrochloride pharmaceutical composition (40 mg/mL cocaine hydrochloride), stored under the long term stability conditions of 25±2° C. and 60±5% relative humidity over 20 months.

Table 41 reports the long-term stability data for the pharmaceutical composition samples tested in Example 5.

specified time point and tested for pH, preservative content, related substances, methanol content, microbial limits at the required time point, and cocaine hydrochloride content. Storage of the stability samples was completed using a calibrated environmental chamber. Testing of the stability samples was completed using High Pressure Liquid Chromatography.

Shelf life of the 4% cocaine hydrochloride pharmaceutical composition was estimated at approximately 6 months at the accelerated stability conditions, based upon the short term (6 months) stability assay results shown in Table 42 and FIGS. 19 and 20, which are described below. Both upright and inverted container assays showed greater than 85 percent of

TABLE 41

Long-term conditions stability data results for the pharmaceutical composition including 4% cocaine hydrochloride in a 0.5 oz. bottle at 25° C. ± 2° C. and 60% ± 5% relative humidity over a period of 20 months.

| Test | Specification | Orientation | T = 0 | T = 6 | T = 12 | T = 15 | T = 18 | T = 20 |
|---|---|---|---|---|---|---|---|---|
| Assay | cocaine | Upright | 100.5% | 97.2% | 96.9% | 94.6% | 94.5% | 93.3% |
|  | hydrochloride | Inverted | 100.5% | 97.1% | 95.7% | 93.1% | 92.4% | 92.2% |
| Preservative | sodium | Upright | 0.100% | 0.103% | 0.112% | 0.116% | 0.118% | 0.125% |
| Content | benzoate | Inverted | 0.100% | 0.102% | 0.109% | 0.114% | 0.117% | 0.124% |
| pH | 2.0-4.0 | Upright | 3.5 | 3.1 | 2.9 | 2.8 | 2.6 | 2.7 |
|  |  | Inverted | 3.5 | 3.1 | 2.9 | 2.8 | 2.7 | 2.7 |
| Related | benzoyl | Upright | 0.1% | 2.3% | 4.3% | 5.0% | 5.8% | 6.5% |
| Substances | ecgonine | Inverted | 0.1% | 2.3% | 4.3% | 4.9% | 5.7% | 6.4% |
|  | unspecified | Upright | <0.1% | <0.1% | <0.1% | <0.1% | <0.1% | <0.1% |
|  | impurities | Inverted | <0.1% | <0.1% | <0.1% | <0.1% | <0.1% | <0.1% |
|  | Total | Upright | 0.1% | 2.3% | 4.3% | 5.0% | 5.8% | 6.5% |
|  |  | Inverted | 0.1% | 2.3% | 4.3% | 4.9% | 5.7% | 6.4% |
| Microbial | Total Aerobic | Upright | conforms | N/A | conforms | conforms | conforms | conforms |
| Limits | Microbial Counts (NMT 100 cfu/g) | Inverted | conforms | N/A | conforms | conforms | conforms | conforms |
|  | Total Combined Mold and Yeast (NMT 10 cfu/g) | Upright | conforms | N/A | conforms | conforms | conforms | conforms |
|  |  | Inverted | conforms | N/A | conforms | conforms | conforms | conforms |
|  | Pseudomonas aeruginosa (Absent) | Upright | conforms | N/A | conforms | conforms | conforms | conforms |
|  |  | Inverted | conforms | N/A | conforms | conforms | conforms | conforms |
|  | Staphylococcus aureus (Absent) | Upright | conforms | N/A | conforms | conforms | conforms | conforms |
|  |  | Inverted | conforms | N/A | conforms | conforms | conforms | conforms |
| Methanol Content (ppm) |  | Upright | N/A | 188 | 215 | 245 | 284 | 394 |
|  |  | Inverted | N/A | 189 | 203 | 238 | 281 | 396 |

N/A—not available

N/A—not available

An accelerated stability study of the same manufactured batch lot (batch lot S35900113) pharmaceutical composition as used in the long-term stability study described above (and contained in the closure system) was conducted over a period of 6 months to determine the rate of physical or chemical degradation of the pharmaceutical composition including 4% cocaine hydrochloride over accelerated environmental conditions.

All accelerated stability samples (each sample containing 4 mL of the pharmaceutical composition including 40 mg/mL cocaine hydrochloride) were placed upright or inverted in an environmental chamber and maintained in an upright or inverted position during the stability study. All of the containers were maintained at 40° C.±2° C. and 75%±5% relative humidity, uninterrupted, (except for the adding or withdrawal of test samples) for a period of six months. Samples were removed from conditions at the the cocaine hydrochloride was retained in the pharmaceutical composition over the course of the accelerated term stability assay for 6 months.

Figure 19:
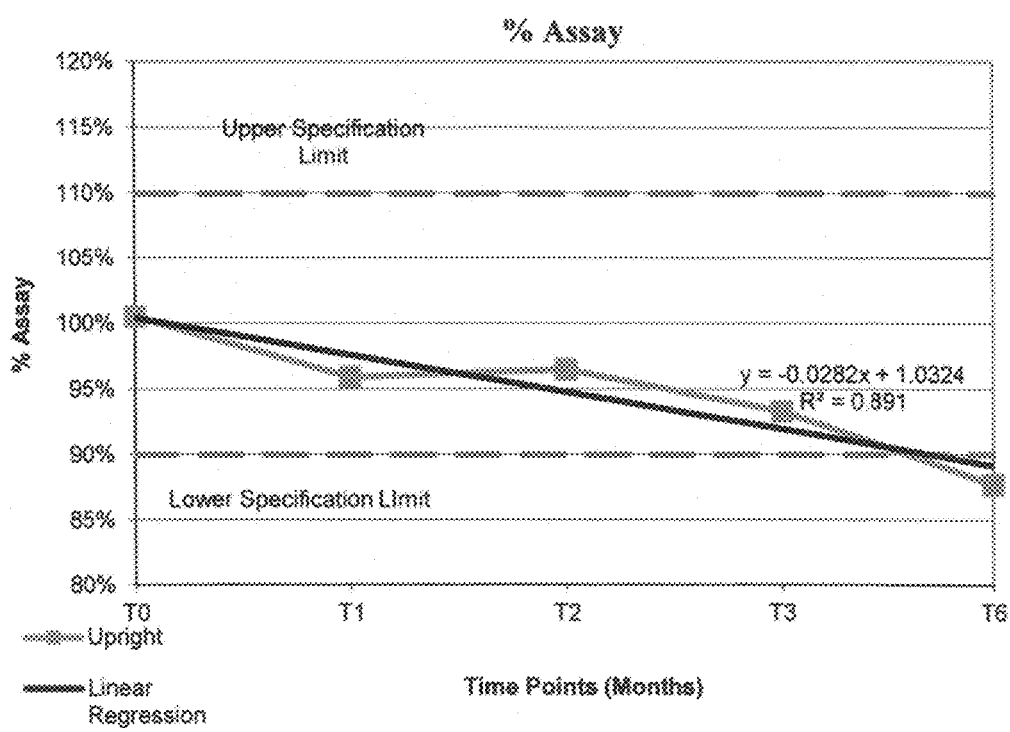
FIG. 19 is a plot of the cocaine hydrochloride assay percentage as a function of time for a pharmaceutical composition (batch lot S35900113) stored in an upright container over a 6-month period at 40° C.±2° C. and 75%±5% relative humidity, thereby providing an assessment of the shelf life stability of the pharmaceutical composition.

FIG. 19 is a plot of the percent detectable cocaine hydrochloride versus time for the 4 mL filled upright container of the 4% cocaine hydrochloride pharmaceutical composition (40 mg/mL cocaine hydrochloride) over a 6-month period at 40° C.±2° C. and 75%±5% relative humidity, thereby providing an assessment of the shelf life stability of the pharmaceutical composition.

Figure 20:
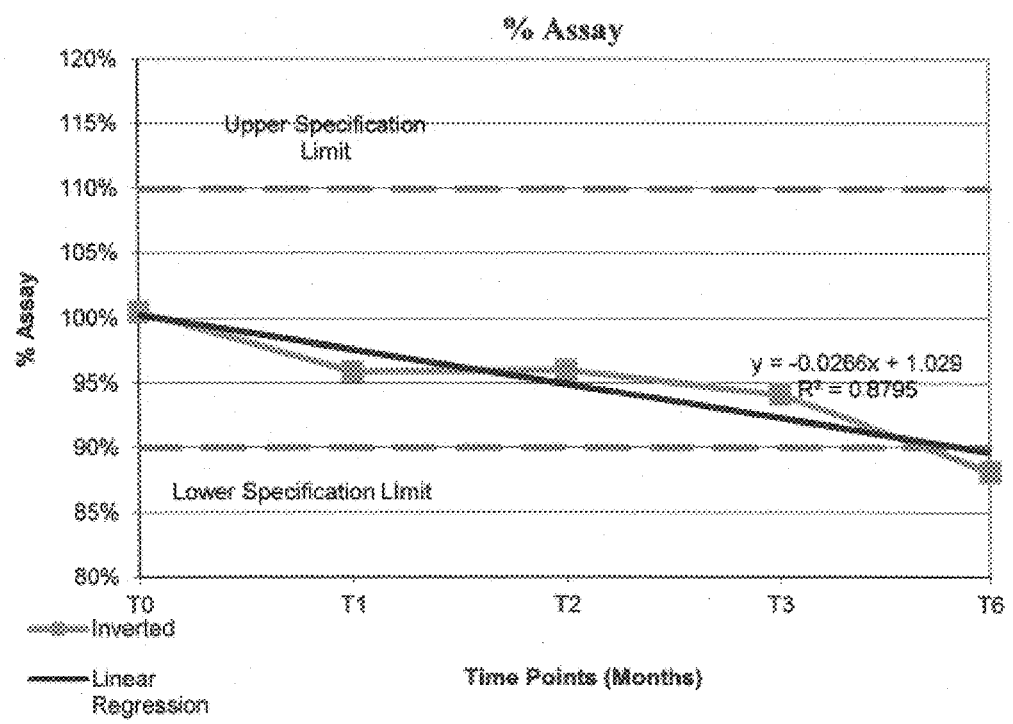
FIG. 20 is a plot of the cocaine hydrochloride assay percentage as a function of time for a pharmaceutical composition (batch lot S35900113) stored in an inverted container over a 6-month period at 40° C.±2° C. and 75%±5% relative humidity, thereby providing an assessment of the shelf life stability of the pharmaceutical composition.

FIG. 20 is a plot of the percent detectable cocaine hydrochloride versus time for the 4 mL filled inverted container of the 4% cocaine hydrochloride pharmaceutical composition (40 mg/mL cocaine hydrochloride) over a 6-month period at 40° C.±2° C. and 75%±5% relative humidity, thereby providing an assessment of the shelf life stability of the pharmaceutical composition.

Table 42 reports the accelerated conditions stability data for the samples tested in Example 5.

TABLE 42

Accelerated conditions stability data results for the pharmaceutical composition including 4% cocaine hydrochloride in a 0.5 oz. bottle at 40 ± 2° C. and 75% ± 5% relative humidity over a period of 4 months.

| Test | Specification | Orientation | Time (months) | | | | |
|---|---|---|---|---|---|---|---|
| | | | T = 0 | T = 1 | T = 3 | T = 4 | T = 6 |
| Assay | cocaine | Upright | 100.5% | 95.9% | 93.3% | 92.0% | 87.7% |
| | hydrochloride | Inverted | 100.5% | 95.9% | 94.1% | 92.3% | 88.1% |
| Preservative | sodium | Upright | 0.100% | 0.103% | 0.114% | 0.120% | 0.147% |
| Content | benzoate | Inverted | 0.100% | 0.102% | 0.114% | 0.120% | 0.145% |
| pH | 2.0-4.0 | Upright | 3.5 | 3.2 | 2.8 | 2.7 | 2.5 |
| | | Inverted | 3.5 | 3.2 | 2.8 | 2.7 | 2.5 |
| Related | benzoyl | Upright | 0.1% | 2.0% | 4.9% | 5.9% | 8.8% |
| Substances | ecgonine | Inverted | 0.1% | 1.9% | 5.0% | 5.9% | 8.7% |
| | unspecified | Upright | <0.1% | <0.1% | <0.1% | <0.1% | <0.1% |
| | impurities | Inverted | <0.1% | <0.1% | <0.1% | <0.1% | <0.1% |
| | Total | Upright | 0.1% | 2.0% | 4.9% | 5.9% | 8.8% |
| | | Inverted | 0.1% | 1.9% | 5.0% | N/A | 8.7% |
| Microbial | Total Aerobic | Upright | conforms | N/A | N/A | N/A | conforms |
| Limits | Microbial Counts (NMT 100 fu/g) | Inverted | conforms | N/A | N/A | N/A | conforms |
| | Total Combined Mold and Yeast (NMT 10 cfu/g) | Upright | conforms | N/A | N/A | N/A | conforms |
| | | Inverted | conforms | N/A | N/A | N/A | conforms |
| | Pseudomonas aeruginosa (Absent) | Upright | conforms | N/A | N/A | N/A | conforms |
| | | Inverted | conforms | N/A | N/A | N/A | conforms |
| | Staphylococcus aureus (Absent) | Upright | conforms | N/A | N/A | N/A | conforms |
| | | Inverted | conforms | N/A | N/A | N/A | conforms |
| Methanol Content (ppm) | | Upright | N/A | N/A | N/A | <50 | 114 |
| | | Inverted | N/A | N/A | N/A | <50 | 111 |

N/A—not available

N/A—not available

An intermediate stability study of the same manufactured batch lot (batch lot S35900113) pharmaceutical composition as used in the long-term and accelerated stability studies described above (and contained in the closure system) was conducted over a period of 12 months to determine the rate of physical or chemical degradation of the pharmaceutical composition including 4% cocaine hydrochloride over intermediate environmental conditions.

All intermediate stability samples (each sample containing 4 mL of the pharmaceutical composition including 40 mg/mL cocaine hydrochloride) were placed upright or inverted in an environmental chamber and maintained in an upright or inverted position during the stability study. All of the containers were maintained at 30° C.±2° C. and 65%±5% relative humidity, uninterrupted, (except for the adding or withdrawal of test samples) for a period of twelve months. Samples were removed from conditions at the specified time point and tested for pH, preservative content, related substances, methanol content, microbial limits at the required time point, and cocaine hydrochloride content. Storage of the stability samples was completed using a calibrated environmental chamber. Testing of the stability samples was completed using High Pressure Liquid Chromatography.

Shelf life of the 4% cocaine hydrochloride pharmaceutical composition was estimated at approximately 12 months at intermediate conditions, based upon the 12-month term stability assay results shown in Table 43 and FIGS. 21 and 22, which are described below. Both upright and inverted container assays show greater than 90 percent of the cocaine hydrochloride was retained in the pharmaceutical composition over the course of the intermediate term stability assay for 12 months.

Figure 21:
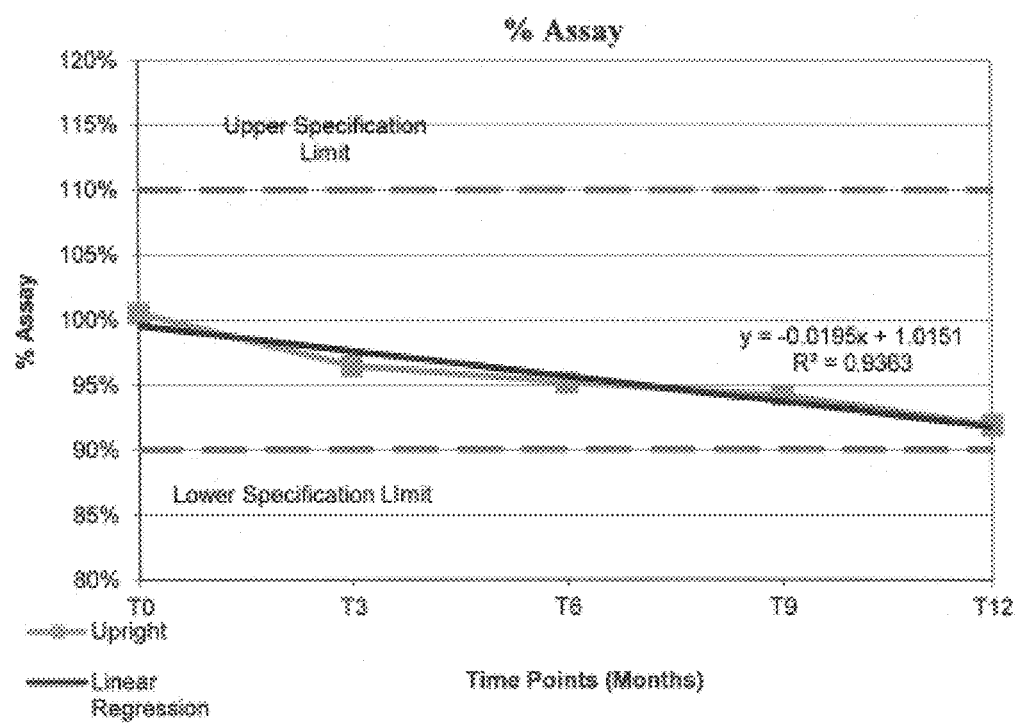
FIG. 21 is a plot of the cocaine hydrochloride assay percentage as a function of time for a pharmaceutical composition (batch lot S35900113) stored in an upright container over a 12-month period at 30° C.±2° C. and 65%±5% relative humidity, thereby providing an assessment of the shelf life stability of the pharmaceutical composition.

FIG. 21 is a plot of the percent detectable cocaine hydrochloride versus time for the 4 mL filled upright container of the 4% cocaine hydrochloride pharmaceutical composition (40 mg/mL cocaine hydrochloride) over a 12-month period at 30° C.±2° C. and 65%±5% relative humidity, thereby providing an assessment of the shelf life stability of the pharmaceutical composition.

Figure 22:
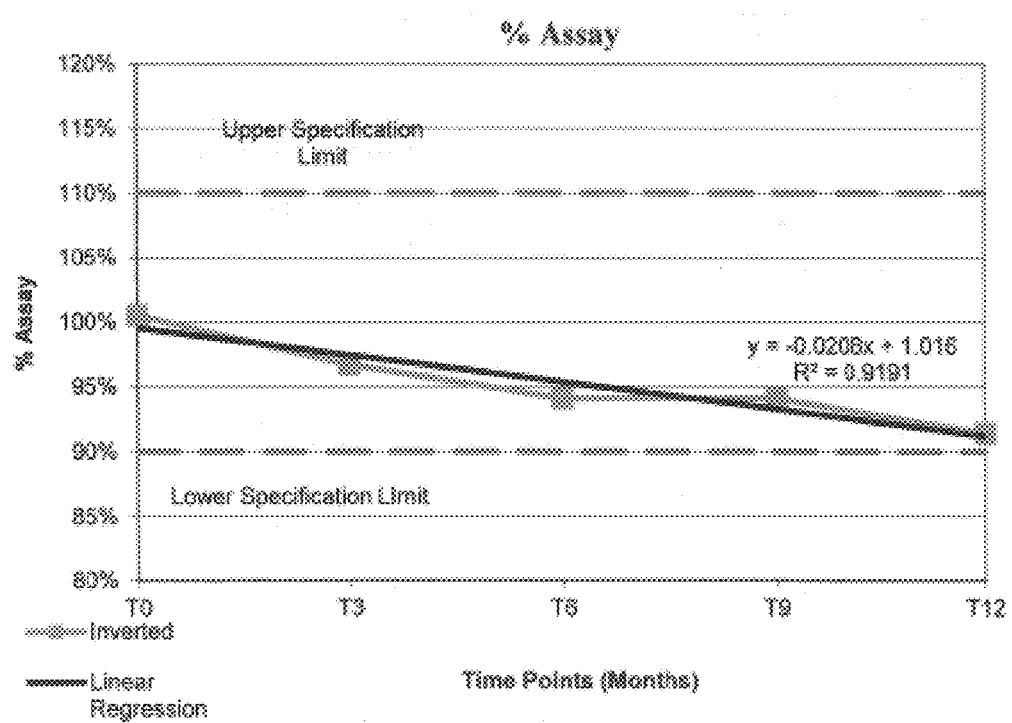
FIG. 22 is a plot of the cocaine hydrochloride assay percentage as a function of time for a pharmaceutical composition (batch lot S35900113) stored in an inverted container over a 12-month period at 30° C.±2° C. and 65%±5% relative humidity, thereby providing an assessment of the shelf life stability of the pharmaceutical composition.

FIG. 22 is a plot of the percent detectable cocaine hydrochloride versus time for the 4 mL filled inverted container of the 4% cocaine hydrochloride pharmaceutical composition (40 mg/mL cocaine hydrochloride) over a 12-month period at 30° C.±2° C. and 65%±5% relative humidity, thereby providing an assessment of the shelf life stability of the pharmaceutical composition.

Table 43 reports the intermediate conditions stability data for the samples tested in Example 5.

TABLE 43

Intermediate conditions stability data results for the pharmaceutical composition cocaine hydrochloride, 40 mg/mL, in a 0.5 oz. bottle at 30 ± 2° C. and 65 ± 5% relative humidity over a period of 12 months.

| Test | Specification | Orientation | T = 0 | T = 3 | T = 6 | T = 9 | T = 12 |
|---|---|---|---|---|---|---|---|
| Assay | cocaine | Upright | 100.5% | 96.5% | 95.2% | 94.2% | 91.9% |
| | hydrochloride | Inverted | 100.5% | 96.7% | 94.1% | 94.1% | 91.4% |
| Preservative | sodium | Upright | 0.100% | 0.104% | 0.111% | 0.119% | 0.129% |
| Content | benzoate | Inverted | 0.100% | 0.103% | 0.109% | 0.118% | 0.128% |
| pH | 2.0-4.0 | Upright | 3.5 | 3.1 | 2.8 | 2.6 | 2.7 |
| | | Inverted | 3.5 | 3.1 | 2.8 | 2.6 | 2.7 |
| Related | benzoyl | Upright | 0.1% | 2.5% | 4.1% | 5.5% | 7.1% |
| Substances | ecgonine | Inverted | 0.1% | 2.5% | 4.0% | 5.5% | 7.1% |
| | unspecified | Upright | <0.1% | <0.1% | <0.1% | <0.1% | <0.1% |
| | impurities | Inverted | <0.1% | <0.1% | <0.1% | <0.1% | <0.1% |
| | Total | Upright | 0.1% | 2.5% | 4.1% | 5.5% | 7.1% |
| | | Inverted | 0.1% | 2.5% | 4.0% | 5.5% | 7.1% |
| Microbial | Total Aerobic | Upright | conforms | N/A | N/A | N/A | conforms |
| Limits | Microbial Counts (NMT 100 cfu/g) | Inverted | conforms | N/A | N/A | N/A | conforms |
| | Total Combined | Upright | conforms | N/A | N/A | N/A | conforms |
| | Mold and Yeast (NMT 10 cfu/g) | Inverted | conforms | N/A | N/A | N/A | conforms |
| | Pseudomonas | Upright | conforms | N/A | N/A | N/A | conforms |
| | aeruginosa (Absent) | Inverted | conforms | N/A | N/A | N/A | conforms |
| | Staphylococcus | Upright | conforms | N/A | N/A | N/A | conforms |
| | aureus (Absent) | Inverted | conforms | N/A | N/A | N/A | conforms |
| Methanol Content (ppm) | | Upright | N/A | N/A | 429 | 250 | 343 |
| | | Inverted | N/A | N/A | 429 | 251 | 343 |

N/A—not available

N/A—not available

Stability data for the pharmaceutical composition including cocaine hydrochloride, 80 mg/mL, was completed up to a 12 month time point for long-term stability conditions. Table 44 shows the results of the 12 month long-term conditions stability study.

Stability data for 4% cocaine hydrochloride pharmaceutical composition was completed up to the 12 month time point for long-term stability conditions. Table 45 shows the results of the 12 month long-term conditions stability study.

TABLE 44

Long-term conditions stability data results for the pharmaceutical composition, cocaine hydrochloride, 80 mg/mL, in a 0.5 oz. bottle at 25 ± 2° C. and 60 ± 5% relative humidity over 12 months.

| Test | Specification | | Orientation | T = 0 | T = 12 |
|---|---|---|---|---|---|
| Assay | cocaine hydrochloride | | Upright | 100.0% | 96.1% |
| | | | Inverted | 100.0% | 96.1% |
| Preservative content | sodium benzoate | | Upright | 0.100% | 0.126% |
| | | | Inverted | 0.100% | 0.125% |
| pH | 2.0-4.0 | | Upright | 3.5 | 2.5 |
| | | | Inverted | 3.5 | 2.6 |
| Related Substances | Benzoyl Ecgonine | | Upright/Inverted | 0.1%/0.1% | 3.7%/3.8% |
| | Unspecified impurities | | Upright/Inverted | <0.1%/<0.1% | <0.1%/<0.1% |
| | Total | | Upright/Inverted | 0.1%/0.1% | 3.7%/3.8% |
| Microbial Limits | Total Aerobic Microbial Counts | NMT 100 cfu/g | Upright | conforms | conforms |
| | | | Inverted | conforms | conforms |
| | Total Combined Mold and Yeast Counts | NMT 10 cfu/g | Upright | conforms | conforms |
| | | | Inverted | conforms | conforms |
| | Pseudomonas aeruginosa | Absent | Upright | conforms | conforms |
| | | | Inverted | conforms | conforms |
| | Staphylococcus aureus | Absent | Upright | conforms | conforms |
| | | | Inverted | conforms | conforms |
| | Methanol Content | | Upright | 22 ppm | 366 ppm |
| | | | Inverted | 22 ppm | 355 ppm |

NMT—not more than, NLT—not less than, NA—not available

TABLE 45

Long-term conditions stability data results for the pharmaceutical composition, cocaine hydrochloride, 40 mg/mL, (batch lot S35900115) in a 0.5 oz. bottle at 25 ± 2° C. and 60 ± 5% relative humidity over 12 months.

| | | | Time (month) | |
|---|---|---|---|---|
| Test | Specification | Orientation | T = 0 | T = 12 |
| Assay | cocaine hydrochloride | Upright | 100.8% | 92.7% |
| | | Inverted | 100.8% | 93.2% |
| Preservative content | sodium benzoate | Upright | 0.099% | 0.111% |
| | | Inverted | 0.099% | 0.109% |
| pH | 2.0-4.0 | Upright | 3.6 | 3.0 |
| | | Inverted | 3.6 | 3.0 |
| Related Substances | Benzoyl Ecgonine | Upright/Inverted | 0.1%/0.1% | 4.3%/4.3% |
| | Unspecified impurities | Upright/Inverted | <0.1%/<0.1% | <0.1%/<0.1% |
| | Total | Upright/Inverted | 0.1%/0.1% | 4.3%/4.3% |
| Microbial Limits | Total Aerobic Microbial Counts | NMT 100 cfu/g | Upright | conforms | conforms |
| | | | Inverted | conforms | conforms |
| | Total Combined Mold and Yeast Counts | NMT 10 cfu/g | Upright | conforms | conforms |
| | | | Inverted | conforms | conforms |
| | *Pseudomonas aeruginosa* | Absent | Upright | conforms | conforms |
| | | | Inverted | conforms | conforms |
| | *Staphylococcus aureus* | Absent | Upright | conforms | conforms |
| | | | Inverted | conforms | conforms |
| Methanol Content | | | Upright | <37 ppm | 189 ppm |
| | | | Inverted | <37 ppm | 192 ppm |

NMT—not more than, NLT—not less than, NA—not available

Example 6

A stability study was conducted on 4% and 8% cocaine hydrochloride pharmaceutical compositions as described in Example 4 stored in the container closure system used in Example 5.

Three studies were conducted on the stability of the 4% and 8% cocaine hydrochloride pharmaceutical compositions. The stability studies involved the following compositions, testing periods and conditions:
  4% cocaine hydrochloride, 24 months under refrigerated conditions (5° C.±2° C.).
  8% cocaine hydrochloride, 24 months under refrigerated conditions (5° C.±2° C.).
  8% cocaine hydrochloride, 21 months under long term conditions (25° C.±2° C. and 60%±5% relative humidity).

A stability study of the pharmaceutical composition contained in the closure system was conducted over a period of 24 months at refrigerated conditions to determine the rate of physical or chemical degradation of the pharmaceutical composition including 4% cocaine hydrochloride.

All refrigerated stability samples (each sample containing 4 mL of the pharmaceutical composition including 40 mg/mL cocaine hydrochloride, lot C35900114A) were placed upright or inverted in an environmental chamber and maintained in an upright or inverted position during the stability study. All of the containers were maintained at 5° C.±2° C., uninterrupted, (except for the adding or withdrawal of test samples) for a period of twenty four months. Samples were removed from the indicated conditions at the specified time point and tested for pH, preservative content, related substances, methanol content, microbial limits at the required time point, and cocaine hydrochloride content. Storage of the stability samples was completed using a calibrated environmental chamber. Testing of the stability samples was completed using High Pressure Liquid Chromatography.

Shelf life of the 4% cocaine hydrochloride pharmaceutical composition was estimated to be at least 24 months at the refrigerated conditions used, based upon the 24-month term stability assay results shown in Table 46 and FIGS. 23 and 24, which are described below. Both upright and inverted container assays showed that greater than 95 percent of the cocaine hydrochloride was retained in the pharmaceutical composition over the course of the refrigerated stability assay for 24 months.

TABLE 46

Refrigerated conditions stability data results for the pharmaceutical composition including 40 mg/mL cocaine hydrochloride in a 0.5 oz. bottle at 5° C. ± 2° C. over a period of 20 months. (Lot C35900114A)

| | | | Time (months) | | | | | |
|---|---|---|---|---|---|---|---|---|
| Test | Specification | Orientation | T = 0 | T = 6 | T = 12 | T = 18 | T = 21 | T = 24 |
| Assay | cocaine hydrochloride | Upright | 99.2% | 102.4% | 99.6% | 99.5% | 100.1% | 99.4% |
| | | Inverted | 99.2% | 102.2% | 100.9% | 99.3% | 99.9% | 99.6% |
| Preservative Content | sodium benzoate | Upright | 0.100% | 0.102% | 0.102% | 0.102% | 0.102% | 0.103% |
| | | Inverted | 0.100% | 0.101% | 0.101% | 0.102% | 0.101% | 0.103% |
| pH | 2.0-4.0 | Upright | 3.5 | 3.4 | 3.4 | 3.4 | 3.4 | 3.4 |
| | | Inverted | 3.5 | 3.4 | 3.4 | 3.4 | 3.4 | 3.4 |

TABLE 46-continued

Refrigerated conditions stability data results for the pharmaceutical composition including 40 mg/mL cocaine hydrochloride in a 0.5 oz. bottle at 5° C. ± 2° C. over a period of 20 months. (Lot C35900114A)

| Test | Specification | Orientation | T = 0 | T = 6 | T = 12 | T = 18 | T = 21 | T = 24 |
|---|---|---|---|---|---|---|---|---|
| Related Substances | benzoyl ecgonine | Upright | 0.2% | 0.4% | 0.6% | 0.8% | 1.0% | 1.0% |
| | | Inverted | 0.2% | 0.4% | 0.6% | 0.8% | 1.0% | 1.0% |
| | unspecified impurities | Upright | <0.1% | <0.1% | <0.1% | <0.1% | <0.1% | <0.1% |
| | | Inverted | <0.1% | <0.1% | <0.1% | <0.1% | <0.1% | <0.1% |
| | Total | Upright | 0.2% | 0.4% | 0.6% | 0.8% | 1.0% | 1.0% |
| | | Inverted | 0.2% | 0.4% | 0.6% | 0.8% | 1.0% | 1.0% |
| Microbial Limits | Total Aerobic Microbial Counts (NMT 100 cfu/g) | Upright | conforms | N/A | conforms | conforms | conforms | conforms |
| | | Inverted | conforms | N/A | conforms | conforms | conforms | conforms |
| | Total Combined Mold and Yeast (NMT 10 cfu/g) | Upright | conforms | N/A | conforms | conforms | conforms | conforms |
| | | Inverted | conforms | N/A | conforms | conforms | conforms | conforms |
| | Pseudomonas aeruginosa (Absent) | Upright | conforms | N/A | conforms | conforms | conforms | conforms |
| | | Inverted | conforms | N/A | conforms | conforms | conforms | conforms |
| | Staphylococcus aureus (Absent) | Upright | conforms | N/A | conforms | conforms | conforms | conforms |
| | | Inverted | conforms | N/A | conforms | conforms | conforms | conforms |
| Methanol Content (ppm) | | Upright | 13 | <37 | <37 | 38 | 52 | 50 |
| | | Inverted | 13 | <37 | <37 | <37 | 54 | 49 |

Figure 23:
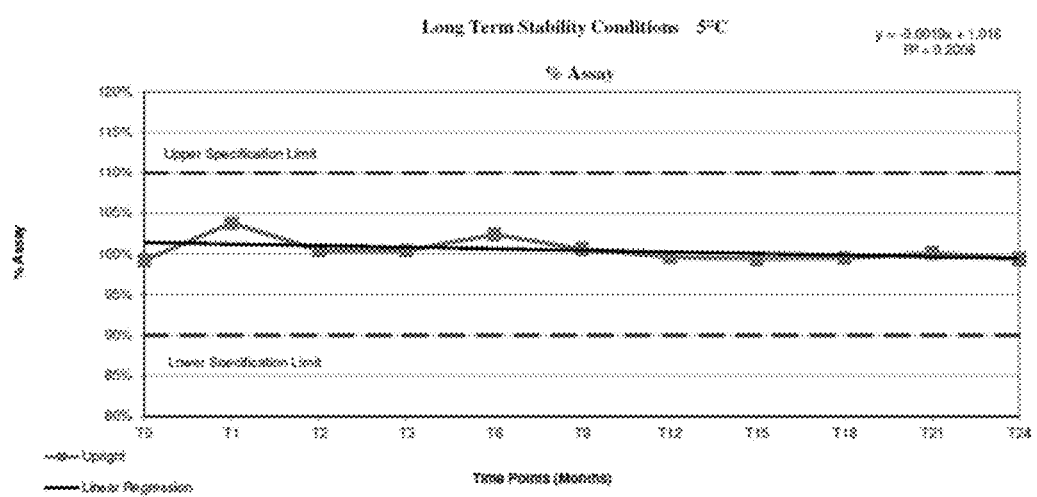
FIG. 23 is a plot of the cocaine hydrochloride assay percentage as a function of time for a pharmaceutical composition (batch lot C35900114A) stored in an upright container over a 24-month period at 5° C.±2° C., thereby providing an assessment of the shelf life stability of the pharmaceutical composition under refrigerated conditions.

FIG. 23 is a plot of the percent detectable cocaine hydrochloride versus time for the 4 mL filled upright container of the 4% cocaine hydrochloride pharmaceutical composition (40 mg/mL cocaine hydrochloride, lot C35900114A) over a 24-month period at 5° C.±2° C.

Figure 24:
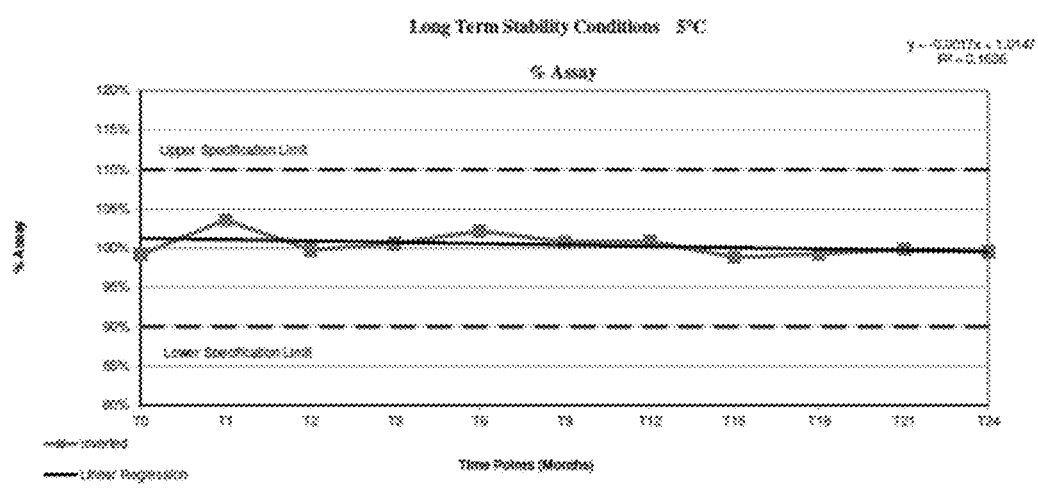
FIG. 24 is a plot of the cocaine hydrochloride assay percentage as a function of time for a pharmaceutical composition (batch lot C35900114A) stored in an inverted container over a 24-month period at 5° C.±2° C., thereby providing an assessment of the shelf life stability of the pharmaceutical composition under refrigerated conditions.

FIG. 24 is a plot of the percent detectable cocaine hydrochloride versus time for the 4 mL filled inverted container of the 4% cocaine hydrochloride pharmaceutical composition (40 mg/mL cocaine hydrochloride, lot C35900114A) over a 24-month period at 5° C.±2° C.

A refrigerated long term stability study of the pharmaceutical composition including 8% cocaine hydrochloride (batch lot S36000214A) contained in the same closure system as used in the stability studies described above was conducted over a period of 24 months to determine the rate of physical or chemical degradation of the pharmaceutical composition when stored under refrigerated environmental conditions.

All refrigerated stability samples (each sample containing 4 mL of the pharmaceutical composition including 80 mg/mL cocaine hydrochloride) were placed upright or inverted in an environmental chamber and maintained in an upright or inverted position during the stability study. All of the containers were maintained at 5° C.±2° C., uninterrupted, (except for the adding or withdrawal of test samples) for a period of twenty four months. Samples were removed from conditions at the specified time point and tested for pH, preservative content, related substances, methanol content, microbial limits at the required time point, and cocaine hydrochloride content. Storage of the stability samples was completed using a calibrated environmental chamber. Testing of the stability samples was completed using High Pressure Liquid Chromatography.

Shelf life of the 8% cocaine hydrochloride pharmaceutical composition was estimated to be at least 24 months at refrigerated conditions, based upon the 24-month term stability assay results shown in Table 47. Both upright and inverted container assays show greater than 95 percent of the cocaine hydrochloride was retained in the pharmaceutical composition over the course of the refrigerated stability assay for 24 months.

TABLE 47

Refrigerated conditions stability data results for the pharmaceutical composition including 80 mg/mL cocaine hydrochloride in a 0.5 oz. bottle at 5° C. ± 2° C. over a period of 24 months. (Lot S36000214A)

| Test | Specification | Orientation | T = 0 | T = 6 | T = 12 | T = 18 | T = 21 | T = 24 |
|---|---|---|---|---|---|---|---|---|
| Assay | cocaine hydrochloride | Upright | 102.1% | 102.2% | 101.1% | 100.4% | 101.9% | 100.5% |
| | | Inverted | 102.1% | 102.3% | 101.4% | 99.6% | 102.0% | 100.2% |
| Preservative Content | sodium benzoate | Upright | 0.097% | 0.099% | 0.101% | 0.101% | 0.103% | 0.103% |
| | | Inverted | 0.097% | 0.099% | 0.100% | 0.100% | 0.103% | 0.103% |
| pH | 2.0-4.0 | Upright | 3.4 | 3.5 | 3.4 | 3.4 | 3.3 | 3.3 |
| | | Inverted | 3.4 | 3.5 | 3.4 | 3.4 | 3.3 | 3.3 |
| Related Substances | benzoyl ecgonine | Upright | 0.1% | 0.3% | 0.5% | 0.7% | 0.8% | 0.9% |
| | | Inverted | 0.1% | 0.3% | 0.5% | 0.7% | 0.8% | 0.9% |
| | unspecified impurities | Upright | <0.1% | <0.1% | 0.1% @ RRT 1.16 | 0.1% @ RRT 1.16 | <0.1% | 0.1% @ RRT 1.16 |

TABLE 47-continued

Refrigerated conditions stability data results for the pharmaceutical composition including 80 mg/mL cocaine hydrochloride in a 0.5 oz. bottle at 5° C. ± 2° C. over a period of 24 months. (Lot S36000214A)

| Test | Specification | Orientation | T = 0 | T = 6 | T = 12 | T = 18 | T = 21 | T = 24 |
|---|---|---|---|---|---|---|---|---|
| | | Inverted | <0.1% | <0.1% | 0.1% @ RRT 1.16 | 0.1% @ RRT 1.16 | <0.1% | 0.1% RRT 1.16 |
| | Total | Upright | 0.1% | 0.3% | 0.6% | 0.8% | 0.8% | 0.9% |
| | | Inverted | 0.1% | 0.3% | 0.6% | 0.7% | 0.8% | 0.9% |
| Microbial Limits | Total Aerobic Microbial Counts (NMT 100 cfu/g) | Upright | conforms | N/A | conforms | conforms | conforms | conforms |
| | | Inverted | conforms | N/A | conforms | conforms | conforms | conforms |
| | Total Combined Mold and Yeast (NMT 10 cfu/g) | Upright | conforms | N/A | conforms | conforms | conforms | conforms |
| | | Inverted | conforms | N/A | conforms | conforms | conforms | conforms |
| | Pseudomonas aeruginosa (Absent) | Upright | conforms | N/A | conforms | conforms | conforms | conforms |
| | | Inverted | conforms | N/A | conforms | conforms | conforms | conforms |
| | Staphylococcus aureus (Absent) | Upright | conforms | N/A | conforms | conforms | conforms | conforms |
| | | Inverted | conforms | N/A | conforms | conforms | conforms | conforms |
| Methanol Content (ppm) | | Upright | 12 | 37 | 51 | 124 | 82 | 87 |
| | | Inverted | 12 | <37 | 49 | 77 | 82 | 81 |

RRT: relative retention time.

A long term stability study of the pharmaceutical composition (lot S36000214A) contained in the same closure system as used in the stability studies described above was conducted over a period of 21 months to determine the rate of physical or chemical degradation of the pharmaceutical composition including 8% cocaine hydrochloride over long term environmental conditions.

All stability samples (each sample containing 4 mL of the pharmaceutical composition including 80 mg/mL cocaine hydrochloride) were placed upright or inverted in an environmental chamber and maintained in an upright or inverted position during the stability study. All of the containers were maintained at 25° C.±2° C. and 60%±5% relative humidity, uninterrupted, (except for the adding or withdrawal of test samples) for a period of twenty one months. Samples were removed from conditions at the specified time point and tested for pH, preservative content, related substances, methanol content, microbial limits at the required time point, and cocaine hydrochloride content. Storage of the stability samples was completed using a calibrated environmental chamber. Testing of the stability samples was completed using High Pressure Liquid Chromatography.

Shelf life of the 8% cocaine hydrochloride pharmaceutical composition was estimated at approximately 21 months at long term conditions, based upon the 21-month term stability assay results shown in Table 48. Both upright and inverted container assays show greater than 85 percent of the cocaine hydrochloride was retained in the pharmaceutical composition over the course of the long term stability assay for 21 months.

TABLE 48

Long term condition stability data results for the pharmaceutical composition including 80 mg/mL cocaine hydrochloride in a 0.5 oz. bottle at 25° C. ± 2° C. and 60% ± 5% relative humidity over a period of 21 months. (Lot S36000214A)

| Test | Specification | Orientation | T = 0 | T = 6 | T = 12 | T = 15 | T = 18 | T = 21 |
|---|---|---|---|---|---|---|---|---|
| Assay | cocaine hydrochloride | Upright | 102.1% | 99.5% | 96.3% | 94.0% | 93.5% | 93.1% |
| | | Inverted | 102.1% | 99.5% | 97.2% | 94.3% | 92.9% | 91.9% |
| Preservative Content | sodium benzoate | Upright | 0.097% | 0.109% | 0.124% | 0.135% | 0.148% | 0.166% |
| | | Inverted | 0.097% | 0.107% | 0.123% | 0.133% | 0.146% | 0.163% |
| pH | 2.0-4.0 | Upright | 3.4 | 2.9 | 2.6 | 2.5 | 2.4 | 2.3 |
| | | Inverted | 3.4 | 2.9 | 2.6 | 2.5 | 2.4 | 2.3 |
| Related Substances | benzoyl ecgonine | Upright | 0.1% | 2.1% | 3.7% | 4.7% | 5.6% | 6.6% |
| | | Inverted | 0.1% | 2.0% | 3.8% | 4.7% | 5.5% | 6.6% |
| | unspecified impurities | Upright | <0.1% | <0.1% | 0.1% @ RRT 1.16 | 0.1% @ RRT 1.16 | 0.1% @ RRT 1.16 | <0.1% |
| | | Inverted | <0.1% | <0.1% | 0.1% @ RRT 1.16 | 0.1% @ RRT 1.16 | 0.1% @ RRT 1.16 | <0.1% |
| | Total | Upright | 0.1% | 2.1% | 3.8% | 4.7% | 5.6% | 6.6% |
| | | Inverted | 0.1% | 2.0% | 3.8% | 4.7% | 5.6% | 6.6% |

TABLE 48-continued

Long term condition stability data results for the pharmaceutical composition including 80 mg/mL cocaine hydrochloride in a 0.5 oz. bottle at 25° C. ± 2° C. and 60% ± 5% relative humidity over a period of 21 months. (Lot S36000214A)

| Test | Specification | Orientation | T = 0 | T = 6 | T = 12 | T = 15 | T = 18 | T = 21 |
|---|---|---|---|---|---|---|---|---|
| Microbial Limits | Total Aerobic Microbial Counts | Upright | conforms | conforms | conforms | conforms | conforms | conforms |
| | | Inverted | conforms | conforms | conforms | conforms | conforms | conforms |
| | Total Combined Mold and Yeast | Upright | conforms | conforms | conforms | conforms | conforms | conforms |
| | | Inverted | conforms | conforms | conforms | conforms | conforms | conforms |
| | Pseudomonas aeruginosa | Upright | conforms | conforms | conforms | conforms | conforms | conforms |
| | | Inverted | conforms | conforms | conforms | conforms | conforms | conforms |
| | Staphylococcus aureus | Upright | conforms | conforms | conforms | conforms | conforms | conforms |
| | | Inverted | conforms | conforms | conforms | conforms | conforms | conforms |
| Methanol Content (ppm) | | Upright | 12 | 185 | 347 | 420 | 442 | 604 |
| | | Inverted | 12 | 181 | 353 | 430 | 460 | 598 |

Example 7

A stability study was conducted on the 4% cocaine hydrochloride pharmaceutical composition as described in Example 4 stored in the container closure system used in Example 5 to determine the rate of physical and chemical degradation under the influence of environmental factors such as temperature and humidity.

Two studies were conducted to demonstrate the stability of the 4% cocaine hydrochloride pharmaceutical composition. The stability studies involved the following testing periods and conditions:

20 months under long term conditions (25° C.±2° C. and 60%±5% relative humidity).

6 months under accelerated conditions (40° C.±2° C. and 75%±5% relative humidity).

A long-term stability study of the pharmaceutical composition contained in the closure system was conducted over a period of 20 months to determine the rate of physical or chemical degradation of the pharmaceutical composition including 4% cocaine hydrochloride.

All long-term stability samples (each sample containing 4 mL of the pharmaceutical composition including 40 mg/mL cocaine hydrochloride, batch lot S35900115A) were placed upright or inverted in an environmental chamber and maintained in an upright or inverted position during the stability study. All of the containers were maintained at 25° C.±2° C. and 60%±5% relative humidity conditions, uninterrupted, (except for the adding or withdrawal of test samples) for a period of twenty months. Samples were removed from conditions at the specified time point and tested for pH, preservative content, related substances, methanol content, microbial limits at the required time point, leachables, antimicrobial effectiveness, and cocaine hydrochloride content. Storage of the stability samples was completed using a calibrated environmental chamber. Testing of the stability samples was completed using High Pressure Liquid Chromatography.

Shelf life of the 4% cocaine hydrochloride pharmaceutical composition was estimated to be at least 20 months at ambient conditions, based upon the long term (20 months) stability assay results shown in Table 49 and FIGS. 25 and 26, which are described below. One batch lot of 4% pharmaceutical composition (4 mL containing 40 mg/mL cocaine hydrochloride, batch lot S35900115A) was tested in both upright and inverted container orientation over the long term stability conditions of 25±2° C. and 60±5% relative humidity for a period of 20 months. Both assays showed that greater than 90 percent of the cocaine hydrochloride was retained in the pharmaceutical composition over the course of the long term 20 month stability assay.

Figure 25:
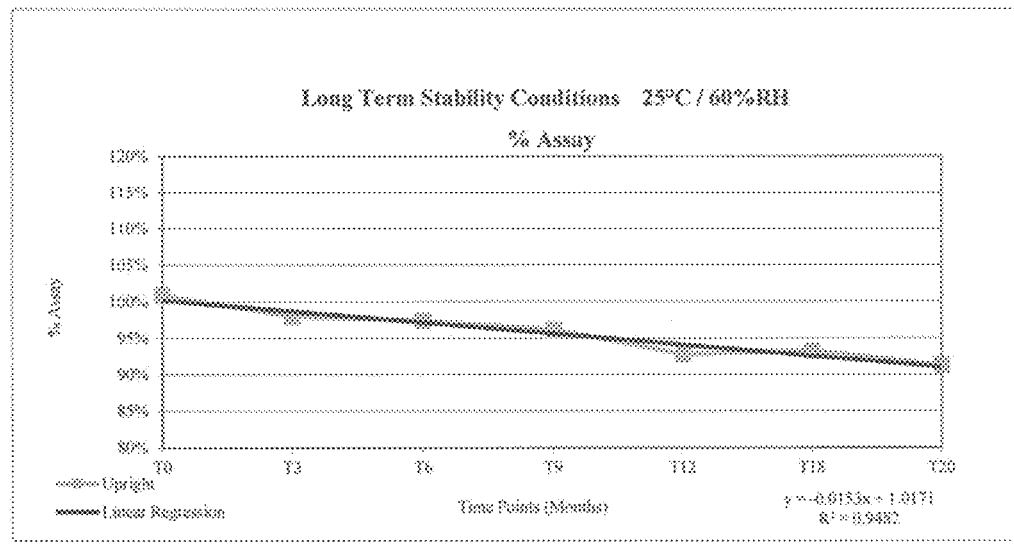
FIG. 25 is a plot of the cocaine hydrochloride assay percentage as a function of time for a pharmaceutical composition (batch lot S35900115A) stored in an upright container over a 20-month period at 25° C.±2° C. and 60%±5° C. relative humidity, thereby providing an assessment of the shelf life stability of the pharmaceutical composition under ambient conditions.

FIG. 25 is a plot of the percent detectable cocaine hydrochloride versus time for the 4 mL filled upright container of the 4% cocaine hydrochloride pharmaceutical composition (40 mg/mL cocaine hydrochloride), stored under the long term stability conditions of 25±2° C. and 60±5% relative humidity over 20 months.

Figure 26:
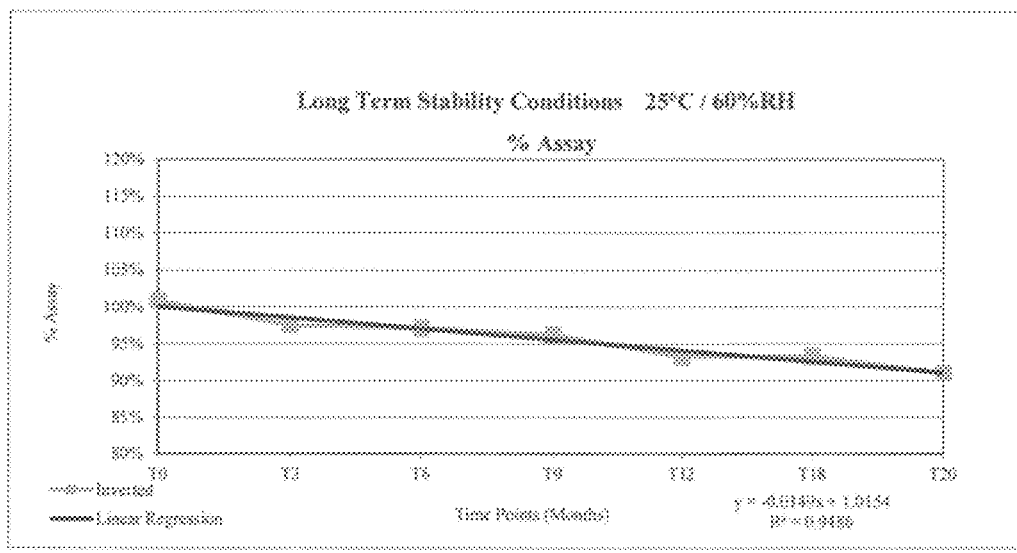
FIG. 26 is a plot of the cocaine hydrochloride assay percentage as a function of time for a pharmaceutical composition (batch lot S35900115A) stored in an inverted container over a 20-month period at 25° C.±2° C. and 60%±5° C. relative humidity, thereby providing an assessment of the shelf life stability of the pharmaceutical composition under ambient conditions.

FIG. 26 is a plot of the percent detectable cocaine hydrochloride versus time for the 4 mL filled inverted container of the 4% cocaine hydrochloride pharmaceutical composition (40 mg/mL cocaine hydrochloride), stored under the long term stability conditions of 25±2° C. and 60±5% relative humidity over 20 months.

The 4% cocaine hydrochloride pharmaceutical composition (4 mL containing 40 mg/mL cocaine hydrochloride, batch lot S35900115A) maintained a pH above 2.5 for at least 20 months at ambient conditions, based upon the long term (20 months) stability assay results shown in Table 49 and FIGS. 27 and 28, which are described below.

Figure 27:
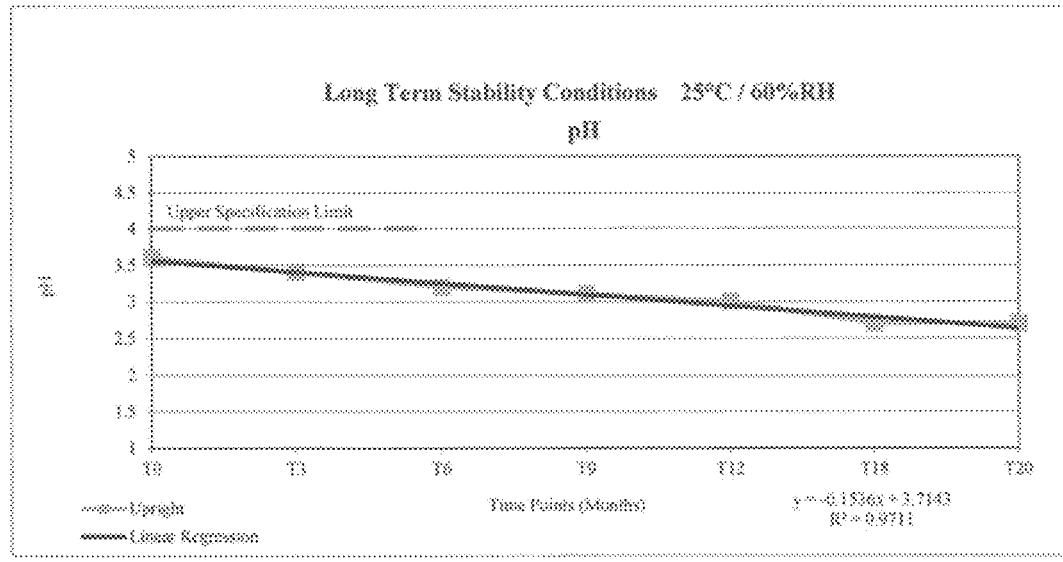
FIG. 27 is a plot of the pH as a function of time for a pharmaceutical composition (batch lot S35900115A) stored in an upright container over a 20-month period at 25° C.±2° C. and 60%±5° C. relative humidity, thereby providing an assessment of the shelf life stability of the pharmaceutical composition under ambient conditions.

FIG. 27 is a plot of the pH versus time for the 4 mL filled upright container of the 4% cocaine hydrochloride pharmaceutical composition (40 mg/mL cocaine hydrochloride), stored under the long term stability conditions of 25±2° C. and 60±5% relative humidity over 20 months.

Figure 28:
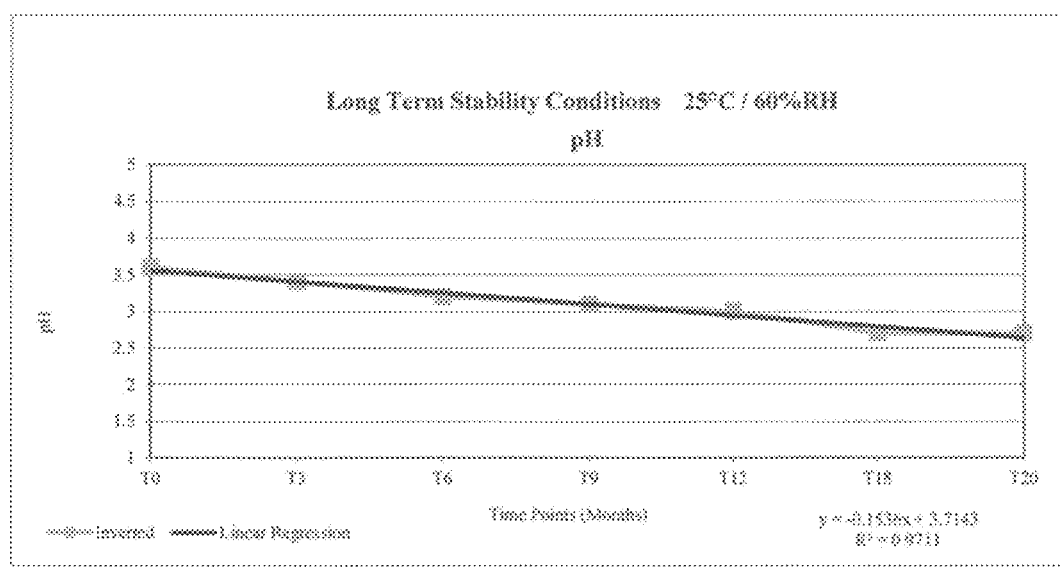
FIG. 28 is a plot of the pH as a function of time for a pharmaceutical composition (batch lot S35900115A) stored in an inverted container over a 20-month period at 25° C.±2° C. and 60%±5° C. relative humidity, thereby providing an assessment of the shelf life stability of the pharmaceutical composition under ambient conditions.

FIG. 28 is a plot of the pH versus time for the 4 mL filled inverted container of the 4% cocaine hydrochloride pharmaceutical composition (40 mg/mL cocaine hydrochloride), stored under the long term stability conditions of 25±2° C. and 60±5% relative humidity over 20 months.

The percent preservatives within the 4% cocaine hydrochloride pharmaceutical composition (4 mL containing 40 mg/mL cocaine hydrochloride, batch lot S35900115A) increased less than 0.03% over the course of 20 months at ambient conditions, based upon the long term (20 months) stability assay results shown in Table 49 and FIGS. 29 and 30, which are described below.

Figure 29:
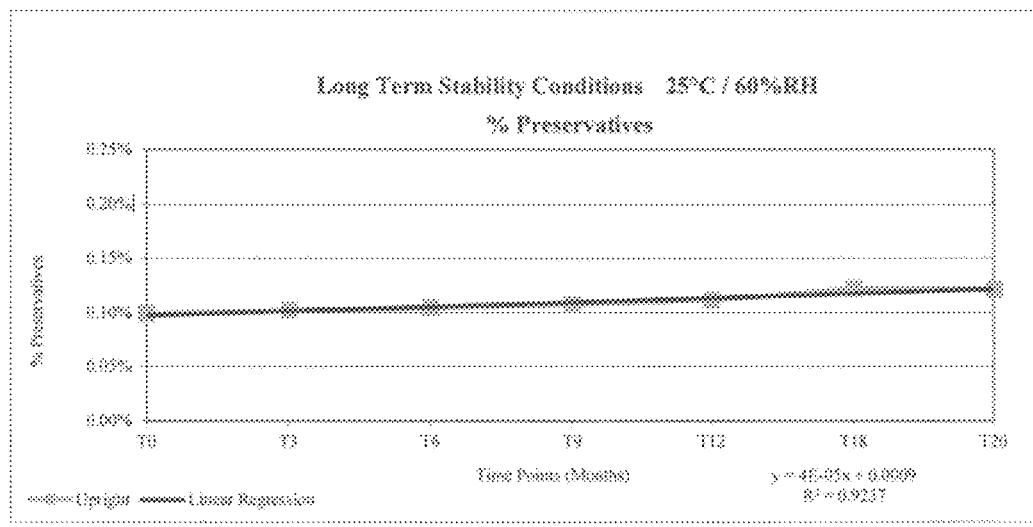
FIG. 29 is a plot of the preservative percentage as a function of time for a pharmaceutical composition (batch lot S35900115A) stored in an upright container over a 20-month period at 25° C.±2° C. and 60%±5° C. relative humidity, thereby providing an assessment of the shelf life stability of the pharmaceutical composition under ambient conditions.

FIG. 29 is a plot of the percent preservatives versus time for the 4 mL filled upright container of the 4% cocaine hydrochloride pharmaceutical composition (40 mg/mL cocaine hydrochloride), stored under the long term stability conditions of 25±2° C. and 60±5% relative humidity over 20 months.

Figure 30:
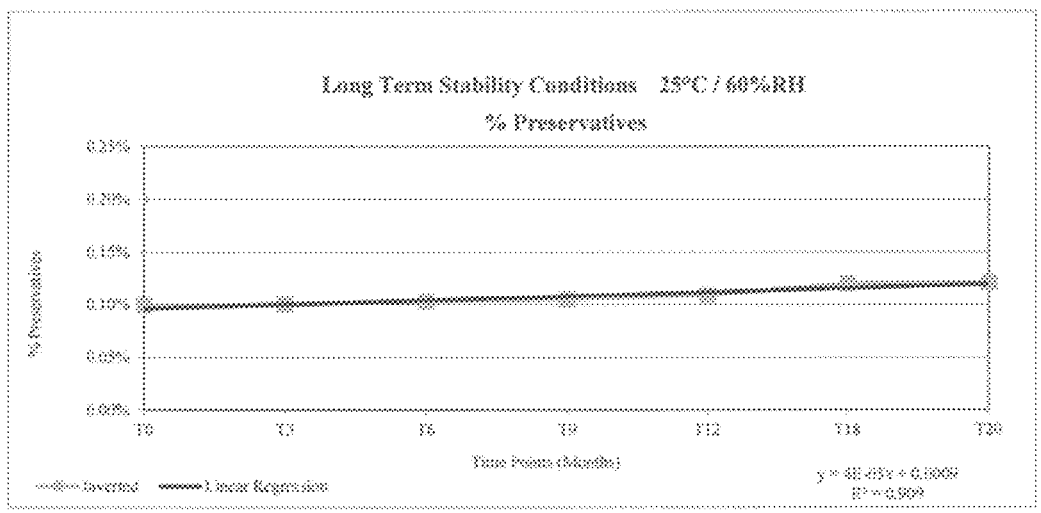
FIG. 30 is a plot of the preservative percentage as a function of time for a pharmaceutical composition (batch lot S35900115A) stored in an inverted container over a 20-month period at 25° C.±2° C. and 60%±5° C. relative humidity, thereby providing an assessment of the shelf life stability of the pharmaceutical composition under ambient conditions.

FIG. 30 is a plot of the percent preservatives versus time for the 4 mL filled inverted container of the 4% cocaine hydrochloride pharmaceutical composition (40 mg/mL cocaine hydrochloride), stored under the long term stability conditions of 25±2° C. and 60±5% relative humidity over 20 months.

Stability test results of the 4% cocaine hydrochloride pharmaceutical composition (4 mL containing 40 mg/mL cocaine hydrochloride, batch lot S35900115A) show an increase in benzoylecgonine content of less than 7% over the course of 20 months at ambient conditions, based upon the long term (20 months) stability assay results shown in Table 49 and FIGS. 31 and 32, which are described below.

Figure 31:
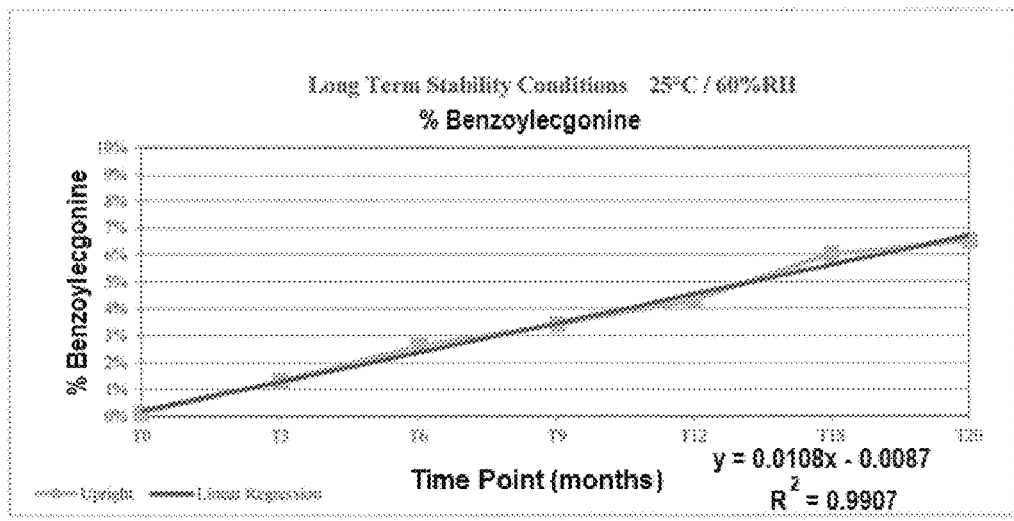
FIG. 31 is a plot of the benzoylecgonine percentage as a function of time for a pharmaceutical composition (batch lot S35900115A) stored in an upright container over a 20-month period at 25° C.±2° C. and 60%±5° C. relative humidity, thereby providing an assessment of the shelf life stability of the pharmaceutical composition under ambient conditions.

FIG. 31 is a plot of the percent benzoylecgonine versus time for the 4 mL filled upright container of the 4% cocaine hydrochloride pharmaceutical composition (40 mg/mL cocaine hydrochloride), stored under the long term stability conditions of 25±2° C. and 60±5% relative humidity over 20 months.

Figure 32:
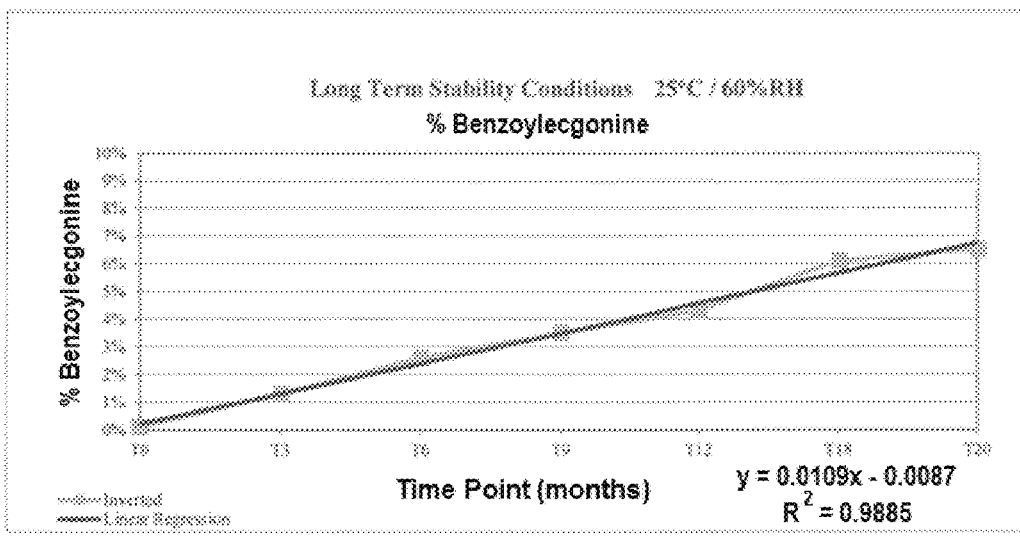
FIG. 32 is a plot of the benzoylecgonine percentage as a function of time for a pharmaceutical composition (batch lot S35900115A) stored in an inverted container over a 20-month period at 25° C.±2° C. and 60%±5° C. relative humidity, thereby providing an assessment of the shelf life stability of the pharmaceutical composition under ambient conditions.

FIG. 32 is a plot of the percent benzoylecgonine versus time for the 4 mL filled inverted container of the 4% cocaine hydrochloride pharmaceutical composition (40 mg/mL cocaine hydrochloride), stored under the long term stability conditions of 25±2° C. and 60±5% relative humidity over 20 months.

Figure 33:
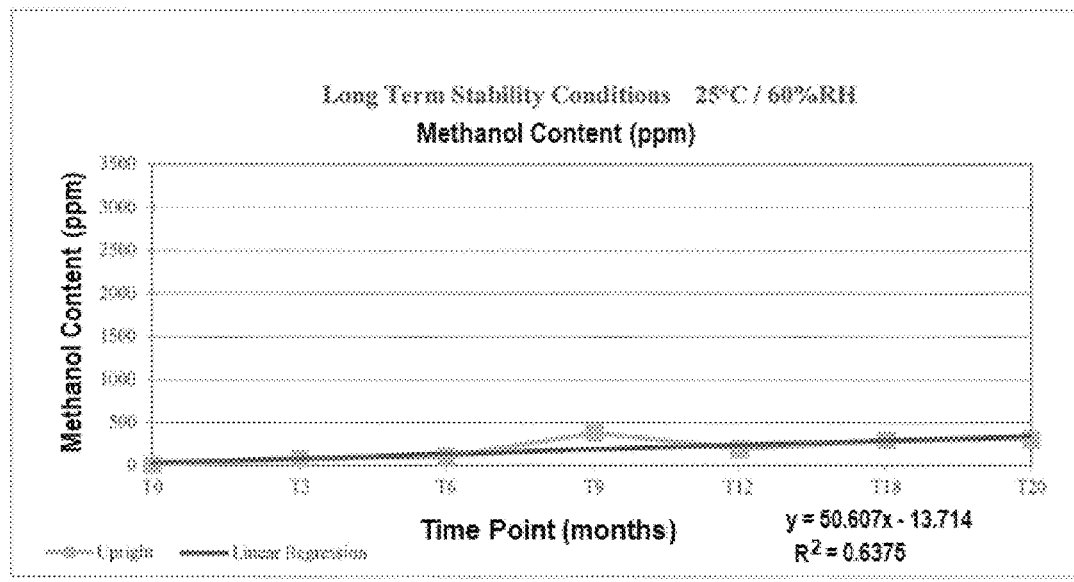
FIG. 33 is a plot of the methanol percentage as a function of time for a pharmaceutical composition (batch lot S35900115A) stored in an upright container over a 20-month period at 25° C.±2° C. and 60%±5° C. relative humidity, thereby providing an assessment of the shelf life stability of the pharmaceutical composition under ambient conditions.

Methanol content of the 4% cocaine hydrochloride pharmaceutical composition (4 mL containing 40 mg/mL cocaine hydrochloride, batch lot S35900115A) increased less than 400 ppm over the course of 20 months at ambient conditions, based upon the long term (20 months) stability assay results shown in Table 49 and FIGS. 33 and 34, which are described below FIG. 33 is a plot of the methanol content (ppm) versus time for the 4 mL filled upright container of the 4% cocaine hydrochloride pharmaceutical composition (40 mg/mL cocaine hydrochloride), stored under the long term stability conditions of 25±2° C. and 60±5% relative humidity over 20 months.

Figure 34:
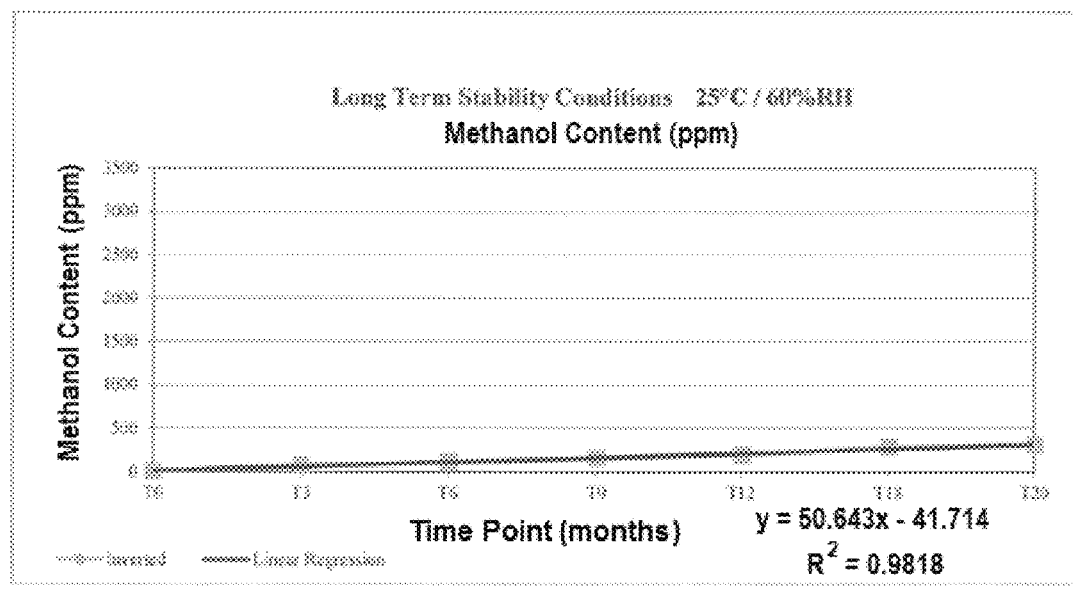
FIG. 34 is a plot of the methanol percentage as a function of time for a pharmaceutical composition (batch lot S35900115A) stored in an inverted container over a 20-month period at 25° C.±2° C. and 60%±5° C. relative humidity, thereby providing an assessment of the shelf life stability of the pharmaceutical composition under ambient conditions.

FIG. 34 is a plot of the methanol content (ppm) versus time for the 4 mL filled inverted container of the 4% cocaine hydrochloride pharmaceutical composition (40 mg/mL cocaine hydrochloride), stored under the long term stability conditions of 25±2° C. and 60±5% relative humidity over 20 months.

Table 49 reports the long-term stability data for the pharmaceutical composition samples tested in Example 7.

TABLE 49

Long-term conditions stability data results for the pharmaceutical composition including 40 mg/mL cocaine hydrochloride in a 0.5 oz. bottle at 25° C. ± 2° C. and 60% ± 5° C. RH over a period of 20 months. (Lot S35900115A)

| Test | Specification | Orientation | T = 0 | T = 3 | T = 6 | T = 9 | T = 12 | T = 18 | T = 20 |
|---|---|---|---|---|---|---|---|---|---|
| Assay | cocaine | Upright | 100.8% | 97.9% | 97.3% | 96.1% | 92.7% | 93.2% | 91.2% |
|  | hydrochloride | Inverted | 100.8% | 97.5% | 97.2% | 96.2% | 93.2% | 93.3% | 91.0% |
| Preservative | sodium | Upright | 0.099% | 0.102% | 0.104% | 0.107% | 0.111% | 0.122% | 0.121% |
| Content | benzoate | Inverted | 0.099% | 0.100% | 0.103% | 0.105% | 0.109% | 0.120% | 0.121% |
| pH | 2.0-4.0 | Upright | 3.6 | 3.4 | 3.2 | 3.1 | 3.0 | 2.7 | 2.7 |
|  |  | Inverted | 3.6 | 3.4 | 3.2 | 3.1 | 3.0 | 2.7 | 2.7 |
| Related | benzoyl | Upright | 0.1% | 1.3% | 2.6% | 3.4% | 4.3% | 6.0% | 6.5% |
| Substances | ecgonine | Inverted | 0.1% | 1.3% | 2.6% | 3.5% | 4.3% | 6.1% | 6.5% |
|  | unspecified | Upright | <0.1% | <0.1% | <0.1% | <0.1% | <0.1% | <0.1% | <0.1% |
|  | impurities | Inverted | <0.1% | <0.1% | <0.1% | <0.1% | <0.1% | <0.1% | <0.1% |
|  | Total | Upright | 0.1% | 1.3% | 2.6% | 3.4% | 4.3% | 6.0% | 6.5% |
|  |  | Inverted | 0.1% | 1.3% | 2.6% | 3.5% | 4.3% | 6.1% | 6.5% |
| Microbial | Total Aerobic | Upright | conforms | N/A | conforms | N/A | conforms | conforms | conforms |
| Limits | Microbial | Inverted | conforms | N/A | conforms | N/A | conforms | conforms | conforms |
|  | Counts (NMT 100 cfu/g) |  |  |  |  |  |  |  |  |
|  | Total Combined | Upright | conforms | N/A | conforms | N/A | conforms | conforms | conforms |
|  | Mold and Yeast | Inverted | conforms | N/A | conforms | N/A | conforms | conforms | conforms |
|  | (NMT 10 cfu/g) |  |  |  |  |  |  |  |  |
|  | Pseudomonas | Upright | conforms | N/A | conforms | N/A | conforms | conforms | conforms |
|  | aeruginosa | Inverted | conforms | N/A | conforms | conforms | conforms | conforms | conforms |
|  | (Absent) |  |  |  |  |  |  |  |  |
|  | Staphylococcus | Upright | conforms | N/A | conforms | N/A | conforms | conforms | conforms |
|  | aureus | Inverted | conforms | N/A | conforms | N/A | conforms | conforms | conforms |
|  | (Absent) |  |  |  |  |  |  |  |  |
| Methanol Content (ppm) |  | Upright | <37 | 74 | 99 | 372 | 189 | 286 | 301 |
|  |  | Inverted | <37 | 48 | 107 | 158 | 192 | 284 | 307 |
| Leachables | Isopropanol | Upright | <QL | <QL | <QL | 358 | 313 | N/A | 428 |
| (ng/mL) |  | Inverted | <QL | <QL | <QL | 345 | 291 | N/A | 415 |
|  | Acetonitrile | Upright | 475 | ND | ND | ND | ND | N/A | ND |
|  |  | Inverted | 475 | ND | ND | ND | ND | N/A | ND |
|  | Timethylsilanol | Upright | 1618 | 1837 | <QL | 595 | <QL | N/A | 651 |
|  |  | Inverted | 1618 | 1295 | 356 | 706 | 439 | N/A | 740 |
|  | Chromium | Upright | 366 | 414 | 391 | 382 | 376 | N/A | 424 |
|  |  | Inverted | 366 | 407 | 405 | 385 | 366 | N/A | 446 |
|  | Nickel | Upright | 175 | 253 | 183 | 176 | 203 | N/A | 196 |
|  |  | Inverted | 175 | 203 | 185 | 174 | 168 | N/A | 202 |
| Antimicrobial | Bacteria | Upright | N/A | N/A | N/A | N/A | N/A | N/A | Conforms |
| Effectiveness |  | Inverted | N/A | N/A | N/A | N/A | N/A | N/A | Conforms |
| Testing | Yeast and | Upright | N/A | N/A | N/A | N/A | N/A | N/A | Conforms |
|  | Molds | Inverted | N/A | N/A | N/A | N/A | N/A | N/A | Conforms |

An accelerated stability study of the same manufactured batch lot (batch lot S35900115A) pharmaceutical composition as used in the long-term stability study described above (and contained in the closure system) was conducted over a period of 6 months to determine the rate of physical or chemical degradation of the pharmaceutical composition including 4% cocaine hydrochloride over accelerated environmental conditions.

All accelerated stability samples (each sample containing 4 mL of the pharmaceutical composition including 40 mg/mL cocaine hydrochloride) were placed upright or inverted in an environmental chamber and maintained in an upright or inverted position during the stability study. All of the containers were maintained at 40° C.±2° C. and 75%±5% relative humidity, uninterrupted, (except for the adding or withdrawal of test samples) for a period of six months. Samples were removed from conditions at the specified time point and tested for pH, preservative content, related substances, methanol content, leachables, microbial limits at the required time point, and cocaine hydrochloride content. Storage of the stability samples was completed using a calibrated environmental chamber. Testing of the stability samples was completed using High Pressure Liquid Chromatography.

Shelf life of the 4% cocaine hydrochloride pharmaceutical composition was estimated at approximately 6 months at the accelerated stability conditions, based upon the short term (6 months) stability assay results shown in Table 50 and FIGS. 35 and 36, which are described below. Both upright and inverted container assays showed greater than 85 percent of the cocaine hydrochloride was retained in the pharmaceutical composition over the course of the accelerated term stability assay for 6 months.

Figure 35:
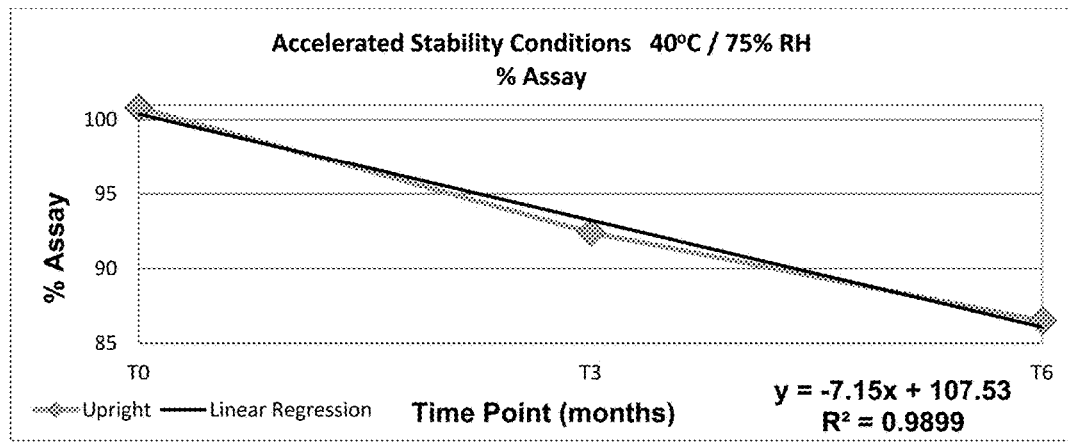
FIG. 35 is a plot of the cocaine hydrochloride assay percentage as a function of time for a pharmaceutical composition (batch lot S35900115A) stored in an upright container over a 6-month period at 40° C.±2° C. and 75%±5° C. relative humidity, thereby providing an assessment of the shelf life stability of the pharmaceutical composition under accelerated conditions.

FIG. 35 is a plot of the percent detectable cocaine hydrochloride versus time for the 4 mL filled upright container of the 4% cocaine hydrochloride pharmaceutical composition (40 mg/mL cocaine hydrochloride) over a 6-month period at 40° C.±2° C. and 75%±5% relative humidity, thereby providing an assessment of the shelf life stability of the pharmaceutical composition.

Figure 36:
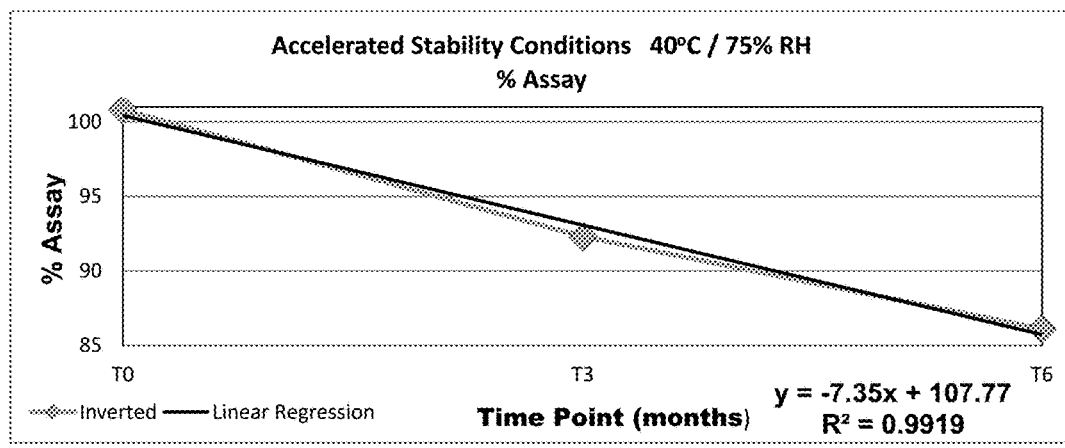
FIG. 36 is a plot of the cocaine hydrochloride assay percentage as a function of time for a pharmaceutical composition (batch lot S35900115A) stored in an inverted container over a 6-month period at 40° C.±2° C. and 75%±5° C. relative humidity, thereby providing an assessment of the shelf life stability of the pharmaceutical composition under accelerated conditions.

FIG. 36 is a plot of the percent detectable cocaine hydrochloride versus time for the 4 mL filled inverted container of the 4% cocaine hydrochloride pharmaceutical composition (40 mg/mL cocaine hydrochloride) over a 6-month period at 40° C.±2° C. and 75%±5% relative humidity, thereby providing an assessment of the shelf life stability of the pharmaceutical composition.

The 4% cocaine hydrochloride pharmaceutical composition (4 mL containing 40 mg/mL cocaine hydrochloride, batch lot S35900115A) maintained a pH of no less than 2.5 for at least 6 months at accelerated conditions, based upon the accelerated term (6 month) stability assay results shown in Table 50 and FIGS. 37 and 38, which are described below.

Figure 37:
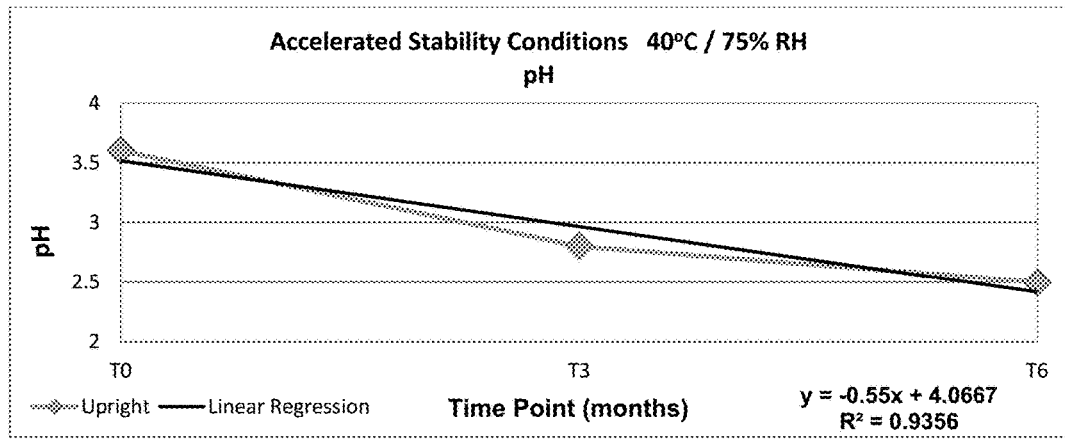
FIG. 37 is a plot of the pH as a function of time for a pharmaceutical composition (batch lot S35900115A) stored in an upright container over a 6-month period at 40° C.±2° C. and 75%±5° C. relative humidity, thereby providing an assessment of the shelf life stability of the pharmaceutical composition under accelerated conditions.

FIG. 37 is a plot of the pH versus time for the 4 mL filled upright container of the 4% cocaine hydrochloride pharmaceutical composition (40 mg/mL cocaine hydrochloride), stored under the accelerated stability conditions of 40° C.±2° C. and 75%±5% relative humidity over 6 months.

Figure 38:
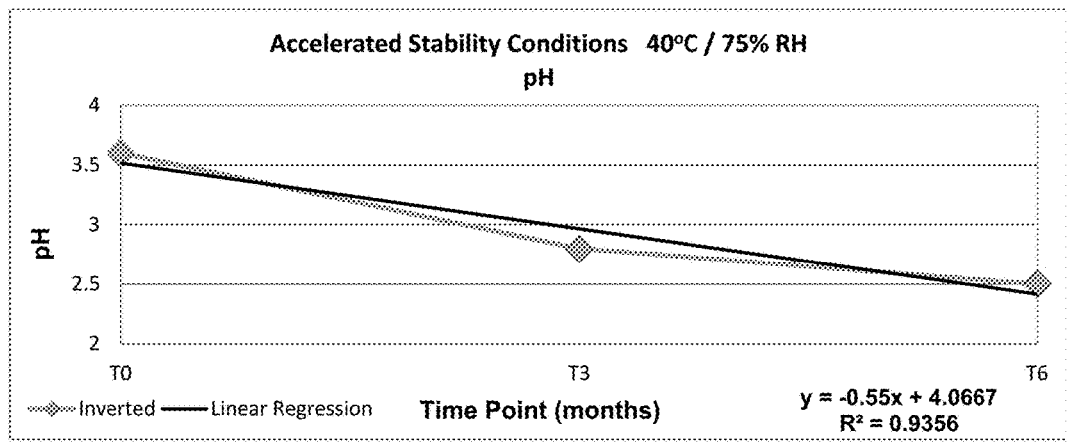
FIG. 38 is a plot of the pH as a function of time for a pharmaceutical composition (batch lot S35900115A) stored in an inverted container over a 6-month period at 40° C.±2° C. and 75%±5° C. relative humidity, thereby providing an assessment of the shelf life stability of the pharmaceutical composition under accelerated conditions.

FIG. 38 is a plot of the pH versus time for the 4 mL filled inverted container of the 4% cocaine hydrochloride pharmaceutical composition (40 mg/mL cocaine hydrochloride), stored under the accelerated stability conditions of 40° C.±2° C. and 75%±5% relative humidity over 6 months.

The percent preservatives within the 4% cocaine hydrochloride pharmaceutical composition (4 mL containing 40 mg/mL cocaine hydrochloride, batch lot S35900115A) increased less than 0.05% over the course of 6 months at accelerated conditions, based upon the accelerated term (6 months) stability assay results shown in Table 50 and FIGS. 39 and 40, which are described below.

Figure 39:
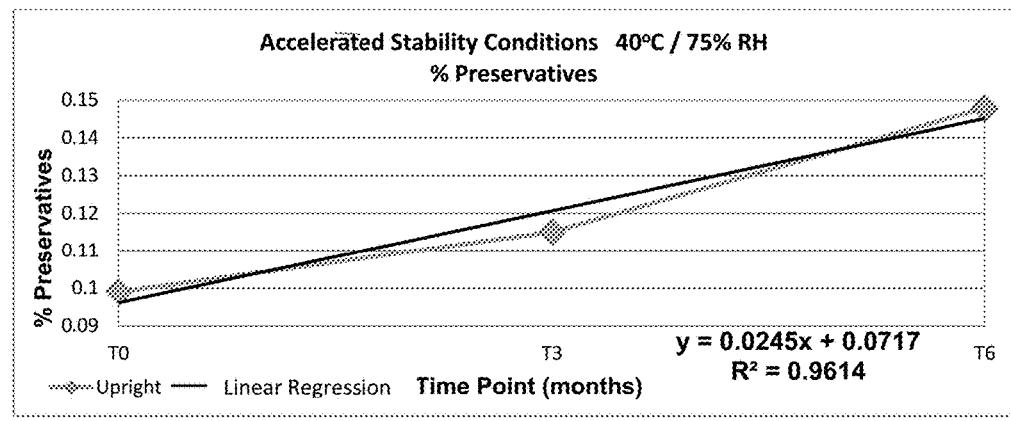
FIG. 39 is a plot of the preservatives percentage as a function of time for a pharmaceutical composition (batch lot S35900115A) stored in an upright container over a 6-month period at 40° C.±2° C. and 75%±5° C. relative humidity, thereby providing an assessment of the shelf life stability of the pharmaceutical composition under accelerated conditions.

FIG. 39 is a plot of the percent preservatives versus time for the 4 mL filled upright container of the 4% cocaine hydrochloride pharmaceutical composition (40 mg/mL cocaine hydrochloride), stored under the accelerated stability conditions of 40° C.±2° C. and 75%±5% relative humidity over 6 months.

Figure 40:
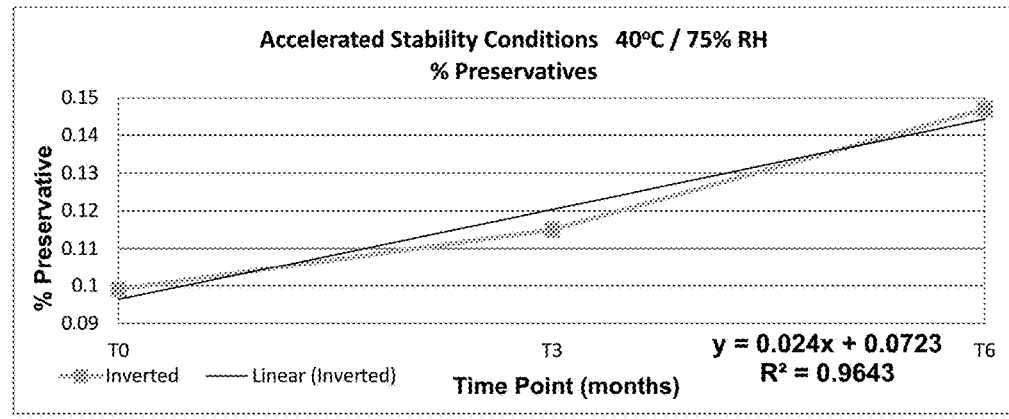
FIG. 40 is a plot of the preservatives percentage as a function of time for a pharmaceutical composition (batch lot S35900115A) stored in an inverted container over a 6-month period at 40° C.±2° C. and 75%±5° C. relative humidity, thereby providing an assessment of the shelf life stability of the pharmaceutical composition under accelerated conditions.

FIG. 40 is a plot of the percent preservatives versus time for the 4 mL filled inverted container of the 4% cocaine hydrochloride pharmaceutical composition (40 mg/mL cocaine hydrochloride), stored under the accelerated stability conditions of 40° C.±2° C. and 75%±5% relative humidity over 6 months.

Stability test results of the 4% cocaine hydrochloride pharmaceutical composition (4 mL containing 40 mg/mL cocaine hydrochloride, batch lot S35900115A) show an increase in benzoylecgonine content of less than 10% over the course of 6 months at accelerated conditions, based upon the accelerated term (6 months) stability assay results shown in Table 50 and FIGS. 31 and 32, which are described below.

Figure 41:
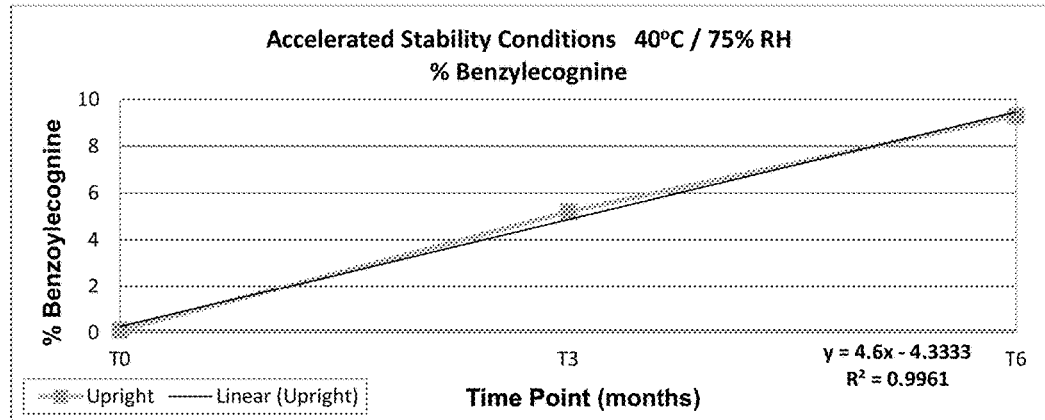
FIG. 41 is a plot of the benzoylecgonine percentage as a function of time for a pharmaceutical composition (batch lot S35900115A) stored in an upright container over a 6-month period at 40° C.±2° C. and 75%±5° C. relative humidity, thereby providing an assessment of the shelf life stability of the pharmaceutical composition under accelerated conditions.

FIG. 41 is a plot of the percent benzoylecgonine versus time for the 4 mL filled upright container of the 4% cocaine hydrochloride pharmaceutical composition (40 mg/mL cocaine hydrochloride), stored under the accelerated stability conditions of 40° C.±2° C. and 75%±5% relative humidity over 6 months.

Figure 42:
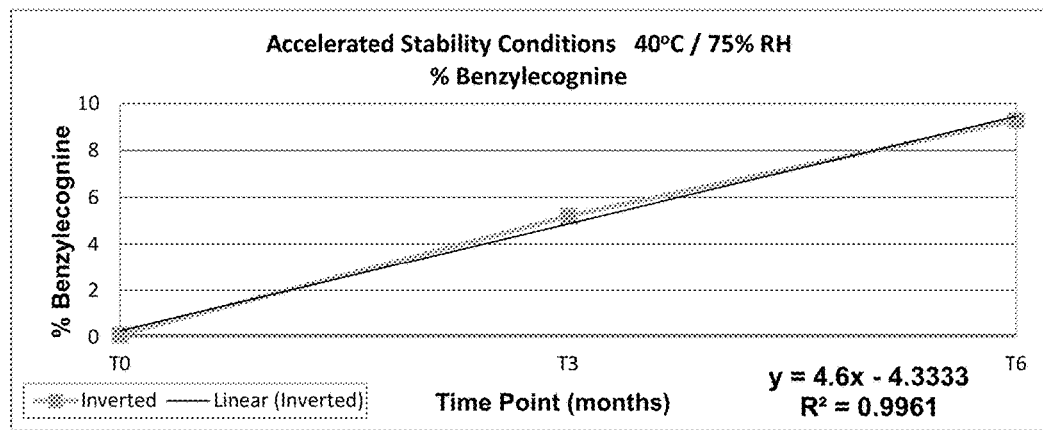
FIG. 42 is a plot of the benzoylecgonine percentage as a function of time for a pharmaceutical composition (batch lot S35900115A) stored in an inverted container over a 6-month period at 40° C.±2° C. and 75%±5° C. relative humidity, thereby providing an assessment of the shelf life stability of the pharmaceutical composition under accelerated conditions.

FIG. 42 is a plot of the percent benzoylecgonine versus time for the 4 mL filled inverted container of the 4% cocaine hydrochloride pharmaceutical composition (40 mg/mL cocaine hydrochloride), stored under the accelerated stability conditions of 40° C.±2° C. and 75%±5% relative humidity over 6 months.

Figure 43:
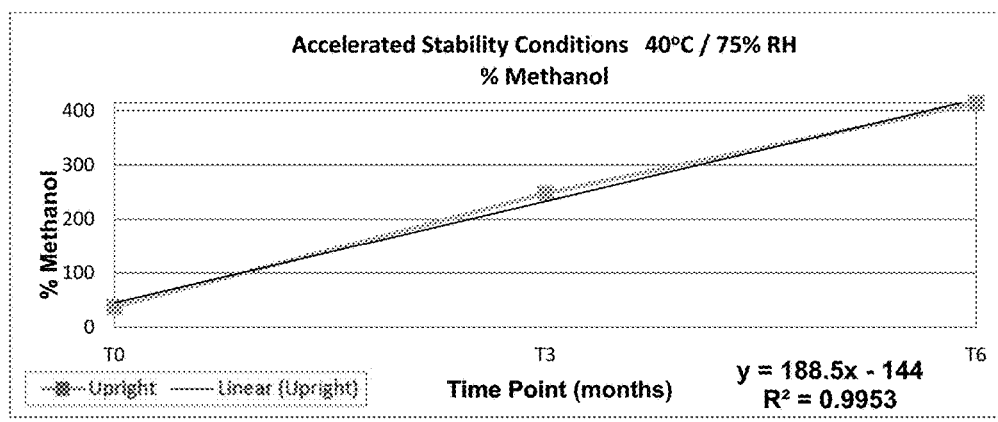
FIG. 43 is a plot of the methanol percentage as a function of time for a pharmaceutical composition (batch lot S35900115A) stored in an upright container over a 6-month period at 40° C.±2° C. and 75%±5° C. relative humidity, thereby providing an assessment of the shelf life stability of the pharmaceutical composition under accelerated conditions.

Methanol content of the 4% cocaine hydrochloride pharmaceutical composition (4 mL containing 40 mg/mL cocaine hydrochloride, batch lot S35900115A) increased less than 400 ppm over the course of 6 months at accelerated conditions, based upon the accelerated term (6 months) stability assay results shown in Table 50 and FIGS. 43 and 44, which are described below FIG. 43 is a plot of the methanol content (ppm) versus time for the 4 mL filled upright container of the 4% cocaine hydrochloride pharmaceutical composition (40 mg/mL cocaine hydrochloride), stored under the accelerated stability conditions of 40° C.±2° C. and 75%±5% relative humidity over 6 months.

Figure 44:
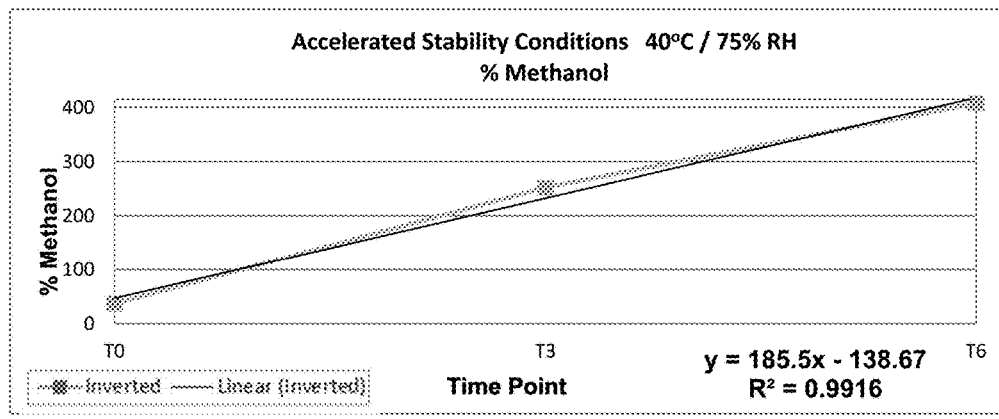
FIG. 44 is a plot of the methanol percentage as a function of time for a pharmaceutical composition (batch lot S35900115A) stored in an inverted container over a 6-month period at 40° C.±2° C. and 75%±5° C. relative humidity, thereby providing an assessment of the shelf life stability of the pharmaceutical composition under accelerated conditions.

FIG. 44 is a plot of the methanol content (ppm) versus time for the 4 mL filled inverted container of the 4% cocaine hydrochloride pharmaceutical composition (40 mg/mL cocaine hydrochloride), stored under the accelerated stability conditions of 40° C.±2° C. and 75%±5% relative humidity over 6 months.

Table 50 reports the accelerated conditions stability data for the samples tested in Example 7.

TABLE 50

Accelerated conditions stability data results for the pharmaceutical composition including 40 mg/mL cocaine hydrochloride in a 0.5 oz. bottle at 40° C. ± 2° C. and 75% ± 5° C. RH over a period of 6 months.
(Lot S35900115A)

| Test | Specification | Orientation | T = 0 | T = 3 | T = 6 |
|---|---|---|---|---|---|
| Assay | cocaine | Upright | 100.8% | 92.4% | 86.5% |
|  | hydrochloride | Inverted | 100.8% | 92.3% | 86.1% |
| Preservative Content | sodium | Upright | 0.099% | 0.115% | 0.148% |
|  | benzoate | Inverted | 0.099% | 0.115% | 0.147% |
| pH | 2.0-4.0 | Upright | 3.6 | 2.8 | 2.5 |
|  |  | Inverted | 3.6 | 2.8 | 2.5 |
| Related Substances | benzoyl ecgonine | Upright | 0.1% | 5.2% | 9.3% |
|  |  | Inverted | 0.1% | 5.2% | 9.3% |
|  | unspecified impurities | Upright | <0.1% | <0.1% | <0.1% |
|  |  | Inverted | <0.1% | <0.1% | <0.1% |
|  | Total | Upright | 0.1% | 5.2% | 9.3% |
|  |  | Inverted | 0.1% | 5.2% | 9.3% |
| Microbial Limits | Total Aerobic Microbial Counts (NMT 100 cfu/g) | Upright | conforms | N/A | conforms |
|  |  | Inverted | conforms | N/A | conforms |
|  | Total Combined Mold and Yeast (NMT 10 cfu/g) | Upright | conforms | N/A | conforms |
|  |  | Inverted | conforms | N/A | conforms |
|  | *Pseudomonas aeruginosa* (Absent) | Upright | conforms | N/A | conforms |
|  |  | Inverted | conforms | N/A | conforms |
|  | *Staphylococcus aureus* (Absent) | Upright | conforms | N/A | conforms |
|  |  | Inverted | conforms | N/A | conforms |
| Methanol Content (ppm) |  | Upright | <37 | 248 | 414 |
|  |  | Inverted | <37 | 252 | 408 |
| Leachables (ng/mL) | Isopropanol | Upright | <QL | 372 | 286 |
|  |  | Inverted | <QL | 341 | 271 |
|  | Acetonitrile | Upright | 475 | ND | ND |
|  |  | Inverted | 475 | ND | ND |
|  | Trimethylsilanol | Upright | 1618 | 1895 | 319 |
|  |  | Inverted | 1618 | 1909 | 292 |
|  | Chromium | Upright | 366 | 408 | 389 |
|  |  | Inverted | 366 | 390 | 391 |
|  | Nickel | Upright | 175 | 188 | 180 |
|  |  | Inverted | 175 | 179 | 183 |

Example 8

Example 8 was a randomized, prospective, double-blind, multicenter, single-dose, placebo and dose-controlled, parallel-group study to evaluate the safety of the 4% and 8% cocaine hydrochloride pharmaceutical compositions as described in Example 4 used as a local anesthetic for diagnostic procedures and surgeries on or through the mucous membranes of the nasal cavities (e.g., nasal/sinus endoscopy, sinusotomy, fracture nasal turbinate(s), lysis intranasal synechia, insertion of nasal septal prosthesis, intranasal biopsy, excision of nasal polyps, excision turbinate(s), removal of an intranasal foreign body, septoplasty, or sinus debridement). Subjects did not receive general anesthesia in this 1-day diagnostic procedure or surgery. After dosing with the 4% or 8% cocaine hydrochloride pharmaceutical composition or Placebo Topical Solution (up to 4 mL), subjects were carefully monitored for safety. A total of 648 male or female subjects, ≥18 years of age, were enrolled and randomized in a 1:3:3 ratio to placebo (95 subjects), 4% cocaine hydrochloride pharmaceutical composition (275 subjects), or 8% cocaine hydrochloride pharmaceutical composition (278 subjects), respectively. The study consisted of a screening period within 14 days of a diagnostic procedure or surgery; a treatment period on the day of the diagnostic procedure or surgery (Day 1); and a follow-up visit (Day 8).

Study Stopping Criteria:

Study stopping criteria were established for Cardiovascular (CV) or Central Nervous System (CNS) events, with data periodically reviewed by a medical clinician to determine if cardiovascular or CNS stopping criteria were met.

Cardiovascular Stopping Criteria:

1. An increase in systolic blood pressure (SBP) or diastolic blood pressure (DBP) greater than or equal to a 25% change above baseline associated with a clinical symptom of chest pain, shortness of breath and/or acute onset of severe headache observed in at least 15% of the active treatment subjects and at least three times the incidence of the placebo treatment subjects after evaluation of at least 100 enrolled subjects.

2. An increase in SBP or DBP greater than or equal to a 40% change above baseline, sustained for at least 10 minutes (i.e., a total of 3 readings 5-6 minutes apart) regardless of symptoms in at least 20% of the active subjects and at least three times the incidence of the placebo treatment subjects after evaluation of at least 100 enrolled subjects.

3. Any serious adverse event associated with a cardiovascular symptom regardless of vital sign measurement in at least 5% of the active subjects and at least three times the incidence of the placebo treatment subjects after evaluation of at least 100 enrolled subjects.

CNS Stopping Criteria:

1. Any serious adverse event associated with CNS symptom in at least 5% of the active subjects and at least three times the incidence of placebo treatment subjects after evaluation of at least 100 enrolled subjects.

2. Any seizure in at least 3% of the active subjects and at least three times the incidence of the placebo subjects after evaluation of at least 100 enrolled subjects.

3. Significant CNS event which causes the Investigator to abort the procedure in at least 10% of the active subject and at least three times the incidence of the placebo subject after evaluation of at least 100 enrolled subjects.

Treatments Administered

Four mL of either the 4% (40 mg/mL) or 8% (80 mg/mL) cocaine hydrochloride pharmaceutical compositions as described in Example 4, or placebo topical solution were poured into a standard medicine cup and 4 cottonoid pledgets (approximately 1.3 cm×4 cm) were added to this solution and allowed to saturate for 10 minutes. Each pledget absorbed approximately 1 mL of solution (i.e., 40 or 80 mg/pledget). Two saturated pledgets were placed into each nasal cavity and up against the septum for 20 minutes. After 20 minutes the pledgets were removed from the subjects.

Brief Summary of Adverse Events

The overall incidence of adverse events (AEs) was 1.1% in the placebo group, 5.1% in the 4% cocaine hydrochloride pharmaceutical composition group, and 4.7% in the 8% cocaine hydrochloride pharmaceutical composition group. No deaths, serious AEs, or discontinuations of study drug or the study due to an AE were reported. The incidence of severe AEs was low (no subjects in placebo and 4% cocaine hydrochloride pharmaceutical composition groups; 0.7% in 8% cocaine hydrochloride pharmaceutical composition group). The results in Table 51 show that the percentage of subjects with at least one AE was 1.1% in the placebo group, 5.1% in the 4% cocaine hydrochloride pharmaceutical composition group, and 4.7% in the 8% cocaine hydrochloride pharmaceutical composition group.

TABLE 51

Overview of adverse events incurred in the safety study of Example 7.

| | Placebo (N = 95) | 4 % Cocaine HCl (N = 275) | 8 % Cocaine HCl (N = 278) | Overall (N = 648) |
|---|---|---|---|---|
| Subjects with AEs, n (%) | 1 (1) | 14 (5.1) | 13 (4.7) | 28 (4.3) |
| Severity | | | | |
| Mild AEs, n (%) | 1 (1) | 10 (3.6) | 8 (2.9) | 19 (2.9) |
| Moderate AEs, n (%) | 0 | 4 (1.5) | 3 (1.1) | 7 (1.1) |
| Severe AEs, n (%) | 0 | 0 | 2 (0.7) | 2 (0.3) |
| Deaths due to AEs, n (%) | 0 | 0 | 0 | 0 |
| Serious AEs, n (%) | 0 | 0 | 0 | 0 |
| Subject discontinued due to an AE, n (%) | 0 | 0 | 0 | 0 |

Comparison of Safety Results

There was no indication of bias in the types or frequency of AEs reported across the treatment groups. Topical nasal doses of 4% and 8% cocaine hydrochloride pharmaceutical compositions were safe and well-tolerated, with a safety profile that was generally similar to placebo. As shown in Table 52, the 4% and 8% hydrochloride pharmaceutical composition treatment groups, headache, epistaxis, and anxiety were the only AEs reported by more than 1 subject. The majority of AEs were of mild severity. No deaths, serious AEs, or discontinuations of either the study or the hydrochloride pharmaceutical composition occurred. Additionally, for vital sign assessments, mean and mean change from baseline over time for heart rate and systolic and diastolic blood pressure were small and transient, resolved without sequelae or treatment, and were not reported as AEs, except in 1 subject in the 4% cocaine group with hypertension and arrhythmia.

TABLE 52

Treatment emergent adverse events (AEs).

| System Organ Class Preferred Term | Placebo (N = 95) n (%) | 4 % Cocaine HCl (N = 275) n (%) | 8% Cocaine HCl (N = 278) n (%) | Overall (N = 648) n (%) |
|---|---|---|---|---|
| ANY PRIMARY SYSTEM ORGAN CLASS | 1 (1.1%) | 14 (5.1%) | 13 (4.7%) | 28 (4.3%) |
| Eye disorders | 0 | 1 (0.4%) | 1 (0.4%) | 2 (0.3%) |
| Foreign body sensation in eyes | 0 | 1 (0.4%) | 0 | 1 (0.2%) |
| Vision blurred | 0 | 0 | 1 (0.4%) | 1 (0.2%) |
| Gastrointestinal disorders | 0 | 1 (0.4%) | 1 (0.4%) | 2 (0.3%) |
| Lip swelling | 0 | 1 (0.4%) | 0 | 1 (0.2%) |
| Nausea | 0 | 0 | 1 (0.4%) | 1 (0.2%) |
| General disorders and administration site conditions | 0 | 1 (0.4%) | 2 (0.7%) | 3 (0.5%) |
| Cold sweat | 0 | 0 | 1 (0.4%) | 1 (0.2%) |
| Facial pain | 0 | 1 (0.4%) | 0 | 1 (0.2%) |
| Fatigue | 0 | 0 | 1 (0.4%) | 1 (0.2%) |
| Injury, poisoning and procedural complications | 0 | 1 (0.4%) | 0 | 1 (0.2%) |
| Medication error | 0 | 1 (0.4%) | 0 | 1 (0.2%) |
| Musculoskeletal and connective tissue disorders | 0 | 1 (0.4%) | 0 | 1 (0.2%) |
| Neck pain | 0 | 1 (0.4%) | 0 | 1 (0.2%) |
| Nervous system disorders | 1 (1.1%) | 5 (1.8%) | 7 (2.5%) | 13 (2.0%) |
| Dizziness | 0 | 1 (0.4%) | 1 (0.4%) | 2 (0.3%) |
| Headache | 1 (1.1%) | 4 (1.5%) | 7 (2.5%) | 12 (1.9%) |
| Psychiatric disorders | 0 | 2 (0.7%) | 0 | 2 (0.3%) |
| Anxiety | 0 | 2 (0.7%) | 0 | 2 (0.3%) |
| Respiratory, thoracic and mediastinal disorders | 1 (1.1%) | 3 (1.1%) | 6 (2.2%) | 10 (1.5%) |
| Dysphonia | 0 | 0 | 1 (0.4%) | 1 (0.2%) |
| Epistaxis | 0 | 2 (0.7%) | 3 (1.1%) | 5 (0.8%) |
| Nasal congestion | 1 (1.1%) | 1 (0.4%) | 0 | 2 (0.3%) |
| Rhinorrhea | 0 | 0 | 1 (0.4%) | 1 (0.2%) |
| Sneezing | 0 | 0 | 1 (0.4%) | 1 (0.2%) |
| Upper-airway cough syndrome | 1 (1.1%) | 0 | 0 | 1 (0.2%) |
| Skin and subcutaneous tissue disorders | 0 | 2 (0.7%) | 0 | 2 (0.3%) |
| Cold sweat | 0 | 1 (0.4%) | 0 | 1 (0.2%) |
| Dermatitis allergic | 0 | 1 (0.4%) | 0 | 1 (0.2%) |
| Vascular disorders | 0 | 0 | 1 (0.4%) | 1 (0.2%) |
| Hypertension | 0 | 0 | 1 (0.4%) | 1 (0.2%) |

As shown in Table 52, one cardiovascular/vascular AE of hypertension, reported as hypertension with arrhythmia, was observed. The subject was treated with 8% cocaine hydrochloride pharmaceutical composition and developed the AE 3 days post-treatment. The subject had a history of hypertension treated with amlodipine. The AE was deemed unlikely related to treatment and was treated with atenolol. In addition to headache, dizziness was the only other CNS-related AE reported in the cocaine hydrochloride pharmaceutical composition treatment groups (0.4% in both the 4% and 8% groups).

Subjects with Low Body Weights

Example 8 included a number of subjects with low body weight (either less than 50 kg or less than 60 kg), and efficacy and safety results were examined resulting in results that ere consistent with those reported for the overall population of subjects, regardless of body weight.

Almost half of subjects treated with the cocaine hydrochloride pharmaceutical compositions (247/552, 45%) received a dose greater than 3 mg/kg. The overall incidence of adverse events (AEs) was similar or slightly higher overall in subjects who received greater than 3 mg/kg (5.7%) versus those who received less than or equal to 3 mg/kg cocaine hydrochloride pharmaceutical composition (4.3%).

To address the potential for the impact of body weight on efficacy and safety, the study conducted the following additional analyses:

Analysis of efficacy (primary endpoint) for 2 subgroups of low weight subjects: <50 kg and <60 kg (see Table 53)

Analysis of safety (AEs) for 2 subgroups of low weight subjects: <50 kg and <60 kg (see Table 54)

Analysis of safety (AEs) for 2 subgroups of subjects based on dose determined on a mg/kg basis (regardless of 4% or 8% dose): ≤3 mg/kg or >3 mg/kg) (Table 55)

Note: There is overlap between the body weight groups examined because the <60 kg group has no lower limit of weight.

The efficacy results were consistently better for the cocaine hydrochloride pharmaceutical composition treatment groups versus placebo, with body weights less than 60 kg showing statistically significant results (see Table 53). Additionally, efficacy and safety results were consistent with those reported for the overall population of subjects, regardless of body weight.

TABLE 53

Analgesic success rates by body weight in Example 8 study (based on primary analysis as defined in the visual numeric rating scale (VNRS).

| | Body Weight <50 kg | | | Body Weight <60 kg | | |
|---|---|---|---|---|---|---|
| | Placebo (N = 3) n (%) | 4% Cocaine HCl (N = 8) n (%) | 8% Cocaine HCl (N = 9) n (%) | Placebo (N = 14) n (%) | 4% Cocaine HCl (N = 40) n (%) | 8% Cocaine HCl (N = 33) n (%) |
| Success | 1 (33.3) | 6 (75.0) | 7 (77.8) | 3 (21.4) | 32 (80.0) | 26 (78.8 |
| Failure | 2 (66.7) | 2 (25.0) | 2 (22.2) | 11 (78.6) | 8 (20.0) | 7 (21.2) |
| P-value* | | 0.4909 | 0.2364 | | 0.0002 | 0.0006 |

*Fisher's Exact Test. Pairwise comparison on active drug to placebo.
HCl = hydrochloride.

As shown in Table 54, the incidence of AEs was low in subjects with low body weight (either <50 kg or <60 kg). In subjects weighing<50 kg, the only AE was severe headache for 1 patient in the 4% cocaine HCl group. AEs reported for subjects weighing<60 kg included this severe headache in the 4% cocaine HCl group as well as 1 patient in the 8% cocaine HCl group with both mild epistaxis and mild foreign body sensation in eyes.

TABLE 54

Comparison of adverse events by body weight

| | Body Weight <50 kg | | | Body Weight <60 kg | | |
|---|---|---|---|---|---|---|
| | Placebo (N = 3) n (%) | 4% Cocaine HCl (N = 8) n (%) | 8% Cocaine HCl (N = 9) n (%) | Placebo (N = 14) n (%) | 4% Cocaine HCl (N = 40) n (%) | 8% Cocaine HCl (N = 33) n (%) |
| Any primary System Organ Class | 0 (0) | 1 (12.5) | 0 (0) | 0 (0) | 1 (2.5) | 1 (3.0) |
| Mild | 0 (0) | 0 (0) | 0 (0) | 0 (0) | 0 (0) | 1 (3.0) |
| Severe | 0 (0) | 1 (12.5) | 0 (0) | 0 (0) | 1 (2.5) | 0 (0) |
| Eye disorders | 0 (0) | 0 (0) | 0 (0) | 0 (0) | 0 (0) | 1 (3.0) |
| Foreign body sensation in eyes | 0 (0) | 0 (0) | 0 (0) | 0 (0) | 0 (0) | 1 (3.0) |
| Mild | 0 (0) | 0 (0) | 0 (0) | 0 (0) | 0 (0) | 1 (3.0) |
| Nervous system disorders | 0 (0) | 1 (12.5) | 0 (0) | 0 (0) | 1 (2.5) | 0 (0) |
| Headache | 0 (0) | 1 (12.5) | 0 (0) | 0 (0) | 1 (2.5) | 0 (0) |
| Severe | 0 (0) | 1 (12.5) | 0 (0) | 0 (0) | 1 (2.5) | 0 (0) |
| Respiratory, thoracic and mediastinal disorders | 0 (0) | 0 (0) | 0 (0) | 0 (0) | 0 (0) | 1 (3.0) |
| Epistaxis | 0 (0) | 0 (0) | 0 (0) | 0 (0) | 0 (0) | 1 (3.0) |
| Mild | 0 (0) | 0 (0) | 0 (0) | 0 (0) | 0 (0) | 1 (3.0) |

Adverse events are classified according to System Organ Class (SOC) and Preferred Term (PT) of MedDRA Version 18.0. Primary system organ classes are presented alphabetically; preferred terms are sorted within primary system organ class alphabetically.

For subjects treated with cocaine hydrochloride pharmaceutical composition, the dose of cocaine hydrochloride was determined on a mg/kg basis (regardless of 4% or 8% dose) and subjects were divided into 2 groups based on those who received ≤3 mg/kg or >3 mg/kg cocaine hydrochloride. Almost half of subjects treated with cocaine hydrochloride (247/552, 45%) received a dose>3 mg/kg. As shown in Table 55, the incidence of AEs was similar or slightly higher overall in subjects who received a dose>3 mg/kg (5.7%) as compared to those who received ≤3 mg/kg cocaine hydrochloride (4.3%). The adverse events observed were non-serious, did not lead to discontinuation, and resolved, supporting a conclusion that cocaine hydrochloride was safe overall in both of these low body weight groups.

TABLE 55

Comparison of adverse events by subjects receiving 3 mg/kg or less cocaine hydrochloride as compared to subjects receiving greater than 3 mg/kg cocaine hydrochloride

| Preferred Term | Placebo (N = 95) n (%) | ≤3 mg/kg Cocaine HCl (N = 305) n (%) | >3% mg/kg Cocaine HCl (N = 247)[a] n (%) |
|---|---|---|---|
| Any AE | 1 (1.1) | 13 (4.3) | 14 (5.7) |
| Eye disorders | 0 | 1 (0.3) | 1 (0.4) |
| Foreign body sensation in eyes | 0 | 0 | 1 (0.4) |
| Vision blurred | 0 | 1 (0.3) | 0 |
| Gastrointestinal disorders | 0 | 1 (0.3) | 1 (0.4) |
| Lip swelling | 0 | 0 | 1 (0.4) |
| Nausea | 0 | 1 (0.3) | 0 |
| General disorders and administration site conditions | 0 | 2 (0.7) | 1 (0.4) |
| Cold sweat | 0 | 1 (0.3) | 0 |
| Facial pain | 0 | 0 | 1 (0.4) |
| Fatigue | 0 | 1 (0.3) | 0 |
| Injury, poisoning and procedural complications | 0 | 0 | 1 (0.4) |
| Medication error | 0 | 0 | 1 (0.4) |
| Musculoskeletal and connective tissue disorders | 0 | 0 | 1 (0.4) |
| Neck pain | 0 | 0 | 1 (0.4) |
| Nervous system disorders | 1 (1.1) | 7 (2.3) | 5 (2.0) |
| Dizziness | 0 | 1 (0.3) | 1 (0.4) |
| Headache | 1 (1.1) | 7 (2.3) | 4 (1.6) |
| Psychiatric disorders | 0 | 0 | 2 (0.8) |
| Anxiety | 0 | 0 | 2 (0.8) |
| Respiratory, thoracic and mediastinal disorders | 1 (1.1) | 6 (2.0) | 3 (1.2) |
| Dysphonia | 0 | 1 (0.3) | 0 |
| Epistaxis | 0 | 3 (1.0) | 2 (0.8) |
| Nasal congestion | 1 (1.1) | 0 | 1 (0.4) |
| Rhinorrhea | 0 | 1 (0.3) | 0 |
| Sneezing | 0 | 1 (0.3) | 0 |
| Upper-airway cough syndrome | 1 (1.1) | 0 | 0 |
| Skin and subcutaneous tissue disorders | 0 | 0 | 2 (0.8) |
| Cold sweat | 0 | 0 | 1 (0.4) |
| Dermatitis allergic | 0 | 0 | 1 (0.4) |
| Vascular disorders | 0 | 1 (0.3) | 0 |
| Hypertension | 0 | 1 (0.3) | 0 |

[a] One patient in the 8% cocaine HCl group was not included as the baseline weight value was missing. Adverse events are classified according to System Organ Class (SOC) and Preferred Term (PT) of MedDRA Version 18.0. Primary system organ classes are presented alphabetically; preferred terms are sorted within primary system organ class alphabetically. HCl = hydrochloride Example 9

The objective of Example 9 was to evaluate the potential toxicity of benzoylecgonine when administered to Sprague Dawley rats as a single intranasal instillation or as a daily intranasal instillation for 14 consecutive days, as well as to assess the recovery, persistence, or progression of any effects following a recovery period of a minimum of 14 days after either treatment regimen.

Single-Dose Phase

Benzoylecgonine in the vehicle (deionized water) was administered by intranasal instillation once to a group (Group 2) of Sprague Dawley rats at a dose level of 8.8 mg/kg. A concurrent control group (Group 1) received the vehicle on a comparable regimen. The dose volume was 0.22 mL/kg, divided between the 2 nares, for both groups. Groups 1 and 2 each consisted of 20 animals/sex. Following dose administration, 9 to 10 animals/sex/group were euthanized on Study Day 1; the remaining 10 animals/sex/group were euthanized following a 14-day nondosing (recovery) period. Criteria for evaluation included daily mortality observations, daily clinical observations, detailed physical observations, body weights, food consumption, clinical pathology (hematology, coagulation, serum chemistry, and urinalysis), organ weights, gross pathology, and microscopic examination of select tissues.

There were no test article-related effects on survival. There were no test article-related clinical observations or effects on body weights, food consumption, clinical pathology parameters, organ weights, or macroscopic or microscopic findings in the nasal cavity or olfactory bulbs.

Repeat-Dose Phase

Benzoylecgonine in the vehicle was administered by intranasal instillation once daily for 14 days to a group (Group 2) of Sprague Dawley rats at a dosage level of 8.8 mg/kg/day. A concurrent control group (Group 1) received the vehicle on a comparable regimen. The dose volume was 0.22 mL/kg, divided between the 2 nares, for both groups. Groups 1 and 2 each consisted of 15 animals/sex. Following 14 days of dose administration, 10 animals/sex/group were euthanized; the remaining 5 animals/sex/group were euthanized following a 14-day nondosing (recovery) period. Criteria for evaluation included daily mortality observations, daily clinical observations, detailed physical observations, body weights, food consumption, clinical pathology (hematology, coagulation, serum chemistry, and urinalysis), organ weights, gross pathology, and microscopic examination of select tissues.

There were no test article-related effects on survival. There were no test article-related clinical observations, or effects on body weights, food consumption, clinical pathology parameters or organ weights, or macroscopic or microscopic findings in the nasal cavity or olfactory.

Preparation

Dosing formulations were prepared at the test article concentrations indicated in Tables 56 and 57 below.

TABLE 56

Dose Formulation Concentration - Single-Dose Phase.

| Group Number | Treatment | Dose Level (mg/kg) | Test Article Concentration [a] (mg/mL) | pH [b] |
|---|---|---|---|---|
| 1 | Vehicle | 0 | 0 | 5.97 |
| 2 | Benzoylecgonine | 8.8 | 40 | 6.32 |

[a] A correction factor of 1.01 was used to account for salt, purity, and/or water content.
[b] pH measurement of the dosing formulations using a pH meter.

TABLE 57

Dose Formulation Concentration - Repeat-Dose Phase

| Group Number | Treatment | Dose Level (mg/kg) | Test Article Concentration [a] (mg/mL) | pH [b] |
|---|---|---|---|---|
| 1 | Vehicle | 0 | 0 | 5.97 |
| 2 | Benzoylecgonine | 8.8 | 40 | 6.32 |

[a] A correction factor of 1.01 was used to account for salt, purity, and/or water content.
[b] pH measurement of the dosing formulations using a pH meter.

The test article formulations were prepared approximately weekly as single formulations for each dosage level, divided into aliquots for daily dispensation, and stored at room temperature (18° C. to 24° C.), protected from light.

Test System, Animal Receipt, and Acclimation

The Sprague Dawley rat was chosen as the animal model for this Example as it is an accepted rodent species for preclinical toxicity testing by regulatory agencies. At this time, studies in laboratory animals provide the best available basis for extrapolation to humans and are required to support regulatory submissions. Acceptable models which do not use live animals currently do not exist.

Sprague Dawley rats (77 males and 77 females) were received in good health and were approximately 41 days old at receipt. Each animal was examined by a qualified technician on the day of receipt and weighed on the following day. Each animal was uniquely identified with a subcutaneous microchip implanted in the dorsoscapular area. All animals were housed for minimum of a 6-day acclimation and each animal was observed twice daily for mortality and changes in general appearance or behavior.

Individual body weights and cage food weights were recorded and detailed physical examinations were performed periodically during acclimation.

Animal Housing

Upon arrival, all animals were housed 2 to 3 per cage by sex in clean, solid bottom cages containing ground corncob bedding material. The animals were temporarily separated as necessary to allow for the performance of protocol-specified activities. Animals were maintained in accordance with the Guide for the Care and Use of Laboratory Animals. The animal facilities at the testing facility are accredited by AAALAC International. Enrichment devices were provided to all animals as appropriate throughout the study for environmental enrichment and to aid in maintaining the animals' oral health, and were sanitized weekly.

Diet, Drinking Water, and Maintenance

The basal diet used in this study is a certified feed with appropriate analyses performed by the manufacturer. Reverse osmosis-treated (on-site) drinking water, delivered by an automatic watering system, and the basal diet were provided ad libitum throughout the study, except during the period of fasting prior to clinical pathology blood collection when food, but not water, was withheld. No contaminants were present in animal feed or water at concentrations sufficient to interfere with the objectives of this study.

Environmental Conditions

All animals were housed throughout acclimation and during the study in an environmentally controlled room. The room temperature and relative humidity controls were set to maintain environmental conditions of 73° F.±5° F. (23° C.±3° C.) and 50%±20%, respectively. Actual mean daily temperature ranged from 72.4° F. to 72.5° F. (22.4° C. to 22.5° C.) and mean daily relative humidity ranged from 36.7% to 47.0% during the study. Fluorescent lighting provided illumination for a 12-hour light (0600 hours to 1800 hours)/12-hour dark photoperiod. The 12-hour light/12-hour dark photoperiod was interrupted as necessary to allow for the performance of protocol-specified activities. Air handling units were set to provide a minimum of 10 fresh air changes per hour.

Assignment of Animals to Treatment Groups

All available rats were weighed and examined in detail for physical abnormalities two and six days prior to the initiation of dose administration for the Repeat-Dose and Single-Dose Phases, respectively. The animals judged suitable for assignment to the study were selected for use in a computerized randomization procedure based on body weight stratification in a block design. The animals were then arranged into treatment groups and housed in social groups. Individual body weights at randomization were within ±20% of the mean for each sex.

For the Single-Dose Phase, the control and 8.8 mg/kg groups (Groups 1 and 2, respectively) each consisted of 20 males and 20 females. For the Repeat-Dose Phase, the control and 8.8 mg/kg/day groups (Groups 1 and 2, respectively) each consisted of 15 males and 15 females. The animals were approximately 7 weeks old at the initiation of dose administration. Individual body weights ranged from 231 g to 283 g for males and from 152 g to 197 g for females in the Single-Dose Phase groups, and from 186 g to 229 g for males and from 139 g to 168 g for females in the Repeat-Dose Phase groups at the initiation of dose administration.

Organization of Test Groups, Dosage Levels, and Treatment Regimen—The vehicle and test article formulations were administered by intranasal instillation into each naris via a syringe equipped with stainless steel-shafted, stainless steel ball-tipped dosing cannula once (Single-Dose Phase) or once daily for 14 consecutive days (Repeat-Dose Phase), through the day prior to the primary necropsy. The same syringe and dosing cannula was used to administer the dose across both nares for a given animal on a given dosing day. The total dose volume administered per dose was split approximately equally across each naris, such that approximately half of the total dose volume was administered into one naris, and the remaining was administered into the other naris. Treatment administration across each naris for an individual animal occurred at approximately the same time. The dose volume for all groups was 0.22 mL/kg. Individual doses were based on the most recently recorded body weights. Adjusted doses became effective the day of collection of the weekly body weights. The first day of dosing was Study Day 0; the first week of dosing was Study Week 0.

Tables 58 and 59 report the study group assignments.

TABLE 58

Study Group Assignments - Single-Dose Phase Groups.

| Group Number | Treatment | Dose Level (mg/kg) | Dose Volume (mL/kg) | Number of Animals | |
|---|---|---|---|---|---|
| | | | | Males | Females |
| 1 | Vehicle | 0 | 0.22 | 20 | 20 |
| 2 | Benzoylecgonine | 8.8 | 0.22 | 20 | 20 |

TABLE 59

Study Group Assignments - Repeat-Dose Phase Groups.

| Group Number | Treatment | Dose Level (mg/kg) | Dose Volume (mL/kg) | Number of Animals | |
|---|---|---|---|---|---|
| | | | | Males | Females |
| 1 | Vehicle | 0 | 0.22 | 15 | 15 |
| 2 | Benzoylecgonine | 8.8 | 0.22 | 15 | 15 |

Deionized water was chosen as the vehicle for this study to avoid any vehicle-related local toxicity. Benzoylecgonine is soluble in water up to approximately 40 mg/mL. Therefore, the maximum feasible dose for both the Single- and Repeat-dose phases of this study was determined to be 8.8 mg/kg based on the solubility and maximum dose volume of 40 µL per naris.

The selected route of administration for this study was intranasal instillation because this is the intended clinical route of exposure.

Parameters Evaluated

Survival

All animals were observed twice daily, once in the morning and once in the afternoon, for mortality and moribundity. Animals found dead were examined macroscopically as soon as possible to ensure that tissues were not lost due to autolysis.

Clinical Observations

Clinical examinations were performed at the time of dose administration and 1 to 2 hours following dose administration. During the recovery period, the animals were observed once daily. The absence or presence of findings was recorded for individual animals at the scheduled intervals. For the Single-Dose Phase, detailed physical examinations were conducted on all animals within 4 days of receipt, on the day of randomization, and on Study Days 0, 1 (for animals scheduled for necropsy), 7, and 14. For the Repeat-Dose Phase, detailed physical examinations were conducted on all animals within 4 days of receipt, on the day of randomization, weekly (t 2 days) during the study period, and on the day of the scheduled necropsies (see Appendix 1—Study Protocol and Deviations). Daily observations during the recovery period were not necessary on days when detailed physical examinations were conducted. In addition, the social groups were observed at the appropriate intervals for findings that could not be attributed to a single animal; only positive findings were recorded.

Body Weights

Individual body weights were recorded within 4 days of receipt, on the day of randomization, Study Day 0 (prior to dosing), weekly (±2 days) during the study period, and on the day prior to the scheduled necropsies (nonfasted). Mean body weights and mean body weight changes were calculated for the corresponding intervals. Final body weights (fasted) were recorded on the day of the scheduled necropsies.

Food Consumption

Cage food weights were recorded once weekly (±2 days) beginning following randomization and throughout the study period. Food consumption was calculated as g/animal/day for the corresponding body weight intervals.

Clinical Pathology

Blood and urine samples for clinical pathology evaluations (hematology, coagulation, serum chemistry, and urinalysis) were collected from all animals assigned to the scheduled necropsies. The animals were fasted overnight prior to blood collection while in metabolism cages for urine collection. Blood was collected for hematology and serum chemistry evaluation via a jugular vein. Blood was collected for coagulation parameters at the time of euthanasia via the vena cava of animals euthanized by inhalation of carbon dioxide. Blood was collected into tubes containing potassium K2EDTA (hematology), sodium citrate (coagulation), or no anticoagulant (serum chemistry).

The hematology and coagulation, serum chemistry, and urinalysis parameters for Example 9 are reported in Tables 60, 61, and 62, respectively.

TABLE 60

Hematology and Coagulation Parameters

Total leukocyte count (WBC)
Erythrocyte count (RBC)
Hemoglobin (HGB)
Hematocrit (HCT)
Mean corpuscular volume (MCV)
Mean corpuscular hemoglobin (MCH)
Mean corpuscular hemoglobin concentration (MCHC)
Platelet count (Platelet)
Prothrombin time (PT)
Activated partial thromboplastin time (APTT)
Reticulocyte count
Percent (RETIC)
Absolute (RETIC Absolute)
Differential leukocyte count
Percent and absolute
Neutrophil (NEU)
Lymphocyte (LYMPH)
Monocyte (MONO)
Eosinophil (EOS)
Basophil (BASO)
Large unstained cell (LUC)
Red cell distribution width (RDW)
Platelet estimate
Red cell morphology (RBC Morphology)

TABLE 61

Serum Chemistry Parameters

Albumin
Total protein
Globulin [by calculation]
Albumin/globulin ratio (A/G Ratio) [by calculation]
Total bilirubin (Total BILI)
Urea nitrogen
Creatinine
Alkaline phosphatase (ALP)
Alanine aminotransferase (ALT)
Aspartate aminotransferase (AST)
Gamma glutamyltransferase (GGT)
Glucose
Total cholesterol (Cholesterol)
Calcium
Chloride
Phosphorus
Potassium
Sodium
Sorbitol dehydrogenase (SDH)
Triglycerides (Triglyceride)
Appearance

TABLE 62

Urinalysis Parameters

Specific gravity (SG)
pH
Total volume (TVOL)
Color (COL)

TABLE 62-continued

Urinalysis Parameters

Clarity (CLA)
Protein (PRO)
Glucose (GLU)
Ketones (KET)
Bilirubin (BIL)
Occult blood (BLD)

Anatomic Pathology

Macroscopic Examination

A complete necropsy was conducted on all animals. The necropsies included, but were not limited to, examination of the external surface, all orifices, and the cranial, thoracic, abdominal, and pelvic cavities, including viscera. Table 63 lists the tissues and organs that were collected for the study.

TABLE 63

Tissues and organs collected for Example 9.

Adrenal glands (2)
Aorta
Bone with marrow
Femur
Sternum
Bone marrow smear (from femur)
Brain
Cervix
Epididymides (2)
Eyes with optic nerves (2)
Gastrointestinal tract
Esophagus
Stomach
Duodenum
Jejunum
Ileum
Cecum
Colon
Rectum
Heart
Kidneys (2)
Larynx
Liver (sections of 2 lobes)
Lungs (including bronchi)
Lymph nodes
Axillary (2)
Mandibular (2)
Mesenteric
Nasal cavity with turbinates
Ovaries (2) with oviducts
Pancreas
Peripheral nerve (sciatic)
Peyer's patches
Pharynx
Pituitary
Prostate
Salivary glands (mandibular (2))
Seminal vesicles (2)
Skeletal muscle (rectus femoris)
Skin with mammary gland
Spinal cord (cervical, thoracic, lumbar)
Spleen
Testes (2)
Thymus
Thyroid (with parathyroids (2))
Tongue
Trachea
Urinary bladder
Uterus
Vagina
Gross lesions (when possible)

Organ Weights

Table 64 shows the organs weighed from animals during the scheduled necropsies of Example 9.

TABLE 64

Organs weighed in Example 9.

Adrenal glands
Brain
Epididymides
Heart
Kidneys
Liver
Ovaries with oviducts
Pituitary
Prostate with seminal vesicles
Spleen
Testes
Thymus
Thyroid with parathyroids
Uterus Paired organs were weighed together. Organ to final body weight and organ to brain weight ratios were calculated.

Histology and Microscopic Examination

After fixation, the nasal cavity with turbinates were trimmed and processed into paraffin blocks, sectioned, mounted on glass microscope slides, and stained with hematoxylin and eosin.

Microscopic examination was performed for the nasal cavity with turbinates from all animals found dead or euthanized at the scheduled necropsies.

Results

Analyses of Dosing Formulations

The analyzed dosing formulations contained 101% to 108% of the test article which was within the protocol-specified target concentrations (90% to 110%). The test article was not detected in the analyzed vehicle formulation that was administered to the control group.

Single-Dose Phase

Survival

There were no test article-related effects on survival. A single male (No. 8885) in the control group was found dead on Study Day 1. This male was noted with macroscopic findings of dark red contents in the ventral neck skeletal muscle and thoracic and oral cavities. Therefore, this death was attributed to blood collection procedures. All other animals survived to the scheduled necropsies.

Clinical Observations

There were no test article-related clinical observations. All clinical observations in the test article-treated group were noted with similar incidence in the control group and/or were limited to single animals.

Body Weights

Body weights were unaffected by test article administration. There were no statistically significant differences when the control and test article-treated groups were compared.

Food Consumption

Food consumption was unaffected by test article administration. There were no statistically significant differences when the control and test article-treated groups were compared.

Clinical Pathology

Hematology and coagulation parameters were unaffected by test article administration. Differences in hematology and coagulation parameters, including those that may have been statistically significant, were not considered test article-related and were attributed to biologic variation because they were of a magnitude of change commonly observed in rats under similar study conditions.

Serum Chemistry

Serum chemistry parameters were unaffected by test article administration. Differences in serum chemistry parameters, including those that may have been statistically significant, were not considered test article-related and were attributed to biologic variation because they were of a magnitude of change commonly observed in rats under similar study conditions.

Urinalysis

Urinalysis parameters were unaffected by test article administration. Differences in urinalysis parameters, including those that may have been statistically significant, were not considered test article-related and were attributed to biologic variation because they were of a magnitude of change commonly observed in rats under similar study conditions.

Anatomic Pathology

Macroscopic Examination

No macroscopic findings were present in the nasal tissues at necropsy. No test article-related macroscopic findings were present at necropsy. All macroscopic observations occurred at a similar incidence between control and test article-dosed rats or are common spontaneous findings in rats of this strain, age, route of administration, and were not considered test article related.

Organ Weights

No test article-related organ weight findings were present at necropsy, and any statistically significant organ weight fluctuations were considered due to individual animal variability, lack of a dose response or lacked a correlating finding in both sexes.

Microscopic Examination

No test article-related microscopic findings were present after a single dose of benzoylecgonine was administered intranasally in Sprague Dawley rats. After a 14-day recovery period from a single dose of benzoylecgonine administered intranasally in Sprague Dawley rats, no test article-related microscopic findings were present. All microscopic findings occurred at similar incidence and severity between control and test article-dosed rats or are common spontaneous findings in rats of this strain, age, route of administration, and were not considered test article related.

Repeat-Dose Phase

Survival

All animals survived to the scheduled necropsies.

Clinical Observations

There were no test article-related clinical observations. All clinical observations in the test article-treated groups were noted with similar incidence in the control group, were limited to single animals, and/or were common findings for laboratory rats of this age and strain.

Body Weights

Body weights were unaffected by test article administration during the dosing period. However, mean body weights for the 8.8 mg/kg/day group males were statistically significantly different than the corresponding control group during the recovery period and the cumulative body weight change for the 8.8 mg/kg/day males was statistically significantly different than the corresponding control group during the study period (Study Days 0-13). These changes were attributed to normal biological variation as the mean body weight changes for the 8.8 mg/kg/day group males during the recovery period were similar to the corresponding control group and the difference in cumulative body weight change was minimal.

Food Consumption

Food consumption was unaffected by test article administration during the dosing period. There were no statistically significant differences when the control and test article-treated group were compared.

Clinical Pathology

Hematology and Coagulation

Hematology and coagulation parameters were unaffected by test article administration. Differences in hematology and coagulation parameters, including those that may have been statistically significant, were not considered test article-related and were attributed to biologic variation because they were of a magnitude of change commonly observed in rats under similar study conditions.

Serum Chemistry

Serum chemistry parameters were unaffected by test article administration. Differences in serum chemistry parameters, including those that may have been statistically significant, were not considered test article-related and were attributed to biologic variation because they were of a magnitude of change commonly observed in rats under similar study conditions.

Urinalysis

Urinalysis parameters were unaffected by test article administration. Differences in urinalysis parameters, including those that may have been statistically significant, were not considered test article-related and were attributed to biologic variation because they were of a magnitude of change commonly observed in rats under similar study conditions.

Anatomic Pathology

Macroscopic Examination

No test article-related macroscopic findings were present at necropsy. All macroscopic observations occurred at a similar incidence between control and test article-dosed rats or are common spontaneous findings in rats of this strain, age, route of administration, and were not considered test article-related.

Organ Weights

No test article-related organ weight findings were present at necropsy, and any statistically significant organ weight fluctuations were considered due to individual animal variability, lack of a dose response or lacked a correlating finding in both sexes.

Microscopic Examination

No test article-related microscopic findings were present after 14 daily doses of benzoylecgonine administered intranasally in Sprague Dawley rats. After a 14-day recovery period from 14 daily doses of benzoylecgonine administered intranasally in Sprague Dawley rats, no test article-related microscopic findings were present. All microscopic findings occurred at similar incidence and severity between control and test article-dosed rats or are common spontaneous findings in rats of this strain, age, route of administration, and were not considered test article related.

Conclusions

Based on the results of this study, intranasal instillation of benzoylecgonine to Sprague Dawley rats at a dose level of 8.8 mg/kg once or once daily for 14 days was well tolerated. Therefore, the no-observed-effect level (NOEL) was considered to be 8.8 mg/kg/day.

Example 10

The objectives of the study were to evaluate the potential toxicity of cocaethylene hydrochloride (HCl) when administered as a single intranasal instillation to Sprague Dawley rats or as a daily intranasal instillation to Sprague Dawley rats for 14 consecutive days, as well as to evaluate the recovery, persistence, or progression of any effects following a recovery period of a minimum of 14 days.

Single-Dose Phase

Cocaethylene HCl in the vehicle (deionized water) was administered by intranasal instillation once to a group (Group 2) of Sprague Dawley rats at a dose level of 2.1 mg/kg. A concurrent control group (Group 1) received the vehicle on a comparable regimen. The dose volume was 0.22 mL/kg, divided between the 2 nares, for both groups. Groups 1 and 2 each consisted of 20 animals/sex. Following dose administration, 10 animals/sex/group were euthanized on Study Day 1; the remaining 10 animals/sex/group were euthanized following a 14-day non-dosing (recovery) period. Criteria for evaluation included daily mortality observations, daily clinical observations, detailed physical observations, body weights, food consumption, clinical pathology (hematology, coagulation, serum chemistry, and urinalysis), organ weights, gross pathology, and microscopic examination of select tissues.

All animals survived to the scheduled necropsies. There were no test article-related clinical observations and macroscopic findings or effects on body weights, food consumption, clinical pathology parameters, or organ weights. In addition, there were no test article-related microscopic findings in the nasal cavity or olfactory bulbs.

Repeat-Dose Phase

Cocaethylene hydrochloride in the vehicle was administered by intranasal instillation once daily for 14 days to a group (Group 2) of Sprague Dawley rats at a dosage level of 2.1 mg/kg/day. A concurrent control group (Group 1) received the vehicle on a comparable regimen. The dose volume was 0.22 mL/kg, divided between the 2 nares, for both groups. Groups 1 and 2 each consisted of 15 animals/sex. Following 14 days of dose administration, 10 animals/sex/group were euthanized; the remaining 10 animals/sex/group were euthanized following a 14-day nondosing (recovery) period. Criteria for evaluation included daily mortality observations, daily clinical observations, detailed physical observations, body weights, food consumption, clinical pathology (hematology, coagulation, serum chemistry, and urinalysis), organ weights, gross pathology, and microscopic examination of select tissues.

All animals survived to the scheduled necropsies. There were no test article-related clinical observations and macroscopic findings or effects on body weights, food consumption, clinical pathology parameters, or organ weights. In addition, there were no test article-related microscopic findings in the nasal cavity or olfactory bulbs.

Preparation

Dosing formulations were prepared at the test article concentrations indicated in the Tables 65 and 66 below.

TABLE 65

Dose Formulation Concentration - Single-Dose Phase.

| Group Number | Treatment | Dose Level (mg/kg) | Test Article Concentration[a] (mg/mL) | pH[b] |
|---|---|---|---|---|
| 1 | Vehicle | 0 | 0 | 5.66 |
| 2 | Cocaethylene HCl | 2.1 | 9.6 | 2.81 |

[a] A correction factor of 1.22 was used to account for salt, purity, and/or water content.
[b] pH measurement of the dosing formulations using a pH meter.

TABLE 66

Dose Formulation Concentration - Repeat-Dose Phase:

| Group Number | Treatment | Dose Level (mg/kg) | Test Article Concentration[a] (mg/mL) | pH[b] |
|---|---|---|---|---|
| 1 | Vehicle | 0 | 0 | 5.66 |
| 2 | Cocaethylene HCl | 2.1 | 9.6 | 2.81 |

[a] A correction factor of 1.22 was used to account for salt, purity, and/or water content.
[b] pH measurement of the dosing formulations using a pH meter.

The test article formulations were prepared approximately twice weekly as single formulations for each dosage level, divided into aliquots for daily dispensation, and stored refrigerated (2° C. to 8° C.), protected from light. The test article formulations were stirred continuously throughout the preparation, sampling, and dose administration procedures.

Test System, Animal Receipt, and Acclimation

The Sprague Dawley rat was chosen as the animal model for this study as it is an accepted rodent species for preclinical toxicity testing by regulatory agencies. At this time, studies in laboratory animals provide the best available basis for extrapolation to humans and are required to support regulatory submissions. Acceptable models which do not use live animals currently do not exist.

Sprague Dawley rats (77 males and 77 females) were received in good health and were approximately 38 days old at receipt. Each animal was examined by a qualified technician on the day of receipt and weighed on the following day. Each animal was uniquely identified with a subcutaneous microchip implanted in the dorsoscapular area. All animals were housed for a minimum 13-day acclimation and each animal was observed twice daily for mortality and changes in general appearance or behavior. Individual body weights and cage food weights were recorded and detailed physical examinations were performed periodically during acclimation.

Animal Housing

Upon arrival, all animals were housed 2 to 4 per cage by sex in clean, solid bottom cages containing ground corncob bedding material. The animals were temporarily separated as necessary to allow for the performance of protocol-specified activities. Animals were maintained in accordance with the Guide for the Care and Use of Laboratory Animals. The animal facilities at the testing facility are accredited by AAALAC International. Enrichment devices were provided to all animals as appropriate throughout the study for environmental enrichment and to aid in maintaining the animals' oral health, and were sanitized weekly.

Diet, Drinking Water, and Maintenance

The basal diet used in this study is a certified feed with appropriate analyses performed by the manufacturer. Reverse osmosis-treated (on-site) drinking water, delivered by an automatic watering system, and the basal diet were provided ad libitum throughout the study, except during the period of fasting prior to clinical pathology blood collection when food, but not water, was withheld. No contaminants were present in animal feed or water at concentrations sufficient to interfere with the objectives of this study.

Environmental Conditions

All animals were housed throughout acclimation and during the study in an environmentally controlled room. The room temperature and relative humidity controls were set to maintain environmental conditions of 73° F.±5° F. (23° C.±3° C.) and 50%±20%, respectively. Actual mean daily temperature ranged from 72.7° F. to 72.9° F. (22.6° C. to 22.7° C.) and mean daily relative humidity ranged from 37.0% to 55.3% during the study. Fluorescent lighting provided illumination for a 12-hour light (0600 hours to 1800 hours)/12-hour dark photoperiod. Air handling units were set to provide a minimum of 10 fresh air changes per hour.

Assignment of Animals to Treatment Groups

All available rats were weighed and examined in detail for physical abnormalities seven days prior to the initiation of dose administration in the Single-Dose Phase. The animals judged suitable for assignment to the study were selected for use in a computerized randomization procedure based on body weight stratification in a block design. The animals were then arranged into treatment groups and housed in social groups. Individual body weights at randomization were within ±20% of the mean for each sex.

For the Single-Dose Phase, the control and 2.1 mg/kg groups (Groups 1 and 2, respectively) each consisted of 20 males and 20 females. For the Repeat-Dose Phase, the control and 2.1 mg/kg groups (Groups 1 and 2, respectively) each consisted of 15 males and 15 females. The animals were approximately 7 weeks old at the initiation of dose administration. Individual body weights ranged from 217 g to 269 g for males and from 167 g to 221 g for females in the Single-Dose Phase groups, and from 228 g to 281 g for males and from 163 g to 224 g for females in the Repeat-Dose Phase groups at the initiation of dose administration.

Organization of Test Groups, Dosage Levels, and Treatment Regimen

The vehicle and test article formulations were administered by intranasal instillation into each naris via a syringe equipped with stainless steel-shafted, stainless steel ball-tipped dosing cannula once (Single-Dose Phase) or once daily for 14 consecutive days (Repeat-Dose Phase), through the day prior to the primary necropsy. The same syringe and dosing cannula was used to administer the dose across both nares for a given animal on a given dosing day. The total dose volume administered per dose was split approximately equally across each naris, such that approximately half of the total dose volume was administered into one naris, and the remaining was administered into the other naris. Treatment administration across each naris for an individual animal occurred at approximately the same time. The dose volume for all groups was 0.22 mL/kg. Individual doses were based on the most recently recorded body weights. Adjusted doses became effective the day of collection of the weekly body weights. The first day of dosing was Study Day 0; the first week of dosing was Study Week 0.

Tables 67 and 68 below report the study group assignments for Single-Dose Phase Groups and Repeat-Dose Phase Groups, respectively.

TABLE 67

Study Group Assignments - Single-Dose Phase Groups

| Group Number | Treatment | Dose Level (mg/kg) | Dose Volume (m L/kg) | Number of Animals | |
|---|---|---|---|---|---|
| | | | | Males | Females |
| 1 | Vehicle | 0 | 0.22 | 20 | 20 |
| 2 | Cocaethlyene HCl | 2.1 | 0.22 | 20 | 20 |

TABLE 68

Study Group Assignments - Repeat-Dose Phase Groups

| Group Number | Treatment | Dose Level (mg/kg) | Dose Volume (m L/kg) | Number of Animals | |
|---|---|---|---|---|---|
| | | | | Males | Females |
| 1 | Vehicle | 0 | 0.22 | 15 | 15 |
| 2 | Cocaethlyene HCl | 2.1 | 0.22 | 15 | 15 |

The selected route of administration for this study was intranasal instillation, because this route was the intended clinical route of administration.

Parameters Evaluated

Survival

All animals were observed twice daily, once in the morning and once in the afternoon, for mortality and moribundity.

Clinical Observations

Clinical examinations were performed at the time of dose administration and 1 to 2 hours following dose administration. During the recovery period, the animals were observed once daily. The absence or presence of findings was recorded for individual animals at the scheduled intervals. For the Single-Dose Phase, detailed physical examinations were conducted on all animals within 4 days of receipt, on the day of randomization, and on Study Days 0, 1, 7, and 14. For the Repeat-Dose Phase, detailed physical examinations were conducted on all animals within 4 days of receipt, on the day of randomization, weekly (±2 days) during the study period, and on the day of the scheduled necropsies. Daily observations during the recovery period were not necessary on days when detailed physical examinations were conducted. In addition, the social groups were observed at the appropriate intervals for findings that could not be attributed to a single animal; only positive findings were recorded.

Body Weights

Individual body weights were recorded within 4 days of receipt, on the day of randomization, Study Day 0 (prior to dosing), weekly (±2 days) during the study period, and on the day prior to the scheduled necropsies (nonfasted). Mean body weights and mean body weight changes were calculated for the corresponding intervals. Final body weights (fasted) were recorded on the day of the scheduled necropsies.

Food Consumption

Cage food weights were recorded once weekly (±2 days) beginning following randomization and throughout the study period. Food consumption was calculated as g/animal/day for the corresponding body weight intervals.

Clinical Pathology

Blood and urine samples for clinical pathology evaluations (hematology, coagulation, serum chemistry, and urinalysis) were collected from all animals assigned to the scheduled necropsies. The animals were fasted overnight prior to blood collection while in metabolism cages for urine collection. Blood was collected from a jugular vein and from the vena cava at the time of necropsy. Blood was collected into tubes containing potassium K2EDTA (hematology), sodium citrate (coagulation), or no anticoagulant (serum chemistry). The hematology and coagulation, serum chemistry, and urinalysis parameters for Example 9 are reported in Tables 69, 70, and 71.

TABLE 69

| Hematology and Coagulation |
| --- |
| Parameters Total leukocyte count (WBC) |
| Erythrocyte count (RBC) |
| Hemoglobin (HGB) |
| Hematocrit (HCT) |
| Mean corpuscular volume (MCV) |
| Mean corpuscular hemoglobin (MCH) |
| Mean corpuscular hemoglobin concentration (MCHC) |
| Platelet count (Platelet) |
| Prothrombin time (PT) |
| Activated partial thromboplastin time (APTT) |
| Reticulocyte count |
| Percent (RETIC) |
| Absolute (RETIC Absolute) |
| Differential leukocyte count |
| Percent and absolute |
| Neutrophil (NEU) |
| Lymphocyte (LYMPH) |
| Monocyte (MONO) |
| Eosinophil (EOS) |
| Basophil (BASO) |
| Large unstained cell (LUC) |
| Red cell distribution width (RDW) |
| Platelet estimate |
| Red cell morphology (RBC Morphology) |

TABLE 70

| Serum Chemistry Parameters. |
| --- |
| Albumin |
| Total protein |
| Globulin [by calculation] |
| Albumin/globulin ratio (A/G Ratio) [by calculation] |
| Total bilirubin (Total BILI) |
| Urea nitrogen |
| Creatinine |
| Alkaline phosphatase (ALP) |
| Alanine aminotransferase (ALT) |
| Aspartate aminotransferase (AST) |
| Gamma glutamyltransferase (GGT) |
| Glucose |
| Total cholesterol (Cholesterol) |
| Calcium |
| Chloride |
| Phosphorus |
| Potassium |
| Sodium |
| Sorbitol dehydrogenase (SDH) |
| Triglycerides (Triglyceride) |
| Appearance a |

TABLE 71

| Urinalysis Parameters. |
| --- |
| Specific gravity (SG) |
| pH |
| Total volume (TVOL) |
| Color (COL) |
| Clarity (CLA) |
| Protein (PRO) |
| Glucose (GLU) |
| Ketones (KET) |
| Bilirubin (BIL) |
| Occult blood (BLD) |

Anatomic Pathology

Macroscopic Examination

A complete necropsy was conducted on all animals. The necropsies included, but were not limited to, examination of the external surface, all orifices, and the cranial, thoracic, abdominal, and pelvic cavities, including viscera. Table 72 reports the tissues and organs collected below.

TABLE 72

| Tissues and organs collected for examination of the animal subjects |
| --- |
| Adrenal glands (2) |
| Aorta |
| Bone with marrow |
| Femur |
| Sternum |
| Bone marrow smear (from femur) |
| Brain |
| Cervix |
| Epididymides (2) |
| Eyes with optic nerves (2) |
| Gastrointestinal tract |
| Esophagus |
| Stomach |
| Duodenum |
| Jejunum |
| Ileum |
| Cecum |
| Colon |
| Rectum |
| Heart |
| Kidneys (2) |
| Larynx |
| Liver (sections of 2 lobes) |
| Lungs (including bronchi) |
| Lymph nodes |
| Axillary (2) |
| Mandibular (2) |
| Mesenteric |
| Nasal cavity with turbinates |
| Ovaries (2) with oviducts |
| Pancreas |
| Peripheral nerve (sciatic) |
| Peyer's patches |
| Pharynx |
| Pituitary |
| Prostate |
| Salivary glands (mandibular (2)) |
| Seminal vesicles (2) |
| Skeletal muscle (rectus femoris) |
| Skin with mammary gland |
| Spinal cord (cervical, thoracic, lumbar) |
| Spleen |
| Testes (2) |
| Thymus |
| Thyroid (with parathyroids (2)) |
| Tongue |
| Trachea |
| Urinary bladder |
| Uterus |
| Vagina |
| Gross lesions (when possible) |

Organ Weights

Table 73, shown below, reports the organs weighed from each of the animals during the scheduled necropsies.

TABLE 64

| Organs weighed from participating animal subjects |
| --- |
| Adrenal glands |
| Brain |
| Epididymides |
| Heart |
| Kidneys |
| Liver |
| Ovaries with oviducts |
| Pituitary |
| Prostate with seminal vesicles |
| Spleen |
| Testes |

TABLE 64-continued

Organs weighed from participating animal subjects

Thymus
Thyroid with parathyroids
Uterus

Paired organs were weighed together. Organ to final body weight and organ to brain weight ratios were calculated Histology and Microscopic Examination After fixation, the nasal cavity with turbinates were trimmed and processed into paraffin blocks, sectioned, mounted on glass microscope slides, and stained with hematoxylin and eosin.

Microscopic examination was performed for the nasal cavity with turbinates from all animals found dead or euthanized at the scheduled necropsies.

Results

Analysis of Dosing Formulations

The analyzed dosing formulations contained 103% to 105% of the test article which was within the protocol-specified target concentrations (90% to 110%). The test article was not detected in the analyzed vehicle formulation that was administered to the control group (Group 1).

Single-Dose Phase

Survival

All animals survived to the scheduled necropsies.

Clinical Observations

There were no test article-related clinical observations. All clinical observations in the test article-treated group were noted with similar incidence in the control group, were limited to a single occurrence in single animals, and/or were common findings for laboratory rats of this age and strain.

Body Weights

Body weights were unaffected by test article administration. There were no statistically significant differences when the control and test article-treated group were compared.

Food Consumption

Food consumption was unaffected by test article administration. There were no statistically significant differences when the control and test article-treated group were compared.

Clinical Pathology

Hematology and Coagulation

Hematology and coagulation parameters were unaffected by test article administration. Differences in hematology and coagulation parameters, including those that may have been statistically significant, were not considered test article-related, were attributed to biologic variation because they were of a magnitude of change commonly observed in rats under similar study conditions.

Serum Chemistry

Serum chemistry parameters were unaffected by test article administration. Differences in serum chemistry parameters, including those that may have been statistically significant, were not considered test article-related, were attributed to biologic variation because they were of a magnitude of change commonly observed in rats under similar study conditions.

Urinalysis

Urinalysis parameters were unaffected by test article administration. There were no statistically significant differences when the control and test article-treated group were compared.

Anatomic Pathology

Macroscopic Examination

There were no test article-related macroscopic findings at the scheduled necropsies. All macroscopic findings noted were considered to be spontaneous and/or incidental in nature and unrelated to test article administration.

Organ Weights

Organ weights were unaffected by test article administration. Differences in organ weights, including those that may have been statistically significant, were not considered test article-related, were attributed to biologic variation because they were of a magnitude of change commonly observed in rats under similar study conditions.

Microscopic Examination

No test article-related microscopic findings were present after a single dose of cocaethylene HCl was administered intranasally in Sprague Dawley rats. After a 14-day recovery period from a single dose of cocaethylene HCl administered intranasally in Sprague Dawley rats, no test article-related microscopic findings were present. All microscopic findings occurred at similar incidence and severity between control and test article-dosed rats or are common spontaneous findings in rats of this strain, age, route of administration, and were not considered test article-related.

Repeat-Dose Phase

Survival

All animals survived to the scheduled necropsies.

Clinical Observations

There were no test article-related clinical observations. At the time of dosing, there was a higher incidence of red nasal discharge in the test article-treated group males and females in comparison to the concurrent control group. Due to the low overall incidence and that the observation was noted in the concurrent control group, this observation was not considered test article-related. The discharge was considered procedural-related as there were no correlating histopathological findings and the act of picking up the animal and dosing them is stressful and this discharge may be porphyrin.

Body Weights

Body weights were unaffected by test article administration. There were no statistically significant differences when the control and test article-treated group were compared. Lower mean body weights were noted in the 2.1 mg/kg group males on Study Days 21 and 27 in comparison to the concurrent control group. However, the control group means were considered to be higher due to a higher than expected weight for Male No. 9813 (0 mg/kg control group). In addition, lower mean body weight gains were noted in the 2.1 mg/kg group males and females from Study Day 13 to 21. The 2.1 mg/kg group means were lower due to body weight loss observed in 1 male and 2 females. Food consumption for these animals was consistent with other weeks on study where body weight loss was not observed. Additionally, these same animals had higher than expected body weight gains from Study Day 21 to 27. Based on the above information, the body-weight effects during Days 13 to 21 were not considered test article-related.

Food Consumption

Food consumption was unaffected by test article administration. There were no statistically significant differences when the control and test article-treated group were compared.

Clinical Pathology

Hematology and Coagulation

Hematology and coagulation parameters were unaffected by test article administration. Differences in hematology and coagulation parameters, including those that may have been statistically significant, were not considered test article-related and were attributed to biologic variation because they were of a magnitude of change commonly observed in rats under similar study conditions.

Serum Chemistry

Serum chemistry parameters were unaffected by test article administration. Differences in serum chemistry parameters, including those that may have been statistically significant, were not considered test article-related, were attributed to biologic variation because they were of a magnitude of change commonly observed in rats under similar study conditions.

Urinalysis

Urinalysis parameters were unaffected by test article administration. There were no statistically significant differences when the control and test article-treated group were compared.

Anatomic Pathology

Macroscopic Examination

There were no test article-related macroscopic findings at the scheduled necropsies. All macroscopic findings noted were considered to be spontaneous and/or incidental in nature and unrelated to test article administration.

Organ Weights

Organ weights were unaffected by test article administration. Differences in organ weights, including those that may have been statistically significant, were not considered test article-related and were attributed to biologic variation because they were of a magnitude of change commonly observed in rats under similar study conditions.

Microscopic Examination

No test article-related microscopic findings were present after 14 daily doses of cocaethylene HCl administered intranasally in Sprague Dawley rats. After a 14-day recovery period from 14 daily doses of cocaethylene HCl administered intranasally in Sprague Dawley rats, no test article-related microscopic findings were present. All microscopic findings occurred at similar incidence and severity between control and test article-dosed rats or are common spontaneous findings in rats of this strain, age, route of administration, and were not considered test article-related.

Conclusions

Based on the results of this study, intranasal instillation administration of cocaethylene HCl to Sprague Dawley rats at a dose level of 2.1 mg/kg once or once daily for 14 days was well tolerated. There were no test article-related macroscopic or microscopic findings in the nasal cavity or olfactory bulbs. Therefore, the no-observed-effect level (NOEL) was considered to be 2.1 mg/kg/day.

Example 11

The objectives of this study were to evaluate the effect of cocaine topical solution on electrocardiogram ("ECG") parameters and to evaluate the safety and tolerability of cocaine topical solution. The pharmaceutical compositions used were aqueous solutions having the compositions of the 4% and 8% cocaine hydrochloride solutions described in Example 4.

Methods and Materials

This was a single-dose, partially blinded, randomized, four-period, four-treatment, crossover study in which 24 healthy adult subjects received separate single doses of cocaine topical solution (8%), cocaine topical solution (4%), placebo, and moxifloxacin HCl tablet (400 mg) in four study periods. Each subject received a different treatment in each study period. Subjects received each of the following treatments in randomized fashion during the four treatment periods: (1) Treatment A: Cocaine hydrochloride, USP, topical solution, 8%; Dose=320 mg (80 mg/mL×4 mL); (2) Treatment B: Cocaine hydrochloride, USP, topical solution, 4%; Dose=160 mg (40 mg/mL×4 mL); (3) Treatment C: Placebo; and (4) Treatment D: AVELOX® (moxifloxacin hydrochloride); Dose=400 mg (1×400 mg tablet).

Treatments A, B, and C were blinded, while Treatment D was open label. Each drug administration was separated by a washout period of at least 4 days. Each dose of cocaine hydrochloride pharmaceutical composition and placebo were administered as follows: 4 mL of cocaine hydrochloride pharmaceutical solution (or placebo vehicle) were poured into a standard medicine cup. Four (4) cottonoid pledgets (approximately 1.3 cm×4 cm) were soaked in the 4 mL of the solution for 10 minutes and allowed to saturate. Each pledget absorbed approximately 1 mL of solution. The soaked pledgets were placed into the nasal cavity (2 per side) and up against the septum at time 0 and removed after 20 minutes. Moxifloxacin HCl was orally administered along with approximately 240 mL (8 fl oz) of room temperature water.

A 25-hour continuous 12-lead ECG recording was performed on Day 1, starting 1 hour before dosing. At the designated time points, up to 10 replicate ECGs were extracted and intervals were measured using the High Precision QT technique. The High Precision QT technique is generally described, for example, in Darpo, et al., "Improving the precision of QT measurements", Cardiology Journal 2011, Vol. 18, No. 4, pp. 401-410, incorporated by reference herein. During protocol-specified ECG extraction windows, 10-second digital 12-lead ECG tracings were extracted from continuous recordings (preceded by a 10-minute supine rest period) at the following time points: predose (3 time points) and 20 minutes (end of cocaine dose; immediately after pledget removal), 40 minutes, and at 1, 1.25, 1.5, 2, 2.5, 3, 4, 6, 8, 12, and 24 hours after pledget insertion/moxifloxacin dosing.

Endpoints

The primary ECG endpoint was ΔQTcF. ΔQTcF is the QTc corrected for heart rate by the Fridericia method. The term "QTc", as used herein, refers to the duration of the QT interval adjusted for the patient's heart rate.

The secondary ECG endpoints were: change-from-baseline heart rate ("HR"), time from beginning of the P-wave to the beginning of the next QRS complex ("PR"), deflections in the tracing of the electrocardiogram comprising the Q, R, and S waves that represent depolarization of the ventricles ("QRS"), time elapsed between two consecutive R waves ("RR"), and measure of the time in the tracing of the electrocardiogram between the start of the Q-wave and the end of the T-wave ("QT"); and T-wave morphological changes.

Results

Overall, cocaine hydrochloride pharmaceutical composition was well-tolerated when administered as a supra-therapeutic (8%) and a therapeutic (4%) intranasal dose to healthy subjects. The results are reported in Tables 74-83 below.

TABLE 74

Change-from-baseline QTcF - QT/QTc Population

| Parameter | Time | Statistics | 160 mg (4%) | 320 mg (8%) | 400 mg (moxifloxacin HCl) | Placebo |
|---|---|---|---|---|---|---|
| ΔQTcF (ms) | 20 min post-dose | n | 24 | 23 | 23 | 24 |
| | | LSMean | 1.6 | 4.0 | −3.1 | −3.0 |
| | | SEM | 1.7 | 1.7 | 1.7 | 1.7 |
| | | 90% CI | (−1.5; 4.6) | (0.9; 7.0) | (−6.1; 0.0) | (−6.1; 0.1) |
| | 40 min post-dose | n | 24 | 24 | 24 | 24 |
| | | LSMean | 2.4 | 5.8 | 4.4 | −1.0 |
| | | SEM | 1.8 | 1.8 | 1.8 | 1.8 |
| | | 90% CI | (−0.6; 5.5) | (2.7; 8.9) | (1.4; 7.5) | (−4.1; 2.1) |
| | 1 hour post-dose | n | 24 | 24 | 24 | 23 |
| | | LSMean | 2.2 | 4.6 | 7.4 | −0.4 |
| | | SEM | 1.7 | 1.7 | 1.7 | 1.7 |
| | | 90% CI | (−0.8; 5.3) | (1.5; 7.6) | (4.4; 10.5) | (−3.4; 2.7) |
| | 1.25 hour post-dose | n | 24 | 24 | 24 | 24 |
| | | LSMean | 1.6 | 2.2 | 9.1 | 0.4 |
| | | SEM | 1.8 | 1.8 | 1.8 | 1.8 |
| | | 90% CI | (−1.5; 4.8) | (−0.9; 5.3) | (5.9; 12.2) | (−2.7; 3.5) |
| | 1.5 hour post-dose | n | 23 | 23 | 23 | 24 |
| | | LSMean | 1.1 | 2.2 | 8.4 | 0.6 |
| | | SEM | 1.7 | 1.7 | 1.7 | 1.7 |
| | | 90% CI | (−2.0; 4.1) | (−0.9; 5.2) | (5.4; 11.5) | (−2.4; 3.6) |
| | 2 hours post-dose | n | 23 | 24 | 23 | 24 |
| | | LSMean | 1.5 | 1.1 | 9.0 | 0.1 |
| | | SEM | 1.7 | 1.7 | 1.7 | 1.7 |
| | | 90% CI | (−1.5; 4.5) | (−2.0; 4.1) | (6.0; 12.0) | (−2.9; 3.1) |
| | 2.5 hours post-dose | n | 23 | 24 | 23 | 24 |
| | | LSMean | 1.7 | 3.1 | 11.5 | 1.7 |
| | | SEM | 1.7 | 1.7 | 1.7 | 1.7 |
| | | 90% CI | (−1.3; 4.8) | (0.1; 6.1) | (8.5; 14.5) | (−1.4; 4.7) |
| | 3 hours post-dose | n | 24 | 23 | 22 | 24 |
| | | LSMean | 3.6 | 2.5 | 13.2 | 0.2 |
| | | SEM | 1.8 | 1.9 | 1.9 | 1.9 |
| | | 90% CI | (0.4; 6.8) | (−0.7; 5.7) | (10.0; 16.5) | (−3.0; 3.5) |
| | 4 hours post-dose | n | 24 | 24 | 24 | 24 |
| | | LSMean | 1.1 | 1.1 | 14.4 | −0.8 |
| | | SEM | 1.8 | 1.8 | 1.8 | 1.8 |
| | | 90% CI | (−2.0; 4.2) | (−2.0; 4.2) | (11.3; 17.6) | (−3.9; 2.3) |
| | 6 hours post-dose | n | 24 | 23 | 24 | 24 |
| | | LSMean | −0.9 | −4.4 | 7.2 | −3.7 |
| | | SEM | 2.0 | 2.1 | 2.0 | 2.0 |
| | | 90% CI | (−4.3; 2.6) | (−7.9; −0.9) | (3.8; 10.7) | (−7.2; −0.2) |
| | 8 hours post-dose | n | 24 | 24 | 24 | 24 |
| | | LSMean | −4.5 | −6.0 | 4.4 | −7.0 |
| | | SEM | 1.8 | 1.8 | 1.8 | 1.8 |
| | | 90% CI | (−7.7; −1.3) | (−9.2; −2.8) | (1.2; 7.6) | (−10.2; −3.9) |
| | 12 hours post-dose | n | 24 | 24 | 24 | 24 |
| | | LSMean | −2.1 | −2.5 | 7.3 | −2.3 |
| | | SEM | 1.8 | 1.8 | 1.8 | 1.8 |
| | | 90% CI | (−5.2; 1.1) | (−5.7; 0.7) | (4.1; 10.4) | (−5.5; 0.8) |
| | 24 hours post-dose | n | 24 | 24 | 23 | 24 |
| | | LSMean | −6.1 | −4.6 | 2.4 | −5.2 |
| | | SEM | 1.9 | 1.9 | 1.9 | 1.9 |
| | | 90% CI | (−9.3; −2.8) | (−7.8; −1.4) | (−0.9; 5.6) | (−8.4; −2.0) |

TABLE 75

Placebo-corrected change-from-baseline QTcF - QT/QTc Population

| Parameter | Time | Statistics | 160 mg (4%) | 320 mg (8%) | 400 mg (moxifloxacin HCl) |
|---|---|---|---|---|---|
| ΔΔQTcF (ms) | 20 min post-dose | LSMean | 4.6 | 7.0 | −0.1 |
| | | SEM | 1.4 | 1.4 | 1.4 |
| | | 90% CI | (2.2; 6.9) | (4.6; 9.3) | (−2.4; 2.3) |
| | 40 min post-dose | LSMean | 3.4 | 6.8 | 5.4 |
| | | SEM | 1.5 | 1.5 | 1.5 |
| | | 90% CI | (1.0; 5.9) | (4.3; 9.2) | (3.0; 7.9) |
| | 1 hour post-dose | LSMean | 2.6 | 4.9 | 7.8 |
| | | SEM | 1.4 | 1.4 | 1.4 |
| | | 90% CI | (0.3; 5.0) | (2.6; 7.3) | (5.5; 10.2) |
| | 1.25 hour post-dose | LSMean | 1.2 | 1.8 | 8.7 |
| | | SEM | 1.6 | 1.6 | 1.6 |
| | | 90% CI | (−1.4; 3.8) | (−0.8; 4.4) | (6.1; 11.3) |
| | 1.5 hour post-dose | LSMean | 0.5 | 1.6 | 7.9 |
| | | SEM | 1.3 | 1.3 | 1.3 |
| | | 90% CI | (−1.8; 2.7) | (−0.7; 3.8) | (5.6; 10.1) |
| | 2 hours post-dose | LSMean | 1.4 | 1.0 | 8.9 |
| | | SEM | 1.4 | 1.3 | 1.4 |
| | | 90% CI | (−0.8; 3.7) | (−1.3; 3.2 ) | (6.7; 11.2) |

TABLE 75-continued

Placebo-corrected change-from-baseline QTcF - QT/QTc Population

| Parameter | Time | Statistics | 160 mg (4%) | 320 mg (8%) | 400 mg (moxifloxacin HCl) |
|---|---|---|---|---|---|
| | 2.5 hours post-dose | LSMean | 0.1 | 1.4 | 9.8 |
| | | SEM | 1.4 | 1.4 | 1.4 |
| | | 90% CI | (−2.3; 2.4) | (−0.9; 3.7) | (7.5; 12.2) |
| | 3 hours post-dose | LSMean | 3.3 | 2.2 | 13.0 |
| | | SEM | 1.7 | 1.7 | 1.7 |
| | | 90% CI | (0.5; 6.1) | (−0.6; 5.1) | (10.1; 15.9) |
| | 4 hours post-dose | LSMean | 1.9 | 1.9 | 15.2 |
| | | SEM | 1.6 | 1.6 | 1.6 |
| | | 90% CI | (−0.7; 4.5) | (−0.8; 4.5) | (12.6; 17.8) |
| | 6 hours post-dose | LSMean | 2.8 | −0.7 | 10.9 |
| | | SEM | 2.1 | 2.1 | 2.1 |
| | | 90% CI | (−0.7; 6.3) | (−4.2; 2.8) | (7.4; 14.4) |
| | 8 hours post-dose | LSMean | 2.6 | 1.1 | 11.5 |
| | | SEM | 1.7 | 1.7 | 1.7 |
| | | 90% CI | (−0.2; 5.4) | (−1.7; 3.9) | (8.7; 14.3) |
| | 12 hours post-dose | LSMean | 0.3 | −0.1 | 9.6 |
| | | SEM | 1.6 | 1.6 | 1.6 |
| | | 90% CI | (−2.5; 3.0) | (−2.9; 2.6) | (6.9; 12.4) |
| | 24 hours post-dose | LSMean | −0.9 | 0.6 | 7.5 |
| | | SEM | 1.7 | 1.7 | 1.7 |
| | | 90% CI | (−3.7; 1.9) | (−2.3; 3.4) | (4.7; 10.4) |

TABLE 76

Change-from-baseline HR - QT/QTc Population

| Parameter | Time | Statistics | 160 mg (4%) | 320 mg (8%) | 400 mg (moxifloxacin HCl) | Placebo |
|---|---|---|---|---|---|---|
| ΔHR (bpm) | 20 min post-dose | n | 24 | 23 | 23 | 24 |
| | | LSMean | 10.9 | 20.5 | 1.0 | 5.4 |
| | | SEM | 1.6 | 1.7 | 1.7 | 1.6 |
| | | 90% CI | (8.2; 13.6) | (17.7; 23.2) | (−1.8; 3.7) | (2.7; 8.1) |
| | 40 min post-dose | n | 24 | 24 | 24 | 24 |
| | | LSMean | 7.9 | 14.0 | 1.3 | 0.9 |
| | | SEM | 1.4 | 1.4 | 1.4 | 1.4 |
| | | 90% CI | (5.6; 10.1) | (11.7; 16.2) | (−1.0; 3.5) | (−1.4; 3.2) |
| | 1 hour post-dose | n | 24 | 24 | 24 | 23 |
| | | LSMean | 5.7 | 11.5 | 1.8 | 0.0 |
| | | SEM | 1.2 | 1.2 | 1.2 | 1.2 |
| | | 90% CI | (3.8; 7.6) | (9.6; 13.4) | (−0.2; 3.7) | (−1.9; 2.0) |
| | 1.25 hour post-dose | n | 24 | 24 | 24 | 24 |
| | | LSMean | 5.6 | 9.0 | 2.6 | −0.1 |
| | | SEM | 1.3 | 1.3 | 1.3 | 1.3 |
| | | 90% CI | (3.4; 7.7) | (6.8; 11.2) | (0.5; 4.8) | (−2.2; 2.1) |
| | 1.5 hour post-dose | n | 23 | 23 | 23 | 24 |
| | | LSMean | 4.8 | 9.7 | 3.9 | 0.1 |
| | | SEM | 1.1 | 1.1 | 1.1 | 1.1 |
| | | 90% CI | (3.0; 6.7) | (7.8; 11.5) | (2.0; 5.7) | (−1.8; 1.9) |
| | 2 hours post-dose | n | 23 | 24 | 23 | 24 |
| | | LSMean | 2.5 | 8.3 | 2.3 | −0.8 |
| | | SEM | 1.0 | 1.0 | 1.0 | 1.0 |
| | | 90% CI | (0.8; 4.3) | (6.6; 10.1) | (0.5; 4.0) | (−2.5; 0.9) |
| | 2.5 hours post-dose | n | 23 | 24 | 23 | 24 |
| | | LSMean | 3.2 | 6.4 | 2.6 | 1.7 |
| | | SEM | 1.1 | 1.1 | 1.1 | 1.1 |
| | | 90% CI | (1.5; 5.0) | (4.6; 8.2) | (0.8; 4.4) | (−0.1; 3.5) |
| | 3 hours post-dose | n | 24 | 23 | 22 | 24 |
| | | LSMean | 3.5 | 6.1 | 2.6 | 0.1 |
| | | SEM | 1.0 | 1.0 | 1.0 | 1.0 |
| | | 90% CI | (1.8; 5.2) | (4.4; 7.8) | (0.8; 4.3) | (−1.6; 1.7) |
| | 4 hours post-dose | n | 24 | 24 | 24 | 24 |
| | | LSMean | 2.2 | 4.5 | 3.4 | 1.9 |
| | | SEM | 1.0 | 1.0 | 1.0 | 1.0 |
| | | 90% CI | (0.5; 3.9) | (2.8; 6.2) | (1.7; 5.2) | (0.1; 3.6) |
| | 6 hours post-dose | n | 24 | 23 | 24 | 24 |
| | | LSMean | 7.1 | 8.3 | 8.2 | 5.8 |
| | | SEM | 1.1 | 1.2 | 1.1 | 1.1 |
| | | 90% CI | (5.2; 9.0) | (6.3; 10.2) | (6.3; 10.1) | (3.9; 7.7) |
| | 8 hours post-dose | n | 24 | 24 | 24 | 24 |
| | | LSMean | 4.4 | 4.9 | 5.7 | 4.1 |
| | | SEM | 1.1 | 1.1 | 1.1 | 1.1 |
| | | 90% CI | (2.5; 6.3) | (3.0; 6.8) | (3.8; 7.6) | (2.2; 6.0) |
| | 12 hours post-dose | n | 24 | 24 | 24 | 24 |
| | | LSMean | 10.3 | 11.3 | 10.7 | 9.1 |
| | | SEM | 1.1 | 1.1 | 1.1 | 1.1 |
| | | 90% CI | (8.5; 12.1) | (9.5; 13.1) | (8.9; 12.5) | (7.3; 11.0) |

TABLE 76-continued

Change-from-baseline HR - QT/QTc Population

| Parameter | Time | Statistics | 160 mg (4%) | 320 mg (8%) | 400 mg (moxifloxacin HCl) | Placebo |
|---|---|---|---|---|---|---|
| | 24 hours post-dose | n | 24 | 24 | 23 | 24 |
| | | LSMean | 4.6 | 5.3 | 4.2 | 4.2 |
| | | SEM | 1.4 | 1.4 | 1.5 | 1.4 |
| | | 90% CI | (2.2; 6.9) | (3.0; 7.7) | (1.8; 6.6) | (1.8; 6.6) |

TABLE 77

Placebo-corrected change-from-baseline HR - QT/QTc Population

| Parameter | Time | Statistics | 160 mg (4%) | 320 mg (8%) | 400 mg (moxifloxacin HCl) |
|---|---|---|---|---|---|
| $\Delta\Delta$HR (bpm) | 20 min post-dose | LSMean | 5.5 | 15.1 | −4.4 |
| | | SEM | 2.2 | 2.2 | 2.2 |
| | | 90% CI | (1.8; 9.2) | (11.4; 18.8) | (−8.1; −0.7) |
| | 40 min post-dose | LSMean | 7.0 | 13.1 | 0.4 |
| | | SEM | 1.8 | 1.8 | 1.8 |
| | | 90% CI | (4.0; 10.0) | (10.1; 16.1) | (−2.6; 3.4) |
| | 1 hour post-dose | LSMean | 5.7 | 11.5 | 1.7 |
| | | SEM | 1.5 | 1.5 | 1.5 |
| | | 90% CI | (3.2; 8.2) | (9.0; 14.0) | (−0.8; 4.2) |
| | 1.25 hour post-dose | LSMean | 5.6 | 9.1 | 2.7 |
| | | SEM | 1.7 | 1.7 | 1.7 |
| | | 90% CI | (2.8; 8.5) | (6.2; 11.9) | (−0.2; 5.6) |
| | 1.5 hour post-dose | LSMean | 4.8 | 9.6 | 3.8 |
| | | SEM | 1.4 | 1.4 | 1.4 |
| | | 90% CI | (2.4; 7.1) | (7.3; 11.9) | (1.5; 6.2) |
| | 2 hours post-dose | LSMean | 3.3 | 9.1 | 3.1 |
| | | SEM | 1.3 | 1.3 | 1.3 |
| | | 90% CI | (1.2; 5.5) | (7.0; 11.3) | (0.9; 5.2) |
| | 2.5 hours post-dose | LSMean | 1.6 | 4.7 | 0.9 |
| | | SEM | 1.4 | 1.3 | 1.4 |
| | | 90% CI | (−0.7; 3.8) | (2.5; 7.0) | (−1.4; 3.2) |
| | 3 hours post-dose | LSMean | 3.4 | 6.0 | 2.5 |
| | | SEM | 1.3 | 1.3 | 1.3 |
| | | 90% CI | (1.4; 5.5) | (3.9; 8.1) | (0.4; 4.6) |
| | 4 hours post-dose | LSMean | 0.3 | 2.6 | 1.6 |
| | | SEM | 1.3 | 1.3 | 1.3 |
| | | 90% CI | (−1.8; 2.5) | (0.5; 4.8) | (−0.6; 3.7) |
| | 6 hours post-dose | LSMean | 1.4 | 2.5 | 2.5 |
| | | SEM | 1.5 | 1.5 | 1.5 |
| | | 90% CI | (−1.1; 3.8) | (0.0; 5.0) | (−0.0; 4.9) |
| | 8 hours post-dose | LSMean | 0.3 | 0.8 | 1.6 |
| | | SEM | 1.5 | 1.5 | 1.5 |
| | | 90% CI | (−2.1; 2.7) | (−1.6; 3.2) | (−0.8; 4.0) |
| | 12 hours post-dose | LSMean | 1.2 | 2.1 | 1.5 |
| | | SEM | 1.4 | 1.4 | 1.4 |
| | | 90% CI | (−1.2; 3.5) | (−0.2; 4.5) | (−0.8; 3.8) |
| | 24 hours post-dose | LSMean | 0.4 | 1.1 | −0.0 |
| | | SEM | 1.9 | 1.9 | 1.9 |
| | | 90% CI | (−2.8; 3.5) | (−0.2; 4.3) | (−3.2; 3.2) |

TABLE 78

Change-from-baseline PR - QT/QTc Population

| Parameter | Time | Statistics | 160 mg (4%) | 320 mg (8%) | 400 mg (moxifloxacin HCl) | Placebo |
|---|---|---|---|---|---|---|
| $\Delta$PR (ms) | 20 min post-dose | n | 24 | 23 | 23 | 24 |
| | | LSMean | −5.5 | −6.9 | 1.1 | −1.0 |
| | | SEM | 1.6 | 1.6 | 1.6 | 1.6 |
| | | 90% CI | (−8.1; −2.8) | (−9.6; −4.2) | (−1.6; 3.8) | (−3.7; 1.6) |
| | 40 min post-dose | n | 24 | 24 | 24 | 24 |
| | | LSMean | 0.2 | −4.2 | 1.4 | 1.3 |
| | | SEM | 1.4 | 1.4 | 1.4 | 1.4 |
| | | 90% CI | (−2.2; 2.7) | (−6.7; −1.8) | (−1.1; 3.9) | (−1.2; 3.8) |
| | 1 hour post-dose | n | 24 | 24 | 24 | 23 |
| | | LSMean | −0.8 | −2.9 | 0.8 | 0.7 |
| | | SEM | 1.5 | 1.5 | 1.5 | 1.5 |
| | | 90% CI | (−3.4; 1.7) | (−5.4; −0.3) | (−1.8; 3.4) | (−1.9; 3.3) |
| | 1.25 hour post-dose | n | 24 | 24 | 24 | 24 |
| | | LSMean | −0.2 | −2.9 | 0.5 | 0.7 |
| | | SEM | 1.4 | 1.4 | 1.4 | 1.4 |
| | | 90% CI | (−2.6; 2.3) | (−5.3; −0.5) | (−1.9; 3.0) | (−1.7; 3.1) |
| | 1.5 hour post-dose | n | 23 | 23 | 23 | 24 |
| | | LSMean | −0.4 | −2.2 | −0.7 | 1.2 |
| | | SEM | 1.4 | 1.4 | 1.4 | 1.4 |
| | | 90% CI | (−2.9; 2.1) | (−4.7; 0.2) | (−3.2; 1.8) | (−1.3; 3.6) |
| | 2 hours post-dose | n | 23 | 24 | 23 | 24 |
| | | LSMean | −1.2 | −4.7 | 0.2 | −0.0 |
| | | SEM | 1.4 | 1.4 | 1.4 | 1.4 |
| | | 90% CI | (−3.7; 1.3) | (−7.2; −2.2) | (−2.3; 2.7) | (−2.5; 2.5) |
| | 2.5 hours post-dose | n | 23 | 24 | 23 | 24 |
| | | LSMean | −0.6 | −4.1 | −0.8 | −1.4 |
| | | SEM | 1.3 | 1.3 | 1.4 | 1.3 |
| | | 90% CI | (−3.0; 1.7) | (−6.5; −1.8) | (−3.2; 1.6) | (−3.8; 1.0) |

TABLE 78-continued

Change-from-baseline PR - QT/QTc Population

| Parameter | Time | Statistics | 160 mg (4%) | 320 mg (8%) | 400 mg (moxifloxacin HCl) | Placebo |
|---|---|---|---|---|---|---|
| | 3 hours post-dose | n | 24 | 23 | 22 | 24 |
| | | LSMean | −0.6 | −4.0 | −2.1 | −0.0 |
| | | SEM | 1.3 | 1.3 | 1.3 | 1.3 |
| | | 90% CI | (−2.9; 1.7) | (−6.3; −1.7) | (−4.5; 0.2) | (−2.4; 2.3) |
| | 4 hours post-dose | n | 24 | 24 | 24 | 24 |
| | | LSMean | −0.6 | −3.8 | −1.5 | −0.1 |
| | | SEM | 1.3 | 1.3 | 1.3 | 1.3 |
| | | 90% CI | (−3.0; 1.7) | (−6.1; −1.4) | (−3.9; 0.9) | (−2.5; 2.2) |
| | 6 hours post-dose | n | 24 | 23 | 24 | 24 |
| | | LSMean | −1.0 | −3.4 | −4.2 | −1.6 |
| | | SEM | 1.6 | 1.6 | 1.6 | 1.6 |
| | | 90% CI | (−3.7; 1.7) | (−6.1; −0.7) | (−6.9; −1.5) | (−4.3; 1.1) |
| | 8 hours post-dose | n | 24 | 24 | 24 | 24 |
| | | LSMean | −2.3 | −3.1 | −5.2 | −3.8 |
| | | SEM | 1.6 | 1.6 | 1.6 | 1.6 |
| | | 90% CI | (−5.0; 0.5) | (−5.8; −0.3) | (−7.9; −2.4) | (−6.5; −1.0) |
| | 12 hours post-dose | n | 24 | 24 | 24 | 24 |
| | | LSMean | −1.7 | −0.4 | −4.7 | −0.8 |
| | | SEM | 1.5 | 1.5 | 1.5 | 1.5 |
| | | 90% CI | (−4.2; 0.8) | (−3.0; 2.1) | (−7.2; −2.1) | (−3.3; 1.8) |
| | 24 hours post-dose | n | 24 | 24 | 23 | 24 |
| | | LSMean | −3.6 | −3.6 | −0.9 | −2.5 |
| | | SEM | 1.5 | 1.5 | 1.5 | 1.5 |
| | | 90% CI | (−6.2; −1.0) | (−6.1; −1.0) | (−3.5; 1.7) | (−5.1; 0.0) |

TABLE 79

Placebo-corrected change-from-baseline PR - QT/QTc Population

| Parameter | Time | Statistics | 160 mg (4%) | 320 mg (8%) | 400 mg (moxifloxacin HCl) |
|---|---|---|---|---|---|
| ΔΔPR (ms) | 20 min post-dose | LSMean | −4.4 | −5.9 | 2.1 |
| | | SEM | 1.8 | 1.9 | 1.9 |
| | | 90% CI | (−7.5; −1.4) | (−9.0; −2.8) | (−1.0; 5.3) |
| | 40 min post-dose | LSMean | −1.0 | −5.5 | 0.1 |
| | | SEM | 1.6 | 1.6 | 1.6 |
| | | 90% CI | (−3.7; 1.6) | (−8.2; −2.8) | (−2.6; 2.8) |
| | 1 hour post-dose | LSMean | −1.5 | −3.6 | 0.1 |
| | | SEM | 1.7 | 1.7 | 1.8 |
| | | 90% CI | (−4.4; 1.4) | (−6.5; −0.7) | (−2.8; 3.1) |
| | 1.25 hour post-dose | LSMean | −0.9 | −3.6 | −0.2 |
| | | SEM | 1.5 | 1.5 | 1.5 |
| | | 90% CI | (−3.4; 1.7) | (−6.2; −1.0) | (−2.7; 2.4) |
| | 1.5 hour post-dose | LSMean | −1.5 | −3.4 | −1.9 |
| | | SEM | 1.6 | 1.6 | 1.6 |
| | | 90% CI | (−4.2; 1.1) | (−6.0; −0.8) | (−4.5; 0.7) |
| | 2 hours post-dose | LSMean | −1.2 | −4.7 | 0.2 |
| | | SEM | 1.6 | 1.6 | 1.6 |
| | | 90% CI | (−3.8; 1.5) | (−7.3; −2.1) | (−2.4; 2.9) |
| | 2.5 hours post-dose | LSMean | 0.7 | −2.8 | 0.5 |
| | | SEM | 1.5 | 1.5 | 1.5 |
| | | 90% CI | (−1.7; 3.2) | (−5.2; −0.3) | (−1.9; 3.0) |
| | 3 hours post-dose | LSMean | −0.5 | −4.0 | −2.1 |
| | | SEM | 1.3 | 1.3 | 1.4 |
| | | 90% CI | (−2.8; 1.7) | (−6.2; −1.7) | (−4.4; 0.2) |
| | 4 hours post-dose | LSMean | −0.5 | −3.6 | −1.4 |
| | | SEM | 1.5 | 1.5 | 1.5 |
| | | 90% CI | (−2.9; 1.9) | (−6.1; −1.2) | (−3.9; 1.0) |
| | 6 hours post-dose | LSMean | 0.6 | −1.8 | −2.6 |
| | | SEM | 1.8 | 1.9 | 1.9 |
| | | 90% CI | (−2.5; 3.7) | (−4.9; 1.3) | (−5.7; 0.5) |
| | 8 hours post-dose | LSMean | 1.5 | 0.7 | −1.4 |
| | | SEM | 1.9 | 1.9 | 1.9 |
| | | 90% CI | (−1.7; 4.7) | (−2.5; 3.9) | (−4.6; 1.8) |
| | 12 hours post-dose | LSMean | −0.9 | 0.3 | −3.9 |
| | | SEM | 1.7 | 1.7 | 1.7 |
| | | 90% CI | (−3.7; 1.9) | (−2.5; 3.1) | (−6.7; −1.1) |
| | 24 hours post-dose | LSMean | −1.0 | −1.0 | 1.7 |
| | | SEM | 1.7 | 1.7 | 1.7 |
| | | 90% CI | (−3.9; 1.8) | (−3.9; 1.9) | (−1.3; 4.6) |

TABLE 80

Change-from-baseline QRS - QT/QTc Population

| Parameter | Time | Statistics | 160 mg (4%) | 320 mg (8%) | 400 mg (moxifloxacin HCl) | Placebo |
|---|---|---|---|---|---|---|
| ΔQRS (ms) | 20 min post-dose | n | 24 | 23 | 23 | 24 |
| | | LSMean | −0.0 | −0.4 | −0.5 | −0.5 |
| | | SEM | 0.3 | 0.3 | 0.3 | 0.3 |
| | | 90% CI | (−0.5; 0.5) | (−0.9; 0.1) | (−1.0; 0.0) | (−1.0; −0.0) |
| | 40 min post-dose | n | 24 | 24 | 24 | 24 |
| | | LSMean | 0.2 | 0.4 | −0.5 | 0.2 |
| | | SEM | 0.2 | 0.2 | 0.2 | 0.2 |
| | | 90% CI | (−0.1; 0.6) | (0.0; 0.7) | (−0.9; −0.2) | (−0.2; 0.5) |

TABLE 80-continued

Change-from-baseline QRS - QT/QTc Population

| Parameter | Time | Statistics | 160 mg (4%) | 320 mg (8%) | 400 mg (moxifloxacin HCl) | Placebo |
|---|---|---|---|---|---|---|
| | 1 hour post-dose | n | 24 | 24 | 24 | 23 |
| | | LSMean | 0.3 | 0.2 | −0.4 | 0.5 |
| | | SEM | 0.3 | 0.3 | 0.3 | 0.3 |
| | | 90% CI | (−0.2; 0.8) | (−0.3; 0.7) | (−0.9; 0.1) | (−0.0; 0.9) |
| | 1.25 hour post-dose | n | 24 | 24 | 24 | 24 |
| | | LSMean | 0.4 | 0.2 | 0.2 | −0.2 |
| | | SEM | 0.2 | 0.2 | 0.2 | 0.2 |
| | | 90% CI | (0.1; 0.7) | (−0.1; 0.5) | (−0.1; 0.5) | (−0.5; 0.1) |
| | 1.5 hour post-dose | n | 23 | 23 | 23 | 24 |
| | | LSMean | 0.2 | 0.1 | 0.0 | −0.3 |
| | | SEM | 0.2 | 0.2 | 0.2 | 0.2 |
| | | 90% CI | (−0.1; 0.5) | (−0.2; 0.3) | (−0.2; 0.3) | (−0.6; −0.0) |
| | 2 hours post-dose | n | 23 | 24 | 23 | 24 |
| | | LSMean | 0.1 | −0.0 | 0.0 | 0.1 |
| | | SEM | 0.2 | 0.2 | 0.2 | 0.2 |
| | | 90% CI | (−0.2; 0.4) | (−0.3; 0.2) | (−0.3; 0.3) | (−0.2; 0.4) |
| | 2.5 hours post-dose | n | 23 | 24 | 23 | 24 |
| | | LSMean | −0.0 | 0.3 | −0.3 | −0.4 |
| | | SEM | 0.2 | 0.2 | 0.2 | 0.2 |
| | | 90% CI | (−0.3; 0.3) | (−0.0; 0.6) | (−0.6; 0.1) | (−0.7; −0.1) |
| | 3 hours post-dose | n | 24 | 23 | 22 | 24 |
| | | LSMean | −0.1 | 0.1 | 0.0 | −0.1 |
| | | SEM | 0.2 | 0.2 | 0.2 | 0.2 |
| | | 90% CI | (−0.4; 0.2) | (−0.2; 0.4) | (−0.3; 0.3) | (−0.4; 0.2) |
| | 4 hours post-dose | n | 24 | 24 | 24 | 24 |
| | | LSMean | −0.2 | −0.0 | −0.0 | 0.2 |
| | | SEM | 0.3 | 0.3 | 0.3 | 0.3 |
| | | 90% CI | (−0.7; 0.3) | (−0.5; 0.4) | (−0.5; 0.4) | (−0.3; 0.6) |
| | 6 hours post-dose | n | 24 | 23 | 24 | 24 |
| | | LSMean | −0.4 | −0.6 | −0.5 | −0.7 |
| | | SEM | 0.3 | 0.3 | 0.3 | 0.3 |
| | | 90% CI | (−0.9; 0.1) | (−1.1; −0.1) | (−1.0; −0.1) | (−1.2; −0.2) |
| | 8 hours post-dose | n | 24 | 24 | 24 | 24 |
| | | LSMean | 0.2 | −0.6 | −0.5 | −0.3 |
| | | SEM | 0.2 | 0.2 | 0.2 | 0.2 |
| | | 90% CI | (−0.2; 0.6) | (−1.0; −0.2) | (−0.9; −0.1) | (−0.7; 0.1) |
| | 12 hours post-dose | n | 24 | 24 | 24 | 24 |
| | | LSMean | 0.2 | −0.2 | −0.0 | −0.3 |
| | | SEM | 0.3 | 0.3 | 0.3 | 0.3 |
| | | 90% CI | (−0.3; 0.6) | (−0.6; 0.3) | (−0.5; 0.5) | (−0.8; 0.2) |
| | 24 hours post-dose | n | 24 | 24 | 23 | 24 |
| | | LSMean | −0.1 | −0.2 | 0.1 | 0.5 |
| | | SEM | 0.3 | 0.3 | 0.3 | 0.3 |
| | | 90% CI | (−0.6; 0.4) | (−0.7; 0.4) | (−0.4; 0.7) | (−0.0; 1.0) |

TABLE 81

Change-from-baseline QT - QT/QTc Population

| Parameter | Time | Statistics | 160 mg (4%) | 320 mg (8%) | 400 mg (moxifloxacin HCl) | Placebo |
|---|---|---|---|---|---|---|
| ΔQT (ms) | 20 min post-dose | n | 24 | 23 | 23 | 24 |
| | | LSMean | −20.4 | −32.0 | −5.3 | −13.5 |
| | | SEM | 2.9 | 2.9 | 2.9 | 2.9 |
| | | 90% CI | (−25.3; −15.6) | (−36.9; −27.1) | (−10.2; −0.4) | (−18.4; −8.7) |
| | 40 min post-dose | n | 24 | 24 | 24 | 24 |
| | | LSMean | −14.1 | −20.8 | 2.2 | −2.3 |
| | | SEM | 2.6 | 2.6 | 2.6 | 2.6 |
| | | 90% CI | (−18.4; −9.8) | (−25.1; −16.5) | (−2.1; 6.4) | (−6.6; 2.0) |
| | 1 hour post-dose | n | 24 | 24 | 24 | 23 |
| | | LSMean | −10.2 | −18.1 | 3.9 | −0.3 |
| | | SEM | 2.3 | 2.3 | 2.3 | 2.3 |
| | | 90% CI | (−14.1; −6.3) | (−22.0; −14.2) | (0.0; 7.8) | (−4.3; 3.6) |
| | 1.25 hour post-dose | n | 24 | 24 | 24 | 24 |
| | | LSMean | −9.6 | −16.3 | 3.9 | 0.9 |
| | | SEM | 2.6 | 2.6 | 2.6 | 2.6 |
| | | 90% CI | (−13.9; −5.3) | (−20.7; −12.0) | (−0.5; 8.2) | (−3.4; 5.2) |
| | 1.5 hour post-dose | n | 23 | 23 | 23 | 24 |
| | | LSMean | −9.4 | −17.6 | 0.8 | 0.8 |

TABLE 81-continued

Change-from-baseline QT - QT/QTc Population

| Parameter | Time | Statistics | 160 mg (4%) | 320 mg (8%) | 400 mg (moxifloxacin HCl) | Placebo |
|---|---|---|---|---|---|---|
| | | SEM | 2.5 | 2.5 | 2.5 | 2.4 |
| | | 90% CI | (−13.5; −5.3) | (−21.7; −13.5) | (−3.3; 4.9) | (−3.3; 4.9) |
| | 2 hours post-dose | n | 23 | 24 | 23 | 24 |
| | | LSMean | −4.4 | −16.1 | 4.2 | 2.2 |
| | | SEM | 2.2 | 2.2 | 2.2 | 2.2 |
| | | 90% CI | (−8.0; −0.7) | (−19.7; −12.4) | (0.5; 7.8) | (−1.5; 5.8) |
| | 2.5 hours post-dose | n | 23 | 24 | 23 | 24 |
| | | LSMean | −5.6 | −10.4 | 6.1 | −1.8 |
| | | SEM | 2.4 | 2.3 | 2.4 | 2.3 |
| | | 90% CI | (−9.5; −1.6) | (−14.4; −6.5) | (2.1; 10.0) | (−5.7; 2.1) |
| | 3 hours post-dose | n | 24 | 23 | 22 | 24 |
| | | LSMean | −4.5 | −10.1 | 7.5 | 0.4 |
| | | SEM | 2.6 | 2.6 | 2.6 | 2.6 |
| | | 90% CI | (−8.8; −0.2) | (−14.4; −5.8) | (3.1; 11.8) | (−3.9; 4.7) |
| | 4 hours post-dose | n | 24 | 24 | 24 | 24 |
| | | LSMean | −4.2 | −8.6 | 6.7 | −4.1 |
| | | SEM | 2.5 | 2.5 | 2.5 | 2.5 |
| | | 90% CI | (−8.4; 0.0) | (−12.8; −4.4) | (2.5; 10.9) | (−8.3; 0.1) |
| | 6 hours post-dose | n | 24 | 23 | 24 | 24 |
| | | LSMean | −15.7 | −22.2 | −9.5 | −15.7 |
| | | SEM | 2.7 | 2.8 | 2.7 | 2.7 |
| | | 90% CI | (−20.2; −11.1) | (−26.8; −17.5) | (−14.1; −5.0) | (−20.2; −11.2) |
| | 8 hours post-dose | n | 24 | 24 | 24 | 24 |
| | | LSMean | −14.2 | −15.8 | −7.6 | −15.2 |
| | | SEM | 2.7 | 2.7 | 2.7 | 2.7 |
| | | 90% CI | (−18.7; −9.7) | (−20.3; −11.3) | (−12.1; −3.1) | (−19.7; −10.7) |
| | 12 hours post-dose | n | 24 | 24 | 24 | 24 |
| | | LSMean | −23.5 | −24.9 | −14.0 | −20.1 |
| | | SEM | 2.5 | 2.5 | 2.5 | 2.5 |
| | | 90% CI | (−27.7; −19.3) | (−29.0; −20.7) | (−18.2; −9.9) | (−24.2; −15.9) |
| | 24 hours post-dose | n | 24 | 24 | 23 | 24 |
| | | LSMean | −14.9 | −15.2 | −6.6 | −14.2 |
| | | SEM | 3.0 | 3.0 | 3.1 | 3.0 |
| | | 90% CI | (−19.9; −9.9) | (−20.2; −10.2) | (−11.7; −1.5) | (−19.2; −9.2) |

TABLE 82

Change-from-baseline RR - QT/QTc Population

| Parameter | Time | Statistics | 160 mg (4%) | 320 mg (8%) | 400 mg (moxifloxacin HCl) | Placebo |
|---|---|---|---|---|---|---|
| ΔRR (ms) | 20 min post-dose | n | 24 | 23 | 23 | 24 |
| | | LSMean | −155.8 | −244.3 | −18.8 | −80.1 |
| | | SEM | 18.0 | 18.2 | 18.2 | 18.0 |
| | | 90% CI | (−185.7; −125.9) | (−274.6; −214.1) | (−49.0; 11.5) | (−110.0; −50.1) |
| | 40 min post-dose | n | 24 | 24 | 24 | 24 |
| | | LSMean | −119.1 | −183.0 | −15.8 | −13.4 |
| | | SEM | 18.9 | 18.9 | 18.9 | 18.9 |
| | | 90% CI | (−150.5; −87.7) | (−214.4; −151.6) | (−47.1; 15.6) | (−44.8; 18.0) |
| | 1 hour post-dose | n | 24 | 24 | 24 | 23 |
| | | LSMean | −92.3 | −159.2 | −24.5 | −3.7 |
| | | SEM | 17.8 | 17.8 | 17.8 | 17.9 |
| | | 90% CI | (−122.0; −62.6) | (−188.9; −129.6) | (−54.2; 5.2) | (−33.5; 26.2) |
| | 1.25 hour post-dose | n | 24 | 24 | 24 | 24 |
| | | LSMean | −81.0 | −132.3 | −35.1 | −1.5 |
| | | SEM | 20.1 | 20.1 | 20.1 | 20.1 |
| | | 90% CI | (−114.6; −47.5) | (−165.9; −98.8) | (−68.7; −1.5) | (−35.1; 32.0) |
| | 1.5 hour post-dose | n | 23 | 23 | 23 | 24 |
| | | LSMean | −73.5 | −141.5 | −58.5 | −1.9 |
| | | SEM | 17.4 | 17.3 | 17.3 | 17.1 |
| | | 90% CI | (−102.4; −44.6) | (−170.4; −112.6) | (−87.4; −29.6) | (−30.4; 26.7) |
| | 2 hours post-dose | n | 23 | 24 | 23 | 24 |
| | | LSMean | −44.3 | −121.6 | −33.8 | 13.6 |
| | | SEM | 16.6 | 16.4 | 16.6 | 16.4 |
| | | 90% CI | (−71.9; −16.6) | (−149.0; −94.1) | (−61.5; −6.2) | (−13.9; 41.0) |
| | 2.5 hours post-dose | n | 23 | 24 | 23 | 24 |
| | | LSMean | −55.1 | −98.0 | −37.0 | −29.1 |
| | | SEM | 16.5 | 16.3 | 16.5 | 16.3 |
| | | 90% CI | (−82.5; −27.6) | (−125.2; −70.9) | (−64.5; −9.5) | (−56.3; −2.0) |

TABLE 82-continued

Change-from-baseline RR - QT/QTc Population

| Parameter | Time | Statistics | 160 mg (4%) | 320 mg (8%) | 400 mg (moxifloxacin HCl) | Placebo |
|---|---|---|---|---|---|---|
| | 3 hours post-dose | n | 24 | 23 | 22 | 24 |
| | | LSMean | −61.5 | −90.8 | −41.1 | −3.9 |
| | | SEM | 15.4 | 15.5 | 15.7 | 15.4 |
| | | 90% CI | (−87.2; −35.9) | (−116.8; −64.9) | (−67.3; −14.9) | (−29.6; 21.7) |
| | 4 hours post-dose | n | 24 | 24 | 24 | 24 |
| | | LSMean | −110.3 | −124.9 | −121.3 | −91.9 |
| | | SEM | 16.0 | 16.0 | 16.0 | 16.0 |
| | | 90% CI | (−68.8; −15.2) | (−97.4; −43.8) | (−82.7; −29.1) | (−55.5; −1.9) |
| | 6 hours post-dose | n | 24 | 23 | 24 | 24 |
| | | LSMean | −110.3 | −124.9 | −121.3 | −91.9 |
| | | SEM | 16.0 | 16.3 | 16.0 | 16.0 |
| | | 90% CI | (−137.0; −83.5) | (−152.1; −97.7) | (−148.1; −94.6) | (−118.7; −65.1) |
| | 8 hours post-dose | n | 24 | 24 | 24 | 24 |
| | | LSMean | −71.3 | −73.2 | −88.8 | −64.7 |
| | | SEM | 16.8 | 16.8 | 16.8 | 16.8 |
| | | 90% CI | (−99.4; −43.2) | (−101.3; −45.1) | (−116.9; −60.7) | (−92.8; −36.6) |
| | 12 hours post-dose | n | 24 | 24 | 24 | 24 |
| | | LSMean | −154.3 | −160.1 | −151.8 | −131.7 |
| | | SEM | 14.2 | 14.2 | 14.1 | 14.2 |
| | | 90% CI | (−178.0; −130.6) | (−183.8; −136.4) | (−175.4; −128.1) | (−155.4; −108.0) |
| | 24 hours post-dose | n | 24 | 24 | 23 | 24 |
| | | LSMean | −66.8 | −76.2 | −65.8 | −71.6 |
| | | SEM | 17.9 | 17.9 | 18.2 | 17.9 |
| | | 90% CI | (−96.6; −37.0) | (−106.1; −46.4) | (−96.2; −35.5) | (−101.4; −41.7) |

TABLE 83

T-wave morphology across treatment groups: treatment emergent changes - QT/QTc Population

| | Category | 160 mg (4%) | 320 mg (8%) | 400 mg (moxifloxacin HCl) | Placebo |
|---|---|---|---|---|---|
| Subject | Total | 24 | 24 | 24 | 24 |
| | Flat | 0 | 0 | 0 | 0 |
| | Notched (+) | 0 | 0 | 0 | 0 |
| | Biphasic | 0 | 0 | 0 | 0 |
| | Normal (−) | 0 | 0 | 0 | 0 |
| | Notched (−) | 0 | 0 | 0 | 0 |
| Timepoint | Total | 309 | 308 | 305 | 311 |
| | Flat | 0 | 0 | 0 | 0 |
| | Notched (+) | 0 | 0 | 0 | 0 |
| | Biphasic | 0 | 0 | 0 | 0 |
| | Normal (−) | 0 | 0 | 0 | 0 |
| | Notched (−) | 0 | 0 | 0 | 0 |

A clear heart rate effect was seen after administration of cocaine hydrochloride pharmaceutical composition, with the largest mean change-from-baseline heart rate (ΔHR) values of 10.9 beats per minute (bpm) and 20.5 bpm observed at 20 min (the time of pledget removal) after administration of 160 mg and 320 mg, respectively. The heart rate response on placebo was small (mean ΔHR: 5.4 bpm) and placebo-corrected ΔHR (ΔΔHR) also peaked at 20 min in the high dose group, with a mean value of 15.1 bpm. For the 320 mg cocaine dose, mean ΔΔHR was 13.1 bpm and 11.5 bpm at 40 and 60 min, respectively, and 9 bpm to 10 bpm for time points up to and including 2 h. The heart rate response was smaller in the subjects administered cocaine hydrochloride (160 mg) pharmaceutical composition, with the highest mean ΔHR values of 5 bpm to 7 bpm observed between 20 and 75 min.

Consistent with the heart rate effect, a small shortening of the PR interval was observed after administration of cocaine 320 mg, with mean placebo-corrected ΔPR (ΔΔPR) of −5.9 ms and −5.5 ms observed at 20 and 40 min, respectively. At 20 min, mean ΔΔPR was −4.4 ms after the lower cocaine dose. Administration of cocaine did not have an effect on the QRS interval. No categorical PR or QRS outliers were observed on cocaine treatment.

After dosing with 320 mg cocaine, a small increase of ΔQTcF was observed, with mean values around 4 ms to 5 ms at the first 3 time points. Smaller changes of QTcF were observed after dosing subjects with the 160 mg cocaine hydrochloride pharmaceutical composition. Moxifloxacin HCl caused a clear increase of ΔQTcF, which peaked at 14.4 ms at 4 hours post-dosing.

Figure 45:
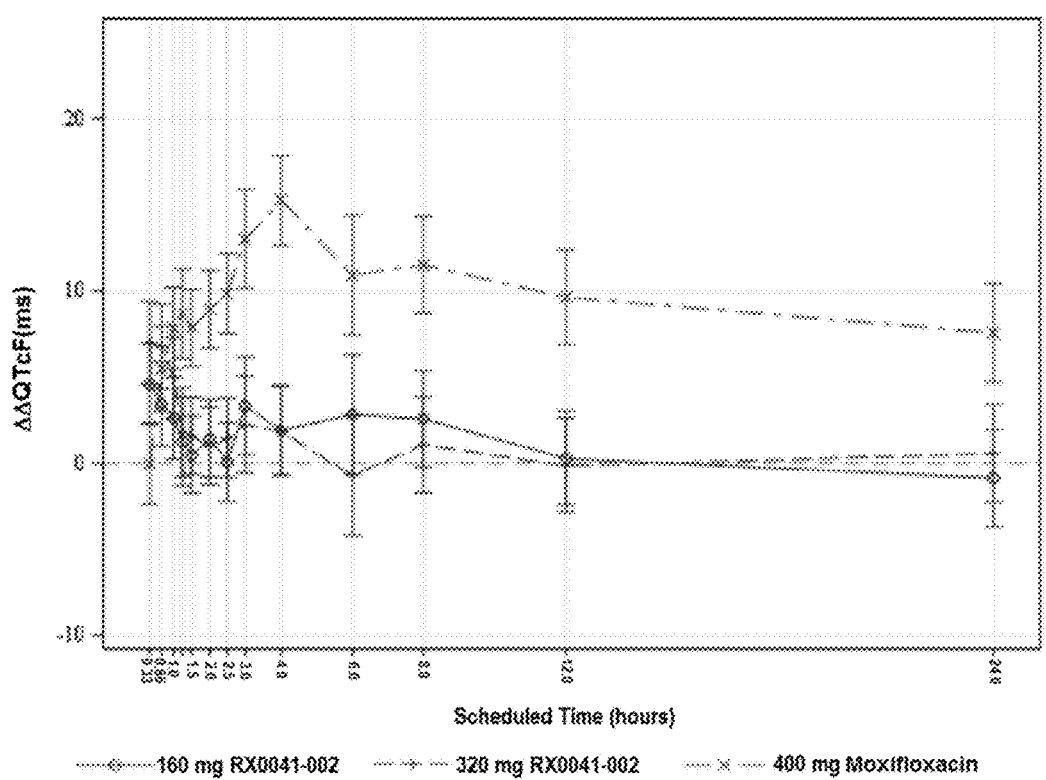
FIG. 45 is a plot of the mean ΔΔQTcF as a function of time as observed during two treatments using a cocaine hydrochloride pharmaceutical composition (160 mg or 320 mg cocaine hydrochloride; batch lot RX0041-002) as compared to treatment with oral moxifloxacin HCl (400 mg).

The mean ΔΔQTcF as a function of time is presented for the three active treatments is shown in the plot of FIG. 45. The values of mean ΔΔQTcF did not exceed 7.0 ms or 4.6 ms for the 320 mg and 160 mg cocaine hydrochloride pharmaceutical composition treatments, respectively; the peak ΔΔQTcF after dosing of 400 mg moxifloxacin HCl was 15.2 ms at 4 h post-dose. There were no categorical outliers in terms of QTcF>450 ms or ΔQTcF>30 ms after administration of cocaine hydrochloride pharmaceutical composition and no treatment emergent T-wave morphology changes.

It will be understood that the present description illustrates those aspects of the invention relevant to a clear understanding of the invention. Certain aspects that would be apparent to those of ordinary skill in the art and that, therefore, would not facilitate a better understanding of the invention have not been presented in order to simplify the present description. Although only a limited number of embodiments of the present invention are necessarily described herein, one of ordinary skill in the art will, upon considering the foregoing description, recognize that many modifications and variations of the invention may be employed. All such variations and modifications of the invention are intended to be covered by the foregoing description and the following claims.

The following numbered clauses are directed to various non-limiting examples of inventions according to the present disclosure:

1. A ready to use pharmaceutical composition comprising:
    about 4% cocaine hydrochloride, by weight; and
    a preservative in an aqueous solution at a pH of 2 to 4,
    wherein the cocaine hydrochloride concentration is greater than about 3.4%, by weight, after the composition has been stored for 24 months at a temperature ranging from 23° C. to 27° C. and a relative humidity ranging from 55% to 65%.
2. A ready to use pharmaceutical composition comprising:
    about 4% cocaine hydrochloride, by weight,
    wherein the cocaine hydrochloride concentration is greater than about 3.4%, by weight, after the composition has been stored for 6 months at a temperature ranging from 28° C. to 32° C., and a relative humidity ranging from 60% to 70%.
3. A ready to use pharmaceutical composition comprising:
    about 4% cocaine hydrochloride, by weight,
    wherein the cocaine hydrochloride concentration is greater than about 3.4%, by weight, after the composition has been stored for 1 month at a temperature ranging from 38° C. to 42° C., and a relative humidity ranging from 70% to 80%.
4. A storage stable pharmaceutical composition comprising:
    about 4% cocaine hydrochloride, by weight,
    wherein the composition comprises no more than 7% of total impurities, by weight, after the composition has been stored for 20 months at a temperature ranging from 23° C. to 27° C., and a relative humidity ranging from 55% to 65%.
5. A storage stable pharmaceutical composition comprising:
    about 4% cocaine hydrochloride, by weight,
    wherein the composition comprises no more than 8% of total impurities, by weight, after the composition has been stored for 12 months at a temperature ranging from 28° C. to 32° C., and a relative humidity ranging from 60% to 70%.
6. A storage stable pharmaceutical composition comprising:
    about 4% cocaine hydrochloride, by weight,
    wherein the composition comprises no more than 10% of total impurities, by weight, after the composition has been stored for 6 months at a temperature ranging from 38° C. to 42° C., and a relative humidity ranging from 70% to 80%.
7. A pharmaceutical composition for reducing sensation in a body region of a subject, the pharmaceutical composition comprising:
    about 4% cocaine hydrochloride, by weight,
    wherein the pharmaceutical composition provides a cocaine $AUC_{inf}$ ranging from about 30.8 ng*h/mL to about 79.0 ng*h/mL, following a topical application of the pharmaceutical composition to the subject for about 20 minutes.
8. A pharmaceutical composition for reducing sensation in a body region of a subject, the pharmaceutical composition comprising:
    about 4% cocaine hydrochloride, by weight,
    wherein the pharmaceutical composition provides a cocaine $C_{max}$ ranging from about 19.7 ng/mL to about 54.3 ng/mL following a topical application of the pharmaceutical composition to the patient for about 20 minutes.
9. A pharmaceutical composition for reducing sensation in a body region of a subject, the pharmaceutical composition comprising:
    about 4% cocaine hydrochloride, by weight,
    wherein the pharmaceutical composition provides a cocaine $T_{max}$ of about 0.09 h to about 0.77 h following a topical application of the pharmaceutical composition to the patient for about 20 minutes.
10. A pharmaceutical composition for reducing sensation in a body region of a patient, the pharmaceutical composition comprising:
    about 4% cocaine hydrochloride, by weight,
    wherein the pharmaceutical composition provides an absorptivity factor for cocaine in the patient ranging from about 0.640 $h^{-1}$ to about 0.687 $h^{-1}$ following a topical application of the pharmaceutical composition to the patient for about 20 minutes.
11. A method of administering a topical anesthetic solution to a patient to reduce sensation in a body region of the patient comprising:
    soaking absorbent articles with a cocaine hydrochloride solution, the cocaine hydrochloride solution including a concentration of cocaine hydrochloride of about 4%, by weight,
    contacting the absorbent articles with a nasal mucous membrane of the patient for at least about 20 minutes,
    wherein the method results in a cocaine $AUC_{inf}$ in the patient from about 30.8 ng*h/mL to about 79.0 ng*h/mL.
12. A method of administering a topical anesthetic solution to a patient to reduce sensation in a body region of the patient comprising:
    soaking a plurality of absorbent articles with an aqueous solution comprising about 4%, by weight, cocaine hydrochloride,
    contacting the absorbent articles with a nasal mucous membrane of a patient for about at least 20 minutes,
    wherein the method results in a cocaine $T_{max}$ in the patient ranging from about 0.09 h to about 0.77 h.
13. A method of administering a topical anesthetic solution to a patient to provide a reduction in sensation in a body region of the patient comprising:
    soaking a plurality of absorbent articles with an aqueous solution comprising about 4% cocaine hydrochloride, by weight,
    contacting the absorbent articles with a nasal mucous membrane of a patient for at least about 20 minutes,
    wherein the method achieves a cocaine $C_{max}$ in the patient ranging from about 19.7 ng/mL to about 54.3 ng/mL.
14. A method of administering a topical localized anesthetic composition to a patient comprising:
    soaking a plurality of absorbent articles with an aqueous solution comprising about 4% cocaine hydrochloride, by weight,
    contacting the absorbent articles with a nasal mucous membrane of a patient for at least about 20 minutes,
    wherein the method results in an absorptivity factor for cocaine in the patient ranging from about 0.640 $h^{-1}$ to about 0.687 $h^{-1}$.
15. A method of administering a topical localized anesthetic composition to a patient comprising:
    soaking a plurality of absorbent articles with an aqueous solution comprising 4% cocaine hydrochloride, by weight,
    contacting the absorbent articles with a nasal mucous membrane of a patient for about 20 minutes;

16. A method of administering a topical anesthetic solution to a patient to reduce sensation in a body region of the patient comprising:
   soaking a plurality of absorbent articles with an anesthetic solution including about 4%, by weight, cocaine hydrochloride,
   contacting the absorbent articles with a nasal mucous membrane of a patient for at least about 20 minutes,
   wherein the method results in an ecgonine methyl ester $C_{max}$ in the patient ranging from about 1.8 ng/mL to about 13.2 ng/mL.

17. A method of administering a topical anesthetic solution to a patient to reduce sensation in a body region of the patient comprising:
   soaking a plurality of absorbent articles with an anesthetic solution including about 4%, by weight, cocaine hydrochloride,
   contacting the absorbent articles with a nasal mucous membrane of a patient for at least about 20 minutes,
   wherein the method results in a benzoylecgonine $C_{max}$ in the patient ranging from about 8.4 ng/mL to about 103 ng/mL.

18. A method for induction of local anesthesia prior to performing a diagnostic procedure on, through, or adjacent the mucous membrane of the nasal cavities of a patient comprising:
   soaking a cottonoid pledget with about 1 mL of an aqueous solution comprising about 4% cocaine hydrochloride, by weight,
   contacting the soaked cottonoid pledget with a mucous membrane of a patient for at least about 20 minutes to reduce sensation in a body region of the patient.

19. A method for inducing local anesthesia prior to performing a post-operative procedure on, through, or adjacent the mucous membrane of the nasal cavities of a patient comprising:
   soaking a cottonoid pledget with about 1 mL of a colored aqueous solution comprising about 4% cocaine hydrochloride, by weight,
   contacting the soaked cottonoid pledget with a mucous membrane of a patient for about at least 20 minutes to reduce sensation in a body region.

20. A method for inducing local anesthesia prior to performing a surgical procedure on, through, or adjacent the mucous membrane of the nasal cavities of a patient comprising:
   soaking a cottonoid pledget with about 1 mL of an aqueous solution comprising about 4% cocaine hydrochloride, by weight,
   contacting the soaked cottonoid pledget with a mucous membrane of a patient for at least about 20 minutes to reduce sensation in a body region.

21. A method of effectively anesthetizing a body region of a patient comprising:
   immersing at least one absorbent article in an aqueous pharmaceutical composition comprising about 3.6% to about 4.4% cocaine hydrochloride, by weight,
   contacting the at least one absorbent article and the aqueous pharmaceutical composition absorbed therein with a mucous membrane of a patient for a time period;
   thereby obtaining a visual numeric rating score of 0 in the body region proximate to the mucous membrane upon von Frey filament testing.

22. A method of effectively anesthetizing a body region of a patient prior to performing a medical procedure on the patient comprising:
   immersing at least one absorbent article in an aqueous pharmaceutical composition comprising about 3.6% to about 4.4% cocaine hydrochloride, by weight,
   contacting the at least one absorbent article and the aqueous pharmaceutical composition absorbed therein with a mucous membrane of a patient for a time period sufficient to result in a visual numeric rating score of 0 in the body region proximate to the mucous membrane upon von Frey filament testing.

23. A method of effectively anesthetizing a body region of a hepatically impaired patient comprising:
   immersing at least one absorbent article in an aqueous pharmaceutical composition comprising about 3.6% to about 4.4% cocaine hydrochloride, by weight,
   contacting the at least one absorbent article and the aqueous pharmaceutical composition absorbed therein with a mucous membrane of a patient for a time period sufficient to result in a visual numeric rating score of 0 in the body region proximate to the mucous membrane upon von Frey filament testing,
   wherein contacting the at least one absorbent article containing the aqueous pharmaceutical composition with the mucous membrane is not repeated within 24 hours.

24. A method of effectively anesthetizing a body region of a renally impaired patient comprising:
   immersing at least one absorbent article in an aqueous pharmaceutical composition comprising about 3.6% to about 4.4% cocaine hydrochloride, by weight,
   contacting the at least one absorbent article and the aqueous pharmaceutical composition absorbed therein with a mucous membrane of a patient for a time period sufficient to result in a visual numeric rating score of 0 in a body region proximate to the mucous membrane upon von Frey filament testing.

25. A ready to use pharmaceutical composition comprising:
   about 4% cocaine hydrochloride, by weight,
   wherein the cocaine hydrochloride concentration is greater than about 3.4%, by weight, after the composition has been stored for 24 months at a temperature ranging from 3° C. to 7° C.

26. A ready to use pharmaceutical composition comprising:
   about 8% cocaine hydrochloride, by weight,
   wherein the cocaine hydrochloride concentration is greater than about 6.8%, by weight, after the composition has been stored for 24 months at a temperature ranging from 3° C. to 7° C.

27. A storage stable pharmaceutical composition comprising:
   about 8% cocaine hydrochloride, by weight,
   wherein the composition comprises no more than 10% of total impurities, by weight, after the composition has been stored for 21 months at a temperature ranging from 23° C. to 27° C., and a relative humidity ranging from 55% to 65%.

28. A storage stable pharmaceutical composition comprising:
about 4% cocaine hydrochloride, by weight,
wherein the composition comprises no more than 6% of total impurities, by weight, after the composition has been stored for 24 months at a temperature ranging from 3° C. to 7° C.

29. A ready to use pharmaceutical composition comprising:
about 4% cocaine hydrochloride, by weight,
wherein the cocaine hydrochloride concentration is greater than about 3.4%, by weight, after the composition has been stored for 9 months at a temperature ranging from 23° C. to 27° C. and a relative humidity ranging from 55% to 65%.

30. A ready to use pharmaceutical composition comprising:
about 4% cocaine hydrochloride, by weight,
wherein the cocaine hydrochloride concentration is greater than about 3.4%, by weight, after the composition has been stored for 3 months at a temperature ranging from 23° C. to 27° C. and a relative humidity ranging from 55% to 65%.

31. A ready to use pharmaceutical composition comprising:
about 4% cocaine hydrochloride, by weight, 32. wherein the cocaine hydrochloride concentration is greater than about 3.4%, by weight, after the composition has been stored for 6 months at a temperature ranging from 23° C. to 27° C. and a relative humidity ranging from 55% to 65%.

33. A ready to use pharmaceutical composition comprising:
about 4% cocaine hydrochloride, by weight,
wherein the cocaine hydrochloride concentration is greater than about 3.4%, by weight, after the composition has been stored for 12 months at a temperature ranging from 23° C. to 27° C. and a relative humidity ranging from 55% to 65%.

34. A ready to use pharmaceutical composition comprising:
about 4% cocaine hydrochloride, by weight,
wherein the cocaine hydrochloride concentration is greater than about 3.4%, by weight, after the composition has been stored for 18 months at a temperature ranging from 23° C. to 27° C. and a relative humidity ranging from 55% to 65%.

35. A ready to use pharmaceutical composition comprising:
about 4% cocaine hydrochloride, by weight,
wherein the cocaine hydrochloride concentration is greater than about 3.4%, by weight, after the composition has been stored for 20 months at a temperature ranging from 23° C. to 27° C. and a relative humidity ranging from 55% to 65%.

36. A ready to use pharmaceutical composition comprising:
about 4% cocaine hydrochloride, by weight,
wherein the cocaine hydrochloride concentration is greater than about 3.5%, by weight, after the composition has been stored for 6 months at a temperature ranging from 38° C. to 42° C., and a relative humidity ranging from 70% to 80%.

37. A ready to use pharmaceutical composition comprising:
about 4% cocaine hydrochloride, by weight,
wherein the cocaine hydrochloride concentration is greater than about 3.4%, by weight, after the composition has been stored for 3 months at a temperature ranging from 38° C. to 42° C., and a relative humidity ranging from 70% to 80%.

38. A storage stable pharmaceutical composition comprising:
about 4% cocaine hydrochloride, by weight,
wherein the composition comprises no more than about 5% of total impurities, by weight, after the composition has been stored for 9 months at a temperature ranging from 23° C. to 27° C., and a relative humidity ranging from 55% to 65%.

39. A storage stable pharmaceutical composition comprising:
about 4% cocaine hydrochloride, by weight,
wherein the composition comprises no more than about 8% of total impurities, by weight, after the composition has been stored for 20 months at a temperature ranging from 23° C. to 27° C., and a relative humidity ranging from 55% to 65%.

40. A storage stable pharmaceutical composition comprising:
about 4% cocaine hydrochloride, by weight,
wherein the composition comprises no more than about 12% of total impurities, by weight, after the composition has been stored for 6 months at a temperature ranging from 38° C. to 42° C., and a relative humidity ranging from 70% to 80%.

41. A method of administering a local anesthetic on a subject undergoing a diagnostic or surgical procedure, comprising:
soaking one or more pledgets in about 4 mL of a ready-to-use composition comprising about 32.0 mg/mL to 39.2 mg/mL of cocaine free-base or an equivalent amount of pharmaceutically acceptable salt of cocaine,
contacting each of the one or more pledgets on a mucous membrane of a subject for up to 20 minutes,
removing each of the one or more pledgets, and
monitoring the subject for seizures during the administration.

42. A method of administering a local anesthetic on a subject not concurrently receiving any other vasoconstrictor agent, comprising:
soaking one or more pledgets in about 4 mL of a ready-to-use composition comprising about 32.0 mg/mL to 39.2 mg/mL of cocaine free-base or an equivalent amount of pharmaceutically acceptable salt of cocaine,
contacting each of the one or more pledgets on a mucous membrane of a subject for up to 20 minutes, and
removing each of the one or more pledgets.

43. A method of effectively anesthetizing a body region of a patient comprising:
immersing at least one absorbent article in an aqueous pharmaceutical composition comprising about 32.0 mg/mL to 39.2 mg/mL of cocaine free-base or an equivalent amount of a pharmaceutically acceptable salt of cocaine,
contacting the at least one absorbent article and the aqueous pharmaceutical composition absorbed therein with a mucous membrane of a patient for a time period such that a total dose to the patient does not exceed 3 mg/kg of body weight, and obtaining a visual numeric rating score of 0 in a body region proximate to the mucous membrane upon von Frey filament testing.

44. A ready to use pharmaceutical composition comprising:
about 4% cocaine hydrochloride, by weight,
wherein the cocaine hydrochloride concentration is greater than about 3.6%, by weight, after the composition has been stored for 24 months at a temperature ranging from 3° C. to 7° C.

45. A ready to use pharmaceutical composition comprising:
about 4% cocaine hydrochloride, by weight,
wherein the cocaine hydrochloride concentration is greater than about 3.4%, by weight, after the composition has been stored for 6 months at a temperature ranging from 38° C. to 42° C. and a relative humidity ranging from 70% to 80%.

46. A storage stable pharmaceutical composition comprising:
about 4% cocaine hydrochloride, by weight,
wherein the composition comprises no more than 6% of total impurities, by weight, after the composition has been stored for 6 months at a temperature ranging from 23° C. to 27° C., and a relative humidity ranging from 55% to 65%.

47. Method of administering a local anesthetic to a subject, comprising:
soaking one or more pledgets in about 4 mL of a composition comprising about 3.8% to about 4.2% cocaine hydrochloride, by weight,
contacting each of the one or more pledgets on a mucous membrane of a subject for about 20 minutes,
removing each of the one or more pledgets from the mucous membrane, and
monitoring a heart rate of the subject,
wherein a change in the subject's baseline heart rate is from about 4 beats per minute to about 8 beats per minute at about 60 minutes after administration of the local anesthetic.

48. Method of administering a local anesthetic to a subject, comprising:
soaking one or more pledgets in about 4 mL of a composition comprising about 3.8% to about 4.2% cocaine hydrochloride, by weight,
contacting each of the one or more pledgets on a mucous membrane of a subject for about 20 minutes,
removing each of the one or more pledgets from the mucous membrane, and
monitoring a heart rate of the subject for about 75 minutes.

49. Method of administering a local anesthetic to a subject, comprising:
soaking one or more pledgets in about 4 mL of a composition comprising about 3.8% to about 4.2% cocaine hydrochloride,
contacting each of the one or more pledgets on a mucous membrane of a subject for about 20 minutes,
removing each of the one or more pledgets from the mucous membrane, and
monitoring an ECG of the subject,
wherein the change in the subject's baseline QTcF is from about 1 ms to about 5 ms at about 60 minutes after administration of a local anesthetic.

What is claimed is:

1. A method of providing induction of local anesthesia of mucous membranes in adult patients comprising:
soaking four cottonoid pledgets in the contents of one bottle containing about 4 mL of a pharmaceutical composition comprising about 36 mg/mL to 44 mg/mL of naturally derived cocaine hydrochloride, until each pledget absorbs about 40 mg of naturally derived cocaine hydrochloride,
contacting two pledgets in each nasal cavity against a septum of a patient for a period ranging from about 10 minutes to about 20 minutes, provided that the method results in a maximum plasma concentration $C_{max}$ in a range from about 19.7 ng/mL to about 54.3 ng/mL of cocaine in the patient; and
performing a procedure on the patient, the procedure selected from the group consisting of a nasal laryngoscopy, a nasopharyngeal laryngoscopy, and a nasal debridement,
provided that the method results in a reduction in pain equivalent to achieving a visual numeric rating score of 0 upon von Frey filament testing.

2. The method of claim 1, wherein the procedure is a nasal laryngoscopy.

3. The method of claim 1, wherein the procedure is a nasopharyngeal laryngoscopy.

4. The method of claim 1, wherein the procedure is a nasal debridement.

5. The method of claim 1, wherein a length of each pledget is from about 3.0 cm to about 8.0 cm.

6. The method of claim 1, wherein a height of each pledget is about 1.3 cm and a length of each pledget is about 4 cm.

7. The method of claim 1, wherein the $C_{max}$ is about 37 ng/mL.

8. A method of providing induction of local anesthesia of mucous membranes in adult patients comprising:
soaking four cottonoid pledgets in the contents of one bottle containing about 4 mL of a pharmaceutical composition comprising about 36 mg/mL to 44 mg/mL of naturally derived cocaine hydrochloride, until each pledget absorbs about 40 mg of naturally derived cocaine hydrochloride;
contacting two pledgets in each nasal cavity against a septum of a patient in a range from about 10 minutes to about 20 minutes, provided that the method results in an $AUC_{inf}$ in a range from about 30.8 ng*h/mL to about 79.0 ng*h/mL of cocaine in the patient; and
performing a procedure on the patient, the procedure selected from the group consisting of a nasal laryngoscopy, a nasopharyngeal laryngoscopy, and a nasal debridement,
provided that the method results in a reduction in pain equivalent to achieving a visual numeric rating score of 0 upon von Frey filament testing.

9. The method of claim 8, wherein a length of each pledget is from about 3.0 cm to about 8.0 cm.

10. The method of claim 8, wherein a height of each pledget is about 1.3 cm and a length of each pledget is about 4 cm.

11. The method of claim 8, wherein the $AUC_{inf}$ is about 54.9 ng*h/mL.

12. The method of claim 8, wherein the procedure is a nasal laryngoscopy.

13. The method of claim 8, wherein the procedure is a nasopharyngeal laryngoscopy.

14. The method of claim 8, wherein the procedure is a nasal debridement.

15. The method of claim 8, wherein the achieved $AUC_{inf}$ ranges from about 30.8 ng*h/mL to about 54.9 ng*h/mL of cocaine in the patient.

16. The method of claim 8, wherein the achieved $AUC_{inf}$ ranges from about 54.9 ng*h/mL to about 79.0 ng*h/mL of cocaine in the patient.

* * * * *